United States Patent
Freedman et al.

(10) Patent No.: US 12,320,800 B2
(45) Date of Patent: Jun. 3, 2025

(54) HIGH-THROUGHPUT AUTOMATION OF ORGANOIDS FOR IDENTIFYING THERAPEUTIC STRATEGIES

(71) Applicant: UNIVERSITY OF WASHINGTON, Seattle, WA (US)

(72) Inventors: Benjamin Freedman, Seattle, WA (US); Nelly M. Cruz Esteves, Seattle, WA (US); Neal Paragas, Seattle, WA (US); Stefan Czerniecki, Seattle, WA (US)

(73) Assignee: University of Washington, Seattle, WA (US)

( * ) Notice: Subject to any disclaimer, the term of this patent is extended or adjusted under 35 U.S.C. 154(b) by 1144 days.

(21) Appl. No.: 17/055,535

(22) PCT Filed: May 16, 2019

(86) PCT No.: PCT/US2019/032754
§ 371 (c)(1),
(2) Date: Nov. 13, 2020

(87) PCT Pub. No.: WO2019/222559
PCT Pub. Date: Nov. 21, 2019

(65) Prior Publication Data
US 2021/0290632 A1    Sep. 23, 2021

Related U.S. Application Data

(60) Provisional application No. 62/739,637, filed on Oct. 1, 2018, provisional application No. 62/672,470, filed on May 16, 2018.

(51) Int. Cl.
*G01N 33/50*    (2006.01)

(52) U.S. Cl.
CPC .................. *G01N 33/5073* (2013.01)

(58) Field of Classification Search
None
See application file for complete search history.

(56) References Cited

U.S. PATENT DOCUMENTS

| | | |
|---|---|---|
| 2003/0008864 A1 | 1/2003 | Schreiner et al. |
| 2005/0118715 A1 | 6/2005 | Hariri et al. |
| 2015/0284689 A1 | 10/2015 | Nigam |
| 2016/0101133 A1 | 4/2016 | Basu et al. |
| 2016/0311764 A1 | 10/2016 | Robinson et al. |
| 2017/0081639 A1* | 3/2017 | Kume ............... G01N 33/74 |

FOREIGN PATENT DOCUMENTS

| | | |
|---|---|---|
| WO | 2013/063588 A1 | 5/2013 |
| WO | 2016/083613 A2 | 6/2016 |
| WO | 2017/041041 A1 | 3/2017 |

OTHER PUBLICATIONS

Radke et al. "Small Molecule-Mediated Refolding and Activation of Myosin Motor Function". eLife. 2014; 3:e01603. (Year: 2014).*
Siller et al. "Development of a rapid screen for the endodermal differentiation potential of human pluripotent stem cell lines" (2016), Scientific Reports, 6:37178, 1-14 (Year: 2016).*
Ho et al. "Disease Modeling Using 3D Organoids Derived from Human Induced Pluripotent Stem Cells" (Mar. 2018), Intern'l J Molecul Sci, 19, 936, 1-17. (Year: 2018).*
Lin et al. "Differentiation, Evaluation, and Applicaiton of Human Induced Pluripotent Stem Cell-Derived Endothelial Cells" (2017), Artioscler Thromb Vasc Biol, DOI: 10.1161/ATVBAHA.117.309962 (Year: 2017).*
Boehnke et al. "Assay Establishment and Validation of a High-Throughput Screening Platform for Three-Dimensional Patient-Derived Colon Cancer Organoid Cultures" (2016), vol. 21(9): 931-941. (Year: 2016).*
Desbordes & Studer "Adapting human pluripotent stem cells to high-throughput and high-content screening" (2012), Nature Protocols, vol. 8, No. 1: 111-130. (Year: 2012).*
Abrahamson, D.R., et al., (2013). Laminin and type IV collagen isoform substitutions occur in temporally and spatially distinct patterns in developing kidney glomerular basement membranes. J. Histochem. Cytochem. 61, 706-718.
Adam, M., et al., (2017). Psychrophilic proteases dramatically reduce single-cell RNA-seq artifacts: A molecular atlas of kidney development. Development 144, 3625-3632.
Astashkina, A.I., et al., (2012). A 3-D organoid kidney culture model engineered for high-throughput nephrotoxicity assays. Biomaterials 33, 4700-4711.
Boletta, A. et al. Polycystin-1, the gene product of PKD1, induces resistance to apoptosis and spontaneous tubulogenesis in MDCK cells. Mol. Cell 6, 1267-1273 (2000).
Brunskill, E.W., et al., (2011). Genes that confer the identity of the renin cell. J. Am. Soc. Nephrol. 22, 2213-2225.
Cai, Y. et al. Altered tracking and stability of polycystins underlie polycystic kidney disease. J. Clin. Invest. 124, 5129-5144 (2014).
Chauvet, V. et al. Expression of PKD1 and PKD2 transcripts and proteins in human embryo and during normal kidney development. Am. J. Pathol. 160, 973-983 (2002).
Chen, S., et al., (2009). A small molecule that directs differentiation of human ESCs into the pancreatic lineage. Nat. Chem. Biol. 5, 258-265.

(Continued)

*Primary Examiner* — Teresa E Knight
(74) *Attorney, Agent, or Firm* — Lee & Hayes, P.C.

(57) ABSTRACT

Methods for testing the effects of therapeutic compound candidates on a phenotypic organoid model is provided. Such a method includes steps of generating the phenotypic organoid model on a high throughput screening platform, treating the organoid with a therapeutic compound candidate, and testing one or more effects resulting from treatment with each of the therapeutic compound candidates. The testing method that has led to identification of a method for treating or preventing cysts is provided. That method may include contacting a population of cells with an inotrope, wherein the inotrope prevents cyst formation, shrinks existing cysts, or both. That method may be used to treat cystogenic diseases or conditions such as Polycystic Kidney Disease (PKD).

11 Claims, 71 Drawing Sheets

(56) References Cited

OTHER PUBLICATIONS

Chuah et al. Stem Cell-Derived Kidney Cells and Organoids: Recent Breakthroughs and Emerging Applications. Biotechnology Advances 35: 150-67 (2017).
Conti, M.A., et al., (2004). Defects in cell adhesion and the visceral endoderm following ablation of nonmuscle myosin heavy chain II-A in mice. J. Biol. Chem. 279, 41263-41266.
Cruz, N. M. et al. Organoid cystogenesis reveals a critical role of microenvironment in human polycystic kidney disease. Nat Mater. Nov. 2017; 16(11): 1112-1119.
Czerniecki, S.M. et al. High-Throughput Screening Enhances Kidney Organoid Differentiation from Human Pluripotent Stem Cells and Enables Automated Multidimensional Phenotyping. Cell Stem Cell. Jun. 1, 2018; 22(6): 929-940.e4.
Daniel, C., et al., (2012). Transgelin is a marker of repopulating mesangial cells after injury and promotes their proliferation and migration. Lab. Invest. 92, 812-826.
Dekel, B., et al., (2003). Human and porcine early kidney precursors as a new source for transplantation. Nat. Med. 9, 53-60.
Dekkers, J.F., et al., (2013). A functional CFTR assay using primary cystic fibrosis intestinal organoids. Nat. Med. 19, 939-945.
Desrochers, T et al. Bioengineered 3D Human Kidney Tissue, a Platform for the Determination of Nephrotoxicity. PLoS One. vol. 8 / Issue 3 (2013).
Doerr, N., et al. (2016). Regulation of polycystin-1 function by calmodulin binding. PLoS ONE 11, e0161525.
Doulatov, S., et al. (2017). Drug discovery for Diamond-Blackfan anemia using reprogrammed hematopoietic progenitors. Sci. Transl. Med. 9, 376.
Freedman, B. S. et al. Reduced ciliary polycystin-2 in induced pluripotent stem cells from polycystic kidney disease patients with PKD1 mutations. J. Am. Soc. Nephrol. 24, 1571-1586 (2013).
Freedman, B. S. et al. Modelling kidney disease with CRISPR-mutant kidney organoids derived from human pluripotent epiblast spheroids. Nat. Commun. 6, 8715 (2015).
Gainullin, V. G., et al., Polycystin-1 maturation requires polycystin-2 in a dose-dependent manner. J. Clin. Invest. 125, 607-620 (2015).
Gattone, V. H. II, et al., Inhibition of renal cystic disease development and progression by a vasopressin V2 receptor antagonist. Nat. Med. 9, 1323-1326 (2003).
Gracz, A.D., et al. (2015). A highthroughput platform for stem cell niche co-cultures and downstream gene expression analysis. Nat. Cell Biol. 17, 340-349.
Grantham, J. J., et al., Cyst formation and growth in autosomal dominant polycystic kidney disease. Kidney Int. 31, 1145-1152 (1987).
Grskovic, M., et al., (2011). Induced pluripotent stem cells—opportunities for disease modelling and drug discovery. Nat. Rev. Drug Discov. 10, 915-929.
Halt, K.J., et al., (2016). CD146(+) cells are essential for kidney vasculature development. Kidney Int. 90, 311-324.
Harari-Steinberg, O., et al. (2013). Identification of human nephron progenitors capable of generation of kidney structures and functional repair of chronic renal disease. EMBO Mol. Med. 5, 1556-1568.
Hayashi, R., et al. (2016). Co-ordinated ocular development from human iPS cells and recovery of corneal function. Nature 531, 376-380.
Huang, L., et al. (2015). Ductal pancreatic cancer modeling and drug screening using human pluripotent stem cell- and patient-derived tumor organoids. Nat. Med. 21, 1364-1371.
Huch, M. et al. Modeling mouse and human development using organoid cultures. Development. (2015) 142: 3113-25.
Ibraghimov-Beskrovnaya, O. et al. Strong homophilic interactions of the Ig-like domains of polycystin-1, the protein product of an autosomal dominant polycystic kidney disease gene, PKD1. Hum. Mol. Genet. 9, 1641-1649 (2000).
ISA, International Search Report and Written Opinion for International Application No. PCT/US2019/032754. Mail Date: Sep. 17, 2019. 13 pages.
Jin, Y., et al. (2017). Endoglin prevents vascular malformation by regulating flow-induced cell migration and specification through VEGFR2 signalling. Nat. Cell Biol. 19, 639-652.
Jinek, M. et al. A programmable dual-RNA-guided DNA endonuclease in adaptive bacterial immunity. Science 337, 816-821 (2012).
Kandasamy, K., et al., (2015). Prediction of drug-induced nephrotoxicity and injury mechanisms with human induced pluripotent stem cellderived cells and machine learning methods. Sci. Rep. 5, 12337.
Kim, Y.K., et al. (2017). Gene-edited human kidney organoids reveal mechanisms of disease in podocyte development. Stem Cells 35, 2366-2378.
Lam, A.Q., et al., (2014). Rapid and efficient differentiation of human pluripotent stem cells into intermediate mesoderm that forms tubules expressing kidney proximal tubular markers. J. Am. Soc. Nephrol. 25, 1211-1225.
Lancaster, M. A. et al. Cerebral organoids model human brain development and microcephaly. Nature 501, 373-379 (2013).
Lantinga-van Leeuwen, I. S. et al. Lowering of Pkd1 expression is sufficient to cause polycystic kidney disease. Hum. Mol. Genet. 13, 3069-3077 (2004).
Liberzon, A. et al. The Molecular Signatures Database (MSigDB) hallmark gene set collection. Cell Syst. 1, 417-425 (2015).
Lienkamp, S.S., et al., (2012). Vertebrate kidney tubules elongate using a planar cell polarity-dependent, rosette-based mechanism of convergent extension. Nat. Genet. 44, 1382-1387.
Lin, S.L., et al., (2008). Pericytes and perivascular fibroblasts are the primary source of collagen-producing cells in obstructive fibrosis of the kidney. Am. J. Pathol. 173, 1617-1627.
Mae, S.I., et al. (2013). Monitoring and robust induction of nephrogenic intermediate mesoderm from human pluripotent stem cells. Nat. Commun. 4, 1367.
Magenheimer, B. S. et al. Early embryonic renal tubules of wild-type and polycystic kidney disease kidneys respond to CAMP stimulation with cystic fibrosis transmembrane conductance regulator/Na+, K+,2Cl− Co-transporter-dependent cystic dilation. J. Am. Soc. Nephrol. 17, 3424-3437 (2006).
Major, M.B., et al. (2008). New regulators of Wnt/beta-catenin signaling revealed by integrative molecular screening. Sci. Signal. 1, ra12.
Mangos, S. et al. The ADPKD genes pkd1a/b and pkd2 regulate extracellular matrix formation. Dis Model Mech. 3, 354-365 (2010).
McCracken, K.W., et al., (2014). Modelling human development and disease in pluripotent stem-cell-derived gastric organoids. Nature 516, 400-404.
Menon, R., et al. (2018). Single-cell analysis of progenitor cell dynamics and lineage specification of the human fetal kidney. bioRxiv.
Mochizuki, T. et al. PKD2, a gene for polycystic kidney disease that encodes an integral membrane protein. Science 272, 1339-1342 (1996).
Morizane, R. et al. Nephron organoids derived from human pluripotent stem cells model kidney development and injury. Nat. Biotechnol. 33, 1193-1200 (2015).
Morizane et al. Kidney Organoids: A Translational Journey. Trends in Molecular Medicine 23: 246-63 (2017).
Nakanishi, K., et al., Proximal tubular cysts in fetal human autosomal recessive polycystic kidney disease. J. Am. Soc. Nephrol. 11, 760-763 (2000).
Neufeld, T. K. et al. In vitro formation and expansion of cysts derived from human renal cortex epithelial cells. Kidney Int. 41, 1222-1236 (1992).
Ong, A. C. et al. Polycystin-1 expression in PKD1, early-onset PKD1, and TSC2/PKD1 cystic tissue. Kidney Int. 56, 1324-1333 (1999).
Pabla, N., et al., (2008). Cisplatin nephrotoxicity: Mechanisms and renoprotective strategies. Kidney Int. 73, 994-1007.
Pagliuca, F.W., et al., (2014). Generation of functional human pancreatic b cells in vitro. Cell 159, 428-439.

(56) References Cited

OTHER PUBLICATIONS

Palpant, N.J., et al., (2017). Generating high-purity cardiac and endothelial derivatives from patterned mesoderm using human pluripotent stem cells. Nat. Protoc. 12, 15-31.

Park-Windhol, C., et al., (2017). Endomucin inhibits VEGF-induced endothelial cell migration, growth, and morphogenesis by modulating VEGFR2 signaling. Sci. Rep. 7, 17138.

Patel, V. et al. Acute kidney injury and aberrant planar cell polarity induce cyst formation in mice lacking renal cilia. Hum. Mol. Genet. 17, 1578-1590 (2008).

Qian, F., et al., The molecular basis of focal cyst formation in human autosomal dominant polycystic kidney disease type I. Cell 87, 979-987 (1996).

Ramm, S., et al., (2016). A high-throughput screening assay to identify kidney toxic compounds. Curr. Protoc. Toxicol. 69, 9.10.1-9.10.26.

Reif, G. A. et al. Tolvaptan inhibits ERK-dependent cell proliferation, Cl− secretion, and in vitro cyst growth of human ADPKD cells stimulated by vasopressin. Am. J. Physiol. Renal Physiol. 301, F1005-F1013 (2011).

Rinkevich, Y., et al. (2014). In vivo clonal analysis reveals lineage-restricted progenitor characteristics in mammalian kidney development, maintenance, and regeneration. Cell Rep. 7, 1270-1283.

Sachs, N., et al. (2018). A living biobank of breast cancer organoids captures disease heterogeneity. Cell 172, 373-386.e10.

Shankland, S.J., et al., (2017). Can podocytes be regenerated in adults? Curr. Opin. Nephrol. Hypertens. 26, 154-164.

Sharma, A., et al. (2017). Highthroughput screening of tyrosine kinase inhibitor cardiotoxicity with human induced pluripotent stem cells. Sci. Transl. Med. 9, 377.

Shillingford, J. M. et al. The mTOR pathway is regulated by polycystin-1, and its inhibition reverses renal cystogenesis in polycystic kidney disease. Proc. Natl Acad. Sci. USA 103, 5466-5471 (2006).

Song, X. et al. Systems biology of autosomal dominant polycystic kidney disease (ADPKD): computational identification of gene expression pathways and integrated regulatory networks. Hum. Mol. Genet. 18, 2328-2343 (2009).

Spence, J.R., et al. (2011). Directed differentiation of human pluripotent stem cells into intestinal tissue in vitro. Nature 470, 105-109.

Straight, A.F., et al., (2003). Dissecting temporal and spatial control of cytokinesis with a myosin II Inhibitor. Science 299, 1743-1747.

Subramanian, A. et al. Gene set enrichment analysis: a knowledge-based approach for interpreting genome-wide expression profiles. Proc. Natl Acad. Sci. USA 102, 15545-15550 (2005).

Sugden, W.W., et al. (2017). Endoglin controls blood vessel diameter through endothelial cell shape changes in response to haemodynamic cues. Nat. Cell Biol. 19, 653-665.

Taguchi, A. et al. Redefining the in vivo origin of metanephric nephron progenitors enables generation of complex kidney structures from pluripotent stem cells. Cell Stem Cell 14, 53-67 (2014).

Takahashi, K., et al., (2007). Induction of pluripotent stem cells from adult human fibroblasts by defined factors. Cell 131, 861-872.

Takakura, A. et al. Renal injury is a third hit promoting rapid development of adult polycystic kidney disease. Hum. Mol. Genet. 18, 2523-2531 (2009).

Takasato, M. et al. Kidney organoids from human iPS cells contain multiple lineages and model human nephrogenesis. Nature 526, 564-568 (2015).

The European Polycystic Kidney Disease Consortium. The polycystic kidney disease 1 gene encodes a 14 kb transcript and lies within a duplicated region on chromosome 16. Cell 77, 881-894 (1994).

The International Polycystic Kidney Disease Consortium. Polycystic kidney disease: the complete structure of the PKD1 gene and its protein. Cell 81, 289-298 (1995).

Thomson, J.A., et al., (1998). Embryonic stem cell lines derived from human blastocysts. Science 282, 1145-1147.

Trudel, M. et al. C-myc-induced apoptosis in polycystic kidney disease is Bcl-2 and p53 independent. J. Exp. Med. 186, 1873-1884 (1997).

Vicente-Manzanares, M., et al., (2009). Non-muscle myosin II takes centre stage in cell adhesion and migration. Nat. Rev. Mol. Cell Biol. 10, 778-790.

Vujic, M. et al. Incompletely penetrant PKD1 alleles mimic the renal manifestations of ARPKD. J. Am. Soc. Nephrol. 21, 1097-1102 (2010).

Yang, Y.M., et al. (2013). A small molecule screen in stem-cell-derived motor neurons identifies a kinase inhibitor as a candidate therapeutic for ALS. Cell Stem Cell 12, 713-726.

Zhang, J.H., et al., (1999). A simple statistical parameter for use in evaluation and validation of high throughput screening assays. J. Biomol. Screen. 4, 67-73.

\* cited by examiner

Cilia/ZO1/DNA pH3/LTL/DNA pH3/DNA podocyte/proximal tubule/
endothelial cells (CD31)/DNA

FIG. 10A

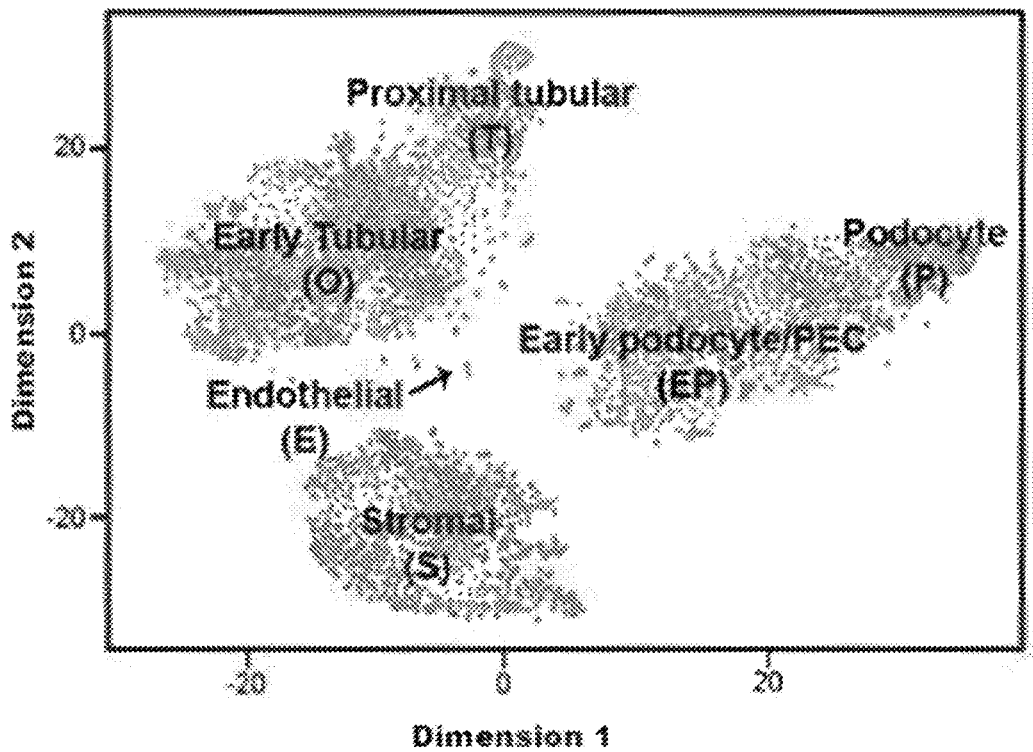

FIG. 10B

| | O | EP | S | T | P | E |
|---|---|---|---|---|---|---|
| Top Differentially Expressed Genes (DEGs) | LIMCH1 | CTGF | COL3A1 | AFP | NPHS2 | CD34 |
| | WFDC2 | MAFB | COL1A2 | GLYATL1 | PTPRO | PECAM1 |
| | CD24 | NPHS1 | POSTN | SLC3A1 | GADD45A | CDS3 |
| | EPCAM | CLIC5 | COL1A1 | TMEM176A | CLIC5 | EGFL7 |
| | MECOM | PODXL | LGALS1 | TMEM176B | PODXL | CALM1 |
| | GNG11 | PTPRO | DNM3OS | SLC34A1 | MAFB | SOX17 |
| | POU3F3 | SPARC | MGP | MPC2 | TGFBR3 | FLT1 |
| | PLEKHA1 | NPHS2 | ACTA2 | DAB2 | SOST | HLX |
| | LDHB | OLFM3 | CALD1 | PDZK1 | TCF21 | ROBO4 |
| | FTL | WT1 | PCOLCE | DPP4 | MPP5 | KDR |
| # Cells | 1931 | 1548 | 1423 | 485 | 353 | 28 |
| DEG p-values | ≤1.45E-203 | ≤1.35E-232 | ≤4.314E-272 | ≤1.82E-110 | ≤1.22E-194 | ≤2.65E-19 |

| | Stromal Subclusters | | | | |
|---|---|---|---|---|---|
| | S0 | S1 | S2 | S3 | S4 |
| Top Differentially Expressed Genes | ENO1 | IGF1 | DLK1 | NCAPG | INHBA |
| | TCF21 | IGFBP5 | SST | MKI67 | FN1 |
| | COL6A3 | POSTN | PAX8 | ZIC1 | IGFBP7 |
| | TBX3 | SRFP2 | GRINA | TOP2A | ANXA1 |
| | CRABP2 | MFAP4 | SHISA3 | FRZB | FLT1 |
| | SEPT11 | TGFBI | SFRP1 | PRC1 | COL4A1 |
| | JUNB | PTN | PCP4 | TK1 | ACTA2 |
| | BDNF | DCN | DNAJC22 | LUM | TPM1 |
| | ID3 | COL3A1 | CTTNBP2 | TGFB1 | ITGA4 |
| | VASP | SFRP1 | GPC3 | TPX2 | MCAM |
| # Cells | 438 | 355 | 271 | 203 | 156 |
| DEG p-values | ≤1.26E-6 | ≤5.43E-15 | ≤3.07E-14 | ≤1.07E-12 | ≤2.46E-39 |

FIG. 16C

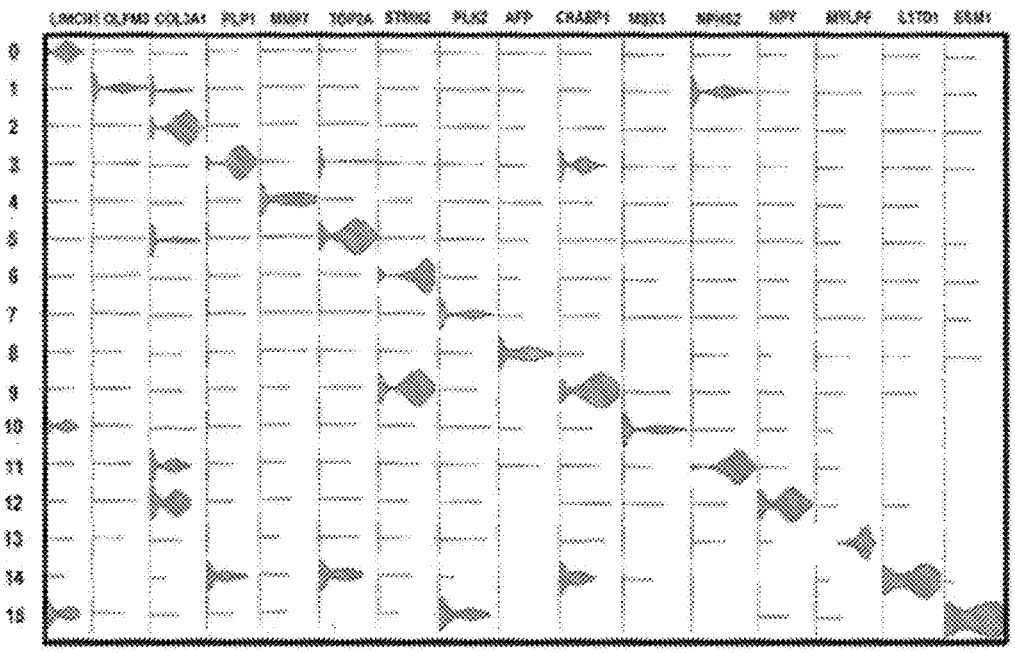

FIG. 16D

| Cell Types | Neural | Epithelial | Proliferating | Neural | Unidentified | Neural | Reproductive/endocrine | Reproductive/endocrine | Muscle/cardiac | Undifferentiated |
|---|---|---|---|---|---|---|---|---|---|---|
| Cluster | C3 | C4 | C5 | C6 | C7 | C9 | C10 | C12 | C13 | C14 |
| Top 20 Differentially Expressed Genes | PLP1 | MMP7 | TCP2A | STMN2 | PLK2 | CRABP1 | MSX1 | NPY | MYLPF | MIR302B |
| | S100B | LAMP5 | HMGB2 | GAP43 | IGF2 | MIAT | SCG2 | SPRR2F | ACTC1 | L1TD1 |
| | POSTN | ARL4C | MKI67 | PPP1R17 | TPM2 | MAP2 | LAPTM4B | FAM213A | TNNC2 | LIN28A |
| | EDNRB | IGFBP7 | CENPF | NEUROD1 | MEST | TUBA1A | THSD4 | NRK | MYL1 | OTX2 |
| | NPR3 | CDH6 | TPX2 | TUBA1A | CDH11 | MAP1B | NTRK2 | STAR | KLHL41 | ESRG |
| | TFAP2B | GSTP1 | UBE2C | RTN1 | CCND2 | TUBB2B | LINC00461 | BEX1 | MYH3 | SOX2 |
| | ERBB3 | DSP | TUBA1B | MAP1B | IGFBP5 | TAGLN3 | ZIC1 | LRRC17 | TPM2 | USP44 |
| | LMO4 | CLDN6 | NUSAP1 | BASP1 | | STMN2 | NLRP1 | MGST3 | TNNI1 | POU5F1 |
| | RPLP1 | CLDN1 | H2AFZ | ELAVL4 | | SOX11 | SOX2 | BEX3 | MYL4 | HMGA1 |
| | MOXD1 | PPFIBP1 | PRC1 | CADM1 | | MIR1242HG | TUBA1A | ATP2B1 | IL17B | SFRP2 |
| | CRABP1 | TPM1 | CCNB1 | CALM2 | | HES6 | DKK1 | ZDHHC8P1 | TNNT1 | CNTNAP2 |
| | SPP1 | MRS2 | CDK1 | STMN1 | | POU3F2 | TPBG | PEG10 | SMPX | IGP2 |
| | RPS12 | TFPI2 | PTTG1 | DCX | | RBP1 | WLS | HMGA2 | ACTA1 | TRIM71 |
| | RPS18 | DCDC2 | SMC4 | ISL1 | | DCX | AP1S2 | CFI | MYBPH | TERM1 |
| | RPS3 | KRT18 | CENPE | MLLT11 | | SOX4 | NEFM | MFGE8 | ACTN2 | SFRP1 |
| | VCAN | TNFRSF12A | CDC20 | POU4F1 | | STMN1 | VIM | TCEAL9 | APCBEC2 | AASS |
| | PABPC1 | EPCAM | BIRC5 | RGS10 | | MLLT11 | PCSK1N | SERINC5 | TNNT3 | SLC2A3 |
| | ITGA4 | JAG1 | NDC80 | C14orf132 | | NHLH2 | MAP1B | LAPTM4B | ENO3 | FEZ1 |
| | ARPC1B | KRT19 | CCNB2 | TUBB2B | | CRMP1 | CDH6 | COL3A1 | CASQ2 | DNMT3B |
| | RPLP0 | ADAMTS1 | CDCA8 | SYT4 | | DCC | SEMA3C | ARL4A | HSPB3 | SALL4 |
| DEG p-values ≤ | 3.44E-140 | 3.45E-62 | 1.96E-226 | 2.07E-232 | 3.75E-06 | 3.36E-134 | 8.70E-52 | 9.50E-12 | 5.33E-93 | 3.32E-14 |

Automated High-Throughput Organoid Differentiation

Application to Biological Questions

FIG. 38

| myosin activating compounds | |
|---|---|
| compound | effect |
| 4'-Hydroxyacetophenone | ↑ myosin IIB, IIC |
| EMD57003 | ↑ myosin |
| CK-1827452 | ↑ cardiac myosin S1 |
| Bis-T-23 | ↑ actin polymerization |
| calpeptin | ↑ Rho-kinase |
| U46619 | ↑ Rho-kinase |
| H-89 | ↓ PKA |
| calcium ionophore | ↑ calmodulin |

HIGH-THROUGHPUT AUTOMATION OF ORGANOIDS FOR IDENTIFYING THERAPEUTIC STRATEGIES

CROSS-REFERENCE TO RELATED APPLICATION(S)

This application is a 35 USC 371 national phase application of PCT/US2019/032754, which claims priority to U.S. Provisional Patent Application No. 62/672,470, filed May 16, 2018, and U.S. Provisional Patent Application No. 62/739,637, filed Oct. 1, 2018, all of which are hereby incorporated by reference in their entirety, as if fully set forth herein.

Organoids are collections of cells in vitro that resemble a bodily organ in structure and function. These next-generation cell-culture systems remain highly accessible to experimental manipulation and analysis but are also sufficiently complex to model tissue-scale development, injury, and disease (Freedman et al., 2015; McCracken et al., 2014). Human organoids have now been derived representing intestine, kidney, eye, and other organs (Freedman et al., 2015; Hayashi et al., 2016; McCracken et al., 2014; Morizane et al., 2015; Spence et al., 2011; Taguchi et al., 2014; Takasato et al., 2015). Many types of organoids can only be derived from human pluripotent stem cells (hPSCs), the cultured equivalents of the early embryonic epiblast, from which all somatic tissues differentiate (Thomson et al., 1998). As hPSC-derived organoids can be generated from any patient, they have great potential for immunocompatible tissue replacement therapies and prediction of individualized outcomes in human clinical populations (Dekkers et al., 2013; Huang et al., 2015; Takahashi et al., 2007).

An attractive potential application is to utilize organoids for automated, high-throughput screening (HTS) of hundreds of thousands of chemical compounds or genes simultaneously, at a scale that could not be accomplished in mammalian model organisms (Major et al., 2008). In contrast to the simple cell cultures typically used for HTS, organoids are capable of reconstituting features of complex disease, such as PKD and brain microcephaly (Cruz et al., 2017; Freedman et al., 2015; Lancaster et al., 2013). Organoids derived from highly regenerative somatic stem cells, such as intestinal crypt cells or mammary cancers, have previously been generated in HTS-compatible formats, to enhance these cultures and identify modifiers of disease (Gracz et al., 2015; Sachs et al., 2018). However, organoids representing many organs can only be derived from hPSCs, involving three-dimensional growth conditions, lengthy stepwise differentiation steps, and special processing for immunofluorescence, all of which pose significant challenges to automation and miniaturization (Freedman et al., 2015; Hayashi et al., 2016; McCracken et al., 2014; Morizane et al., 2015; Spence et al., 2011; Taguchi et al., 2014; Takasato et al., 2015). For this reason, HTS involving hPSC derivatives has been limited to simpler cultures, such as cell monolayers, which are restricted in their capacity to model complex tissue phenotypes (Chen et al., 2009; Doulatov et al., 2017; Pagliuca et al., 2014; Sharma et al., 2017; Yang et al., 2013). There is a need to develop an HTS platform for organoids to develop and optimize therapeutic agents for treatment of diseases lacking a cure or an effective treatment. One such disease is Polycystic Kidney Disease (PKD).

On average, PKD affects 1 in 600 individuals, accounts for 10% of end-stage kidney disease, and causes end-stage renal disease at 60 years of age (Dagaard 1957; Greenberg & Cheung, 2009; Deltas & Papagregoriou; Chow & Ong 2009). The pathognomonic hallmark of PKD is the formation of numerous large, fluid-filled cysts in the kidneys (FIG. 18A). Cysts also arise in other organs, such as the liver. Flank pain, cyst infection, and hypertension are common symptoms preceding organ failure. As no cure exists, treatment traditionally focuses on managing the complications of chronic kidney disease and preparing for renal replacement therapy. The slowly progressive, multi-organ nature of PKD makes it an excellent candidate for the development of chemical therapeutics. Even a small effect on cyst formation could translate into years of preserved function in the kidneys and other organs.

Tolvaptan (Jynarque), a vasopressin receptor antagonist, can modestly slow the growth of total kidney volume (TKV) (~3%/yr) and improve glomerular filtration rate (GFR; ~1.5 ml/min/yr) (Torres et al. 2012; Tangri et al. 2017; Torres et al. 2017; Gross et al. 2019). Tolvaptan received FDA approval in 2018, and this followed approval of TKV as a predictive biomarker for PKD progression in human studies. However, tolvaptan does not shrink PKD cysts or prevent them from forming, has side effects of frequent thirst and occasional severe hepatotoxicity that preclude use in many patients, and actually reduces glomerular filtration rate (GFR, a clinical barometer of kidney function) while patients start taking the drug (Torres et al. 2012; Tangri et al. 2017; Torres et al. 2017; Gross et al. 2019). Furthermore, its mechanism of action is not fully understood (Gattone et al. 2003; Reig et al. 2011). Of the 12 million people with PKD, only a few thousand take tolvaptan. Thus, there is a strong need for safer and more efficacious therapies for PKD, to either supplement tolvaptan or supplant it.

SUMMARY

In some embodiments, a method for preventing or shrinking cysts is provided. That method may include contacting a population of cells with a inotrope, wherein the inotrope prevents cyst formation, shrinks existing cysts, or both. Although the population of cells may be from any organ type, in one embodiment, the population of cells is a population of kidney cells from an organ (in vivo) or a kidney organoid generated from pluripotent stem cells.

In other embodiments, a method of treating Polycystic Kidney Disease (PKD) is provided. The method of treatment may include administering a therapeutically effective amount of a myosin II activator to a subject having PKD, wherein the myosin II activator acts to prevent, reverse, or slow the progression of PKD. The myosin II activator may be administered orally, intravenously, or by injection.

In some embodiments, the inotrope is a myosin II activator. In certain embodiments, the myosin II activator is a thiadiazinone compound of Formula I

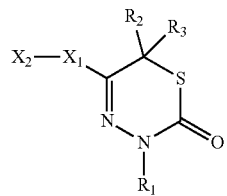

Formula I in which
  $R_1$ is H;
  $R_2$ and $R_3$ are each independently of one another H or A;
  $X_1$ is phenyl, a substituted phenyl, a quinolyl, a substituted quinolyl, a quinolyl derivative, or a substituted quinolyl derivative;
  $X_2$ is benzoyl, a substituted benzoyl, a benzoyl derivative, or a substituted benzoyl derivative; and
  A is $C_{1-6}$ alkyl.

In other embodiments, the myosin II activator is a thiadiazinone compound of Formula II

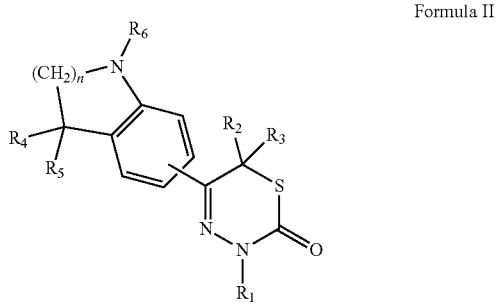

Formula II in which
  $R_1$ is H;
  $R_2$ and $R_3$ are each independently of one another H or A;
  $R_4$ and $R_5$ are each independently of one another H or $C_{1-6}$ alkyl;
  $R_6$ is acyl, alkyl, aryl with or without one or more substitutions;
  A is $C_{1-6}$ alkyl; and
  n is 1, 2, 3, or 4.

In one embodiment, the myosin II activator is EMD57033. In another embodiment, the myosin II activator is 4-hydroxyacetophenone (4-HAP) or a derivative thereof.

In some aspects, the myosin II activator preferentially binds to non-muscle myosin II over cardiac beta myosin, or alternatively, binds to non-muscle myosin II but does not bind cardiac beta myosin.

In some aspects, a myosin II activator as described herein may be used in the treatment Polycystic Kidney Disease (PKD), and may be prepared as a pharmaceutical composition to be administered to a subject having PKD.

In certain embodiments, a method for testing the effects of therapeutic compound candidates on a phenotypic organoid model is provided. Such a method includes steps of generating the phenotypic organoid model on a high throughput screening platform, treating the population of hPSCs plated in each of the plurality of wells with a therapeutic compound candidate, and testing one or more effects resulting from treatment with each of the therapeutic compound candidates. The method for generating the phenotypic organoid model on a high-throughput screening platform may include steps of plating each of a plurality of wells of a high throughput culture vessel with a population of human pluripotent stem cells (hPSCs) and differentiating the population of hPSCs plated in each of the plurality of wells using a single induction step without dissociating or replating the differentiated cells. The method of testing the effects of therapeutic compound candidates may be performed automatically by a liquid handling robot according to some embodiments.

In some aspects, the high throughput culture vessel comprises 384 or more wells. When performing the method for testing the effects of therapeutic compound candidates, every well of the high throughput culture vessel may be utilized, or some wells may not be used. Thus, in some embodiments, the plurality of wells used in the method is the same as the total number of wells in the high throughput culture vessel. IN other embodiment, the plurality of wells is less than the number of wells in the high throughput culture vessel. The population of hPSCs may be plated at a density of less than 5,000 cells per well, or other densities described herein.

In some embodiments, the wells may be treated with a concentration of CHIR99021 optimized using the protocols described herein. In one embodiment, the concentration is between 8 µM and 1 µM.

The method described herein may be used to test myosin II activators described herein, and the test may include determining the effect(s) resulting from treatment with a plurality of therapeutic compound candidates. Those effects may include the compound's effect on cell toxicity, cell differentiation, and efficacy.

In certain embodiments, the wells may be treated with VEGF to stimulate endothelial growth.

In other embodiments, a method for measuring organ specific toxicity and disease phenotypes of an agent on an organoid is provided, the method comprising: a. providing one or more organoids derived from human pluripotent stem cells in a high throughput format; b. admixing the agent with the one or more organoids; and c. detecting one or more outcomes of agent on the one or more organoids, wherein the one or more outcomes indicates toxicity, disease, differentiation state, or a combination thereof of the one or more organoids.

In some embodiments, the method comprises admixing one or more additional agents with the one or more organoids and detecting one or more additional outcomes on the one or more organoids. In some embodiments, the outcome is differentiation state of the one or more organoids.

In some embodiments, the method comprises providing one or more organoids is in adherent culture formats. In some embodiments, the one or more organoids are derived from human iPSCs. In some embodiments, the one or more organoids are kidney organoids.

In some embodiments, the method comprises performing single-cell RNA-seq on the one or more organoids. In some embodiments, the one or more outcomes comprises phenotypic screening of the one or more organoids.

In one embodiments, a system for measuring the organ specific toxicity and disease phenotypes of an agent on one or more organoids is provided, the method comprising providing a non-transitory computer readable medium having computer-executable instructions stored thereon that, if executed by one or more processors of a computing device, cause the computing device to perform one or more steps as described and/or illustrated herein, wherein the computer automatically identifies and analyzes individual organoids based on the presence of an outcome specific for the organoid.

In one embodiment, a method for identifying a threshold concentration of one or more agents on an outcome of one or more organoids is provided, the method comprising a. providing one or more organoids derived from human pluripotent stem cells in a high throughput format; b. admixing one or more agents with the one or more organoids; and c. detecting the threshold concentration of the one or more agents that causes the outcome of the one or more agents on the one or more organoids, wherein the outcome indicates toxicity, disease, differentiation state, or a combination thereof of the one or more organoids.

BRIEF DESCRIPTION OF THE DRAWINGS

FIG. 1A shows still images from a video showing cyst formation from a PKD organoid in adherent culture. FIG. 1B, Schematic of high-efficiency organoid cystogenesis protocol. FIGS. 1C and 1D show representative images of kidney organoids (1C) and quantification of cyst formation after 2 weeks of suspension culture (1D) (CTRL1 versus PKD1$^{-/-}$, n=3 separate experiments, ±s.e.m., t(3.663)=21.05, p=5.8949×10$^{-5}$; CTRL2 versus PKD2$^{-/-}$, n=4 separate experiments, ±s.e.m., t(5.458)=10.66, p=7.3731×10$^{-5}$). FIG. 1E shows 6-well (3.5 cm) dishes containing PKD or control organoids after 9 months of culture. Scale bars, 100 µm (1A-1C) and 1 cm (1E).

FIG. 2A shows paraffin sections dyed with haematoxylin and eosin from PKD oragnoids, or human kidney biopsies taken from patients with autosomal dominant PKD (ADPKD), autosomal recessive PKD (ARPKD), and Meckel syndrome. Identifying labels are provided for orientation and emphasis of specific histological features (c, kidney capsule; z, nephrogenic zone; i, inflammatory infiltrate; cy, large cyst; post, postnatal). FIGS. 2B-2C are sets of confocal immunofluorescence images showing nephron segment markers in PDK organoid cysts (2B) or PKD patient kidneys (2C). Zoom shows close-up of dotted boxed region. Arrow represents an area of specific enrichment for LTL. Glomeruli (g) do not appear cystic. Neither LTL nor ECAD is detected in a large ADPKD cyst, whose epithelium has dedifferentiated (*). FIG. 2D is a graph showing the percentage of PKD organoid cysts labelling positive for LTL, ECAD, or both marker (n=3 separate experiments, ±s.e.m.). FIG. 2E is a set of confocal optical sections showing LTL affinity in a representative cyst in suspension. Higher-magnification (hi mag) image shows LTL in the adjoining organoid remnant portion of this cyst. FIG. 2F is an image showing LTL in cyst-lining epithelial cells. FIG. 2G is an image showing cilia (acetylated α-tubulin) and tight junctions (ZO1) in representative cyst-lining epithelial cells. FIG. 2H is a set of representative confocal images showing stromal markers in PDK organoid cyst and patient cysts. Scale bars, 200 µm or 25 µm (2F, 2G).

FIGS. 3A and 3B show representative images (3A) and quantification of pH3 (3B) in adherent PKD organoid cysts under adherent conditions. Boxes show 25th and 75th percentiles, whiskers indicate min and max values (n=115 tubules pooled from 7 separate experiments and 26 cysts pooled rom 6 separate experiments, ±s.e.m., t(37.16)=3.491, p=0.0013). FIG. 3C shows three-dimensional confocal reconstruction of a large cyst in suspension. Arrowhead indicates anaphases. FIG. 3D shows representative images showing microdissection of large cysts in suspension. FIG. 3E is a graph showing cell counts in organoids immediately after placement in suspension (Org.) or in microdissected cysts grown for several months (Cyst). Dashed lines represent nonlinear breaks in the y-axis. FIG. 3F shows heat maps from microarray analysis of cysts and tubule remnants from cultured organoids, showing differentially expressed genes (p-value s 0.05) contributing to activation of E2F targets, mTORC1 signaling, and MYC. Columns represent samples and rows represent gene; red indicates greater than the mean (white) and blue, less than the mean values. Scale bars, 100 µm.

FIG. 4A shows phase-contrast image of organoid explants on days 1, 4, and 12 after replating. FIGS. 4B-4D show wide-field fluorescence (4B) and confocal sections (4C, 4D) showing epithelial and kidney-specific marker expression in representative kidney organoid cell monolayers. FIGS. 4E-4F shows representative immunoblots of PC1 and PC2 in kidney organoids (4E) and undifferentiated hPSCs (4F). FIG. 4G is a graph showing PC1 protein levels in undifferentiated hPSCs, normalized to b-actin loading control (CTRL, n=6; PKD1$^{-/-}$ and PKD2$^{-/-}$, n=3, ±s.e.m., CTRL versus PKD1$^{-/-}$, t(6.936)=6.603, p=0.00031 (*); CTRL versus PKD2$^{-/-}$, t(4.837)=5.669, p=0.0026 ()). FIG. 4H is a graph showing PC2 protein levels in undifferentiated hPSCs, normalized to b-actin loading control (CTRL, n=6; PKD1$^{-/-}$ and PKD2$^{-/-}$, n=3, ±s.e.m., CTRL versus PKD1$^{-/-}$, t(6.451)=0.9247, p=0.3884 (NS); CTRL versus PKD2$^{-/-}$, t(5)=8.006, p=0.0005 (***)). FIGS. 4I-4K show representative immunoblot (4I) and quantification of PC1 and PC2 levels (4J, 4K) in hPSCs treated with four different PKD2 siRNAs (pooled or individually) or a scrambled (Scr) siRNA control (n=3). FIG. 4J shows results of an unpaired t-test with Welch's correction, Scr versus pool, t(2)=11, p=0.0075; No. 2 versus Scr, t(2)=1.747, p=0.2227; No. 3 versus Scr, t(2)=22.66, p=0.0019; No. 4 versus Scr, t(2) =9.467, p=0.0110; No. 5 versus Scr, t(2)=11.56, p=0.0074. FIG. 4K shows results of an unpaired t-test with Welch's correction, Scr versus pool, t(2)=16.92, p=0.0035; No. 2 versus Scr, t(2)=2.912, p=0.1005 (NS, not significant); No. 3 versus Scr, t(2)=31.93, p=0.0010; No. 4 versus Scr, t(2)=77.64, p=0.0002; No. 5 versus Scr, t(2)=20.28, p=0.0024. Scale bars, 100 µm (a,b) or 10 µm (c,d). NS, not significant.

FIG. 5A is a photograph of organoids implanted into collagen balls and cultured in suspension for two weeks. FIG. 5B shows the diameters of empty (n=17) and organoid-implanted (CTRL, n=19; PKD, n=16) collagen droplets, pooled from three experiments (empty versus CTRL, t(21.96)=13.53, p=3.9334×10$^{-12}$; CTRL versus PKD, t(24.74)=11.33, p=1.7989×10$^{-6}$). Each droplet is indicated by a single data point. FIG. 5C shows a wide-field immunofluorescence image of whole droplet compacted by a PKD organoid, stained for tubule segment markers. Zoom of dashed boxed region is shown for fluorescent channels. FIG. 5D shows confocal immunofluorescence images at the edge of a representative droplet after contraction, adjacent to the collagen interior (col). The dashed boxed region is shown for each individual channel at higher magnification. FIG. 5E shows phase-contrast images showing the edge of a representative droplet at an early stage of compaction. FIG. 5F shows sirius red staining of collagen droplets. FIG. 5G shows TEM 25,000×images of collagen filament structure in the interior of droplets. Zoom of dashed boxed region is shown for each image. FIG. 5H is a schematic of collagen droplet compaction by organoids. KTECs migrate out and surround the scaffold, which contracts towards the outgrowth (curved arrows). Scale bars, 500 µm (5C-5F) or 500 nm (5G).

FIG. 6A is a schematic of organoid plate production. FIG. 6B shows representative wells of 96- and 384-well kidney organoid plates at identical magnification, showing phase-contrast image with proximal tubule (LTL) overlay in green. Zoom of boxed region (arrowhead) is shown below. Images show contiguous microscopic fields that were stitched together to form a larger image. FIG. 6C shows representative wells of a 384-well organoid plate labeled with nephron segment markers of proximal tubule (LTL), distal tubule (ECAD), and podocytes (NPHS1), showing progressive zoom of yellow boxed regions. Scale bars, 100 mm. See also FIG. 13A-13D.

FIG. 7A shows a representative well of a 384-well organoid plate (top row) robotically plated, differentiated, fixed, stained, imaged for proximal tubule (LTL), distal tubule (ECAD), and podocyte (NPHS1) segments. Magenta overlay (bottom row) shows automatically identified structures over actual staining. Scale bar, 1 mm. FIG. 7B illustrates quantification of organoids/well in automated 384-well plates with increasing CHIR concentrations. Each box represents a single well. White boxes represent wells lost to fungal contamination. ZO factors for organoid differentiation in the three lines were calculated to be 0.596 (line 1), 0.034 (line 2), and 0.285 (line 3). FIG. 7C illustrates quantification of proximal tubules (green), distal tubules (yellow), and podocytes (red) at these different CHIR concentrations. Each condition shows the average of 32 wells (2 columns), and 14 mM shows the average of 64 wells. Conditions in which organoids did not differentiate efficiently (<5 organoids total) were not included in the analysis and appear blank. See also FIG. 14A-14E.

FIG. 8A shows representative images of kidney organoids in microwell plates subjected to immunofluorescence analysis for segment-specific markers. Top row shows wide-field immunofluorescence image taken with a 43 objective. Middle row shows confocal image of the organoid highlighted above in the boxed region, taken with a 403 objective. Bottom row shows zoom of boxed region from middle row. ZO-1 (column 2) and CLDN1 (column 3) were labeled in the far red and red channels, respectively, in the same sample. Each of these is pseudocolored red and displayed separately to show co-localization with NPHS1 in the green. FIG. 8B shows 40x images (top) with zoom (bottom) of the same marker combinations in developing kidneys. Arrowheads (CFTR and CLDN1) indicate specific patterns in organoids and tissues. FIGS. 8C and 8D are confocal images of organoids with progressive zooms, showing PEC-like expression of PAX8 (8C) and CLDN1 (8D) in LNL capsules surrounding podocytes (PODXL+), compared to human kidney tissue (8D, right). FIG. 8E is a set of confocal images of collecting duct markers, counterstained with LTL, in organoids and tissues. Scale bars, 100 mm. See also FIG. 15A-15F.

FIG. 9A is a schematic of differentiation protocol used for vascular optimization. FIG. 9B shows one well of a 96-well organoid plate treated with 100 ng/mL VEGF, showing podocytes (SYNPO), proximal tubules (LTL), and ECs (CD31) by wide-field immunofluorescence. FIG. 9C shows wide-field images of VE-cadherin immunofluorescence in organoid cultures±VEGF (left) or endothelial cell-directed cultures (right). FIGS. 9D and 9E are graphs showing the percentage of the total culture area occupied by cells expressing VE-cadherin, averaged from four representative experiments (FIG. 9D), or cells expressing CD31 (FIG. 9E), averaged from two additional representative experiments (±SE). FIG. 9F shows confocal optical sections showing ECs (CD31+) in optimized organoids, compared to human kidney sections. Scale bars, 200 mm.

FIGS. 10A-10J illustrates that single-cell RNA sequencing reveals that enhanced organoids contain epithelial and endothelial cell types analogous to developing human kidneys (A) t-SNE plot showing cell populations in kidney organoids, identified by clustering similar single-cell transcriptomes. FIG. 10B shows that top differentially expressed genes (DEG) within cells of these clusters compared to other cell clusters. All genes are present in corresponding developing human kidney (DHK) cell clusters, and bold if also in P1 mouse kidney cell clusters of same lineage. FIG. 10C shows a correlation matrix comparing average gene expression of kidney organoid and DHK cell clusters. FIG. 10D is a set of violin plots of genes of interest within these cell clusters. FIG. 10E is a set of overlay t-SNE plots from 4 individual datasets±VEGF differentiation. Inset highlights mature endothelial cell cluster. Data are representative of 3 experimental replicates. FIG. 10F is a t-SNE plot. FIG. 10G shows the top differentially expressed genes of cells in subclusters of stromal cluster from FIG. 10A. The dotted line around subcluster S4 (see FIGS. 10F, 10H, and 10I) highlights cells only detected with VEGF treatment. FIG. 10H is a set of overlay t-SNE plots of stromal subclusters FIG. 10F is for 4 individual datasets±VEGF differentiation, colored as in FIG. 10E. FIG. 10I features (t-SNE) plots highlighting MCAM expression in stromal subclusters (FIGS. 10F and 10H) relative to VEGF treatment. FIG. 10J shows representative wide-field immunofluorescent images of MCAM and CD31 in cells in organoid cultures±VEGF. Scale bar, 500 mm. Gene names are not italicized for ease of viewing in FIGS. 10B, 10D, and 10G. See also FIG. 16A-16H.

FIGS. 11A-11D show individual organoids treated with increasing cisplatin doses showing phase-contrast effects on tubular integrity (11A), quantification of cell survival (11B), KIM-1 expression detected by ELISA (11C), and KIM-1 immunofluorescence (11D). FIG. 11E is a set of immunofluorescence images of a cyst formed in a 384-well plate from a kidney organoid with mutations disrupting the PKD2 gene. FIG. 11F is a set of phase-contrast images of organoids tubules with or without forskolin treatment. FIG. 11G shows quantification of cystogenesis induced by forskolin at increasing concentrations. FIG. 11H is a schematic of multi-dimensional data in HTS organoids. Each position represents a different treatment condition. A positive hit showing normal differentiation, low toxicity, and high efficacy (phenotypic rescue) is highlighted with an asterisk in the efficacy dataset. Scale bars, 100 mm. Error bars, SD. *p<0.05 (n=3 or more experiments).

FIG. 12A shows Cyst formation (% of cyst/organoid) from PKD organoids cultured in 96-well and treated with different compounds. Gradient triangles represent the increasing doses used for each compound. BSP, bone sialoprotein; Vitr., Vitronectin. FIG. 12B shows representative images of untreated and blebbistatin-treated PKD organoids in suspension. Arrowheads indicate cysts. FIG. 12C is a graph showing cyst quantification 3 days after blebbistatin treatment in suspension culture (n=4 separate experiments, 15 organoids, ±SEM, p=0.0002). The difference between blebbistatin treated and untreated is shown (Δ cyst/organoid). FIG. 12D shows cyst diameters after 7 days of blebbistatin treatment in suspension culture from 4 separate experiments pooled together. Each square represents a cyst (control+blebb., n=10; PKD−blebb., n=24; PKD+blebb., n=118; ±SEM, p<0.0001). FIG. 12E shows representative images and quantification of PKD cyst area after removal of blebbistatin (n=8 from 2 separate experiments, ±SEM; d0 versus d3, p=0.0015). Drug was removed (d0) after 7 days of treatment. A representative organoid before and after washout is shown. FIG. 12F is a set of confocal immunofluorescence images showing nephron segment markers in PKD organoid cysts (cy) induced with blebbistatin. LTL was used for labeling proximal tubules, ECAD for distal tubules, NPHS1 for podocytes and DAPI for DNA. FIG. 12G is a set of representative confocal images showing NMIIB expression in PKD organoids. Proximal, LTL; DNA, DAPI. Arrowhead, non-cystic tubules. Scale bars, 200 mm. See also FIG. 17A-17B.

FIGS. 13A and 13B show wide-field images showing proximal tubules (LTL) co-localized with endothelial cells (CD31) and podocytes (PODXL) (13A) or nephron progenitor cells (SIX2), using two distinct differentiation protocols (13B). FIG. 13C shows schematic and representative images of experiment testing the effect of replating of the formation of tubules. FIG. 13D shows Immunofluorescence images in cultures replated during the process of differentiation, showing associations between nephron progenitor cells (SIX2+) and proximal tubules (LTL+). Scale bars, 20 µm.

FIGS. 14A-14E illustrate automated identification of organoid differentiation from hPSCs enables high content analysis. FIG. 14A shows a representative well of a 384-well plate showing LTL labeling of proximal tubules (top) and automated identification of tubules as separate objects (bottom). FIG. 14B shows quantification of LTL+ organoids/well in automated 384-well plates plated with three different starting cell numbers and two different CHIR concentrations (N>200 well/condition). The y-axis shows the number of wells containing the quantity of organoids specified on the x-axis. FIG. 14C shows a representative well of a 384-well organoid plate (top row) robotically plated, differentiated, fixed, stained, and imaged for proximal tubule (LTL), distal tubule (ECAD), and podocyte (NPHS1) segments. Overlay (bottom row) shows automatically-identified structures over actual staining. FIG. 14D shows quantification of nephron-like structures in automated 384-well plates with increasing CHIR concentrations and cell densities. Data from four subclones of the WA09 hPSC line are shown: three labeled as in FIG. 7A-7C, plus one additional subclone (Line 4). Each shaded box in the heat map represents one unique condition with four replicate wells. FIG. 14E shows paraffin sections of teratomas from these lines, stained with hematoxylin and eosin (H & E).

FIGS. 15A-15C show immunofluorescence images from FIGS. 8A-8B showing separated channels for LTL and ECAD. Arrowhead indicates an ECAD$^+$LTL$^{lo}$CUBN$^-$ distal tubular segment. FIG. 15D shows separated channels from FIG. 8A for ZO1 and CLDN1 in an organoid. ZO1 enrichment (arrow) and CLDN1 enrichment (arrowhead) are observed in different parts of the organoid epithelium. FIGS. 15E-15G show separated channels from FIGS. 8C-8D showing separated channels of LTL and PAX8 in kidney organoids (S3E), or LTL and CLDN1 in kidney organoids (15F) and developing human kidneys (15G).

FIGS. 16A-16H illustrates that single cell RNA sequencing reveals kidney, endothelial and non-kidney cell types in organoids. FIG. 16A is a t-SNE plot including all cell clusters generated from Drop-seq analysis of organoids±VEGF treatment, from which kidney specific cluster were identified and selected for FIG. 10A (labeled here). Quality metrics for cell clustering in FIG. 16A include: individual datasets with comparable genes, transcripts and mitochondrial content following batch correction (top), resulting heatmap of gene expression following cell clustering of combined datasets (bottom) as shown in FIG. 16B, and violin plots of selected differentially expressed genes for each cell cluster as shown in FIG. 16C. FIG. 16D shows the top differentially expressed genes for each non-kidney cell cluster in FIG. 16A with cell type assignment based on analysis of gene expression patterns using Human Protein Atlas tissue proteome. FIG. 16E shows expression of kidney cell-type specific genes in bulk RNA-seq from cells in organoids grown without VEGF treatment in replica wells from the same experiment as those analyzed in FIG. 16A (scale is logarithmic). FIG. 16F shows relative expression levels as assessed by bulk RNA-seq of selected endothelial and cell cycle genes from cells in organoids grown±VEGF treatment (as in FIGS. 16A and 16E). FIG. 16G shows feature plots (overlaying kidney cluster t-SNE from FIG. 10A) that reveal expression of EMCN and ENG within stromal cluster cells (red circles). FIG. 16H shows feature plots (overlaying t-SNE from A) of genes potentially involved in glomerular vascularization based on expression of ligands in podocytes (top, black dotted line) and receptors sin stromal and mature endothelial cells (bottom, red dotted and solid lines, respectively). (Gene names not italicized for ease of viewing).

FIG. 17A shows separated channels from FIG. 7F for distal tubules (ECAD), proximal tubules (LTL), podocytes (NPHS1), DNA (DAPI) and phase in PKD organoid cysts (cy) induced with blebbistatin. FIG. 17B shows separated channels from FIG. 7G for NMIIB, proximal tubules (LTL), DNA (DAPI) and phase in untreated and blebbistatin-treated PKD organoid. Arrowhead, non-cystic tubules.

FIG. 18A is a photograph of healthy and diseased human kidneys. The PKD kidney is sectioned to show cysts. FIG. 18B is a schematic that shows tubules in cross-section. In healthy kidney, the PC½ complex activates actomyosin to constrict tubular epithelial cells apically and anchor them to the ECM basally. Loss of PC½ reduces actomyosin, resulting in dilation and cell detachment (red arrows). EMD activates actomyosin without PC½ to rescue these effects.

FIG. 20A is a set of confocal images showing podocytes (nephrin), distal tubules (ECAD), and proximal tubules (LTL) in kidney organoids or human kidneys. FIG. 20B is a set of photographs of low-adhesion plates and FIG. 20C is a graph showing cyst formation rates in PKD mutants (red) or isogenic controls.

FIG. 21A shows low magnification fields of PKD organoids in suspension on day 14 of treatment and FIG. 21B shows quantification of cyst size. n≥14 organoids per condition.

FIG. 23A shows PKD organoids in suspension at the day of treatment (day 0) and 7 days after treatment with vehicle control (DMSO) or 5 µM EMD. Scale bar, 500 µm. FIG. 23B is a graph showing the quantification of change in organoid area from day 0 to day 7.

FIG. 24A is a schematic of EMD treatment in PKD1$^{RC/RC}$ and control mice. FIG. 24B shows photographs of inferior poles of unfixed PKD1$^{RC/RC}$ kidneys treated with vehicle or EMD. FIGS. 24C and 24D show the effects of EEMD on total kidney weight (24C) and BUN (24D).

FIG. 25A shows live confocal z-sections through bottom and top of a PKD organoid expressing NMIIB-GFP. Arrow indicates a budding cyst. FIG. 25B shows NMIIA (red) staining in human kidney tissue, with DAPI.

FIG. 26A shows representative mouse kidney sections. FIGS. 26B-26C show quantification of αSMA area (26B) and cyst size (26C).

FIG. 27A shows PKD organoids that were labeled with Calcein AM and propidium iodide (PI) 7 days after treatment. Scale bar, 200 µm. FIG. 27B is a graph showing quantification of live/dead cell viability using relative fluorescent units from labeled organoids after treatments.

FIG. 28A shows docking of EMD into the crystal structure of cardiac MYH7, with FIG. 28B showing a zoom in space-filling model, from Radke et al, eLife, 2014. FIG. 28C shows the alignment of the SH3-like domain consensus sequence with MYH7, compared to non-muscle MYH9 and MYH10. A residue involved in EMD binding is highlighted with red arrow.

FIG. 29A shows the principles of stretching NMII under vertical magnetic tweezers. FIG. 29B shows an example of protein folding/unfolding force changes induced by adding its binding partners measured by method shown in FIG. 29A. The unfolding force of cold shock protein (Csp) increases from 10 pN to 43 pN when single-stranded (ss) DNA is added.

FIGS. 31A-31B show immunoblots of PC1 and PC2 in genome-modified PKD hPSCs or isogenic controls, from a representative experiment. Band intensity quantification of mature PC1 or PC2, normalized to β-actin, is shown (FIG. 31A, n=3 separate experiments, ±s.e.m., t(2.111)=12.64, p=0.0050; FIG. 31B, n=5 separate experiments, t(4.048)=10.4, p=0.0005). FIG. 31C shows a schematic of adherent cyst formation. Adherent cues (gradient rectangle) and stroma (pink cells) surround PKD tubules (green), which rarely form cysts. FIG. 31D shows phase-contrast images showing time courses of representative organoids in adherent cultures. Arrowheads indicate formation of the pre-cyst. Detachment is complete by day 35. Images are representative of >20 cysts or tubules. Scale bar, 100 µm. FIG. 31E shows a schematic of suspension cyst formation from a PKD organoid.

FIG. 32A shows paraffin sections dyed with hematoxylin and eosin from additional PKD patients. OFD, orofaciodigital syndrome. c, kidney capsule; i, inflammatory infiltrate. FIG. 32B shows confocal immunofluorescence showing ECAD and LTL in a representative PKD organoid cyst. FIG. 32C shows a set of confocal immunofluorescence images showing nephron segment markers. FIG. 32D shows confocal optical sections of samples shown in FIG. 2H showing individual channels. FIG. 32E shows Masson's trichrome staining in paraffin sections of PKD organoid cysts and human PKD kidneys. Blue staining indicates collagen deposits. Scale bars, 200 µm.

FIG. 33A shows a confocal z-slice through a PKD1$^{-/-}$ cyst in suspension. Orthogonal planes are shown for the z planes indicated by dashed lines. FIG. 33B shows still frames from a movie showing confocal volumetric reconstruction of this cyst from different perspectives. FIG. 33C. shows phase contrast images of a kidney organoid explant (p1; red arrow) and two subsequent passages (p2, p3; red arrows). FIG. 33D. shows a phase contrast image of passage 1 KTECs showing cobblestone morphology. FIG. 32E shows comparative marker expression in outgrowth KTECs compared to LTL$^+$ cells sorted from organoid cultures. Scale bars, 50 µm.

FIG. 34A shows representative RNA-Seq alignments for PKD1 in hPSCs. Three independent experiments are shown for each genotype. Sequences are aligned to the reference sequence (blue diagram). FIG. 34B shows reads per kilobase million for PKD1 in the three individual experiments depicted in FIG. 34A (individual data points are shown). FIG. 34C shows representative immunofluorescence images of PC2 and cilia in undifferentiated PKD1$^{-/-}$ and PKD2$^{-/-}$ hPSCs, compared to isogenic controls. FIG. 34D shows quantification of ciliary PC2 in PKD1$^{-/-}$ and PKD2$^{-/-}$ lines (n=9 and 2 each of PKD1$^{-/-}$ and PKD2$^{-/-}$ with ≥300 cilia counted per condition, ±s.e.m; ctrl vs. PKD1$^{-/-}$, t(8)=17.99, p=9.3564×1Q$^{-8}$; ctrl vs. PKD2$^{-/-}$, t(8.285)=17.68, p=7.1680×10$^{-8}$). FIG. 34E shows ciliary PC2 immunofluorescence in kidney organoid cells. Scale bars, 10 µm.

FIG. 35A shows representative stills from a movie showing individual PKD organoids or isogenic controls treated for 72 hours with 30 µM forskolin, and subsequently returned to normal media for 72 hours (washout). FIG. 35B shows quantification of cyst formation in PKD or control organoids treated with forskolin, 8-Br-cAMP, or vehicle control. Doses of 8-Br-cAMP<1 mM did not produce cysts. FIG. 35C shows dynamics of cystic expansion in thirty PKD or control organoids after treatment with 30 µM forksolin. Each trace represents a single organoid, pooled from two experiments. Average of all traces is shown with bold black line.

FIG. 36A shows confocal immunofluorescence images showing iPSC-derived organoids and human kidney tissue, showing podocytes (NPHS1), distal tubules (ECAD), and proximal tubules (LTL). FIG. 36B shows a chart a quantification of organoids per well. FIG. 36C shows representative images of kidney organoid differentiation in a cohort of one ESC line, two control iPSC lines, and three PKD iPSC lines. Two different differentiation protocols were performed. Individual data points are shown. Arrowheads indicate cyst-like structures in these cultures. ARPKD, autosomal recessive PKD. Scale bars, 100 μm.

FIGS. 37A, 37B, and 37C show original western blots for FIGS. 4E, 4F, and 4I, respectively, as labeled on each figure. Cropped areas used in FIGS. 4E, 4F, and 4I are shown in the bracket boxes. Prestained protein standards were visible on the blots and annotated manually by overlay of the film onto the nitrocellulose membrane. kDa sizes of the standards are indicated for clarity.

FIG. 38 is a table of myosin activating compounds and their respective effects.

DETAILED DESCRIPTION

Figure 30:
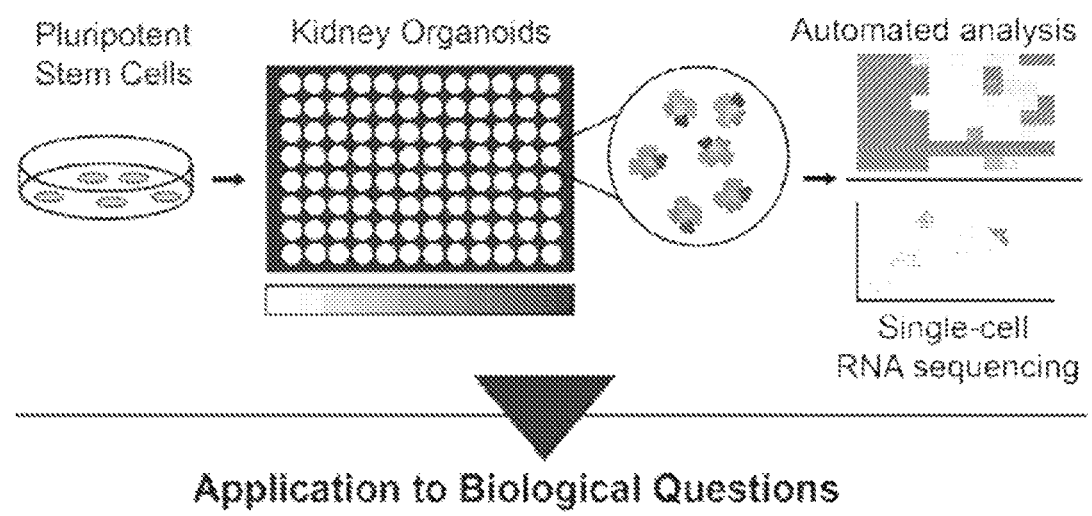
FIG. 30 is an overview of the automated high-throughput system for organoid differentiation and how it is applicable to biological questions.
Figure 30:
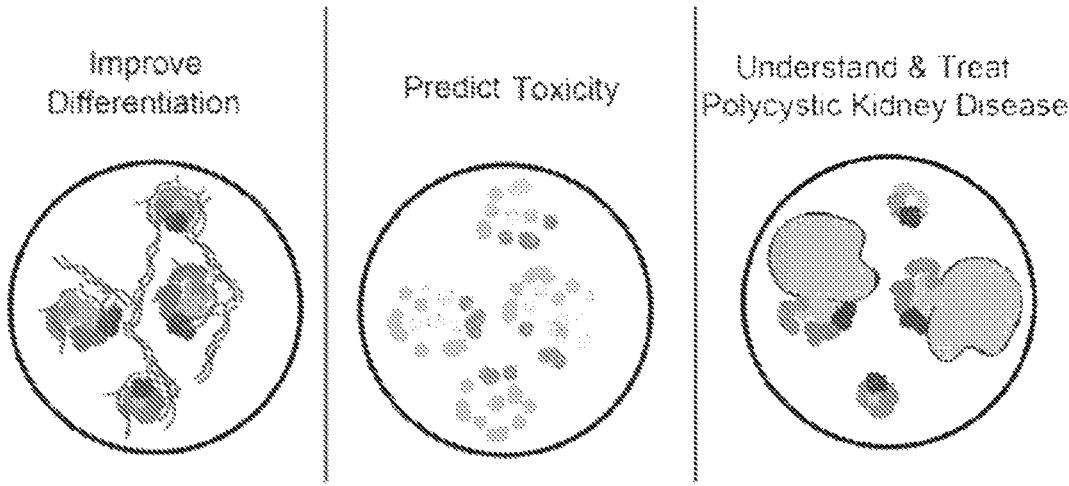

The embodiments described herein provide phenotypic organoid models derived from pluripotent stem cells and optimization of said models, high-throughput screening methods using said models, and therapeutic targets and therapeutic candidates identified using those methods. Organoids derived from human iPSCs have great potential for drug screening, but their complexity has, until now, posed a challenge for miniaturization and automation. The system and methods described herein establish an automated high-throughput organoid model derived from any pluripotent stem cell line that may be used to (i) optimize culture conditions and improve differentiation, (ii) measure toxicity and comprehend disease, and (iii) test the effects of therapeutic compound candidates on a phenotypic organoid model. See FIG. 30. As described below, a robotic pipeline is established using the methods described herein for the manufacture and analysis of organoids in microwell arrays suitable for high-throughput screening.

Automated High-Throughput Screening Platform Using a Phenotypic Organoid Model

In certain embodiments, methods for generating a phenotypic organoid model on a high-throughput screening platform from human pluripotent stem cells (hPSCs) are provided. In certain embodiments, the phenotypic organoid models are generated, optimized, and utilized for testing using an automated system that carries out automated protocols and are compatible with high throughput screening methods. The term "automated" as used herein refers to automation of processes involved in the cell culture including protocols for generating, optimizing and testing for effects of therapeutic compound candidates. Automation of cell culture protocols is performed fully or partially by liquid handling robots or other instrumentation in order to improve the consistency of the cell culture process and to reduce the chances for cell contamination where there is high volume cell culture needs. Any suitable liquid handling robot or instrumentation such as multi-channel pipettes may be used to execute instructions to carry out the methods and protocols described herein including, but not limited to liquid handling robots, instrumentation and other systems sold by Hamilton Company, Celartia, BioTek, Beckman Coulter, WellMate, CyBio, Integra Biosciences, Agilent Technologies, BMG Labtech, DRG International, Inc., Hudson Robotics, Labcyte, Molecular Devices, Tecan Trading AG, Thermo Fisher Scientific, Bio Molecular Systems, Analytik Jena AG, or any other commercially available system.

Cell culture methods that have traditionally used liquid handling robots are generally shorter in duration than the differentiation process for stem cells, so the use of robots to automate the entire process of plating, differentiation, and other manipulation and/or treatment of human pluripotent stem cells has presented challenges, including programming the robot for long duration experiments and the risk of contamination by fungus or other microbes during the long term handling by the robot. Thus, in one embodiment, the automated methods described herein include a step of introducing an antifungal agent to the cell media during the differentiation process. In certain embodiments, the antifungal agent is Amphotericin B, which may be introduced after the first week of treating the population of cells.

A phenotypic organoid model may be generated for any type of organoid including, but not limited to, kidney organoids, gut organoids, liver organoids, pancreatic organoids, ovary organoids, brain organoids, and cancer organoids. The organoids generated in accordance with the methods described herein may act as a model for a phenotype related to a disease or condition. Each type of organoid may be generated from differentiation of one or more hPSC cell line, and each cell line may require different optimal differentiation conditions to form the phenotypic organoid. Thus, automated methods for optimizing differentiation cell line are provided herein to optimize a desired cell line for use in a high throughput screening system.

In some embodiments, generating the phenotypic organoid model includes a step of plating one or more wells of a high-throughput culture vessel with a low-density population of human pluripotent stem cells (hPSCs). The population of hPSCs may be a population from any suitable hPSCs cell line including, but not limited to, a primary human embryonic stem cell line (hESCs, e.g. the H9 ES cell line), an induced pluripotent stem cell line (iPSC, e.g. the WTC11 iPS cell line), or a genetically modified hPSC cell line. In one embodiment, the population of hPSCs is a PKD1$^{-/-}$ or PKD2$^{-/-}$ cell line (as described in the examples below). The high-throughput culture vessel may be of any size suitable for high-throughput screening or testing and may include a microwell cell culture plate having 96 wells, 384 wells, 1536 wells, 3456 wells, 9600 wells, or any other large format microwell culture plate. In certain embodiments, the high-throughput culture vessel is a 384 well microwell culture plate or a plate that includes more than 384 wells.

The plates may first be coated with Matrigel, diluted 1:100 in cold DMEM/F12, and then added to each well of the high-throughput culture vessel at a volume of 30 μL per well. The dilution of Matrigel used in the embodiments described herein was modified from the typical dilution to reduce cell clumping effects of other dilutions such as a 1:60 dilution.

The low-density population of human pluripotent stem cells (hPSCs) used in the methods described herein means that the population of hPSCs are "low-density" as compared with plating densities that are typically used in larger, low-throughput formats. For example, the plating density (as defined by number of cells per unit surface area of the well) depends on the size of the well and is lower than would be predicted based on a linear scale. As discussed further below, one result of the optimization of organoid differentiation to produce a fully automated organoid platform compatible with high-throughput screening or testing was that the optimal number of cells for the initial plating step was found to be of a lower density. The optimal number of cells may vary based on the human pluripotent stem cell line used to produce the organoids. For example, the optimal number of cells for plating the H9 cell line is approximately 2,000 cells per well, but the H9 cell line or another cell line could be plated within a range of similar densities discussed herein based on methods for optimizing differentiation conditions.

In certain embodiments, the human pluripotent stem cells are plated at a density of fewer than 5,000 cells per well, fewer than 4,000 cells per well, fewer than 3,000 cells per well, fewer than 2,000 cells per well, fewer than 1,000 cells per well, or fewer than 500 cells per well. In other embodiments, the human pluripotent stem cells are plated at a density of between approximately 1,000 to 5,000 cells per well, between approximately 1,000 to 4,000 cells per well, between approximately 1,000 to 3,000 cells per well, or between approximately 1,000 to 2,000 cells per well. In some embodiments, the optimal number of cells plated are at a density below 1,000 cells per well. For example, the optimal number of cells for plating the WTC11 cell line is approximately 200 cells per well, but the WTC11 cell line or another cell line could be plated within a range of similar densities discussed herein based on methods for optimizing differentiation conditions. In certain embodiments, the hPSCs are plated at a density of between approximately 100-200 cells per well, between approximately 200-300 cells per well, between approximately 300-400 cells per well, or between approximately 400-500 cells per well. The hPSCs may be plated in a volume of approximately 50 µL that includes mTeSR+Rock (or any other suitable plating media). In certain embodiments, the cell densities discussed above are applicable for a 384-well plate.

After initially plating the cells, the method includes a differentiating step, whereby the population of hPSCs are differentiated using a differentiating factor specific to the desired somatic cell types that make up the desired organoid. For example, in one embodiment, the desired organoid is a kidney organoid and the differentiating factor is a CHIR factor such as CHIR 99021. In the automated methods described herein, the CHIR treatment is generally shorter than typical differentiation methods and is added at a higher volume and concentration than is typical for lower-throughput plates. For example, treatment with a CHIR compound may be at 14 µM and up to about 6 hours shorter than normal treatment (~20% of the total treatment time). Further, the differentiating step is may be a single induction step without dissociating or replating the differentiated cells as discussed below.

Additionally, as described in the examples below, the microenvironment of the differentiated cells is important for developing a desired phenotypic organoid model. Thus, the method may include adding additional phenotypic factors to stimulate a phenotypic change in the organoid development. For example, VEGF may be added in order to enhance endothelial cell differentiation in an organoid model as discussed in the examples below. Other microenvironmental factors such as 8-bromoadenosine, cyclic adenosine monophosphate (cAMP), forskolin, or blebbistatin, which induces cysts in kidney organoids, may be introduced to the population of cells as well including, but not limited to the factors discussed below in the working examples.

In one embodiment, the method of generating the phenotypic organoid model is a protocol that includes the following steps:
Step 1: coat a 384-well plate with Matrigel diluted 1:100 in cold DMEM/F12, use 30 µL per well. (Due to issues with cell clumping 1:100 works better than 1:60 dilution).
Step 2 (Day 0): Plate cells in mTeSR+Rock, in a final volume of 50 µL per well. Cell density may vary per cell line, as discussed above.
Step 3 (Day 1): Sandwich with mTeSR+Matrigel, 1:60 dilution.
Step 4 (Day 2): Skip feeding on Day 2.
Step 5 (Day 3): Remove media (preferably in the morning) and add 50 µL/well of RPMI+14 µM CHIR (+/−Noggin)
Step 6 (Day 4): Remove media (preferably in the afternoon), add 50 µL/well of RB (Advanced RPMI+Glutamax+B27 Supplement, from Life Technologies)
Step 7 (Day 5): feed plates with RB (50 µL/well)
Step 8 (Day 8): feed plates with RB (50 µL/well)
Ongoing steps (through day 21-25): Feed plates twice a week, typically Mondays and Thursdays or Tuesdays and Fridays. Use 50 µL/well RB for feedings. Introduce an antifungal during this time period (e.g. Amphotericin B) at this point to help prevent fungal contamination (0.250 µg/mL final concentration in RB). The use of this antifungal is not typically used in these differentiations in low throughput formats, but is particularly important in high throughput preparations using automated machines in which the tubing is re-used. The tubing of the liquid handling instrumentation is washed with water followed by 70% ethanol in water after every use to prevent contamination.

Additional protocols are described in the working examples below.

In certain embodiments, the organoid models generated by the methods and protocols described herein model a disease or condition that causes cysts to form on or in an affected tissue or organ (i.e. a cystogenic disease or condition). In some embodiments, conditions or diseases that may cause cysts to form may include, but are not limited to, genetic conditions, tumors, infections, errors in embryonic development, cellular defects, chronic inflammatory conditions, blockages of ducts in the body, parasites, and injuries to skin or vessels. According to some embodiments, certain types of cysts that are caused by the disease or condition may form the basis of the phenotypic organoid model and include, but are not limited to, acne cysts, arachnoid cysts, Baker's cysts, Bartholin's cysts, breast cysts, Chalazion cysts, colloid cysts, dentigerous cysts, dermoid cysts, epidiymal cysts, ganglion cysts, hydatid cysts, ovarian cysts, pancreatic cysts, periapical cysts, pilar cysts, pilonidal cysts, renal (or kidney) cysts, autosomal dominant PKD, autosomal recessive PKD, ciliopathy syndromes, Bardet Biedl Syndrome, Joubert Syndrome, nephronophthisis, polycystic liver disease, pineal gland cysts, sebaceous cysts, tarlov cysts (also known as perineural or perinurial cysts), vocal fold cysts (e.g., mucus retention cysts, epidermoid cysts).

In the embodiments described above, the population of cells used in the method for generating a cystogenic organoid model may be a PKD1$^{-/-}$ or PKD2$^{-/-}$ cell line that may be supplemented with cAMP, forskolin, blebbistatin, or any combination thereof to induce cyst development. And, in one embodiment, the organoid models generated by the methods and protocols described herein model polycystic kidney disease (PKD), as discussed in detail in the working examples below.

Automated Methods for Optimizing Differentiation of Organoid Model

Each cell line used to generate the phenotypic organoid models generated above may be optimized using an automated process as described below in the examples. For example, the concentration of the differentiation factor (e.g., CHIR99021), the number of cells for the initial plating, and other factors may affect the differentiation of the organoids and the proportion of different cell types within the organoids. In some embodiments, a computer may be trained to automatically identify and analyze individual organoids based on a particular cell type or marker. As a non-limiting example, a software program such as but not limited to CellProfiler may be trained as discussed in Example 2 below to identify individual kidney organoids in microscope images based on the presence and proportion of proximal tubules, distal tubules, or podocytes. Other analyses are also possible to use in accordance with these embodiments, e.g., ELISA and others discussed in the examples below.

Automated Methods for Screening Therapeutic Compounds

Phenotypic organoid models generated using the methods described above may be used to test the effects of therapeutic compound candidates on the model. The high-throughput culture vessel allows for multiple treatments and outcomes to be tested at one time to enable a side-by-side comparison of different effects by different compounds as discussed below in Example 2. Thus, after generating the phenotypic organoid model in a high-throughput culture vessel, each of a plurality of wells in the vessel may be treated with a therapeutic compound candidate, then evaluated for one or more effects of that treatment. Among other things, the method allows for testing of cell toxicity of the compound, its effect on the phenotype of the organoid, and/or the efficacy of the compound. In certain embodiments, each well may be treated with a different compound and the same effect may be tested for each compound. Alternatively, certain wells on a single culture vessel may be treated with the same compound, and different effects of the compound may be tested on the same culture vessel. Liquid handling robots can be programmed to analyze the results of screening methods also, as discussed below in Example 3.

Methods for Treating Cystogenic Conditions Using Myosin Activating Inotropes

Using the methods described herein for high-throughput screening of potential modulators of disease may lead to the identification of candidate targets and therapeutic compounds for the treatment of a condition or disease. In one example the high throughput methods led to the identification of myosin as a target for the development of therapeutic compounds for cystogenic conditions like polycystic kidney disease (PKD), which was an unexpected finding, as myosin has been implicated in some human diseases, but not for PKD or other diseases that include cysts as a clinical manifestation of the disease or condition (see Example 2 below). Consequently, methods for treating or preventing cystogenesis in a population of cells—either in vivo or in vitro—are provided herein. Such methods include contacting the population of cells with a inotrope that modulates myosin activity, or otherwise activates myosin. In some embodiments, the inotrope may be any suitable contractile agent or positive inotrope including, but not limited to, Digoxin, Berberine, Calcium, Calcium sensitizers, Catecholamines, Angiotensin II, Eicosanoids, Phosphodiesterase inhibitors, Glucagon, Insulin. In other embodiments, the positive inotrope may be a direct myosin activator or a myosin modulator. For example, the positive inotrope may activate any myosin class including, but not limited to, myosin I, II, III, IV, V, VI, VII, VIII, IX, X, XI, XII, XIII, XIV, XV, XVI, XVII, XVIII. In one embodiment, the positive inotrope is a myosin II activator. Myosin II activators may modulate the function of MYH1, MYH2, MYH3, MYH4, MYH6, MYH7, MYH7B, MYH8, MYH9, MYH10, MYH11, MYH13, MYH14, MYH15, or MYH16. And in one embodiment, the positive inotrope preferably activates-or only activates-non-muscle myosin II (NMII) isoforms (e.g., NMIIA, NMIIB, NMIIC, corresponding to the MYH9, MYH10, and MYH14 genes) over cardiac myosin. Negative inotropes such as blebbistatin may also modulate the cystogenesis phenotype.

In some embodiments, the inotrope may be Rho kinase inhibitor e.g. Y-27632, Focal adhesion kinase inhibitor e.g. FAK inhibitor 14, PD 325901 inhibitor of mitogen activated protein kinase (MEK or MAPKK), ezrin inhibitor NSC668394, cytochalasin D, nocodazole, ML141, latrunculin B, jasplakinolide, tubacin, HA-1077, phalloidin, tacolimus, Bis-T-23, SB-413542, or one of the compounds listed in Table 5 below.

| compound | effect |
| --- | --- |
| 4'-Hydroxyacetophenone | ↑ myosin IIB, IIC |
| EMD57003 | ↑ myosin |
| CK-1827452 | ↑ cardiac myosin S1 |
| Bis-T-23 | ↑ actin polymerization |
| calpeptin | ↑ Rho-kinase |
| U46619 | ↑ Rho-kinase |
| H-89 | ↓ PKA |
| calcium ionophore | ↑ calmodulin |

In one embodiment, the method for treating or preventing cystogenesis is a method that includes a step of contacting a population of kidney cells (e.g., a kidney organoid in vitro or a kidney in vivo) with a inotrope, wherein the inotrope prevents cyst formation, shrinks existing cysts, or both. And in certain embodiments, the method is related to treatment of a cystogenic disease or condition where the disease or condition causes cysts to form on or in an organ like those described above. For example, in one embodiment, a method for treating polycystic kidney disease (PKD) is provided.

"Treating" or "treatment" of a condition may refer to preventing the condition, slowing the onset or rate of development of the condition, reducing the risk of developing the condition, preventing or delaying the development of symptoms associated with the condition, reducing or ending symptoms associated with the condition, generating a complete or partial regression of the condition, or some combination thereof. The methods of treatment described herein may include a step of administering a therapeutically effective amount of a inotrope to a subject (e.g., a human or other mammal) having PKD, wherein the inotrope acts to prevent, reverse, or slow the progression of PKD.

In one aspect, the inotrope used in accordance with the treatment methods above is a myosin II activator. Myosin II activators that may be used in accordance with the embodiments described herein may include a thiadiazinone compound, 4-hydroxyacetophenone (4-HAP), or a derivative thereof.

In some embodiments a thiadiazinone compound that may be used is a thiadiazinone compound of Formula I:

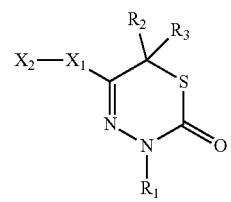

Formula I in which
R₁ is H;
R₂ and R₃ are each independently of one another H or A;
X₁ is phenyl, a substituted phenyl, a quinolyl, a substituted quinolyl, a quinolyl derivative, or a substituted quinolyl derivative;

$X_2$ is benzoyl, a substituted benzoyl, a benzoyl derivative, or a substituted benzoyl derivative; and A is $C_{1-6}$ alkyl.

In other embodiments a thiadiazinone compound that may be used is a thiadiazinone compound of Formula II:

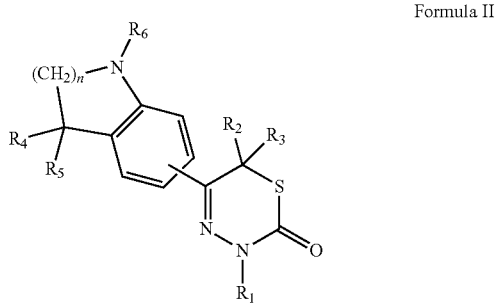

Formula II in which
$R_1$ is H;
$R_2$ and $R_3$ are each independently of one another H or A;
$R_4$ and $R_5$ are each independently of one another H or $C_{1-6}$ alkyl;
$R_6$ is acyl, alkyl, aryl with or without one or more substitutions;
A is $C_{1-6}$ alkyl; and
n is 1, 2, 3, or 4.

In one embodiment, the thiadiazinone compound is EMD57033, also referred to as (+)-5-(1-(3,4-Dimethoxybenzoyl)-1,2,3,4-tetrahydroquinolin-6-yl)-6-methyl-3,6-dihydro-2H-1,3,4-thiadiazin-2-one, or (+)-6-(3,6-Dihydro-6-methyl-2-oxo-2H-1,3,4-thiadiazin-5-yl)-1-(3,4-dimethoxybenzoyl)-1,2,3,4-tetrahydroquinoline.

In other embodiments, the thiadiazinone may be any of the thiadiazinone compounds disclosed in EP Patent Application Publication Nos. EP0145236, EP0679651, or in U.S. Pat. Nos. U.S. Pat. Nos. 4,616,013, 4,788,194, 4,861,773, 4,916,128, 4,933,336, 5,137,885, 5,206,363, 5,276,027, 5,378,702, US567799, U.S. Pat. Nos. 5,747,489, 5,434,149, 5,705,497, 5,859,008, 7,534,785, 7,902,186, 8,211,886, all of which are hereby incorporated by reference as if fully set forth herein.

The inotropes described above may be administered in combination with another agent to help prevent any toxic effects of the inotrope. For example, the inotrope (e.g., myosin II activator or modulator, thiadiazinone compound, etc.) may be blebbistatin or a drug that competes with binding to cardiac myosin.

The methods for treating diseases or conditions described herein include administering a therapeutically effective amount of the inotrope (e.g., myosin II activator or modulator, thiadiazinone compound, etc.) or a therapeutic or pharmaceutical composition that includes the inotrope. An "effective amount," "therapeutically effective amount" or "effective dose" is an amount of a composition (e.g., a therapeutic or pharmaceutical composition or agent) that produces a desired therapeutic effect in a subject, such as preventing or treating a target condition or alleviating symptoms associated with the condition. The precise therapeutically effective amount is an amount of the composition that will yield the most effective results in terms of efficacy of treatment in a given subject. This amount will vary depending upon a variety of factors, including but not limited to the characteristics of the therapeutic compound (including activity, pharmacokinetics, pharmacodynamics, and bioavailability), the physiological condition of the subject (including age, sex, disease type and stage, general physical condition, responsiveness to a given dosage, and type of medication), the nature of the pharmaceutically acceptable carrier or carriers in the formulation, and the route of administration. One skilled in the clinical and pharmacological arts will be able to determine a therapeutically effective amount through routine experimentation, namely by monitoring a subject's response to administration of a compound and adjusting the dosage accordingly. For additional guidance, see Remington: The Science and Practice of Pharmacy 21st Edition, Univ. of Sciences in Philadelphia (USIP), Lippincott Williams & Wilkins, Philadelphia, PA, 2005.

The therapeutic or pharmaceutical composition may also include one or more pharmaceutically acceptable carriers. A "pharmaceutically acceptable carrier" refers to a pharmaceutically acceptable material, composition, or vehicle that is involved in carrying or transporting a compound of interest from one tissue, organ, or portion of the body to another tissue, organ, or portion of the body. For example, the carrier may be a liquid or solid filler, diluent, excipient, solvent, or encapsulating material, or some combination thereof. Each component of the carrier must be "pharmaceutically acceptable" in that it must be compatible with the other ingredients of the formulation. It also must be suitable for contact with any tissue, organ, or portion of the body that it may encounter, meaning that it must not carry a risk of toxicity, irritation, allergic response, immunogenicity, or any other complication that excessively outweighs its therapeutic benefits.

The method of treating Polycystic Kidney Disease (PKD) comprising administering a therapeutically effective amount of a myosin II activator to a subject having PKD, wherein the myosin II activator acts to prevent, reverse, or slow the progression of PKD, wherein the myosin II activator is administered orally, intravenously, or by injection.

The therapeutic compositions described herein may be administered by any suitable route of administration. A route of administration may refer to any administration pathway known in the art, including but not limited to aerosol, enteral, nasal, ophthalmic, oral, parenteral, rectal, transdermal (e.g., topical cream or ointment, patch), or vaginal. "Transdermal" administration may be accomplished using a topical cream or ointment or by means of a transdermal patch. "Parenteral" refers to a route of administration that is generally associated with injection, including infraorbital, infusion, intraarterial, intracapsular, intracardiac, intradermal, intramuscular, intraperitoneal, intrapulmonary, intraspinal, intrasternal, intrathecal, intrauterine, intravenous, subarachnoid, subcapsular, subcutaneous, transmucosal, or transtracheal. In certain embodiments, the inotrope (e.g., myosin II activator, thiadiazinone compound, etc.) or a therapeutic or pharmaceutical composition thereof is administered orally, intravenously, or by injection.

Having described the invention with reference to the embodiments and illustrative examples, those in the art may appreciate modifications to the invention as described and illustrated that do not depart from the spirit and scope of the invention as disclosed in the specification. The examples are set forth to aid in understanding the invention but are not intended to and should not be construed to limit its scope in any way. The examples do not include detailed descriptions of conventional methods. Such methods are well known to those of ordinary skill in the art and are described in numerous publications. Further, all references cited above and in the examples below are hereby incorporated by reference in their entirety, as if fully set forth Herein.

WORKING EXAMPLES

Example 1—Generating a Model of PKD Cystogenesis Reveals a Critical Role of Microenvironment in Human Polycystic Kidney Disease Polycystic kidney disease (PKD) is a life-threatening disorder, commonly caused by defects in polycystin-1 (PC1) or polycystin-2 (PC2), in which tubular epithelia form fluid-filled cysts (The European PKD Consortium 1994; Mochizuki et al. 1996). A major barrier to understanding PKD is the absence of human cellular models that accurately and efficiently recapitulate cystogenesis (Neufeld et al. 1992; Boletta et al. 2000). Previously, a genetic model of PKD was generated using human pluripotent stem cells and derived kidney organoids (Freedman et al. 2013; Freedman et al. 2015a). Here, it was shown that systematic substitution of physical components can dramatically increase or decrease cyst formation, unveiling a critical role for microenvironment in PKD. Removal of adherent cues increases cystogenesis 10-fold, producing cysts phenotypically resembling PKD that expand massively to 1-centimetre diameters. Removal of stroma enables outgrowth of PKD cell lines, which exhibit defects in PC1 expression and collagen compaction. Cyclic adenosine monophosphate (AMP), when added, induces cysts in both PKD organoids and controls. These biomaterials establish a highly efficient model of PKD cystogenesis that directly implicates the microenvironment at the earliest stages of the disease.

Materials and Methods

Kidney organoid differentiation. WA09 (H9) hPSCs with CRISPR-targeted PKD1$^{-/-}$ or PKD2$^{-/-}$ mutations, or passage- and procedure-matched non-mutant isogenic controls, were maintained feeder-free on 1% Reduced Growth Factor GelTrex (Life Technologies) in mTeSR1 (Stem Cell Technologies) and dissociated with Accutase (Stem Cell Technologies), as previously described (Freedman et al. 2015a). hPSC lines were derived from either the WA09 hESC line (WiCell) or theWTC11 iPSC line (Gladstone Institute). 60,000 cells from each cell line were plated per well of a 24-well plate pre-coated with GelTrex in mTeSR1 supplemented with 10 µM Rho-kinase inhibitor Y27632 (StemGent). The media was replaced with 500 µl mTeSR1+1.5% GelTrex at 16 h, 500 µl mTeSR1 at 36 h, Advanced RPMI+ Glutamax (from Life Technologies)+12 µM CHIR99021 (Stemgent) at 50 h, and RB (Advanced RPMI+Glutamax+ B27 Supplement, from Life Technologies) at 86 h. RB was changed two days later and every three days thereafter. Alternatively (Protocol B, FIG. 35B), undifferentiated hPSCs were plated overnight and then treated with 8 µM CHIR99021 in APEL media (Stem Cell Technologies) for 48-72 h, 30 ng ml$^{-1}$ FGF9 or FGF2 (Peprotech)+1 µgml$^{-1}$ heparin (Stem Cell Technologies) in APEL for 96 h, and subsequently cultured in APEL, which was replaced every three days. Organoids typically became visible by light microscopy 12-18 days after plating.

Cyst formation. In adherent cultures (untreated), 'cysts' were identified as large, balloon-like, translucent structures that swayed in response to agitation. Flat rings and dilated tubules were not counted as cysts and occasionally appeared even in non-PKD controls. Forskolin and 8-Br-cAMP (Sigma) were added to adherent cultures on the twenty-first day of differentiation, resulting in rapid formation of cysts that typically did not sway in response to agitation. Wells were imaged using a Nikon TiE inverted wide-field microscope and cysts were quantified using ImageJ cell counter. To generate large cysts in suspension, adherent organoids were microdissected with a 23-gauge syringe needle from 24-well plates on an inverted phase-contrast microscope, and carefully transferred using a transfer pipette into a low-adhesion 6-well plate (Corning) containing 2 ml RB. The organoids were isolated on the twenty-first day of differentiation, before cysts formed. RB media was changed by gravity every three days, and cystogenesis was assessed at two weeks after replating.

Generation of KTEC lines from organoid. To prepare monolayers of kidney cells for analysis, freshly isolated organoids were immediately plated onto tissue culture dishes pre-coated with 1% GelTrex (Thermo Scientific) and cultured for one week in RB, and the resulting epithelial outgrowths were processed for immunoblot and immunofluorescence. Alternatively, to isolate KTECs using flow cytometry, entire organoid cultures were incubated with fluorescein-conjugated LTL (FL-1321, Vector Labs) diluted 1:500 into RB for four hours, dissociated with Accutase, pelleted, resuspended in flow sorting buffer: 1% FBS, 10 mM HEPES buffer in phosphate buffered saline (PBS) (Thermo Scientific). LTL+ cells were isolated on a FACS Aria Cell Sorter (BD Biosciences) and replated onto GelTrex-coated tissue plates in RB.

Figure 37:
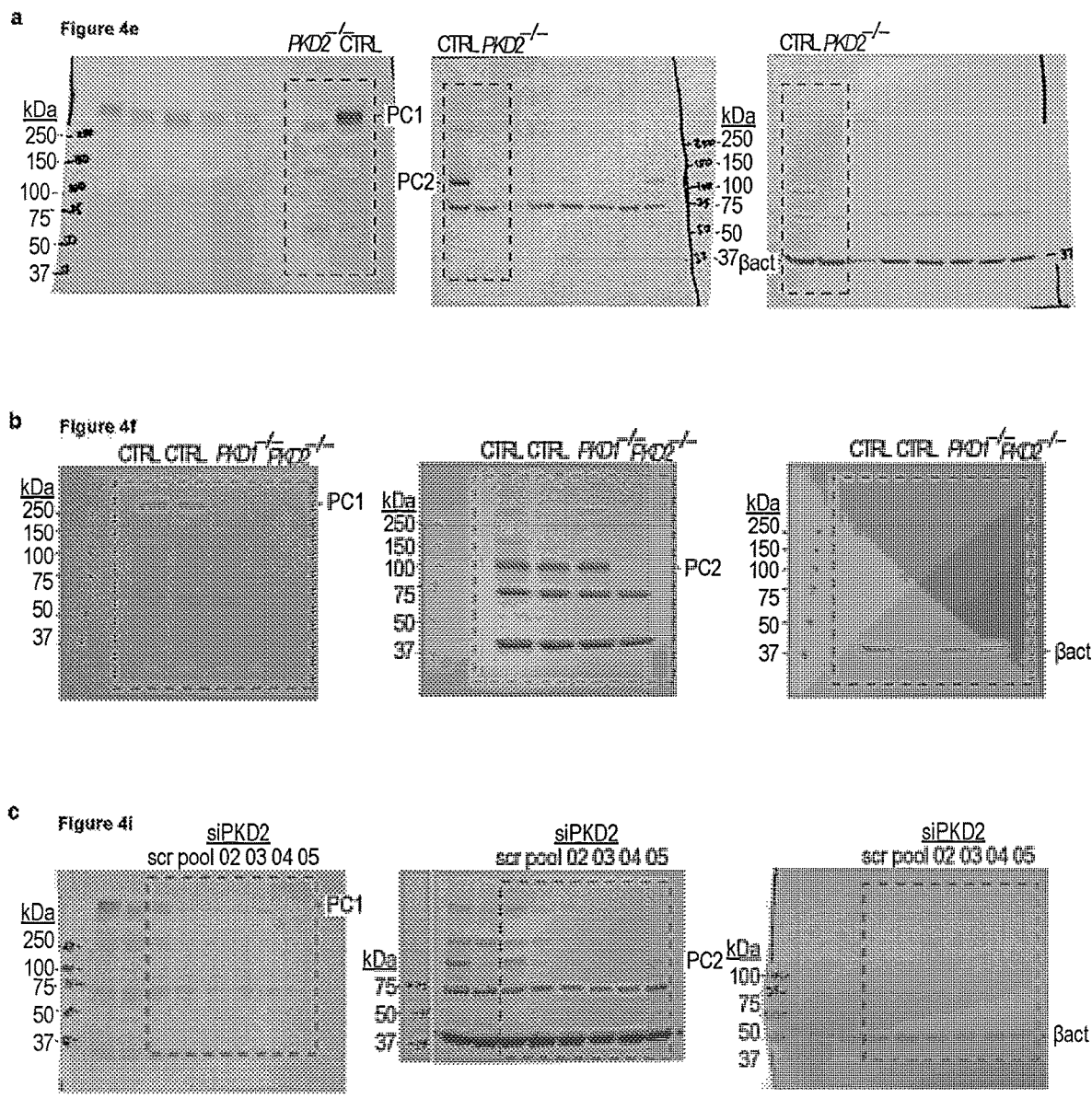
FIGS. 37A-37C show full-length western blot images showing PC1 depends on PC2.

Organoid embedding in collagen droplet. To embed organoids in collagen droplets, a sheet of Parafilm was soaked in 70% ethanol, air dried, and pressed against the holes of a box of gel-loading pipette tips (1-200 µl, Fisher Scientific 02-707-138) to create a dimpled mould (Lancaster et al. 2013). One organoid was placed in each dimple and 30 µl of 7 mg ml$^{-1}$ collagen I (Corning) was added. The droplets were incubated 25 min at 37° C. and carefully resuspended in 3 ml of RB media in an untreated 6-well plate. The media was changed weekly and the droplets were imaged after two weeks of incubation using a Nikon Ti Inverted Wide-field microscope and a Nikon 1 J1 Camera. Droplet diameters were measured using NIS Elements imaging software (Nikon) and normalized to the diameter of empty droplets from the same set, for a total of three sets. Droplets that failed to undergo compaction (~20% in control and ~50% in PKD samples) were excluded. Droplets were fixed with 4% paraformaldehyde (PFA) for 20 min at room temperature, incubated 16 h in 30% sucrose (Sigma) in water, mounted in Tissue-Tek (Sakura), flash frozen, and cryosectioned onto Superfrost Plus slides (Fisher). Sections were stained in Picro-sirius red solution (Sky-Tek laboratories) for one hour, rinsed in two changes of 0.5% acetic acid solution, and dehydrated in two changes of absolute ethanol before mounting. Immunofluorescence was performed as described below.

siRNA and immunoblotting. 16 h after plating, hPSCs were transfected with Dharmacon Smartpool siRNAs (Fisher Scientific) directed against PKD2 or scrambled control in mTeSR1 without antibiotics. Media was changed 24 h later. 72 h after siRNA treatment, cells were lysed in RIPA buffer (Thermo Scientific) containing 1× Complete mini EDTA-free protease inhibitor, PhosSTOP, and benzonase nuclease (all Sigma). Protein lysates were quantified using a BCA protein assay kit (Thermo Fisher). To prepare the samples, 50 µg of protein were mixed with Pierce LaneMarker Reducing Sample (Thermo Fisher) and incubated at 40° C. for 5 min. Samples were separated in a 4-20% protein gel (Bio-Rad) and transferred into a PVDF membrane using standard protocols and 0.01% SDS in the transfer buffer (0.25M Tris Base, 1.92M Glycine, 0.1% SDS). Gels included prestained molecular weight markers (Precision Plus Protein Kaleidoscope Standards, Bio-Rad), which were annotated manually by overlay of the film onto the nitrocellulose membrane. The antibodies used for the immunoblots were anti-PC1 (sc-130554, Santa Cruz), anti-PC2 (sc-10376, Santa Cruz) and anti-β-actin (4970S, Cell signaling). The intensity ratio of the experimental band to the loading control was normalized to 1 in the negative control (unmodified or untreated hPSCs). The remaining bands were normalized to the control and averaged for at least three independent experiments. Examples of unprocessed immunoblots with the original standards hand-marked are provided in FIG. 37.

Global gene expression and bioinformatics analysis. For systems biology analysis of cysts, cystic epithelium or tubule remnants were manually separated from PKD1$^{-/-}$ organoids (71-87 days of culture from three experiments) using a 22-gauge needle under a dissecting microscope and flash frozen separately in liquid nitrogen. Total RNA containing small RNA was extracted from seven paired samples (cysts and tubule remnants from the same organoid) using RNeasy Micro Kit (Qiagen) with an on-column DNA digestion step to minimize genomic DNA contamination. The sample integrity of the RNA was assessed using the RNA 6000 Nano Assay on 2100 Bioanalyzer (Agilent Technologies) to ensure that RNA integrity number (RIN) was greater than 7. Microarray experiments were performed at The Centre for Applied Genomics (TCAG) at the Hospital for Sick Children. Following the manufacturer's protocol, 10 ng of total RNA was labelled using the GeneChipWT Pico Reagent K t (Affymetrix). Fragmented and biotin-labelled ss-cDNAs were then hybridized to GeneChip Human Gene 2.0 ST Arrays (Affymetrix) for 16 h at 4° C. Hybridized arrays were stained and washed in the Affymetrix Fluidics Station 450. Thereafter, the arrays were scanned on an Affymetrix GeneChip Scanner 3000 and the image (.DAT) files were preprocessed using the Affymetrix GeneChip Command Console (AGCC) software v.4.3 to generate cell intensity (.CEL) files. After image processing, the array data were uploaded to the Affymetrix Expression Console software v1.4.1 for further processing and quality control. All quality assessment metrics, including spike-in controls during target preparation and hydrization were found within the boundaries. The probe set signal intensities were then extracted and normalized using the robust multi-array average (RMA) algorithm embedded in the Expression Console software, which includes convolution background correction, quantile normalization, and median polish summarization. Downstream paired sample t-test was carried out via Partek Genomics Suite 6.6 (Partek) to determine differentially expressed genes between cysts and tubules. Gene set enrichment analysis (GSEA, http://software.broadinstitute.org/gsea/index.jsp) was used as the primary tool to identify potential gene pathways or gene sets that may modulate cystic kidney organoid growth (Subramanian et al. 2005). Before running GSEA, Affymetrix probe sets were collapsed to one gene level, paired sample t-test statistics scores were used to create a ranked list of genes of the entire data set (in total, 29406 unique genes with gene symbols). GSEA was performed using the Hallmark gene sets from Molecular Signatures Database (MSigDB, http://software.broadinstitute.org/gsea/msigdb/collections.jsp#H) (Liberzon et al. 2015). The description of each gene set can be found on the MSigDB website. Overrepresented gene sets were defined with a false discovery rate (FDR)≤0.25. For RNA-Seq analysis of hPSCs, RNA was prepared from isogenic sets of cell lines using the RNEasy Mini Kit (Qiagen), checked for high integrity on an Agilent Bioanalyzer, prepared using the TruSeq stranded mRNA library kit (Illumina), and sequenced on an Illumina NextSeq500 75×75 paired-end high-output run. Samples were aligned to an hg19 reference sequence.

Immunofluorescence. To fix organoids, an equal volume of 8% paraformaldehyde (Electron Microscopy Sciences) in PBS was added to the culture media (4% final concentration) for 15 min at room temperature. After fixing, samples were washed in PBS, blocked in 5% donkey serum (Millipore)/0.3% Triton X-100/PBS, and incubated overnight in 3% bovine serum albumin/PBS with primary antibodies. The next day, samples were washed in PBS and incubated overnight with Alexa-Fluor secondary antibodies and DAPI (Thermo Scientific), followed by PBS washes. For frozen tissue sections, fresh tissues were incubated in 4% paraformaldehyde for one hour at 4° C., incubated 16 h in 30% sucrose (Sigma) in water, mounted in Tissue-Tek (Sakura), flash frozen, and cryosectioned onto SuperfrostPlus slides (Fisher) before blocking. Paraffin sections were prepared by fixing overnight in methacarn (60% absolute methanol, 30% chloroform, 10% glacial acetic acid, Sigma) or in 4% PFA, followed by paraffin embedding, sectioning, deparaffinization in 100% xylene (3 washes, 5 min each), dehydration in graded 70%-100% ethanol (5 min each), and heating in citrate buffer pH 6.0 (Sigma) in a pressure cooker (Instant Pot IPDUO60) for three minutes prior to immunostaining. Kidney organoid cysts were embedded in 2% agarose prior to paraffin embedding. Histology stains (Haematoxylin and eosin, or Masson's trichrome) were applied to paraffin sections by UW Pathology. Primary antibodies included acetylated alpha-tubulin (051M4770; Sigma), ZO-1 (339100; Invitrogen), LTL (FL-1321, Vector Labs), PC2 (sc-25749, Santa Cruz), NPHS1 (R&D AF4269, 1:500), KIM-1 (MAB1750, R&D), PODXL (R&D AF1658, 1:500), ECAD (Abcamab11512), SMA (Sigma A2547, 1:500), LAMA1 (Sigma L9393a, 1:500), and pH3(sc-8656, Santa Cruz). Fluorescence images were captured using a Nikonepifluorescence 90-1 (upright), Nikon Ti Inverted-Wide-field microscope, or NikonA1R and C1 confocal microscopes. pH3+ cells were scored manually in cysts or tubular organoids of similar sizes.

Electron microscopy. Droplets were gently transferred with a cut-off transfer pipette into EM fix: 0.15 M sodium cacodylate trihydrate (Sigma) dissolved in water (pH 7.3) containing 4% formaldehyde and 2% glutaraldehyde (Electron Microscopy Sciences), and stored overnight. Samples were post-fixed with osmium tetroxide solution (Sigma), dehydrated in serial ethanol dilutions (Sigma), and embedded in epoxy resin. Ultrathin sections (80 nm) were mounted on 200 mesh copper grids and stained with uranyl acetate and lead citrate (Electron Microscopy Sciences). Imaging was performed with a JEOL JEM-1010 TEM and a FEI Tecnai G2 Spirit TEM.

PKD patients. All human samples were obtained with informed consent and in compliance with all ethical regulations under the auspices of protocols approved by the UW Institutional Review Board. These included an ADPKD kidney donated by a 46-yr-old female (generous gift of Virginia Mason Hospital), an anonymized biopsy of a 15-week control kidney (UW Laboratory of Developmental Biology), and anonymized biopsies of kidneys with clinically diagnosed Meckel syndrome (20 weeks), ARPKD (29 weeks, 6 months, or 6 years), and orofaciodigital syndrome (18 yr.) from Seattle Children's Hospital Histopathology. Patients with kidney disease were enrolled in the study for the purposes of collecting cells and tissues as positive controls. These samples were collected from patients of all ages without any discrimination with respect to gender, age, race, family history, or other co-variates. PKD samples were chosen from this collection at random and based on availability to represent a range of disease severities, ages, and genotypes.

Statistical analysis. Experiments were performed using a cohort of PKD hPSCs, generated as described previously (Freedman et al. 2015a), including three $PKD1^{-/-}$ and two $PKD2^{-/-}$ hPSC lines, and a total of six isogenic control lines that were subjected to CRISPR mutagenesis but were found to be unmodified at the targeted locus. Quantification was performed on experiments performed side by side on at least three different occasions. Error bars are mean±standard error (s.e.m.). Statistical analyses were performed using Graph-Pad Prism Software. To test significance, p values were calculated using two-tailed, unpaired t-test with Welch's correction (unequal variances). Statistical significance was defined as $p<0.05$. Exact p values, t values and degrees of freedom are provided in the Figure legends.

Data availability. Microarray data are MIAME compliant and publicly available in Gene Expression Omnibus (GEO, http://www.ncbi.nlm.nih.gov/geo) (ID: GSE101308). All remaining datasets are available from the corresponding author upon reasonable request.

Results and Discussion

Figure 1A:
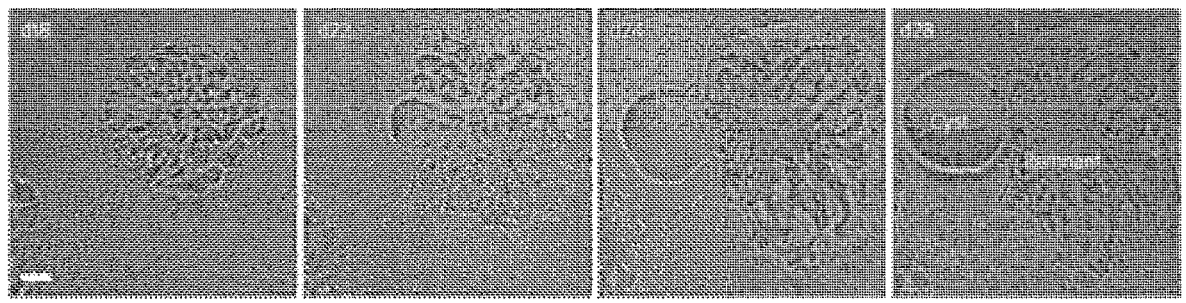
FIGS. 1A-1E show that removal of adherent cues establishes a highly efficient model of PKD cystogenesis.
Figure 31:
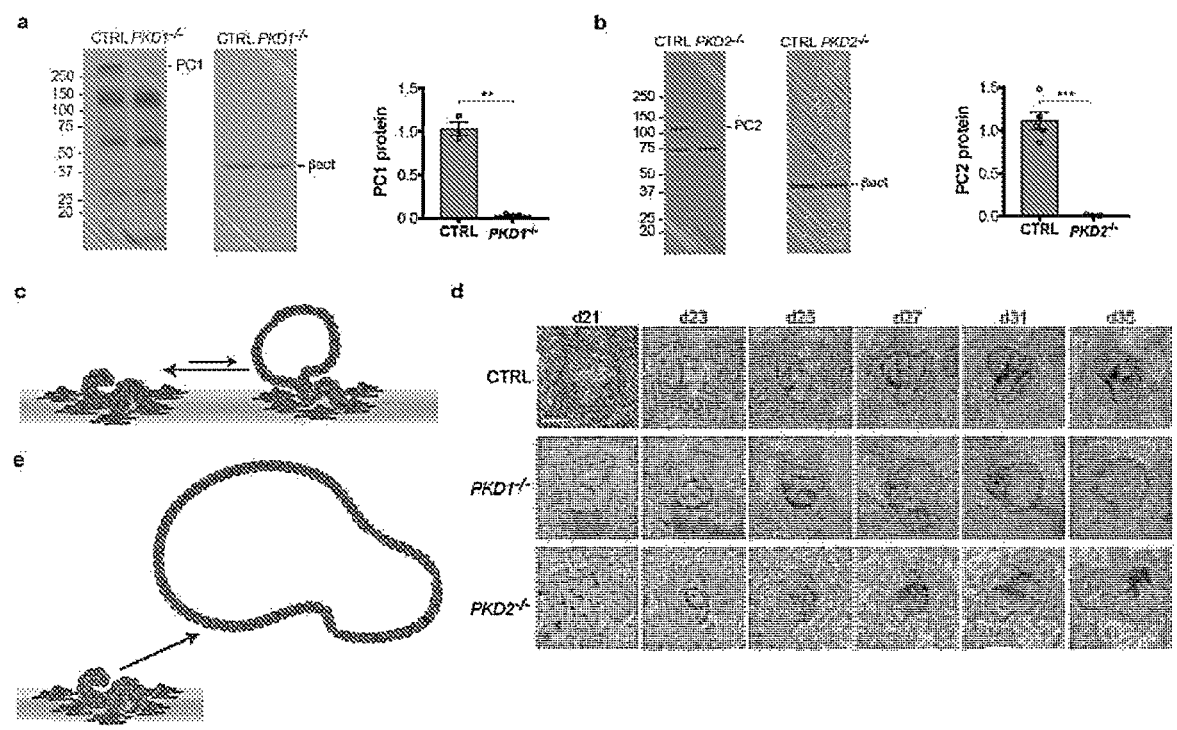
FIGS. 31A-31E show that analysis of adherent PKD organoids reveals tubule-to-cyst transitions.

PKD affects one in ~1,000 people worldwide, with no known cure (The European PKD Consortium 1994; Mochizuki et al. 1996). Animal models do not fully genocopy or phenocopy human PKD, and are too complex physiologically for a minimal reconstitution approach (Lantinga-van Leeuwen et al. 2004; Shillingford et al. 2006; Trudel et al. 1997; Gattone et al. 2003). A human cellular model is needed to complement animal models and reveal the early pathophysiology of PKD. Human pluripotent stem cells (hPSCs) were generated with targeted, biallelic mutations that lack the mature form of PC1, or any detectable PC2, using the Cas9/CRISPR (clustered regularly interspaced short palindromic repeats) gene editing system (FIGS. 31A-31B) (Freedman et al. 2015a; Jinek et al. 2012). Under adherent culture conditions, kidney organoids derived from $PKD1^{-/-}$ or $PKD2^{-/-}$ hPSCs form fluid-filled cysts, although cystogenesis is highly inefficient (~7% of organoids), and its mechanism has not been determined (Freedman et al. 2015a). This system was used as a starting point to investigate how cysts form and identify modulators of cystogenesis. Time-lapse imaging revealed that cyst formation involved two steps: first, rearrangement of a tubule within an organoid, resulting in deformation of linear shape to form a 'pre-cyst' surrounding an hollow pocket; and second, partial detachment of the pre-cyst from the underlying stratum followed immediately by rapid expansion, resulting in a buoyant cyst tethered to an adherent organoid remnant (FIGS. 1A, 31C, 31D). Cysts therefore arose from whole tubular segments that expanded and partially detached from the adherent surface.

Figure 1B:
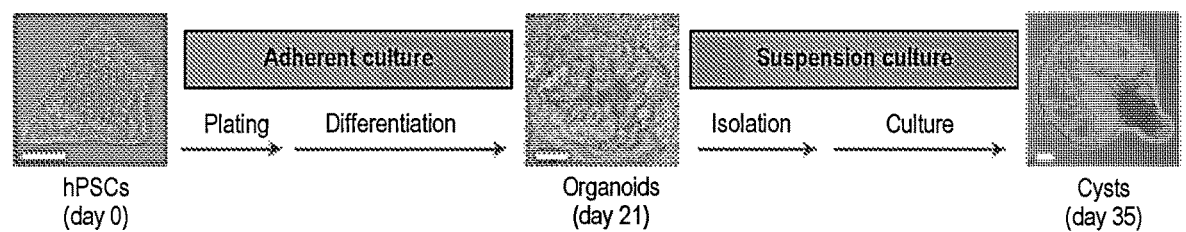
Figure 1C:
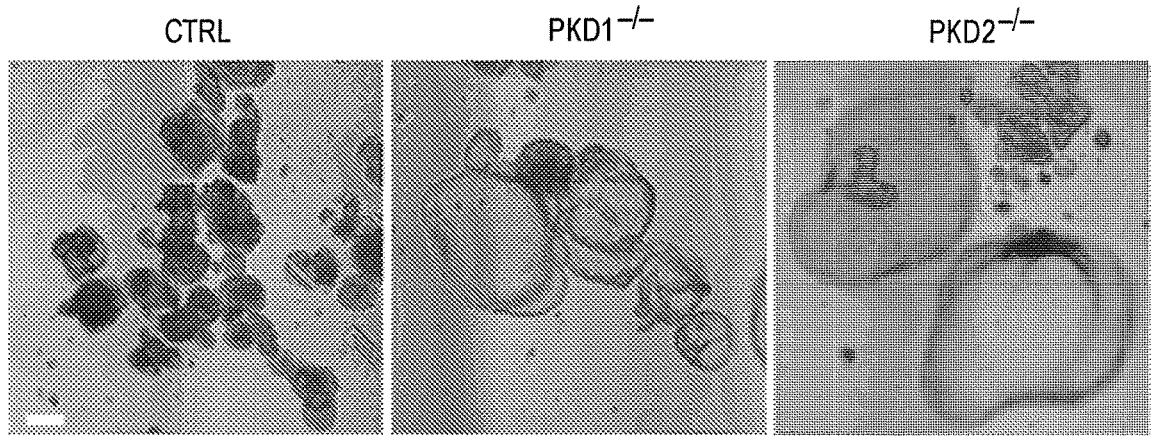
Figure 1D:
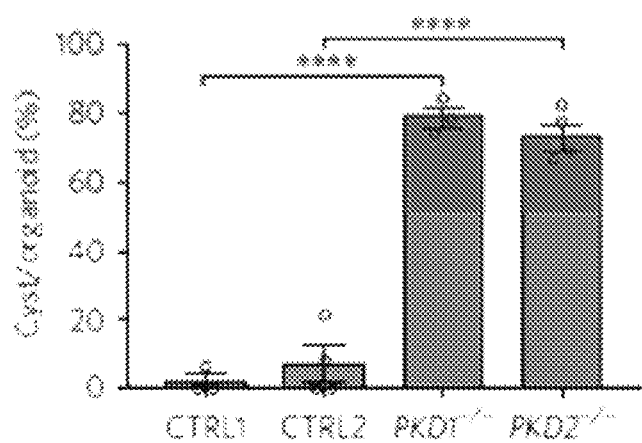
Figure 1E:
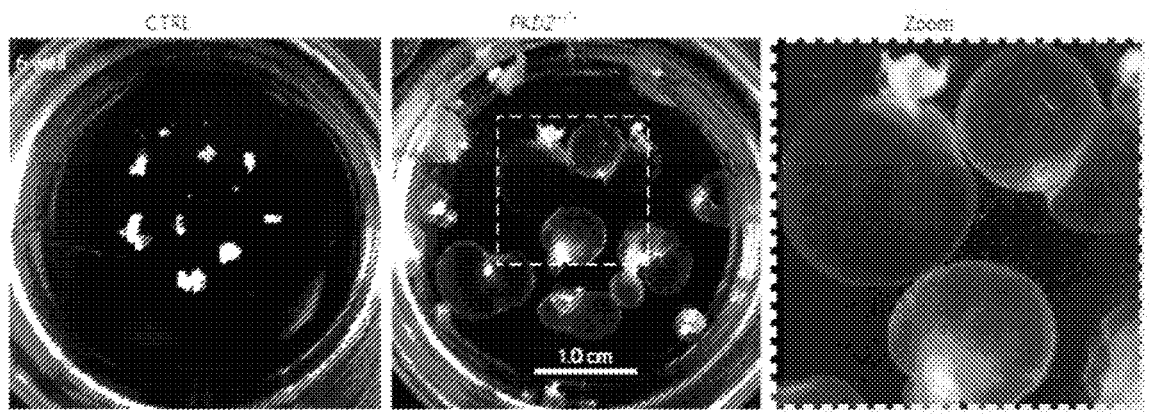

To test whether adherent forces played a critical role in limiting tubular deformation and subsequent cyst formation, organoids were purified on day 21 of differentiation, prior to the formation of cysts, and transferred to wells coated with an anti-adhesive hydrogel to generate suspension cultures (FIGS. 1B and 31E). After two weeks in suspension, ~75% of PKD organoids formed large, free-floating cysts (FIGS. 1C-1D), a 10-fold increase in cyst formation over adherent cultures (Freedman et al. 2015a). Control organoids of identical genetic background formed cysts only very rarely under these conditions, indicating that cystogenesis remained a specific consequence of the PKD mutations (FIGS. 1C-1D). As an inherent property of this differentiation system in both PKD and control cultures, each of the organoids placed into suspension was relatively small (~250 µm in diameter) and contained only ~5 tubules, therefore a significant proportion (~15%) of individual tubules deformed into cysts. In long-term cultures, PKD cysts further expanded massively and reached diameters of ~1 centimetre, reflecting a 4,000-fold increase in size over the original organoid (FIG. 1E). Even after many months in suspension, cysts remained rare among control organoids, which formed smaller, denser aggregates (FIGS. 1D-1E). Thus, modification of the material environment enabled the establishment of a highly efficient minimal reconstitution system for PKD cystogenesis.

Figure 2A:
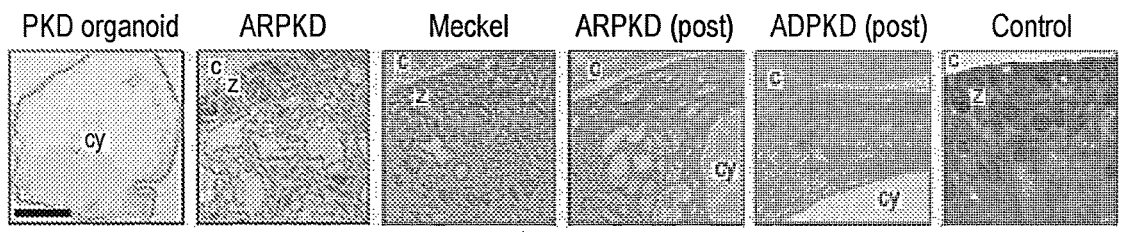
FIGS. 2A-2H show that organoid PKD cysts phenotypically resemble PKD patient cysts.
Figure 32:
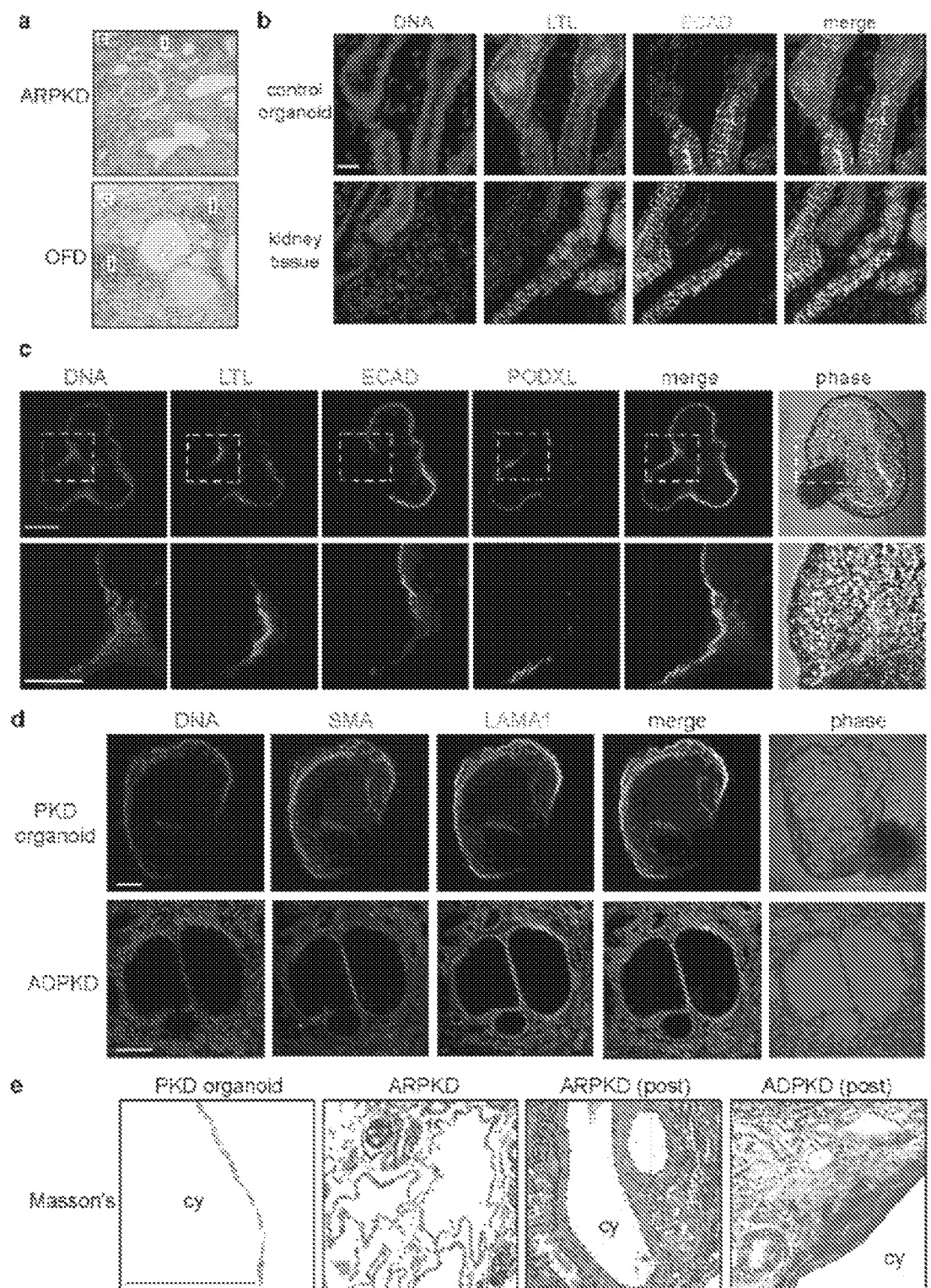
FIGS. 32A-32E illustrate organoid PKD cysts share features of PKD patient cysts.

Histological analysis revealed that PKD organoid cysts were lined with a thin, squamous epithelial layer, approximately one single cell in thickness, with irregular edges, surrounding a hollow lumen (FIG. 2A). When compared to cysts from various stages and subtypes of clinical PKD in vivo, organoid cysts most closely resembled cysts in prenatal PKD, which extended radially from the medulla to the cortex and appeared prominent just beneath the nephrogenic zone (FIGS. 2A and 32A). Similar cysts were previously reported in patients with biallelic mutations in PKD1 (Vujic et al. 2010). In contrast, postnatal cysts from patients exhibited a more smooth-edged and multi-layered appearance and were accompanied by interstitial nephritis and inflammatory infiltrates not observed prenatally or in organoids (FIGS. 2A and 32A).

Figure 2B:
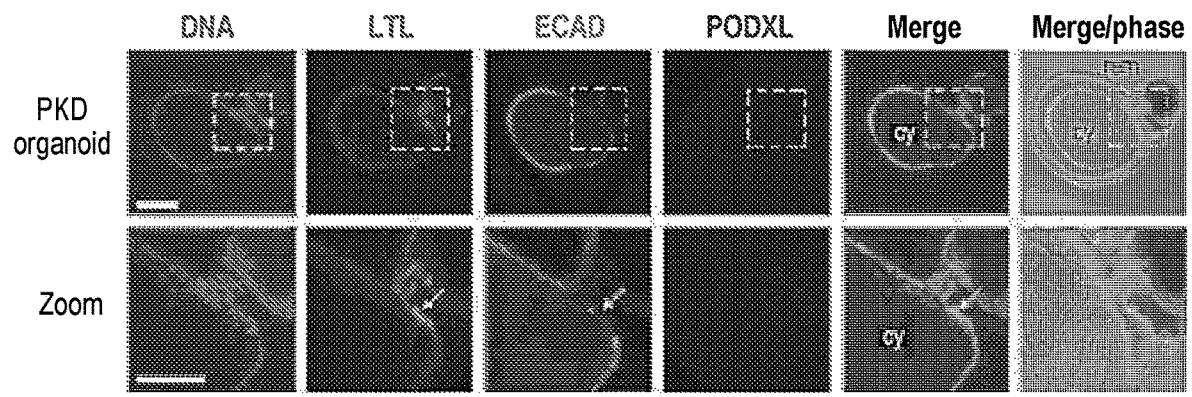
Figure 2C:
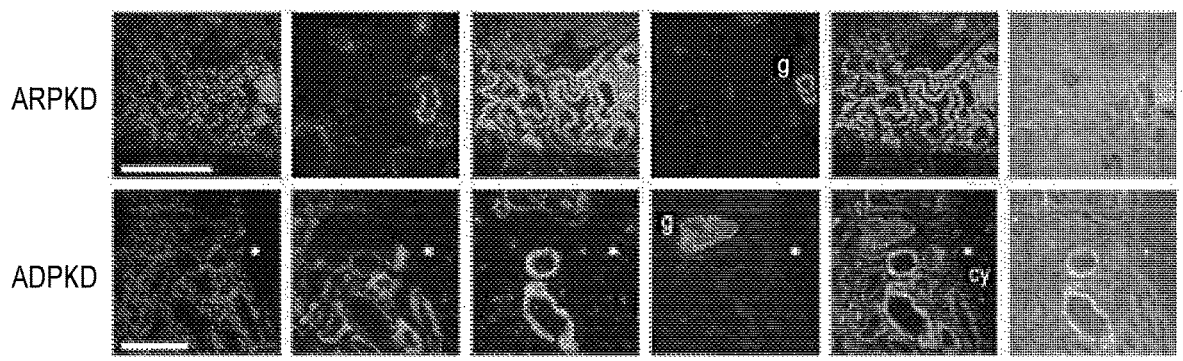
Figure 2D:
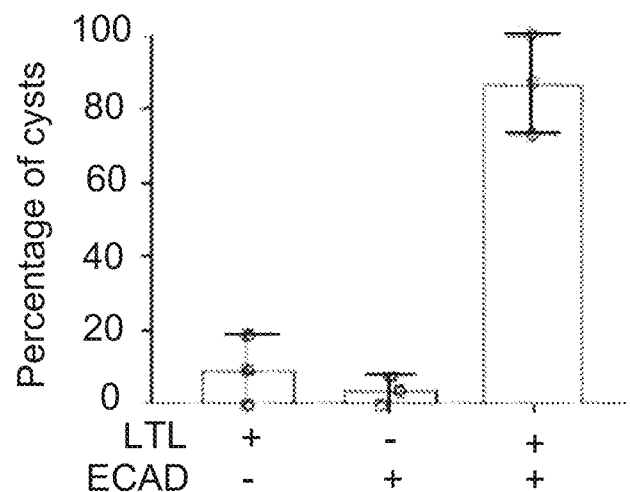
Figure 2E:
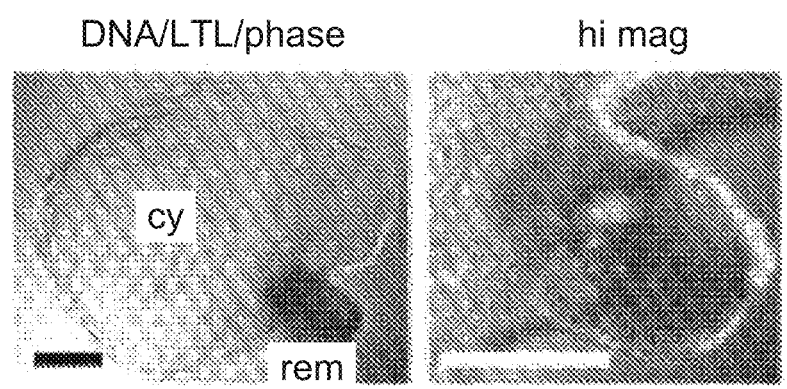
Figure 2F:
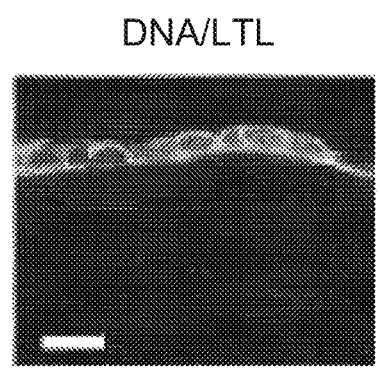
Figure 2G:
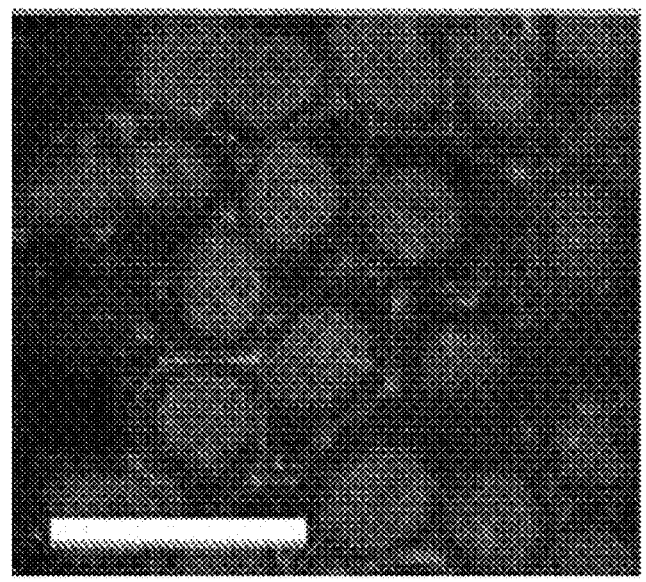
Figure 2H:
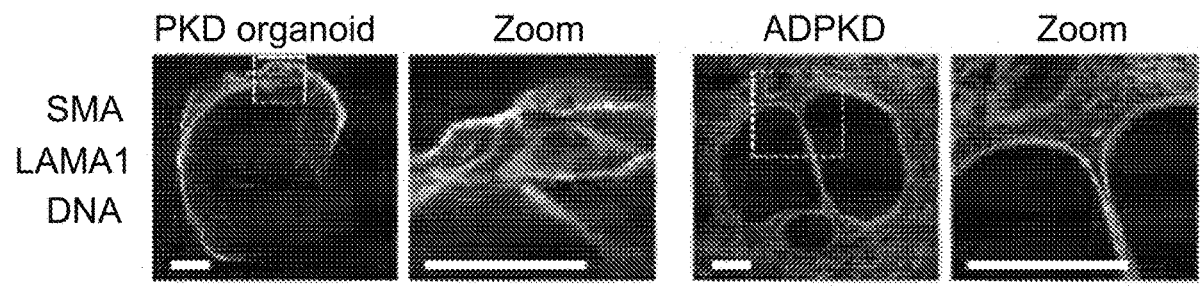

Lotus tetragonolobus lectin (LTL) and E-cadherin (ECAD), respectively, have been identified as markers of organoid proximal and distal tubules in these cultures (Freedman et al. 2015a). In non-cystic organoids and tissues, these markers were not mutually exclusive, but rather formed a continuum, with enrichment in their respective nephron segments (FIG. 2B). In PKD organoid cysts, LTL and ECAD largely overlapped within the cyst-lining epithelium, exhibiting patches of specific enrichment, whereas PODXL, a marker enriched in kidney podocytes, was not detected in cysts, similar to prenatal and postnatal PKD patient kidneys (FIGS. 2B, 2C, and 32C) (Vujic et al. 2010; Jinek et al. 2012; Grantham et al. 1987). Approximately 80% of organoid cysts expressed both LTL and ECAD, which were also detected within the tubular remnants continuous with these cysts (FIGS. 2B-2F and 32C). Cyst-lining cells in organoids were heavily coated with primary cilia and formed tight junctions between cells in a cobblestone pattern (FIG. 2G). Interestingly, organoid cysts in long-term suspension cultures also contained a subpopulation of stromal cells that co-expressed smooth muscle α-actin (SMA) and laminin, markers expressed in cystic stroma of PKD patient kidneys (FIGS. 2H and 32D). Collagen deposition in these cysts remained scant, similar to cysts in prenatal PKD kidneys, whereas postnatal PKD kidney cysts exhibited prominent fibrosis (FIG. 32E). PKD organoid cysts in vitro therefore recapitulated hallmark features of PKD patient cysts, particularly the very early stages of PKD.

Figure 3A:
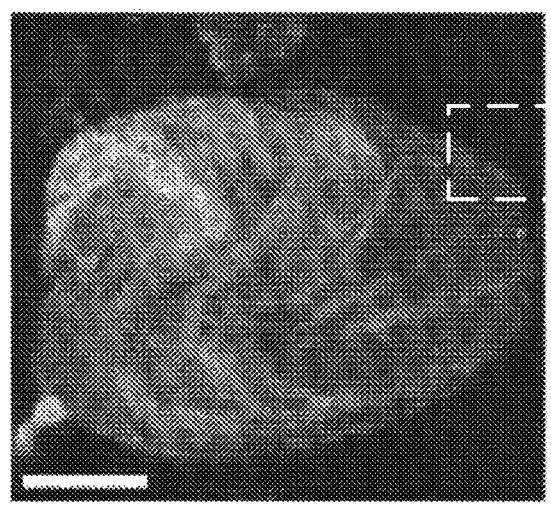
FIGS. 3A-3F show that PDK organoid cysts arise from hyperproliferative KTECs.
Figure 3B:
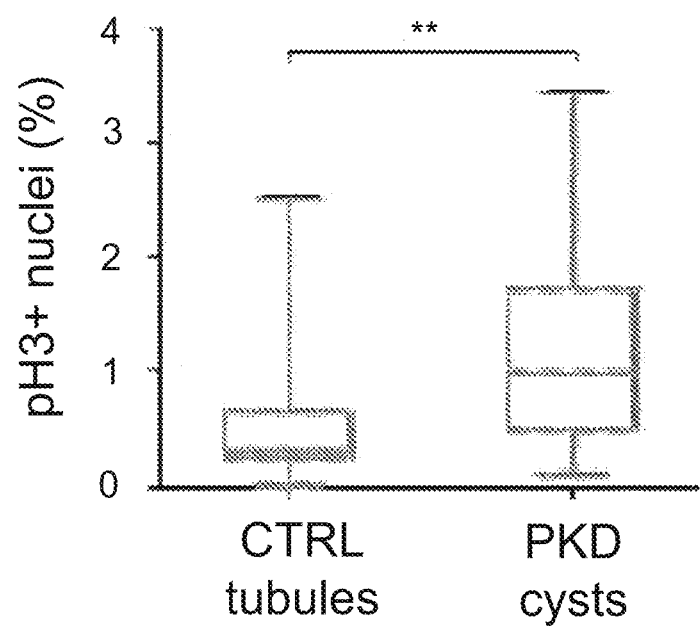
Figure 3C:
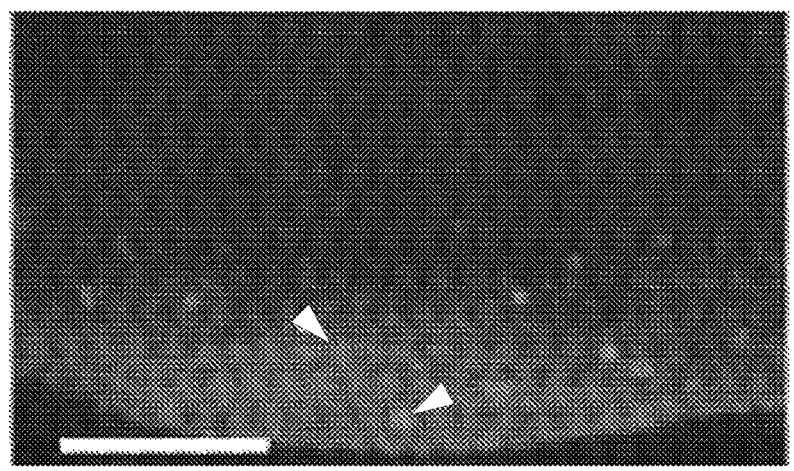
Figure 3D:
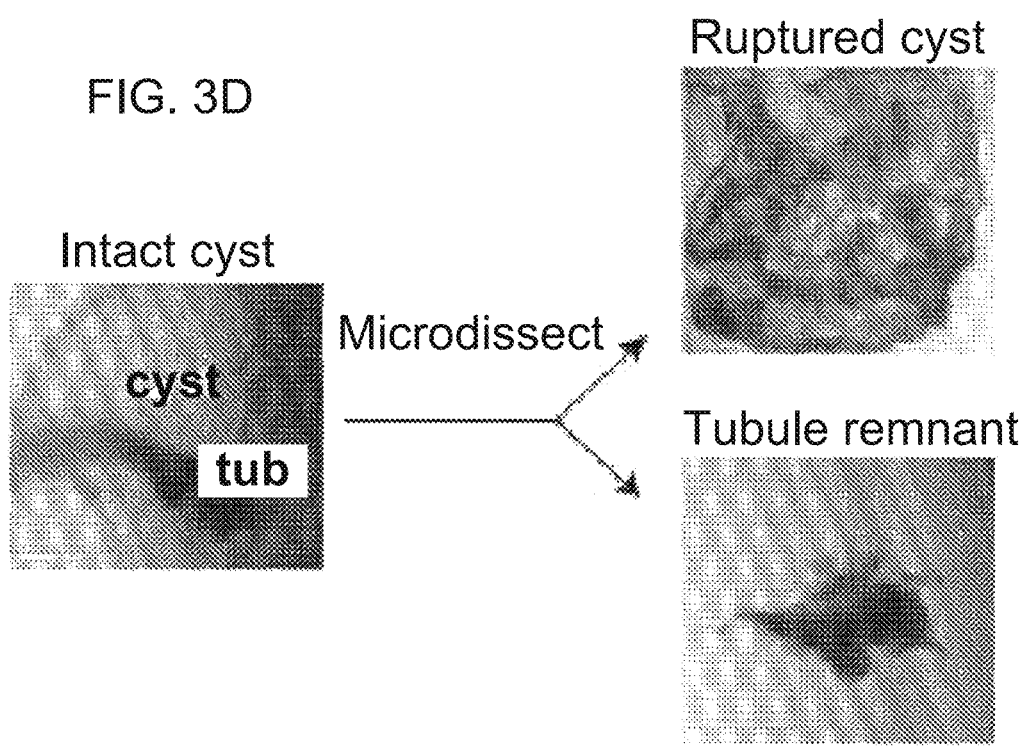
Figure 3E:
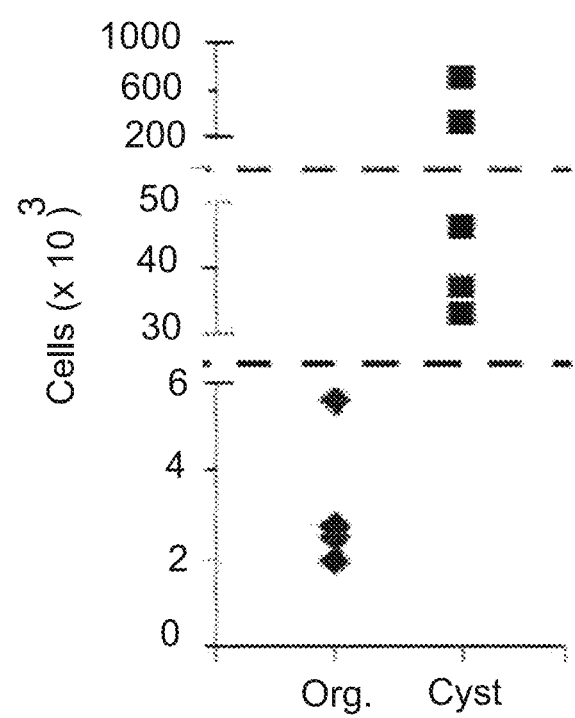
Figure 3F:
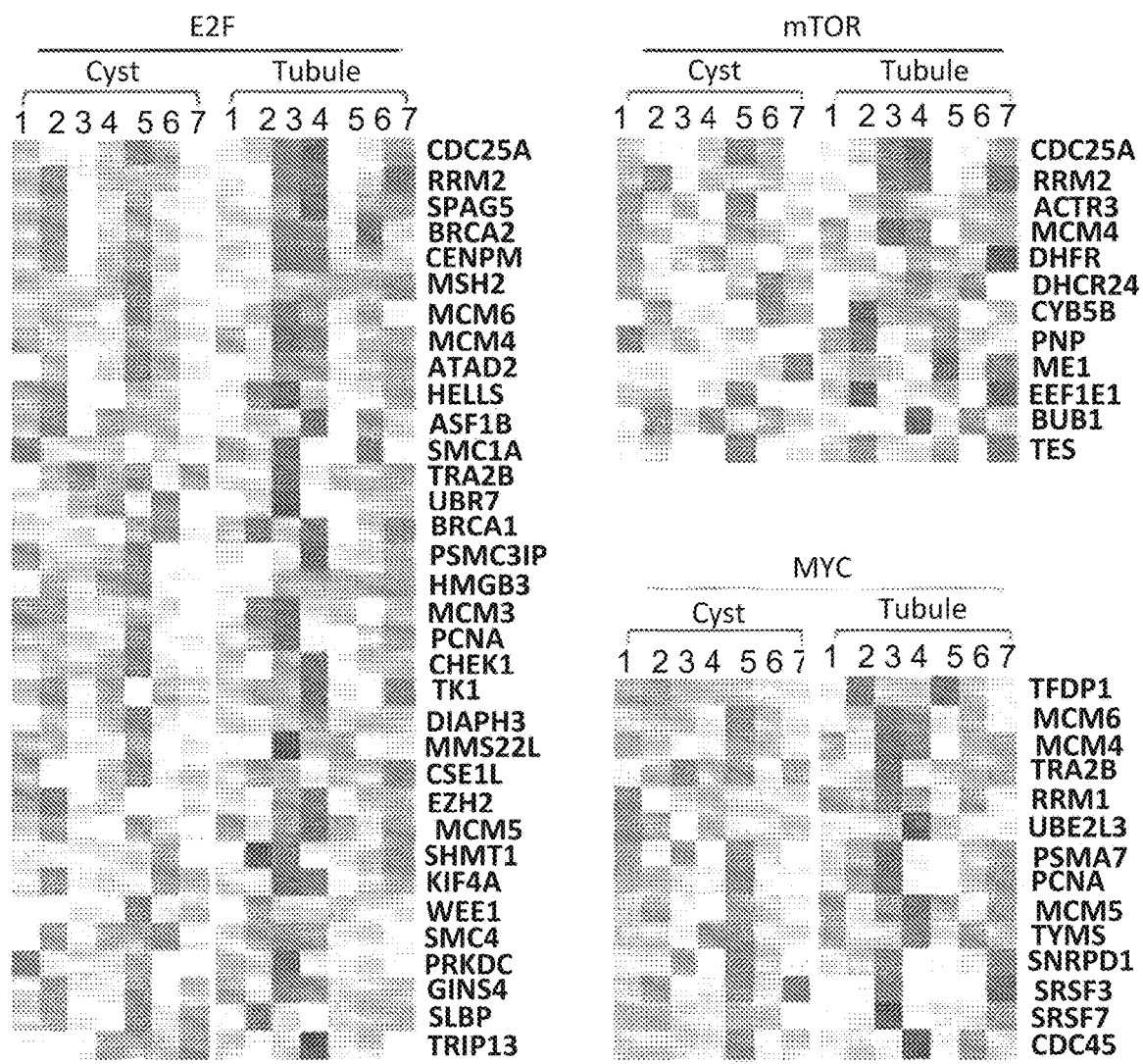
Figure 33:
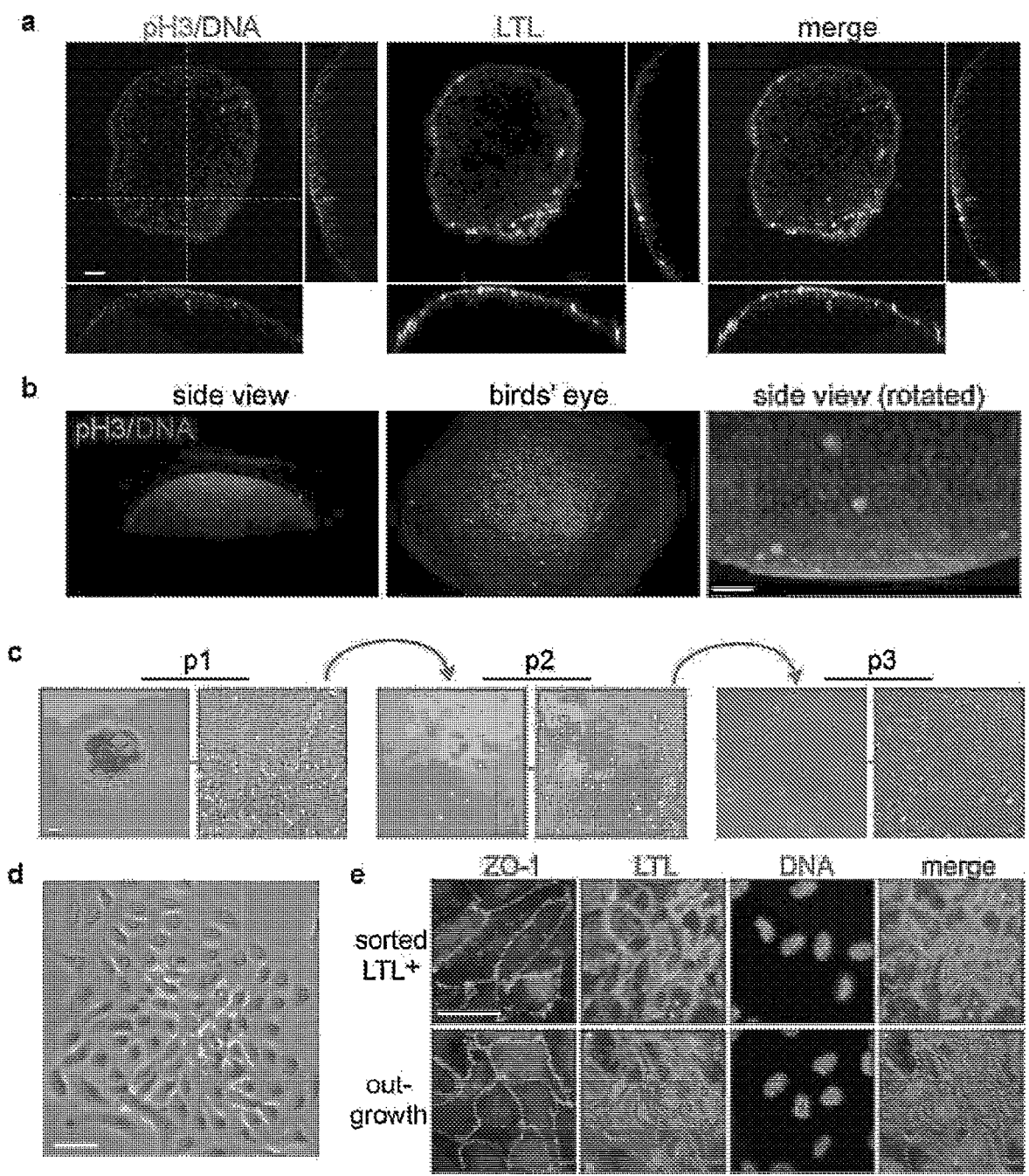
FIGS. 33A-33E illustrate cysts arise from proliferative KTECs.

PKD organoid cysts in adherent cultures exhibited a two-fold increase in phosphorylated histone H3 (pH3), compared to LTL+ tubular cells from non-mutants, indicating increased proliferation (FIGS. 3A-3B). Similarly, in large cysts in long-term suspension cultures, dividing cells were detected within the cyst-lining epithelium and in anaphases oblique and internal to the plane of the cyst (FIGS. 3C, 33A, 33B). When large PKD cysts were microdissected away from their remnant tubules, they immediately deflated, reflecting the loss of accumulated fluid (FIG. 3D). Cysts contained from ~30,000 to ~600,000 cells, whereas the original organoids from which they derived contained only ~3,000 cells, indicating extensive proliferation (FIG. 3E). Pathway-based global gene expression microarray analysis revealed significant enrichment of hallmark gene sets for cell cycle progression, mTOR signaling, and MYC activity in cysts, compared to remnant tubules (FIG. 3F). PKD cysts therefore arose from hyperproliferative kidney tubular epithelial cells (KTECs). A hallmark of mouse and human autosomal dominant PKD (ADPKD) (Shillingford et al. 2006; Trudel et al. 1997; Grantham et al. 1987; Song et al. 2009).

Figure 4A:
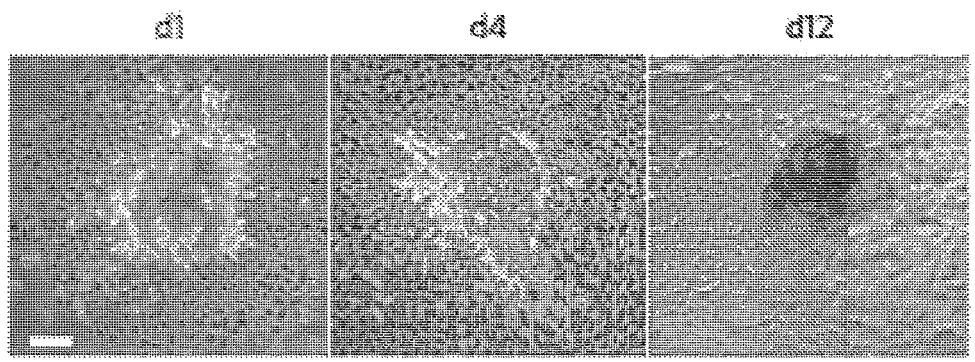
FIGS. 4A-4K show that outgrowth of PKD cell lines reveals a critical deficiency in PC1 expression.
Figure 4B:
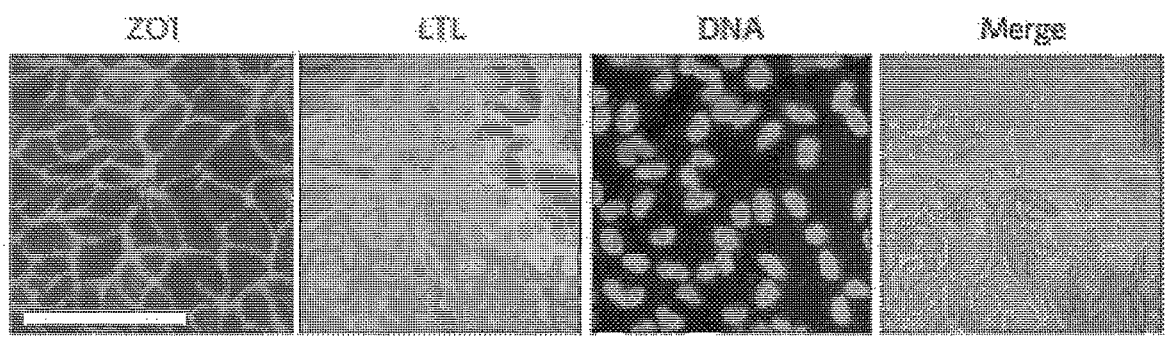
Figure 4C:
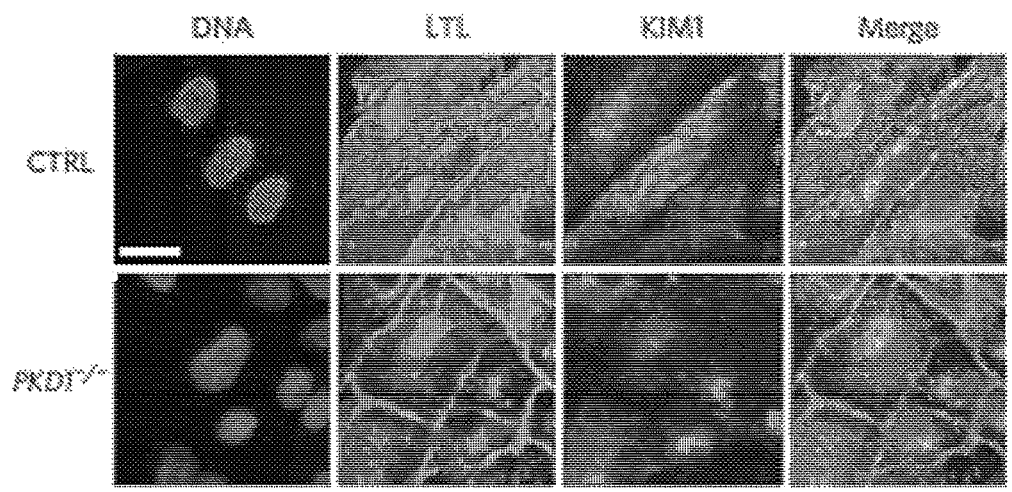
Figure 4D:
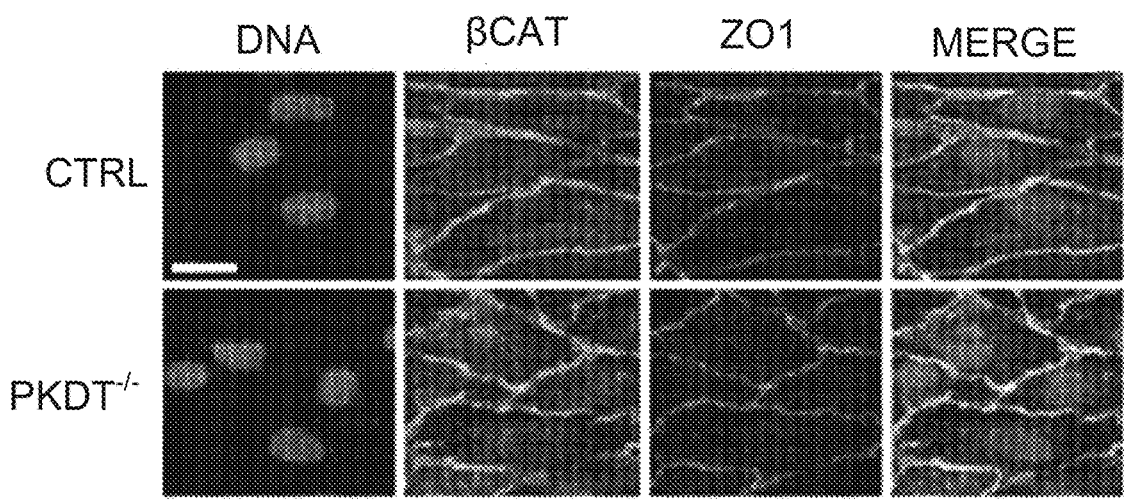

The process of purifying organoids and transferring them into suspension might induce cyst formation by provoking an injury response (Takakura et al. 2009; Patent et al. 2008). To test this, organoids were purified and immediately replated onto wells coated with a thin layer of extracellular matrix (ECM) but lacking stroma. The replated organoids re-adhered but did not form cysts, indicating that injury alone was not sufficient to promote cystogenesis (FIG. 4A). Under these conditions, it was observed that both control and PKD organoids formed expanding cell outgrowths very quickly, which could be further expanded as monolayers up to three passages (FIGS. 4A and 33C). Cells derived from organoid outgrowths exhibited a cobblestone-like epithelial morphology and predominantly expressed markers specific to KTECs, including LTL and kidney injury molecule-1 (KIM-1), similar to flow-sorted LTL+ cells from organoid cultures (FIGS. 4B-4D and 33D-33E). Removal of stroma thus stimulated proliferation and migration of organoid cells.

Figure 4E:
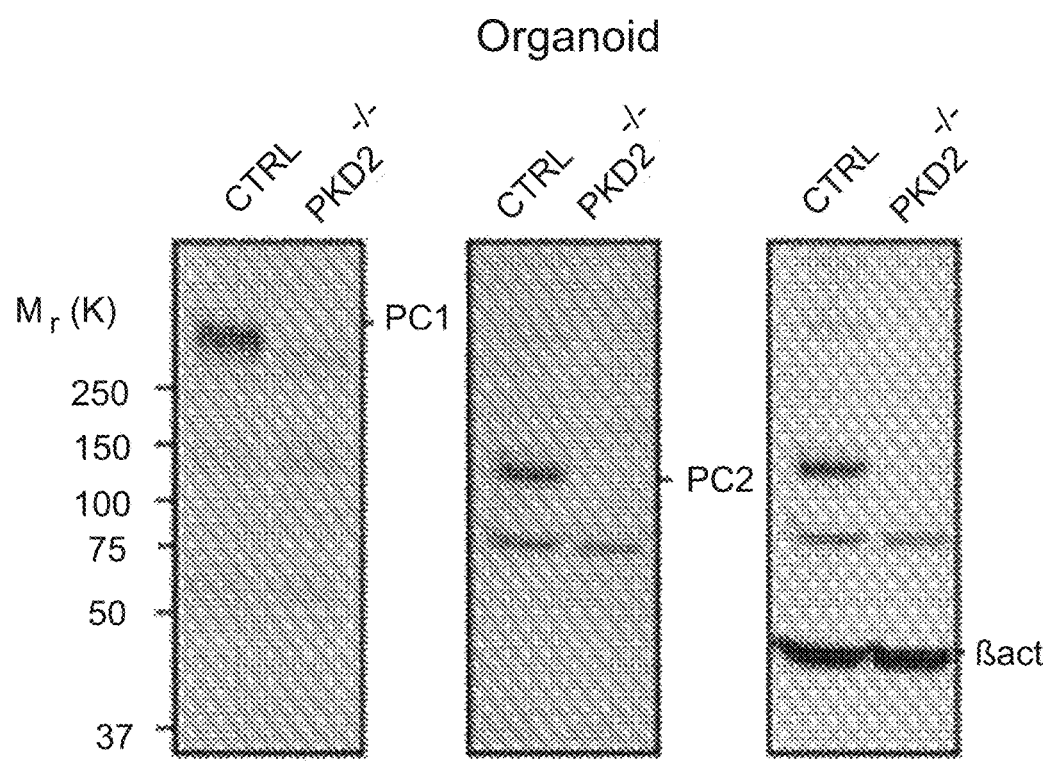
Figure 4F:
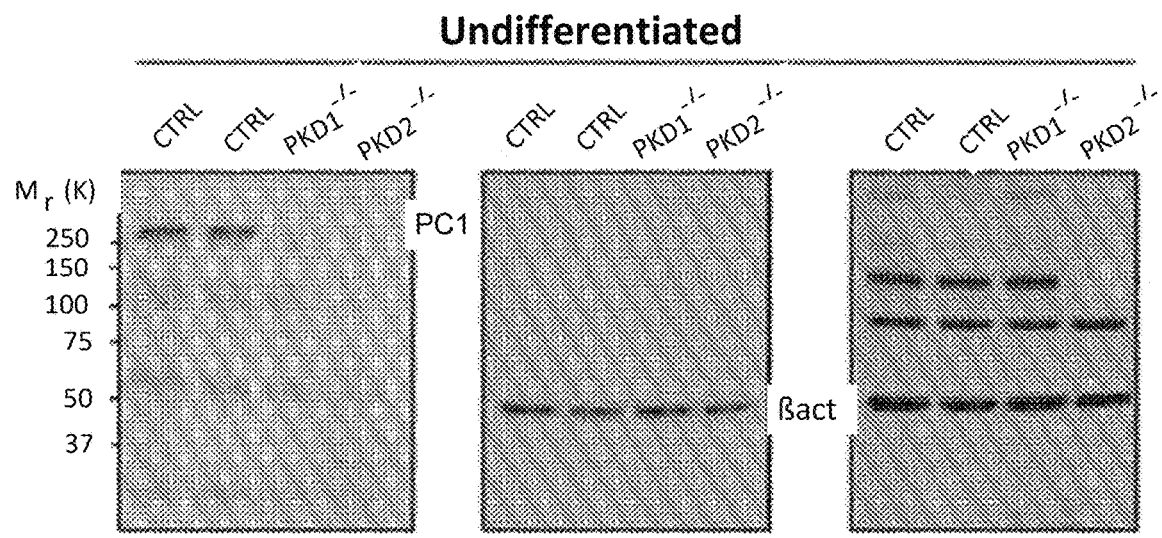
Figure 4G:
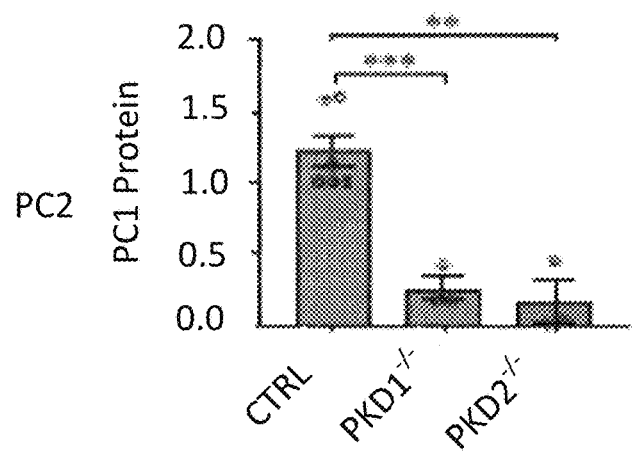
Figure 4H:
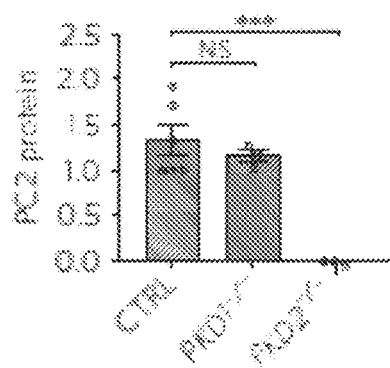
Figure 4I:
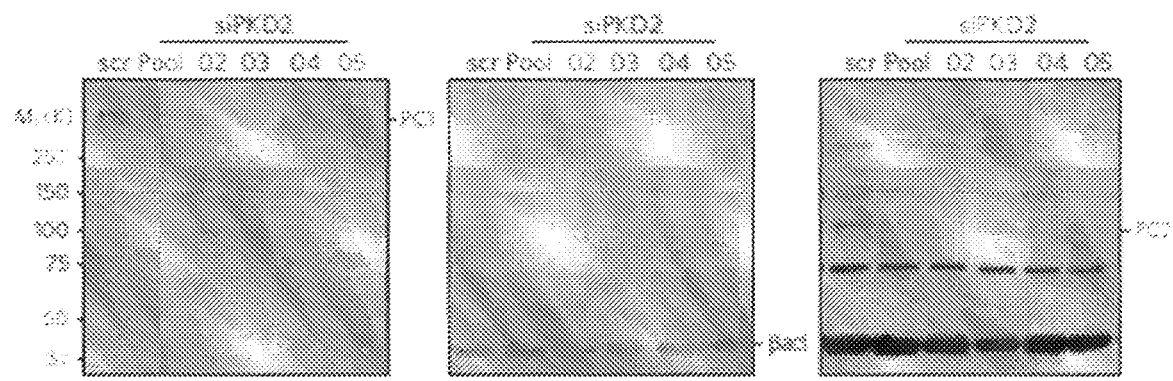
Figure 4J:
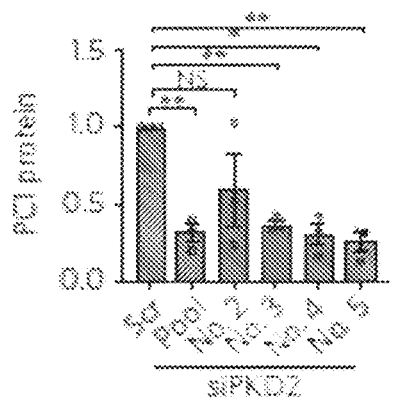
Figure 4K:
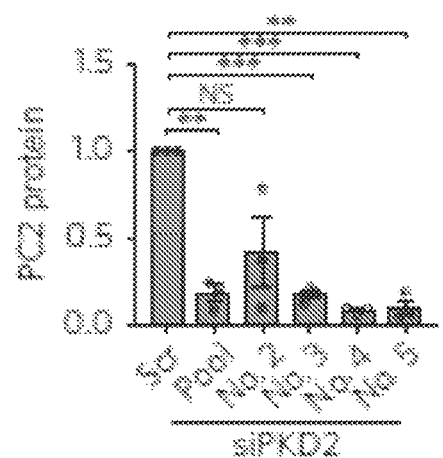
Figure 34:
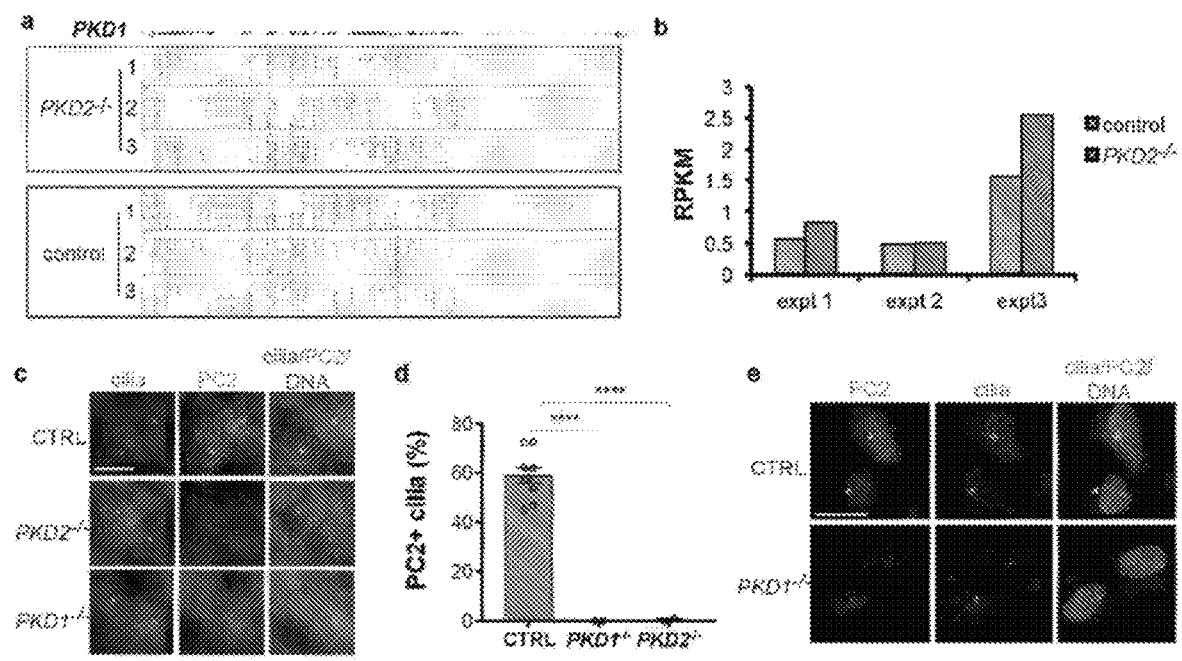
FIGS. 34A-34E show that PC1 and PC2 interdependence is post-transcriptional.

Further, the organoid KTEC cell lines to investigate the expression of PC1, whose structure suggests a possible role in cell adhesion (The International PKD Consortium, 1995; Ibraghimov-Beskrovnaya et al. 2000). In contrast to many cell types, KTECs derived from organoid outgrowths expressed sufficient quantities of endogenous PC1 to detect in lysates by immunoblot (FIG. 4E) (Cai et al. 2014; Gainullin et al. 2015). Surprisingly, it was found that PC1 protein was nearly undetectable in KTECs derived from PKD2$^{-/-}$ organoids, using an antibody against the amino terminal fragment (FIG. 4E) (Ong et al. 1999). Undifferentiated PKD2$^{-/-}$ exhibited a similarly strong decrease in PC1 expression levels (FIGS. 4F-4G). PKD1 transcripts were expressed at normal levels in PKD2$^{-/-}$ hPSCs, suggesting that PC1 loss occurs through a post-transcriptional mechanism (FIGS. 34A-34B). Conversely, in PKD1$^{-/-}$ cells, PC2 expression levels were unchanged from isogenic controls, although its localization to primary cilia was strikingly decreased, consistent with previous reports (FIGS. 4F, 4H, 34C, and 34D) (Freedman et al. 2015a; Cai et al. 2014; Gainullin et al. 2015). Furthermore, treatment of control hPSCs with three different siRNAs, which knocked down PC2 protein to 12.6±0.02% of normal levels (avg. ±s.e.m.), induced a corresponding decrease in PC1 protein to 30.5±0.03% of normal levels (FIGS. 4I-4K). These studies revealed, unexpectedly, that PC2 was required for PC1 amino-terminus expression in human cells, in contrast to reports in mouse Pkd2$^{-/-}$ cells (Cai et al. 2014; Gainullin et al. 2015). Differences between species, cell types, or exogenous versus endogenous expression levels may account for this discrepancy, as PC1 is a low-abundance protein in humans, who appear to be highly sensitive to reductions in its expression, compared to mice (Freedman et al. 2015a; Lantinga-van Leeuwen et al. 2004; Qian et al. 1996; Chauvet et al. 2002).

Figure 5A:
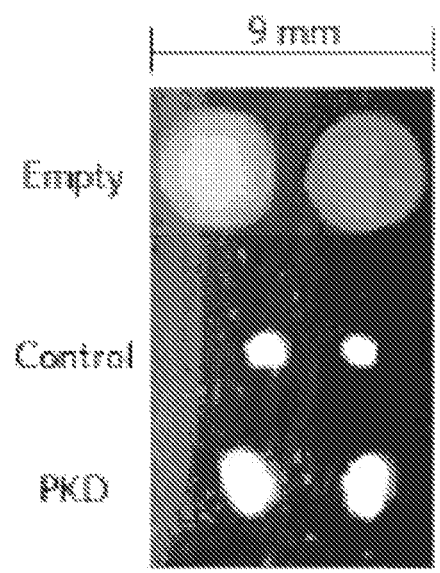
FIGS. 5A-5H show that organoids remodel their matrix microenvironment in a PKD-dependent manner.
Figure 5B:
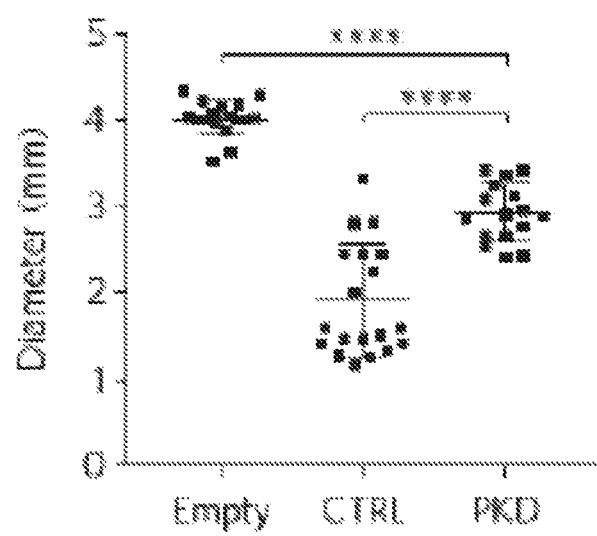
Figure 5C:
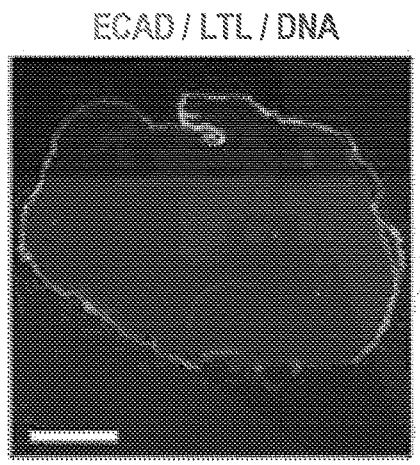
Figure 5D:
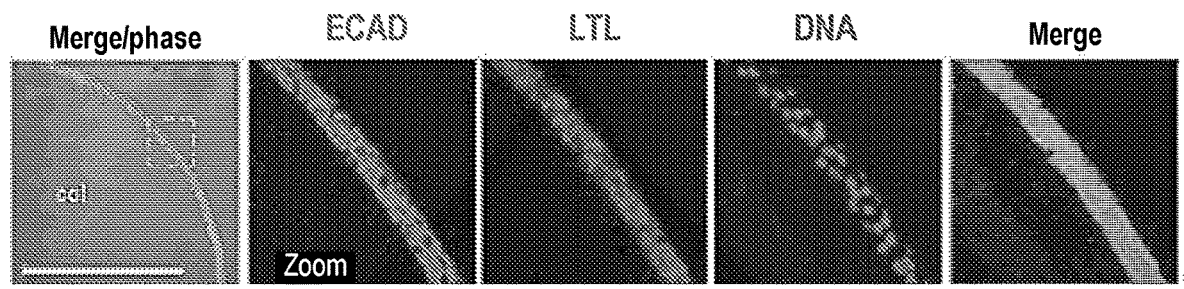
Figure 5E:
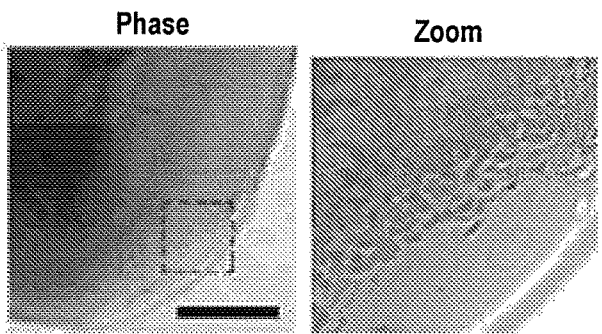
Figure 5F:
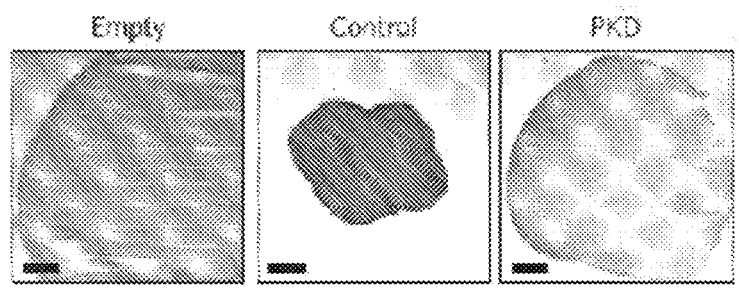
Figure 5G:
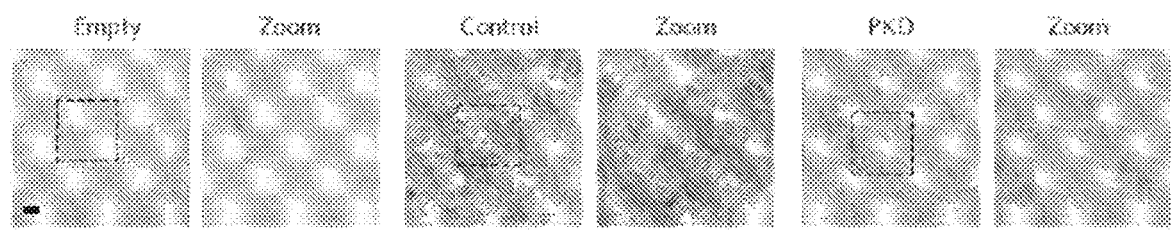
Figure 5H:
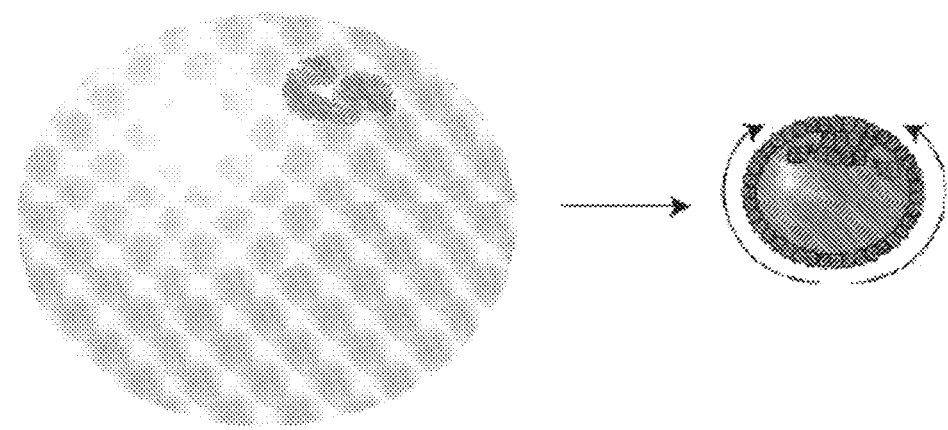

Based on these studies, the ECM microenvironment likely functions to maintain tubular shape and adhesion through interactions involving PC1's long, extracellular domain (The International Playcystic Kidney Disease Consortium, 1995; Ibraghimov-Beskrovnaya et al. 2000; Mangos et al. 2010). To directly test the effect of PKD mutations on the matrix microenvironment, individual organoids (~250 μm diameter) were embedded into larger collagen droplets (~4 mm diameter) and placed these in suspension. Droplets implanted with organoids did not form cysts, but rather contracted dramatically over a period of approximately 1-2 weeks (FIG. 5A). PKD1$^{-/-}$ organoids were quantitatively impaired in their ability to compact collagen droplets, compared to isogenic controls (FIG. 5B). Contracted droplets comprised an inner core of solid collagen encompassed by a thin, continuous epithelium of LTL+ECAD+KTECs (FIGS. 5C-5D). During the formation of these structures, KTECs could be observed migrating out of the implanted organoid to coat the surface of the droplet (FIG. 5E). Collagen staining appeared more intense after contraction, and collagen fibres appeared denser ultrastructurally, indicating that the changes in droplet size involved physical compression (FIGS. 5F-5G). Collectively, these findings revealed that kidney organoid epithelia were capable of dramatically remodeling their ECM microenvironment through migratory forces, and that this property was partially dependent on PC1 (FIG. 5H).

Figure 35:
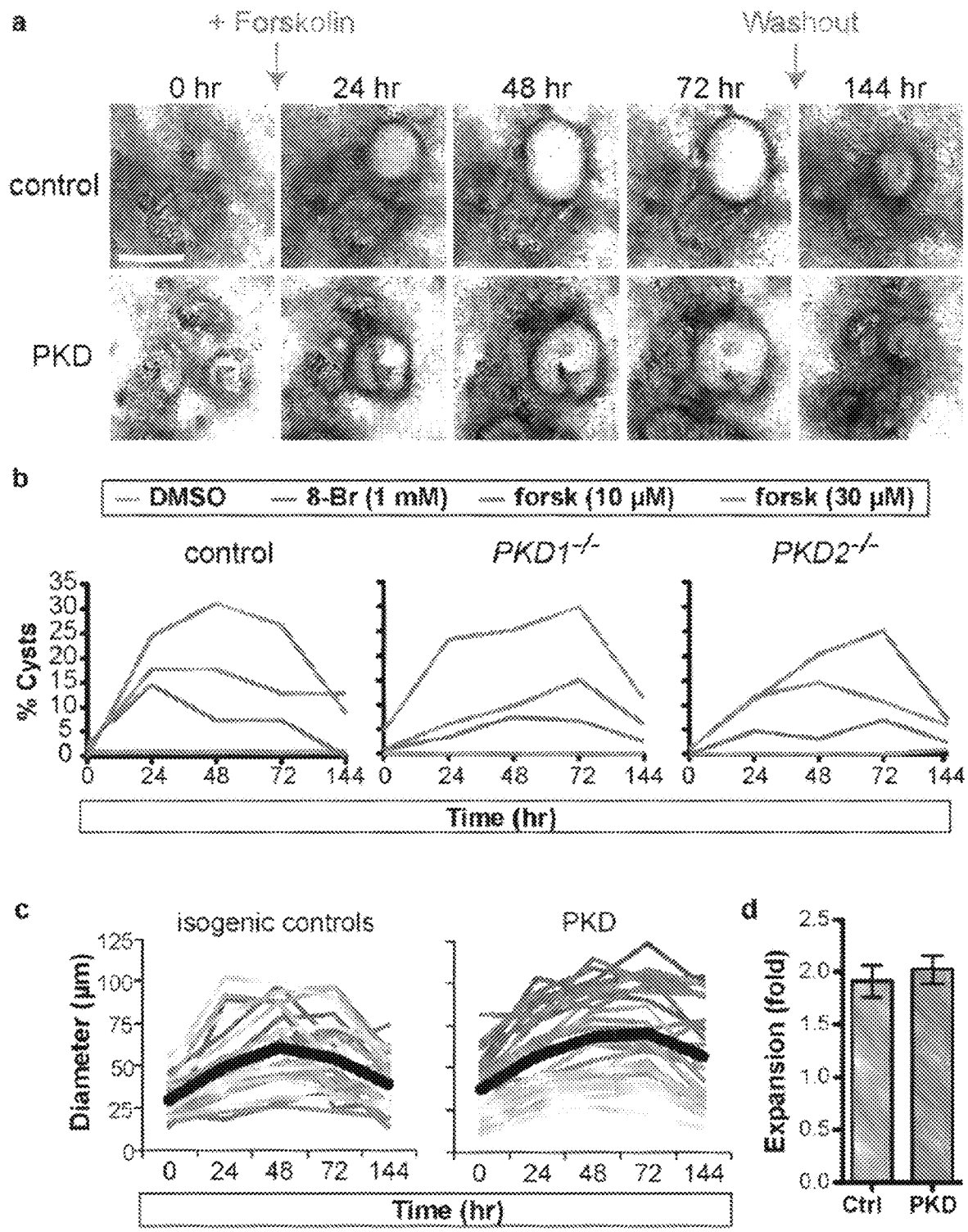
FIGS. 35A-35D show cyclic Cyclic AMP promotes cystogenesis in PKD organoids and isogenic controls.

Cyclic AMP (cAMP) signaling may contribute significantly to PKD, but can also promote fluid accumulation in non-PKD epithelia (Neufeld et al. 1992; Magenheimer et al. 2006). Forskolin, a powerful agonist of adenylyl cyclase, induced rapid and dose-dependent swelling of adherent organoids into round, cyst-like structures that retained the shape of the original tubules (FIGS. 35A-35B). The non-degradable cAMP analog 8-Br-cAMP also induced swelling, although the effect was much less pronounced (FIGS. 35B-35C). Upon withdrawal of these agents, the swollen structures deflated and the organoids returned towards their original size (FIGS. 35A-35C). Both PKD and non-PKD organoids swelled and deflated to a similar degree after cAMP stimulation, indicating a modifier effect (FIGS. 35A-35D). One limitation of this system is that the collecting ducts could not be examined, which are the primary target of cAMP-mediated candidate therapeutics (Gattone et al. 2003; Reif et al. 2011), because these structures do not mature in kidney organoids (Freedman et al. 2015a; Taguchi et al. 2014; Takasato et al. 2015; Morizane et al. 2015).

Figure 36:
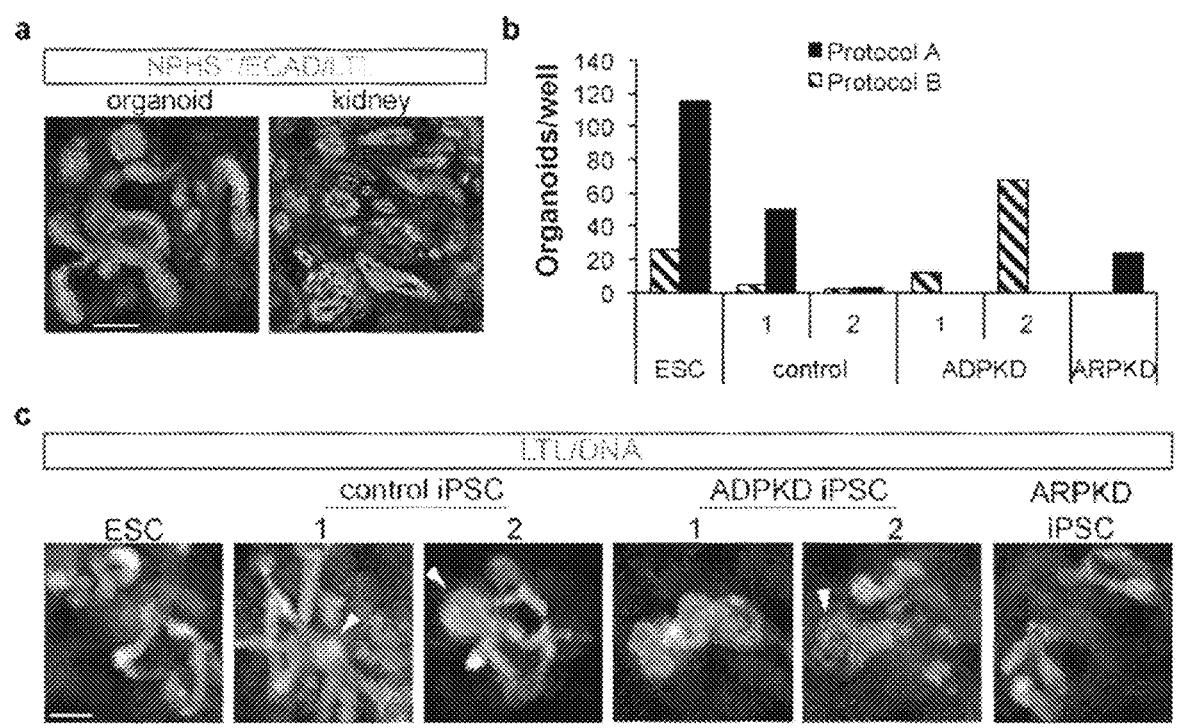
FIG. 36D shows average expansion at 72 hours (±s.e.m.). No significant difference is observed (p=0.59). Scale bars, 100 µm.
FIGS. 36A-36C show hPSCs from different patients exhibit variability in kidney organoid differentiation.

In addition to gene-edited mutants, the potential of using induced pluripotent stem cells (iPSCs) derived from PKD patients was investigated to model disease (Freedman et al. 2013). It was found that iPSCs from human patients exhibited dramatic line-to-line variability in their abilities to form organoids, regardless of PKD genotype and organoid differentiation protocol (FIGS. 36A-36C). The morphology of tubular structures also varied noticeably between different lines (FIG. 36C). As such differences reflected a degree of heterogeneity that would confound analysis of PKD-specific effects, the studies were focused on the CRISPR-mutant hPSCs. Although patient-derived organoids presented much variability, they could eventually represent valuable tools to develop personalized medicine approaches.

In conclusion, by combining PKD organoids with modular physical environments, a human cellular system that models PKD with high efficiency and specificity was established. Comparison of PKD and non-PKD organoids suggests a specific, primary role for microenvironment and adhesion in early stages of the disease. Interventions that strengthen stromal or scaffolding components can provide a critical cue favouring migratory repair over cystogenesis. The biochemical studies indicate a central requirement for PC1, which may function as an adhesion regulator that maintains tubular architecture through interactions with the microenvironment. The efficiency, specificity, and modularity of organoid cultures provide critical insight into the biomaterial basis of human disease, with great potential for mechanistic studies and therapeutics development.

Example 2: High-Throughput Screening Enhances Kidney Organoid Differentiation from Human Pluripotent Stem Cells and Enables Automated Multidimensional Phenotyping Protocols for the miniaturization and automation of human organoid differentiation from hPSCs are described below, using the kidney as a representative organ lineage. Further, the feasibility of using this system to enhance organoid differentiation and model disease was demonstrated.

Organoids derived from human pluripotent stem cells, such as those generated in accordance with the methods described above, are a potentially powerful tool for high-throughput screening (HTS), but the complexity of organoid cultures has traditionally posed a significant challenge for miniaturization and automation. Described below is a fully automated, HTS-compatible platform for enhanced differentiation and phenotyping of human kidney organoids. The entire 21-day protocol, from plating to differentiation to analysis, may be performed automatically by liquid-handling robots, or alternatively by manual pipetting. High-content imaging analysis reveals both dose-dependent and threshold effects during organoid differentiation. Immunofluorescence and single-cell RNA sequencing identify previously undetected parietal, interstitial, and partially differentiated compartments within organoids and define conditions that greatly expand the vascular endothelium. Chemical modulation of toxicity and disease phenotypes can be quantified for safety and efficacy prediction. Screening in gene-edited organoids in this system reveals an unexpected role for myosin in polycystic kidney disease. Organoids in HTS formats thus establish an attractive platform for multidimensional phenotypic screening.

Materials and Methods

The main resources were sourced as indicated in Table 4 below

TABLE 4

| REAGENT or RESOURCE | SOURCE | IDENTIFIER |
|---|---|---|
| Antibodies | | |
| Fluorescein *Lotus tetragonolobus* Lectin | Vector Labs | FL-1321; RRID:AB_2336559 |
| Rat Anti-Human E-Cadherin antibody [DECMA-1] | Abcam | Ab11512; RRID:AB_298118 |
| Sheep Anti-Human Nephrin (NPHS1) | R&D Systems | AF4269; RRID:AB_2154851 |
| Mouse Anti-Human ZO-1 antibody | Invitrogen | 339100; RRID:AB_2533147 |
| Mouse Anti-Human CD31 | BD Biosciences | 555444; RRID:AB_395837 |
| Biological Samples | | |
| Developing kidney tissue (days 60-130) | Laboratory of Developmental Biology (University of Washington) | 26805, 26846, 26847, 26848 |
| Chemicals, Peptides, and Recombinant Proteins | | |
| GSK-3β inhibitor CHIR99021 | StemGent | 04-0004-10; CAS 252917-06-9 |
| Rho-kinase inhibitor Y27632 | StemGent | 04-0012; CAS 146986-50-7 |
| Cisplatin | Sigma | 1134357; CAS 15663-21-1 |
| Forskolin | LC Laboratories | FF-9929; CAS 66575-29-9 |
| Recombinant human VEGF165 | Peprotech | 100-20 |
| Critical Commercial Assays | | |
| CellTiter-Glo | Promega | G75070 |
| Kidney Injury Panel 3 Human Kit | Meso Scale Diagnostics | K15189D-1 |
| Deposited Data | | |
| scRNA-seq samples | This paper | GEO: GSE109718 |
| Human Developing Kidney scRNA-seq | Menon et al., 2018 | GEO: GSE109205 |
| CHIR99021 titration in 384-well plates of human pluripotent stem cells-analysis of nephron segment differentiation | This paper | Mendeley Data; https://doi.org/10.17632/988tyf4th8.1 |
| Experimental Models: Cell Lines | | |
| WA09 (H9) human ESCs | WiCell | WAe009-A |
| WTC11 human iPSCs | Laboratory of Bruce Conklin, MD | GM25256; RRID:CVCL_Y803 |
| CRISPR-mutant PKD hPSC and isogenic controls | Freedman et al., 2015 | PKD1$^{-/-}$ A3, F1, C6 |

TABLE 4-continued

| REAGENT or RESOURCE | SOURCE | IDENTIFIER |
|---|---|---|
| CRISPR-mutant PKD hPSC and isogenic controls | Cruz et al., 2017 | $PKD2^{-/-}$ G4, 12 |
| CRISPR-mutant PKD hPSC and isogenic controls | Cruz et al., 2017 | control 07, B4, B5, H1, H7 |
| Experimental Models: Organisms/Strains | | |
| NOD-scid mice (NOD.CB17-Prkdc$^{scid}$/J) | Jackson Laboratory | RRID:IMSR_JAX:001303 |
| Software and Algorithms | | |
| GE INCELL Investigator/Developer | GE | http://www.geifesciences.com/ |
| GraphPad Prism | GraphPad | https://graphpad.com |
| NIS Elements | Nikon | https://nikoninstruments.com |
| ImageJ | NIH | http://imagej.nih.gov |

Experimental Model and Subject Details

Human studies were performed with informed consent under the auspices of the University of Washington IRB. Studies with human pluripotent stem cells were performed with approval by the University of Washington ESCRO. WA09 (H9) female embryonic stem cells (WiCell) or WVTC11 iPSCs derived from a Japanese male donor (gift of Dr. Bruce Conklin, Gladstone Institute) were maintained in 6-well tissue-culture treated dishes (Falcon) at 37 degrees using feeder-free on 3% Reduced Growth Factor GelTrex (Life Technologies) in 2 mL mTeSR1 (Stem Cell Technologies). Experiments in mice were performed in compliance with the strict ethical requirements and regulations of the UW IACUC under a pre-approved animal protocol. A colony of NOD.CB17-Prkdcscid/J mice (NOD-scid, Jackson Laboratory) was maintained under specific pathogen free conditions. Littermate animals of equally mixed genders and 6 weeks of age were used for all experiments.

Method Details

Kidney differentiation in microwell plates. hPSCs were dissociated with Accutase (Stem Cell Technologies) and plated onto microwell plates pre-coated with GelTrex in mTeSR1 supplemented with 10 mMRho-kinase inhibitor Y27632 (StemGent). The media was replaced with mTeSR1+1.5% GelTrex at 16 hours, 12 mMCHIR99021 in Advanced RPMI+Glutamax (Life Technologies) at 60 hours, and RB (Advanced RPMI+Glutamax+B27 Supplement, from Life Technologies) at 96 hours. Volumes used are as follows: 500 µL for 24-well plates, 100 µL for 96-well plates, and 50 µL for 384-well plates. RB was changed two days later and every three days thereafter. For experiments involving modulation of endothelial cell media was supplemented with VEGF165 (Peprotech, 12.5 to 200 ng/ml). Alternatively (Protocol B, FIG. 31A), the protocol described by Takasato et al. was adapted for adherent culture: undifferentiated hPSCs were plated overnight and treated the following morning with 8 mM CHIR99021 in APEL media (StemCell Technologies) for 48-72 hr, 30 ng/ml FGF9 (Peprotech)+1 mg/ml heparin (StemCellTechnologies) in APEL for 96 hr, and cultured thereafter in APEL, replaced every three days. Alternatively, to generate endothelial cells without kidney organoids, 100,000 hPSCs/cm2 were plated in mTeSR1+10 mM Y27632+1 mM CHIR99021, replaced with RPMI+B27 minus insulin+1.5% Geltrex+50 ng/mL Activin A (R&D) at 24 h, RPMI+B27 minus insulin+40 ng/mL BMP4 (Peprotech)+1 mL CHIR99021 at 61 h, and StemPro 34 (Thermo Fisher Scientific)+2 mM Glutamax+50 mg/mL ascorbic acid (Sigma)+10 ng/mL BMP4+5 ng/mL bFGF (Peprotech)+300 ng/mL VEGF165 at 85 h for a 72-hour incubation. Robotic instrumentation consisted of a BioTek EL406 plate washer with microplate stacker from Beckman-Coulter Matrix Technologies, WellMate Dispenser and Stacker and a CyBio CyBi-Well Vario Workstation which allows dispensing of small amounts of reagents, cells, and compounds. Manual instrumentation consisted of Integra Voyager and Viaflo II electronic multichannel pipets.

Teratoma formation. Dissociated hPSCs (400,000/well) were plated in three wells of a 6-well plate and grown to confluence in mTeSR1 for six days. Cells were dissociated, pelleted, resuspended in 500 ml of an ice-cold 1:1 mixture of DMEM/F12 (Fisher) and Matrigel (Corning). The cells were immediately injected beneath the neck scruff of immunodeficient, NOD-scid mice using a 22-gauge syringe needle. Growths were harvested 15 weeks after injection, photographed, fixed in methacarn (60% methanol, 30% chloroform, 10% acetic acid, all from Sigma), embedded in paraffin, sectioned, and stained with hematoxylin and eosin for histological analysis.

Immunohistochemistry. For confocal microscopy, kidney organoids were differentiated on 96-well No, 1.5 coverslip glass-bottom plates (Mat-Tek). To fix, an equal volume of 8% paraformaldehyde (Electron Microscopy Sciences) was added to the culture media (4% final concentration) for 15 minutes at room temperature. After fixing, samples were washed in PBS, blocked in 5% donkey serum (Millipore)/ 0.3% Triton X-100/PBS, incubated overnight in 3% bovine serum albumin/PBS with primary antibodies, washed, incubated overnight with Alexa Fluor secondary antibodies and DAPI (Invitrogen), and washed in PBS. Primary antibodies included ZO-1 (339100; Invitrogen), PAX8 (10336-1-AP, Proteintech), NPHS1 (AF4269, R&D), OAT1 (PA6-26244, Thermo Fisher), CLDN-1 (ab15098, Abcam), SYNPO (sc-21537; Santa Cruz), E-CAD (ab11512, Abcam), WT1 (sc-192; Santa Cruz), CFTR (570 antibody; University of North Carolina), Myosin IIB (3404S, Cell Signaling), CUBN (gift of Dr. Dennis Brown, Massachusetts General Hospital), AQP2 (HPA046834, Sigma), CD144NE-cadherin (2500T, Cell Signaling), CD146/MCAM (ab75769, Abcam), and CD31/PECAM (555444; BD). LTL (FL-1321, Vector Laboratories) and DBA (B-1035, Vector Laboratories) were similarly applied. Fluorescence images were captured using an inverted Nikon epifluorescence Eclipse Ti or A1R confocal microscope. Automated imaging was performed using a GE INCELL 2000 Analyzer.

Automated organoid optimization and analysis. Organoids were produced in a fully-automated manner and developed to an age of 25 days, then fixed and stained with NPHS1, LTL, and ECAD to mark podocytes, proximal tubules, and distal tubules respectively. Each well was imaged at a standardized exposure using an In Cell Analyzer 2000 (GE Healthcare). Representative images were collected using the GE INCELL investigator suite. An algorithm was then generated using the INCELL developer suite to accurately identify each population of cells while simultaneously excluding background fluorescence. This algorithm was used to count and measure the cell populations in each well, as well as across dosages of CHIR99021. These results were displayed using the Spotfire software (TIBCO) with the definition of an organoid as being a discrete group of cells that contains overlapping staining for podocytes, proximal tubule and distal tubule. To assess nephrotoxicity, organoids were purified manually and subjected to a dose titration of cisplatin (Sigma) for 24 hours in 96-well plates. Organoids were imaged and then fixed for immunofluorescence, or alternatively lysed and a KIM-1 ELISA (MesoScale Discovery) was performed. Organoid viability was assessed with CellTiter-Glo (Promega) and quantified using a PerkinElmer Envision plate reader.

Cyst generation. PKD1$^{-/-}$ and PKD2$^{-/-}$ hPSCs or isogenic controls were differentiated in microwell plates in adherent cultures. Forskolin (Sigma) was added to microwell plates during automated liquid handling on the 21st day after differentiation. Large swellings rapidly developed and grew to full size over 72 hours. Cysts were identified by comparing images with captured with high-content imaging prior to forskolin treatment, and after 72 hours. Screening of PKD cystogenesis was performed in duplicate in 96-well plates to provide sufficient space and numbers of organoids per well. Factors were plated at four different concentrations for seven days, and the organoids were scanned visually on a phase-contrast microscope for increased or decreased cyst formation. Factors included blebbistatin (Cayman Chemicals, used at 0.1 mM, 0.5 mM, 2.5 mM, 12.5 mM), gelatin (StemCell Technologies, used at 0.1 mM, 0. mM, 2.5 mM, 12.5 mM), collagenase type IV (StemCell Technologies, used at 0.1 mM, 0. mM, 2.5 mM, 12.5 mM), GM 6001 (Cayman Chemicals, used at 0.1 mM, 0.5 mM, 2.5 mM, 12.5 mM), synthetic peptide derived from Vitronectin (kindly provided by Cole DeForest at UW Chemical Engineering, used at 10 mM, 50 mM, 250 mM, 1.25 mM), synthetic peptide derived from bone sialoprotein (kindly provided by Cole DeForest at UWChemical Engineering, used at 10 mM, 50 mM, 250 mM, 1.25 mM), synthetic RGD peptide (kindly provided by Cole DeForest at UW Chemical Engineering, used at 10 mM, 50 mM, 250 mM, 1.25 mM), rMMP8, human (kindly provided by Cole DeForest at UW Chemical Engineering, used at 30 mg/ml, 6 mg/ml, 1.2 mg/ml, 0.24 mg/ml). To test cystogenesis in suspension, adherent organoids were microdissected with a 23-gauge syringe needle from 24-well plates on an inverted phase-contrast microscope, and transferred into a low-adhesion 6-well plate (Corning) containing 2 mL RB or 2 mL RB with 12.5 mM blebbistatin. Organoids were imaged daily on a Nikon Ti Inverted Widefield microscope for a period of 7 days. Cyst diameters were measured using NIS Elements imaging software (Nikon). Contiguous microscopic fields were collected using an automated stage and stitched together using NIS Elements software to generate large images of wells or plates.

scRNA-seq and cell clustering analysis. Organoids were collected by scraping cells from whole wells into ice-cold DPBS, dissociated with cold activate protease, and Dropseq was performed as on an Illumina HiSeq 2500 in rapid run mode. Sequences were aligned to NCBI human genome assembly GRCh38, with 70%-80% overall alignment. Organoid differentiation was performed from WA09 hPSCs (WiCell, Madison WI) in 24-well plates to provide sufficient cells for analysis. Unsupervised cell clustering, principal components analysis and data presentation were performed with the following modifications/specifics: datasets from Drop-seq analyses of individual wells were combined and batch corrected. Unsupervised subclustering was performed following supervised selection of stromal cells from the initial clustering analysis. Cells were excluded if genes expressed were <500 or R 4000 (to exclude cell doublets) or if mitochondrial gene expression was >25% all genes (to exclude non-healthy cells). Publicly available data were used for cell type identification and gene expression comparison: GUDMAP (https://www.gudmap.org/), GenePaint (https://www.genepaint.org), ESBK's Kidney Systems Biology Project's transcriptomic data (https://hpcwebapps.cit.nih.gov/ESBL/Database/), Gene Expression Omnibus accession number GSE94333, and KeyGenes (http://www.keygenes.nl/). A correlation matrix comparing average gene expression in organoid and human kidney clusters was generated using Stats R-package, based on GSE94333. Unless otherwise noted, "top differentially expressed genes" were chosen from top 20 for each organoid cell cluster, based on their appearance in scRNA-seqdata from human developing kidney (corresponding clusters) and mouse P1 kidney (clusters of same lineage). Genes were listed in order of statistical significance with highest p-value for last gene generated based on the number of cells in the cluster. scRNAseq samples were deposited in the Gene Expression Omnibus (NCBI) under accession number GSE109718.

Bulk RNA sequencing. Cells from organoid cultures grown in parallel for scRNA-seq (+ and −VEGF treatment) were lysed with TRIzol Reagent (Invitrogen). Total RNA was isolated using Direct-zol mini prep RNA columns (Zymo Research) with on-column DNase treatment. RNA quality was assessed by Bioanalyzer 2100 platform (Agilent) using a Eukaryote Total RNA Nano array (Agilent), with RIN values of 9.7 and 9.5 for VEGF+ and − samples, respectively. cDNA was generated from 10 ng RNA using the SMART-Seq Low Input RNA kit for sequencing (Takara) applying 8 PCR cycles. Amplified cDNA was purified by Agencourt AMPure XP DNA purification kit (Beckman Coulter) and analyzed on the Bioanalyzer platform using a High Sensitivity DNA array (Agilent). Next-generation sequencing libraries were generated and barcoded using the Nextera XT DNA Library Preparation Kit (Illumina) starting with 100 pg cDNA. cDNA libraries were pooled and sequenced on one lane of a HiSeq500 platform with Illumina TruSeq v4 chemistry (paired-end 2×75 cycles) at the University of Michigan DNA Sequencing Core. Resulting sequences were aligned to human genome (Ensembl GRCh38) using STAR (version 2.5.2) with default parameters. Relative read counts at gene level were estimated using HTSeq (version 2.20.2 and normalized using quantile normalization function in edgeR R statistical package. A total number of 52 and 76 million reads were obtained with alignment rates of 91% and 88% from VEGF+ and − samples, respectively.

Quantification and Statistical Analysis

Data summaries shown in the Figures are representative of three or more separate experiments (biological replicates). Statistical significance was calculated with Graphpad Prism software. For comparisons between two groups, a two-tailed Student's t test for samples with unequal variance (heteroscedastic) was utilized. For comparisons between multiple groups, the analysis of variance (ANOVA) method was used. Z' factor was calculated based on standard deviation as described (Zhang et al., 1999) to assess high throughput assay quality. The Z' factor calculation provides a quantitative measure of the separation between the control (no CHIR99021) condition and the optimal differentiation condition for each line. A Z' factor>0.5 indicates an excellent assay (Zhang et al., 1999).

Data and Software Availability

The accession number for the scRNA-seq samples reported in this paper is GEO: GSE109718. CHIR99021 titration data are provided in Mendeley Data (https://doi.org/10.17632/988tyf4fh8.1).

Results

Differentiation of hPSCs into Organoids in HTS Formats

Figure 6A:
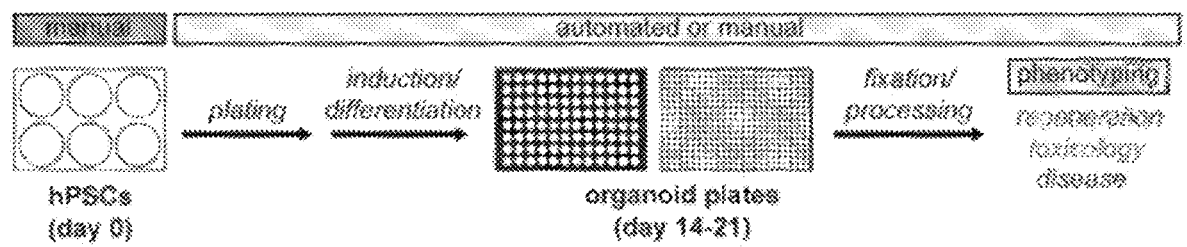
FIGS. 6A-6C show the generation of organoid plates in automated HTS formats.
Figure 6B:
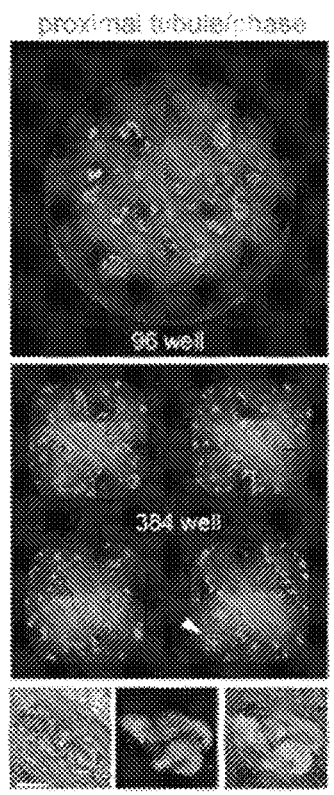
Figure 6C:
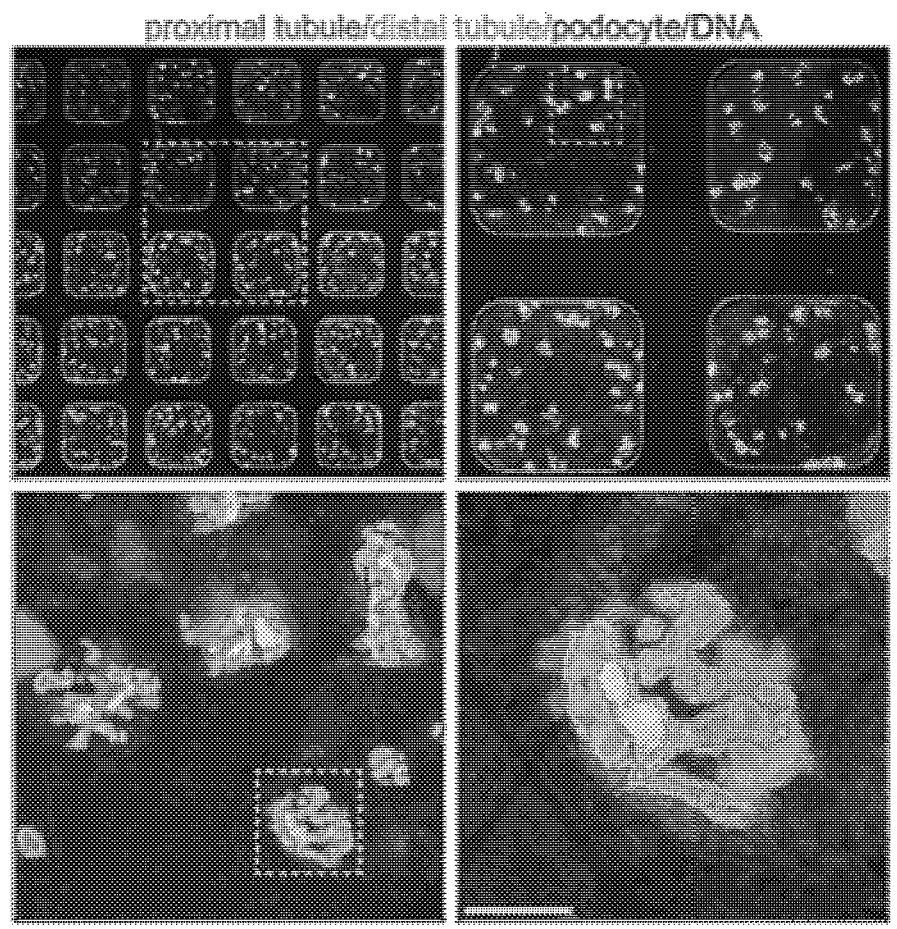

To generate organoids compatible with HTS, hPSCs were plated in 96- and 384-well formats and differentiated into the kidney lineage for 3 weeks (FIG. 6A). Kidney organoids are highly complex and of great biomedical interest for their potential to model disease, toxicity, and regeneration (Freedman et al., 2015; Morizane et al., 2015; Taguchi et al., 2014; Takasato et al., 2015). To establish protocols accessible to a broad range of laboratories, plates were prepared either manually, using multi-channel pipettes, or automatically, using liquid-handling robots to perform all steps of plating, differentiation, fixation, and phenotyping (FIG. 6A). Following differentiation, each well contained numerous kidney organoids, as detected by Lotus tetragonolobus lectin (LTL) binding of the proximal tubular segments (FIG. 6B). In addition to proximal tubular cells, each organoid included distal tubule (ECAD+) and podocyte (NPHS1+) cell populations in distal-to-proximal arrangements (FIG. 6C and Video 1).

Figure 13A:
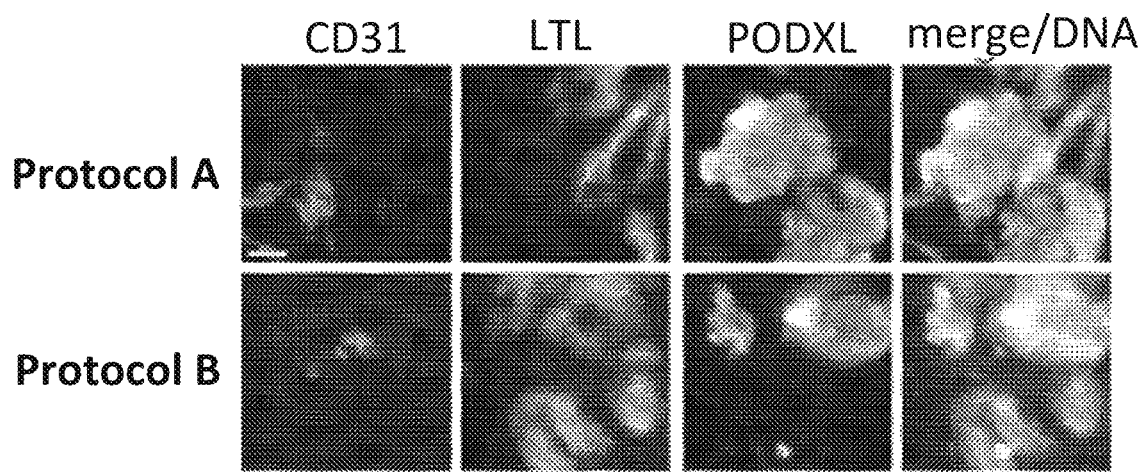
FIGS. 13A-13D show a comparison of differentiation protocols reveals key factors in organoid formation.
Figure 13B:
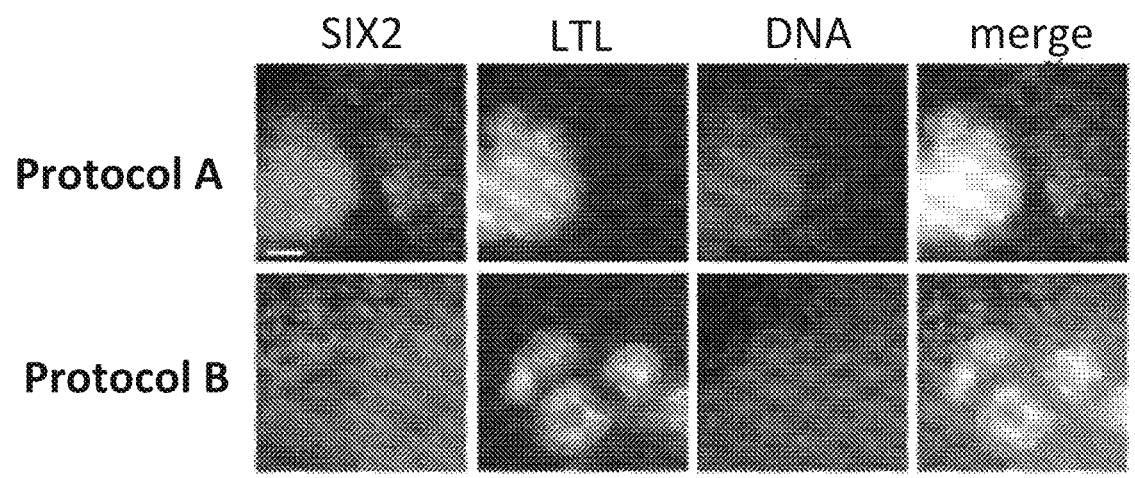

To simplify automation, these experiments adapted for HTS, a differentiation protocol that involves only a single induction step with the kinase inhibitor CHIR99021 (Freedman et al., 2015). In side-by-side experiments, the nephron-like structures within the organoids derived using this protocol closely resembled those observed in organoids derived using protocols from other groups (FIGS. 13A and 13B) (Takasato et al., 2015). To accommodate high throughput applications, differentiation was performed on standard tissue culture plates as previously described in larger wells (Freedman et al., 2015), rather than transwell plates or suspension cultures. This resulted in the formation of numerous kidney organoids per well, each organoid containing 5 nephron-like structures and growing to a natural size of 200 mm in diameter (FIG. 6C), similar to intestinal organoids (Dekkers et al., 2013; Spence et al., 2011).

Figure 13C:
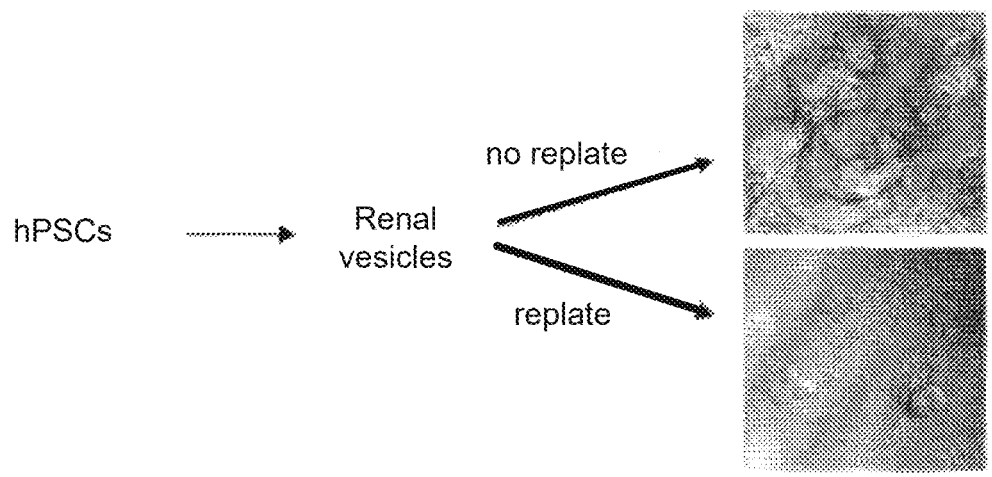
Figure 13D:
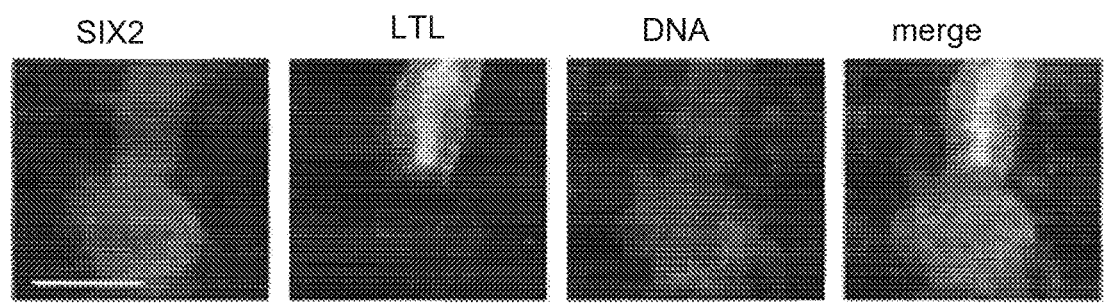

As these cultures were spread out in two dimensions, the kidney organoids formed discrete nests of tubules that could be clearly discerned from surrounding, non-kidney cells with standard microscopes. This contrasts with other differentiation protocols in which the entire culture, including both kidney and non-kidney cells, is dissociated and re-aggregated into a three-dimensional pellet of arbitrary size, also called a kidney organoid (Morizane et al., 2015; Taguchi et al., 2014; Takasato et al., 2015). It was found that such dissociation and replating steps were unnecessary for kidney organoid generation and instead resulted in dramatically fewer and smaller tubular structures (FIGS. 13C and 13D). In addition, genetic models of PKD and nephrotic syndrome were established in adherent organoid cultures, and those organoids were used as the starting point for HTS experiments focusing on disease (Cruz et al., 2017; Freedman et al., 2015; Kim et al., 2017).

Optimization of Organoid Differentiation with Microwell Plates

Figure 14A:
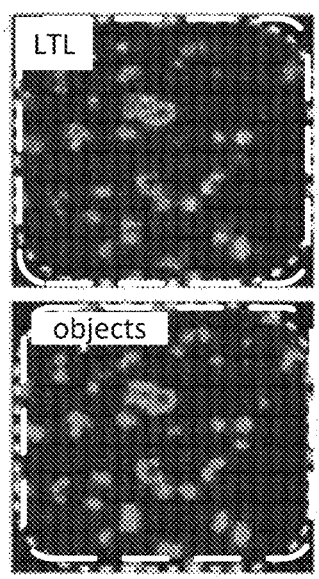
Figure 14B:
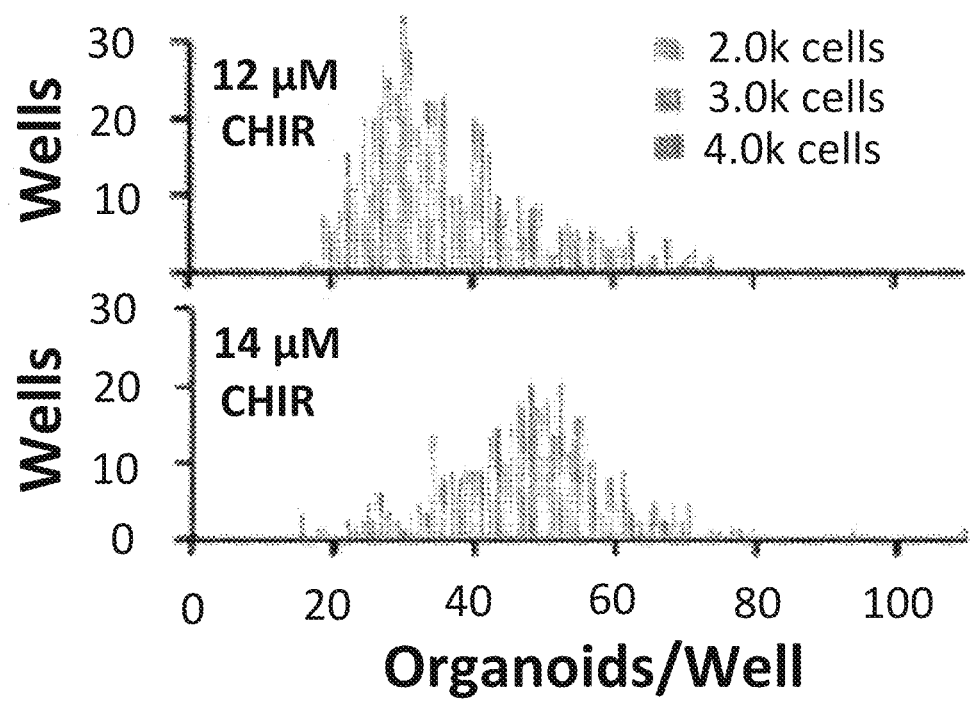

HTS organoid plates were used to quantitatively assess differentiation conditions and optimize their own production. As CHIR99021 has been applied at concentrations ranging from 5 to 12 mM in various kidney organoid differentiation protocols (Freedman et al., 2015; Lam et al., 2014; Mae et al., 2013; Morizane et al., 2015; Taguchi et al., 2014; Takasato et al., 2015), its dose dependence for organoid differentiation remains unclear. For the initial optimization, linear titrations of cell number were plated in 384-well kidney organoid plates and treated with three different concentrations of CHIR99021. On day 21 of differentiation, each well was fixed and stained for LTL and fully imaged using a high-content imager (15 min per plate). A computer was trained to automatically identify and analyze individual organoids based on the presence of proximal tubules (FIG. 14A). Differentiation was robustly achieved at all three CHIR99021 concentrations and cell numbers, with 3,000 cells/well and 14 mM CHIR99021 producing the optimal number of organoids per well (FIG. 14B).

Figure 7A:
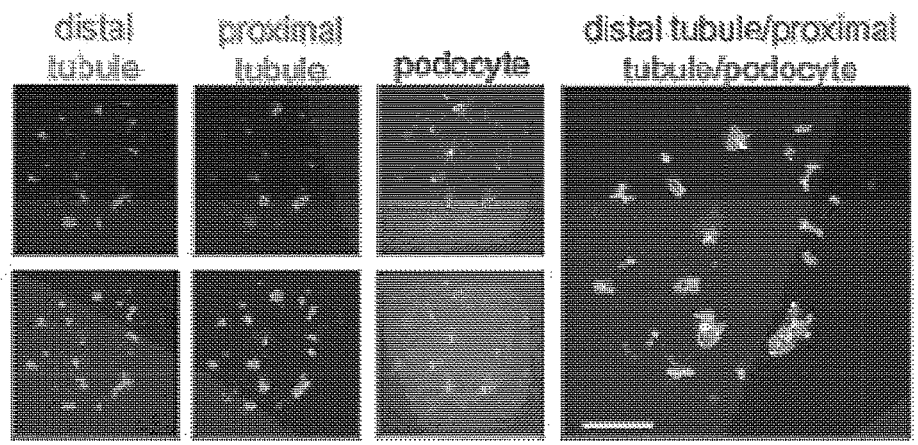
FIGS. 7A-7C shows utilization of organoid HTS plates to optimize differentiation.
Figure 7B:
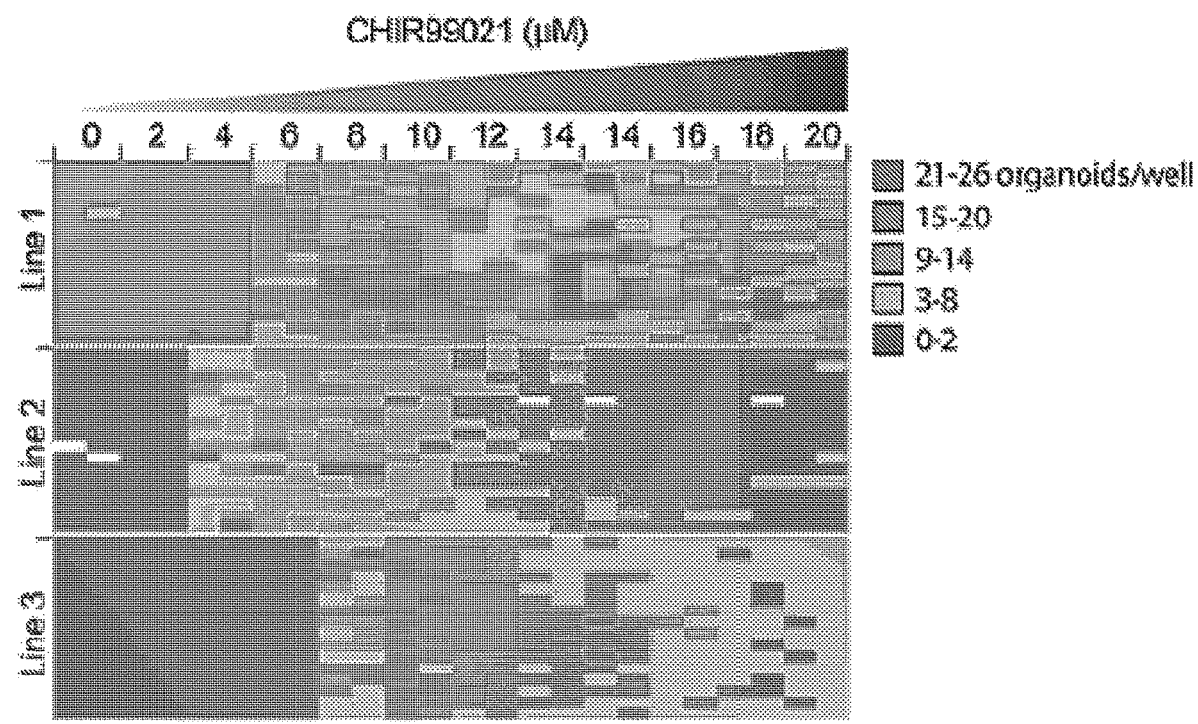
Figure 14C:
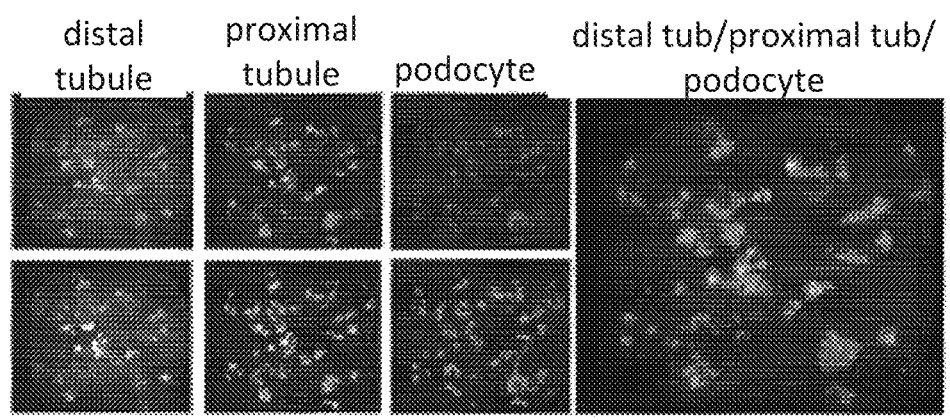

The organoid HTS platform was also used to quantify the effect of CHIR99021 on organoid differentiation and substructure over a broader range of concentrations, ranging from 0 to 20 mM. For these experiments, the software for the IN Cell Analyzer (GE Healthcare) was adapted to recognize organoids as structures containing proximal tubules, distal tubules, and podocytes in close proximity, enabling analysis of these individual subcompartments within each organoid (FIGS. 7A and 14C). Differentiation was quantified in three different subclones of WA09 hPSCs (FIG. 7B). Each differentiated well of a 384-well plate typically contained 10 organoids, representing 50 nephron-like structures (FIGS. 7A, 7B, 14C, and 14D). These experiments revealed an ideal range of CHIR99021 concentrations capable of generating organoids (FIG. 7B).

Figure 14D:
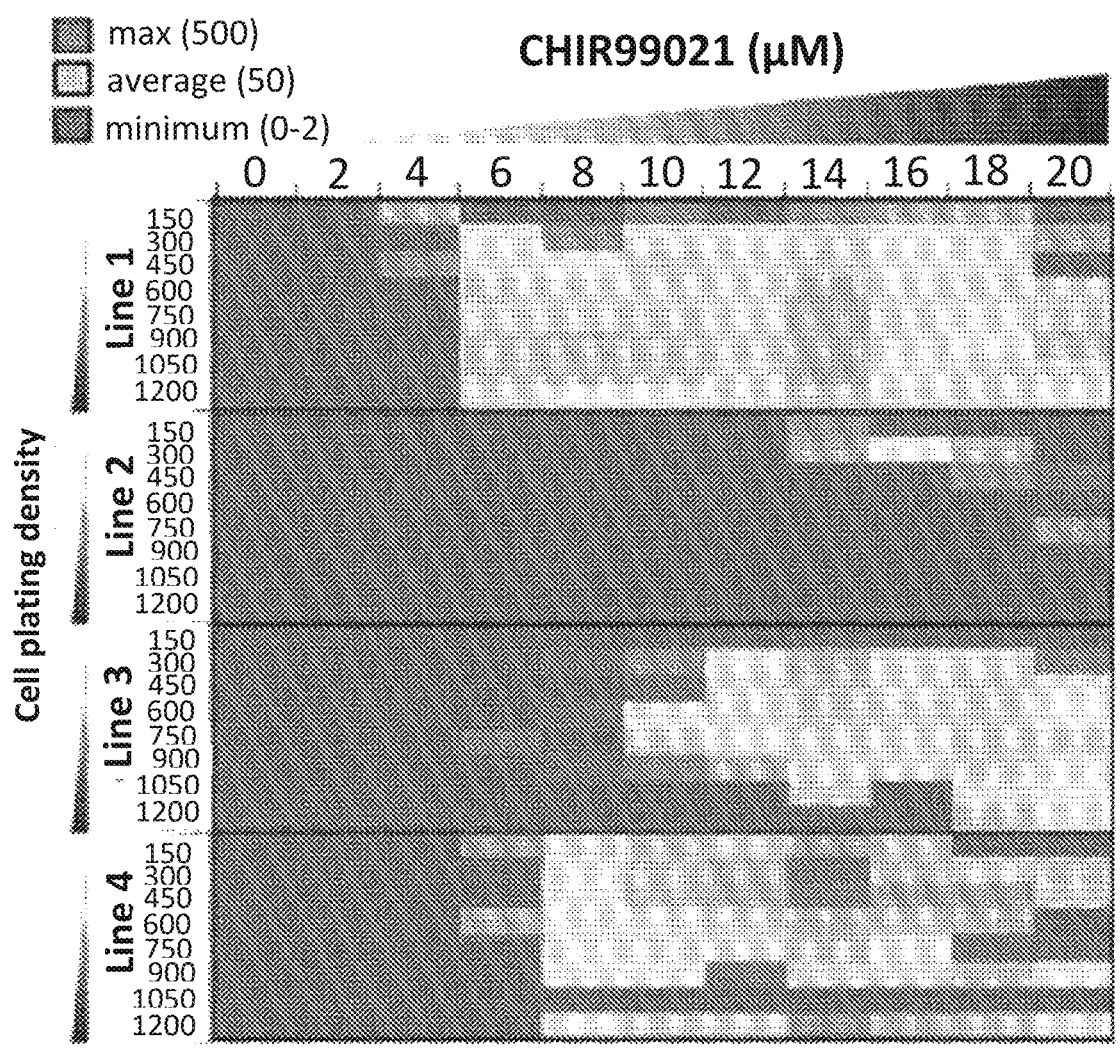
Figure 15A:
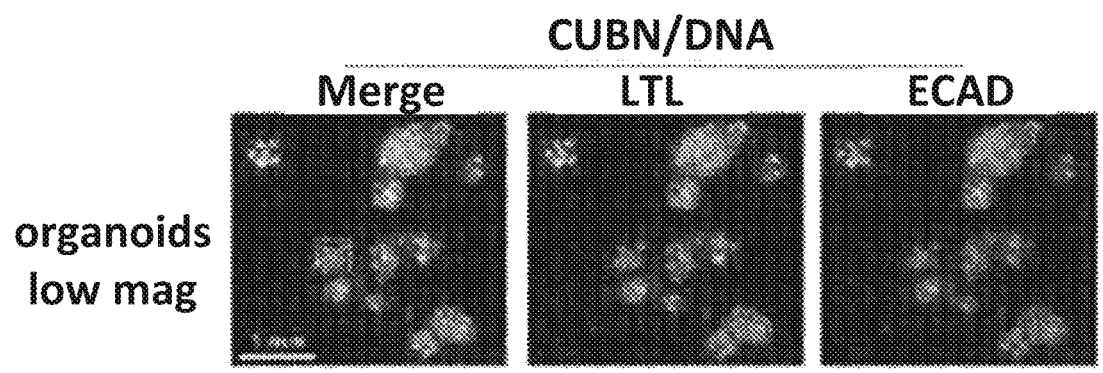
FIGS. 15A-15F show that specific markers distinguish organoid nephron tubular segments.
Figure 15B:
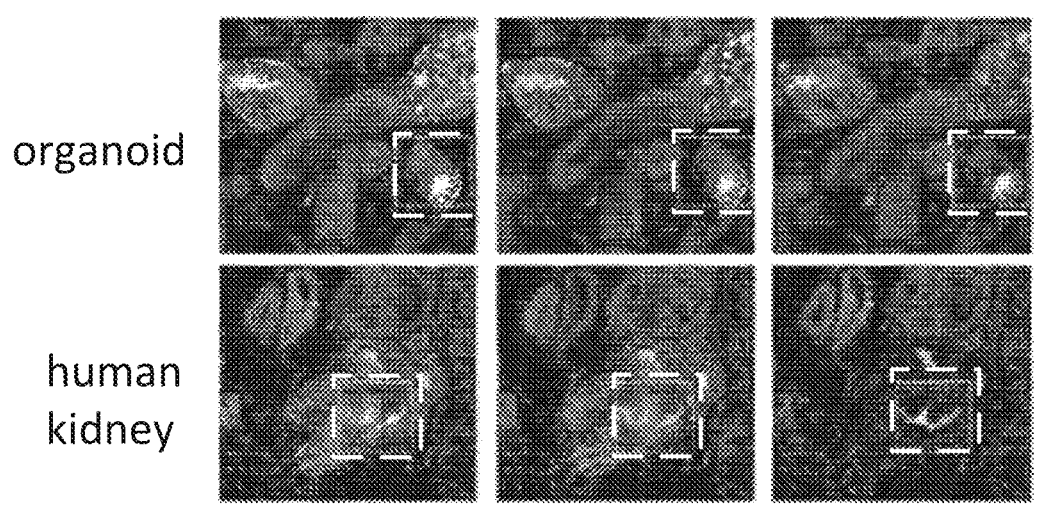
Figure 15C:
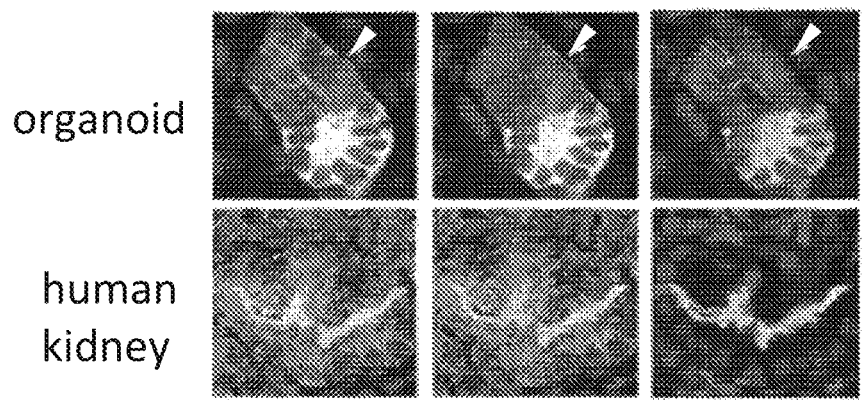
Figure 15A:
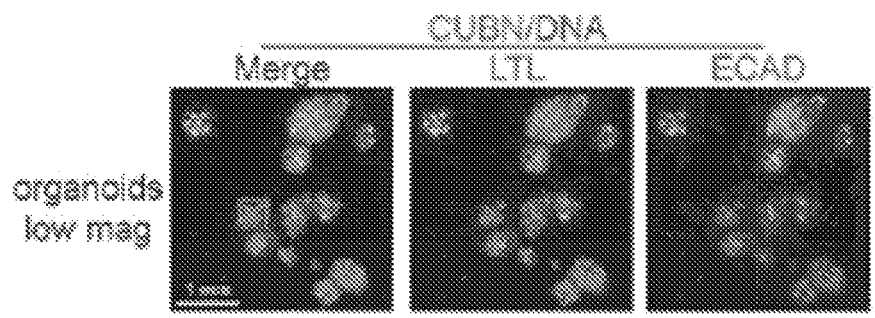
Figure 15B:
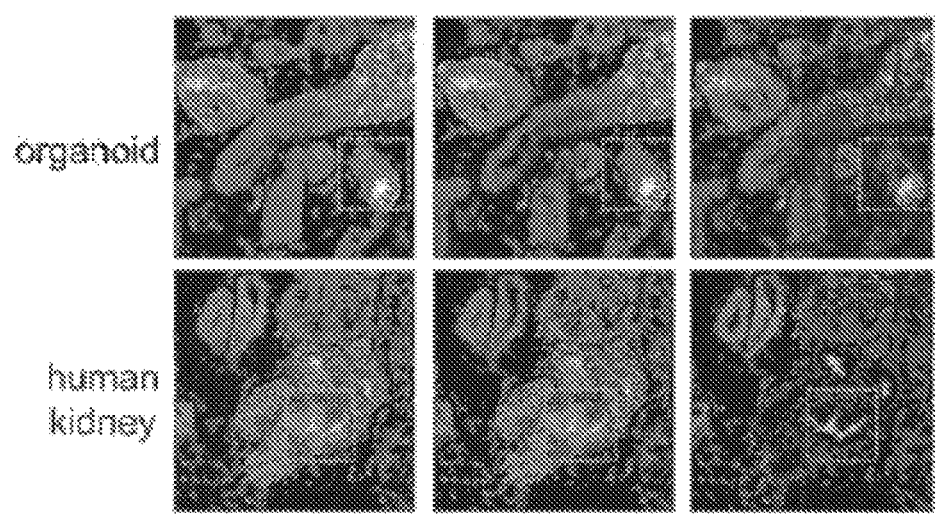
Figure 15C:
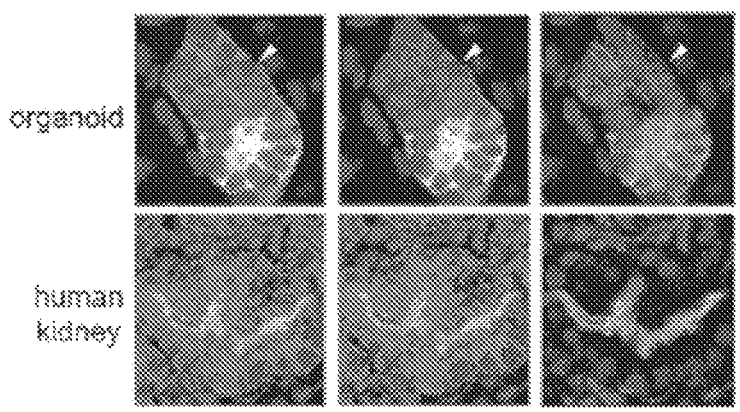
Figure 15D:
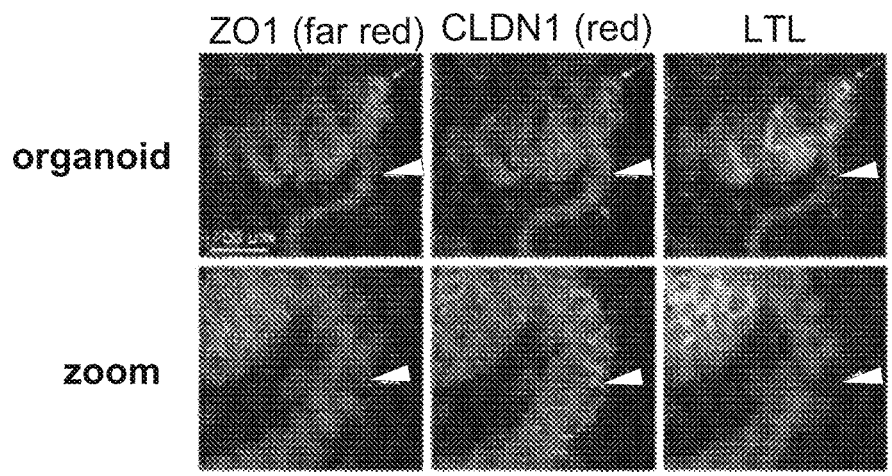
Figure 15E:
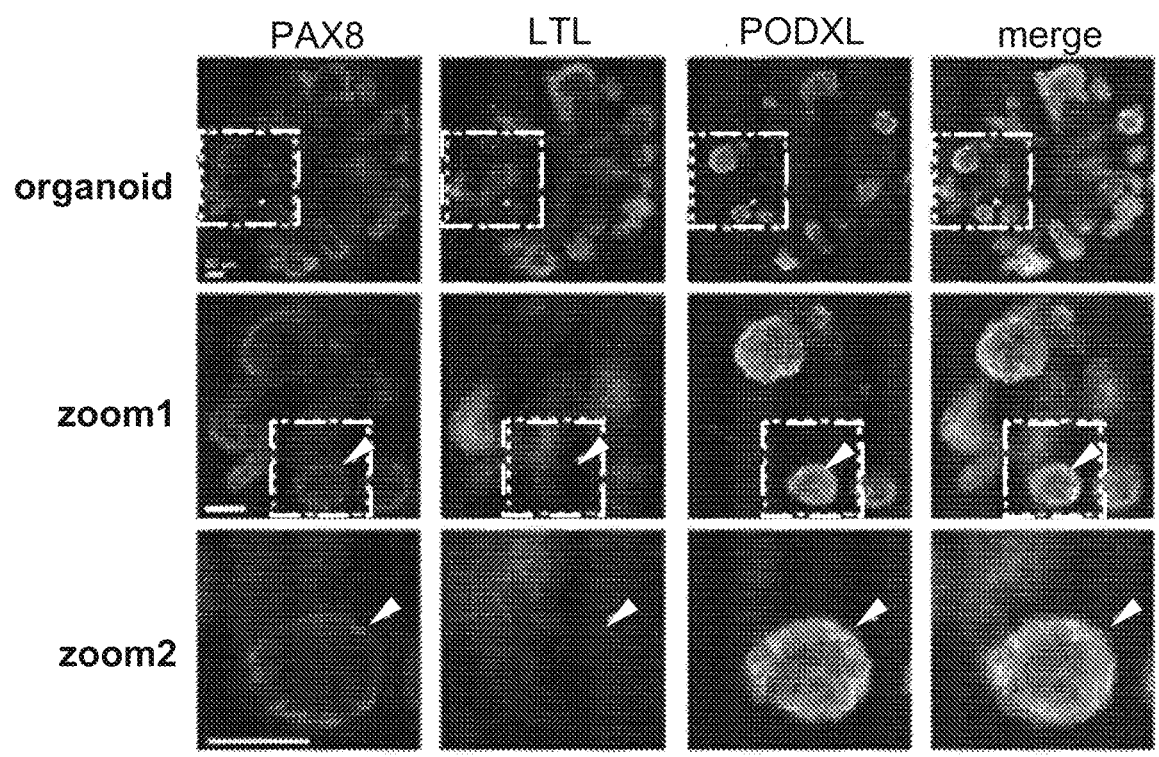
Figure 15F:
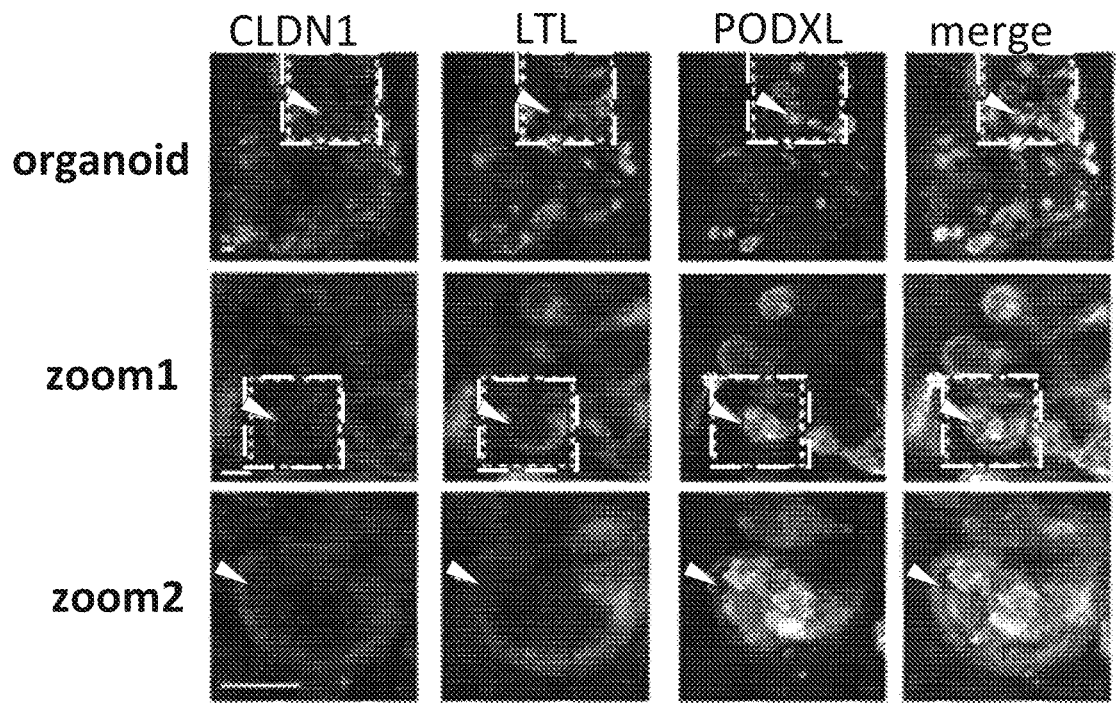
Figure 15G:
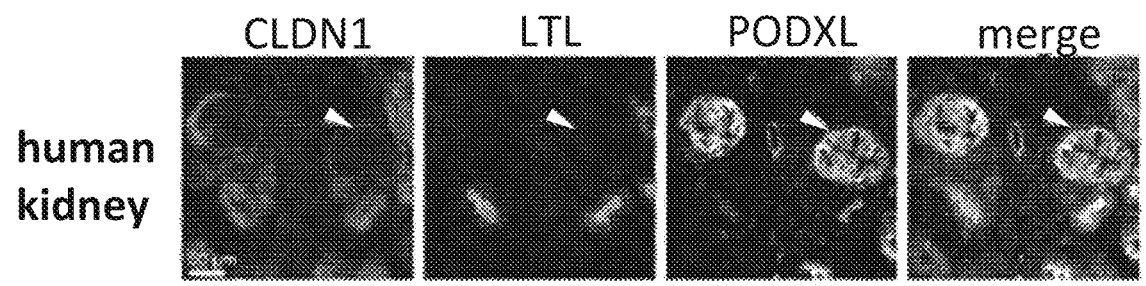

Surprisingly, the optimal CHIR99021 concentration varied significantly for each individual subclone, despite the fact that these were all derived from the same original hPSC line (FIG. 7B). ZO factor calculation indicated that line 1 was excellent for HTS and line 3 was acceptable (FIG. 7B) (Zhang et al., 1999). The overall differentiation tendencies of the three individual subclones were found to be reproducible in multiple experiments, demonstrating that this was an inherent property of the subclones (FIG. 14D). The optimal number of cells for the initial plating varied from 1,000 to 3,000, depending on the experiment, likely owing to stochastic differences between the cells from passage to passage (FIG. 14D). When implanted into immunodeficient animals, each of these subclones formed large teratoma growths containing tissues from the three embryonic germ layers, demonstrating that they remained fully pluripotent (FIG. 14E).

Figure 7C:
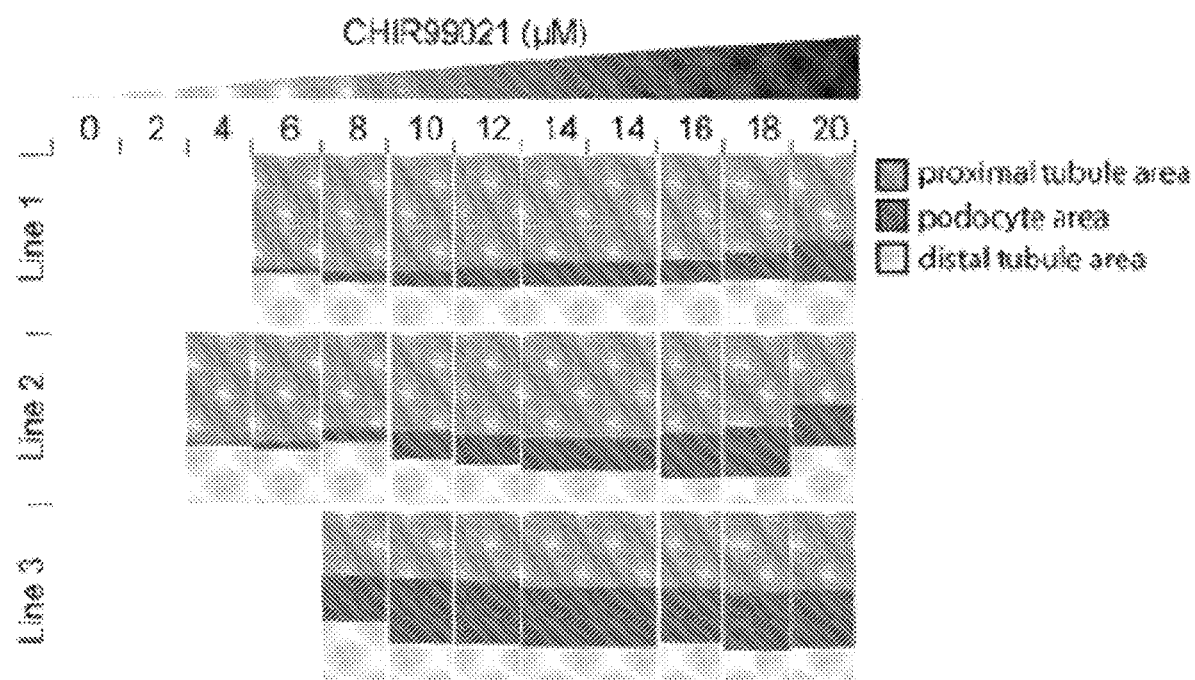

By performing quantitative image analysis with the IN Cell Analyzer, the proportion of each organoid that contained proximal tubules, distal tubules, or podocytes was determined. These experiments revealed a tight correlation between the proportions of these three nephron segments throughout the active range of CHIR99021 concentrations (FIG. 7C). A slight increase in the number of podocytes was observed in middle and high CHIR99021 concentrations, relative to the lowest doses (FIG. 7C). Even at concentrations of CHIR99021 that produced very few organoids, the organoids that did form had similar proportions of the three nephron segments (FIG. 7C). These experiments established a framework for using organoid plates to optimize and investigate differentiation conditions, revealing both dose-dependent and threshold effects.

Marker Analysis Reveals Organoid Segments In Vitro

Characterization of organoids using specific markers is important to determine which cell types are present and how they compare to tissues in vivo. In contrast to many organoid culture systems that require special processing, the organoid microwell plates described herein are adherent cultures that can be grown on glass, processed using standard techniques, and examined by confocal microscopy. A variety of cell types within these cultures have been identified, including podocytes, proximal and distal tubules, endothelial cells, stromal myofibroblasts, and neurons (Cruz et al., 2017; Freedman et al., 2015; Kim et al., 2017). Using this approach, a panel of important markers whose localization patterns in kidney organoids remain poorly characterized were analyzed as compared to human kidney tissues undergoing active nephrogenesis.

Figures 8A, 8B:
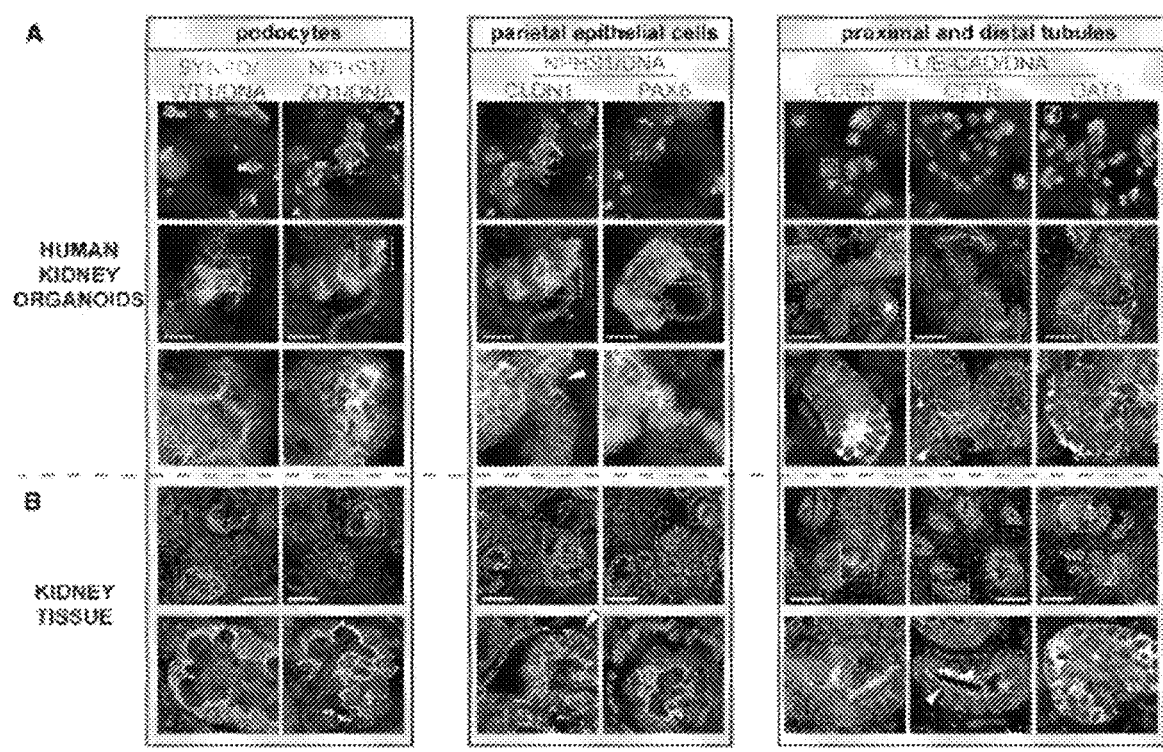
FIGS. 8A-8E establish that microwell pates reveal detailed patterning of organoids similar to tissues in vivo

In both organoids and kidney tissues, proximal tubules exhibited strong LTL binding and weak ECAD expression, whereas distal tubules exhibited weak LTL binding and strong ECAD expression (FIGS. 8A, 8B, and 15A-15C). In contrast to LTL, which was expressed in both proximal and distal tubules, expression of cubilin (CUBN), a receptor important for nutrient and protein reabsorption, was sharply restricted to proximal tubules, localizing strongly to the apical membrane (FIGS. 8A, 8B, 15A, and 15B). The cystic fibrosis transmembrane conductance regulator (CFTR) was detected in apical foci in both proximal and distal tubules, while the organic anion transporter (OAT1) localized to the basolateral membrane, similar to human kidney tissues in vivo (FIGS. 8A and 8B).

Figure 8C:
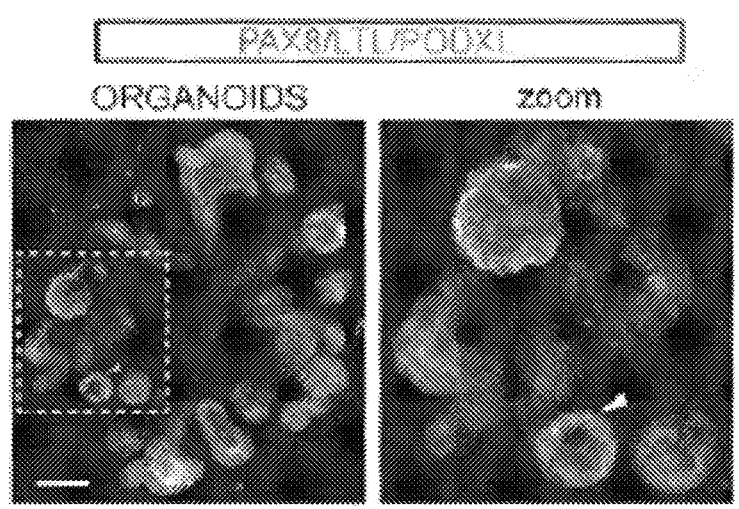
Figure 8D:
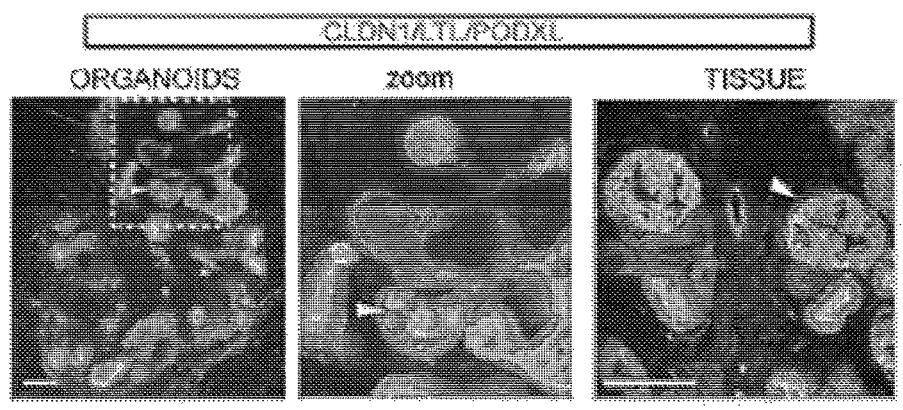

In the glomerular compartment, podocytes formed tightly clustered cell aggregates expressing NPHS1, synaptopodin, and WT1 (FIGS. 8A and 8B). This compartment was further investigated for parietal epithelial cells (PECs), an important cell type for kidney disease and regeneration (Shankland et al., 2017), which have not previously been identified in kidney organoids derived from hPSCs. In the multiwell organoids, a population of cells were detected adjacent to podocytes expressing CLDN1 and PAX8, markers that were absent in podocytes and were expressed by PECs in vivo (FIGS. 8A and 8B). In a subpopulation of organoid structures, these CLDN1+PAX8+ cells surrounded the podocyte clusters in a lining one single-cell layer thick (FIG. 8C). These cells were positioned between the proximal tubular cells (LTL+) and the podocytes (podocalyxin+) but did not bind LTL (FIGS. 8C and 8D). These structures and marker expression patterns were reminiscent of the PEC layer of Bowman's capsule in vivo (FIGS. 8C and 8D).

Figure 8E:
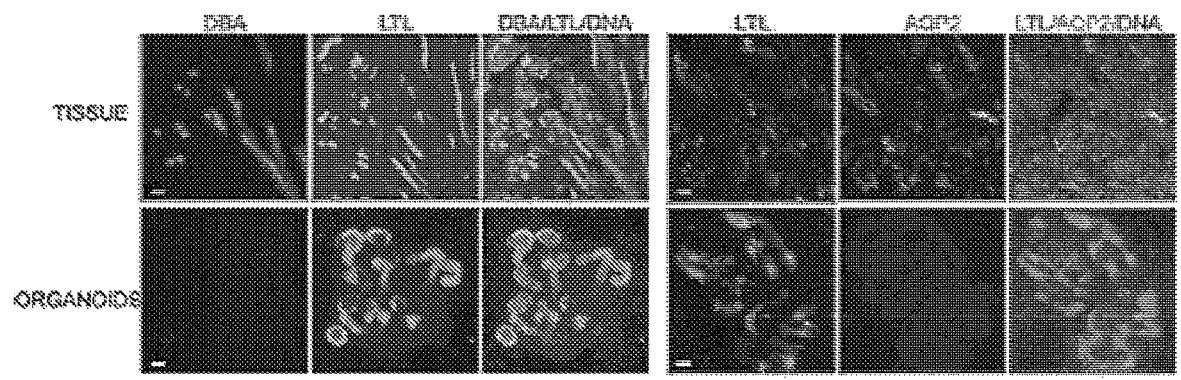

In contrast to these proximal nephron segments, collecting ducts were not detected in organoids with two distinct segment-specific markers, Dolichus bifloris agglutinin (DBA), and aquaporin-2 (AQP2) (FIG. 8E). These markers successfully distinguished ducts from tubules in developing kidney tissues (FIG. 8E). These careful analyses of organoids versus tissues revealed more nuanced expression of nephron compartment markers than previously appreciated.

Enhancement of Endothelial Differentiation in HTS Organoids

Figure 9A:
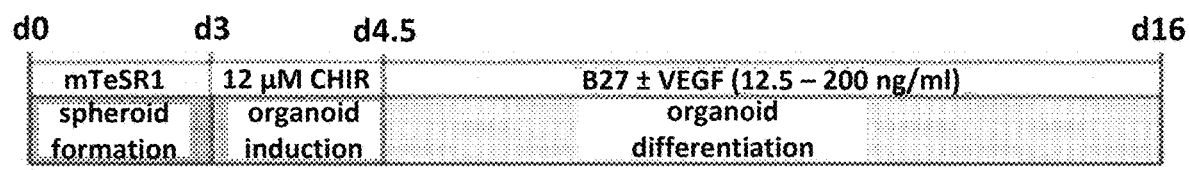
FIGS. 9A-9F shows optimization of vascularization in organoids.
Figure 9B:
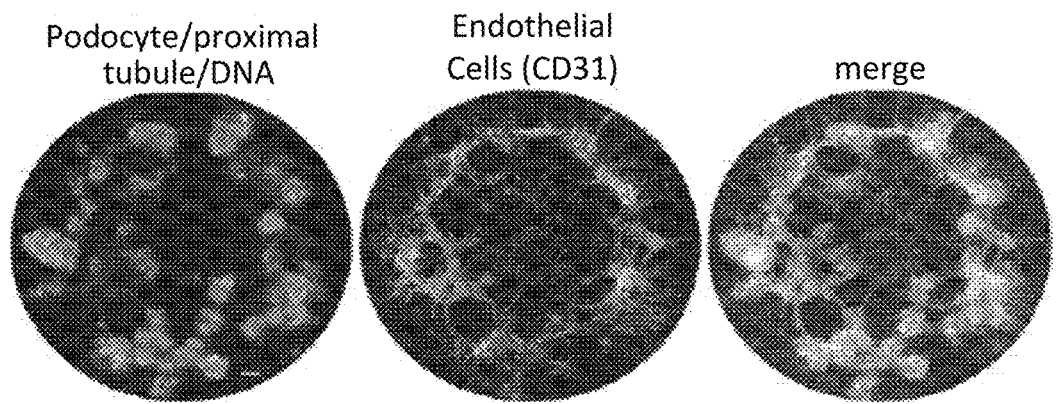
Figure 9C:
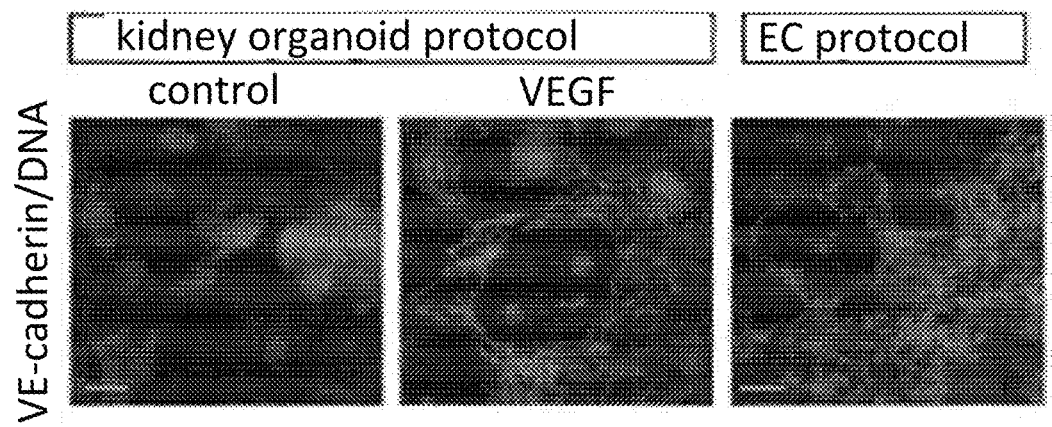
Figure 9D:
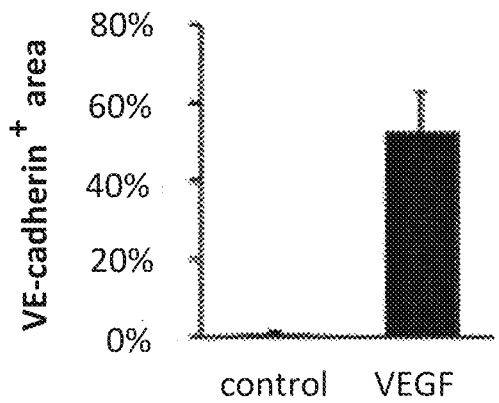
Figure 9E:
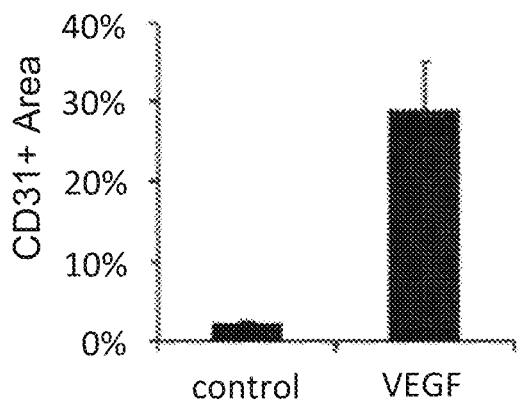
Figure 9F:
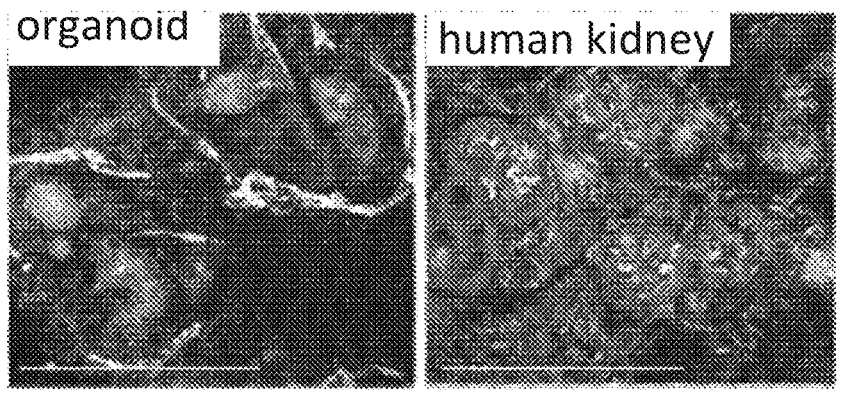

The vasculature is a critical component of all somatic organs, with essential functions in physiology and disease. Organoid cultures derived from hPSCs lack mature vascular networks but can contain subpopulations of endothelial cells (ECs), which form linear chains of cells in contact with the organoids (Freedman et al., 2015; Takasato et al., 2015). As endothelial cells are typically a minor component in these cultures, kidney organoid microwells were used to optimize the differentiation protocol to increase ECs (FIG. 9A). It was discovered that addition of vascular endothelial growth factor (VEGF) during the differentiation process resulted in an approximately 10-fold increase in ECs expressing CD31 and vascular endothelial (VE)-cadherin, without compromising the formation of the organoids (FIGS. 9B-9E). These ECs resembled those obtained in an endothelial cell-directed differentiation protocol (FIG. 9E) (Palpant et al., 2017). Despite their increased numbers, ECs did not invade the podocytes to establish a bona fide glomerular basement membrane (FIG. 9F). Thus, increase in ECs alone was insufficient to induce glomerulus formation in vitro, suggesting a requirement for additional cues such as specific extracellular matrix isoforms (Abrahamson et al., 2013), or a more specific endothelial cell population.

Single-Cell RNA Sequencing Reveals Spectrum of Organoid Maturation States

Figure 10C:
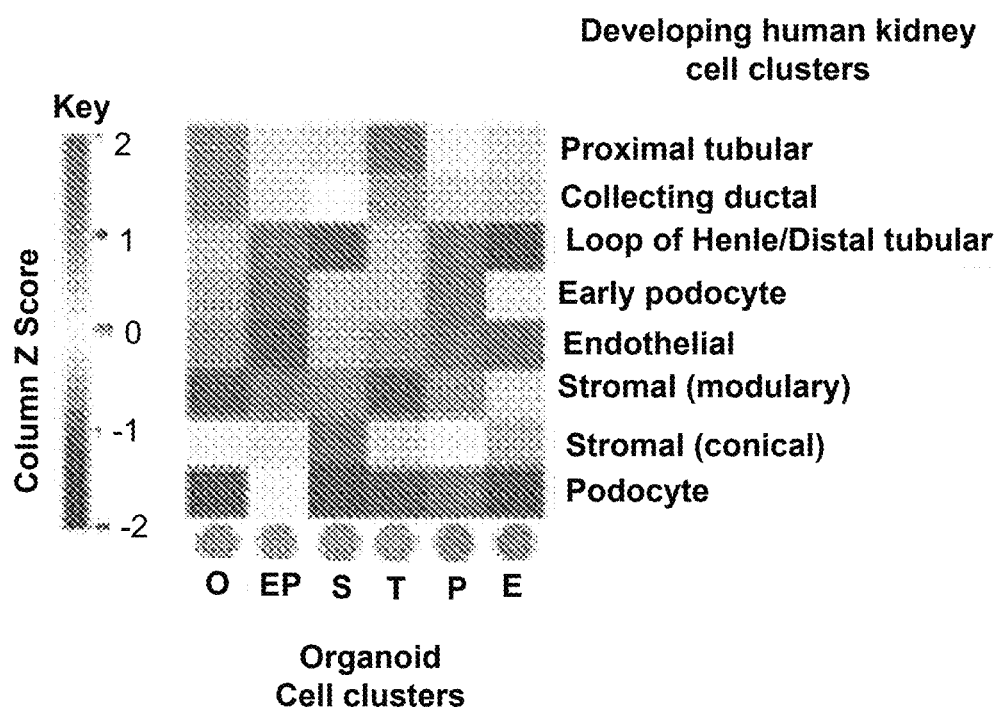
Figure 16A:
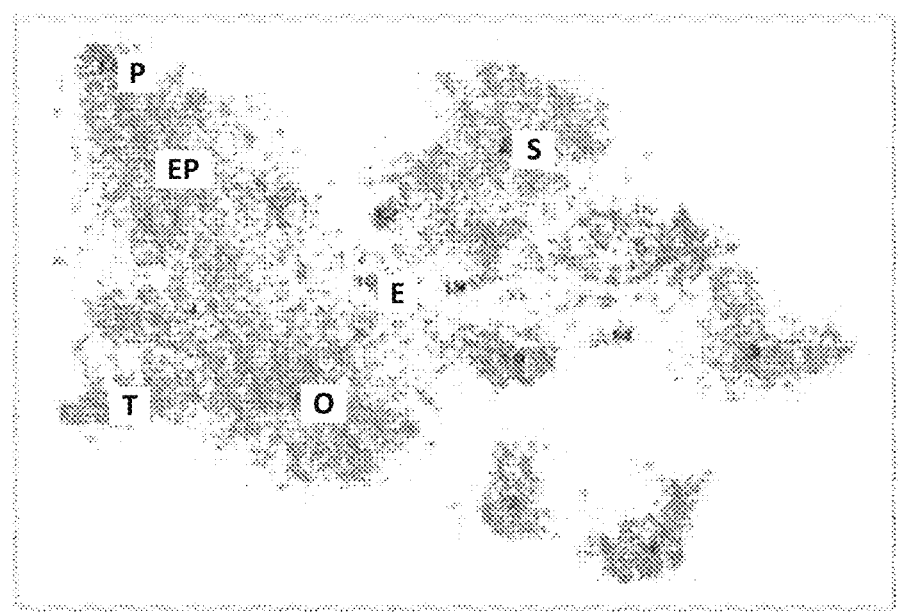
Figure 16B:
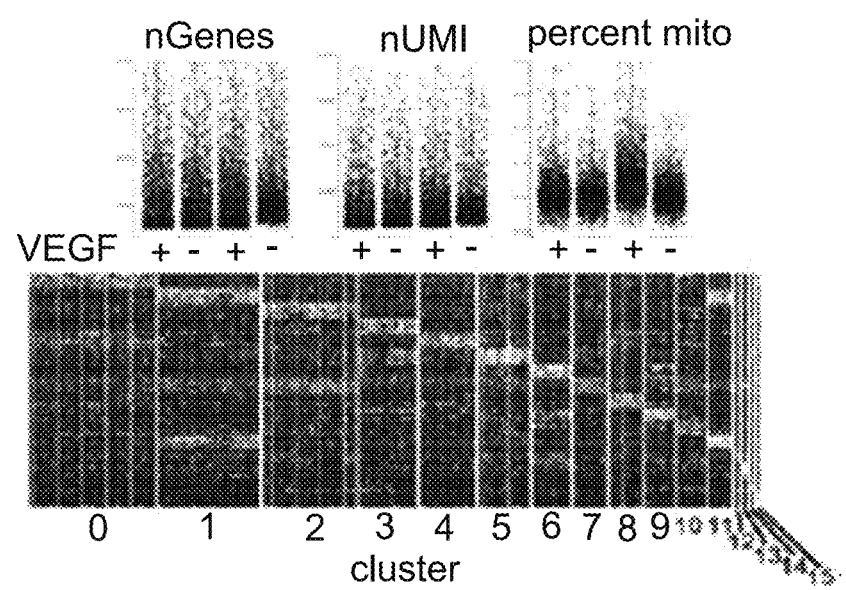
Figure 16E:
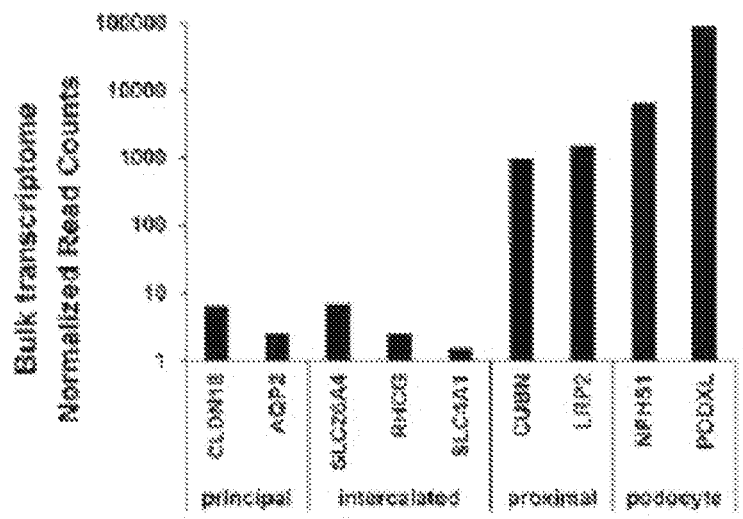

Single-cell RNA sequencing (scRNA-seq) was performed and the results were analyzed to reveal gene expression signatures of individual cell types within the inherently heterogeneous organoids. Unsupervised clustering analysis of transcriptomes from 10,535 cells revealed a total of sixteen cell clusters, as visualized in t-distributed stochastic neighbor embedding (t-SNE) plots (FIGS. 10A and 16A-16D). Six of these clusters were identified as kidney or endothelial cell lineages, based on comparison to gene lists of scRNA-seq clusters generated from developing human kidneys or newborn mouse kidneys (FIGS. 10A and 10B) (Adam et al., 2017; Menon et al., 2018). These included (1) proximal tubules, (2) podocytes, (3) "early tubules" expressing signatures of both proximal and distal tubules and collecting ducts, (4) "early podocytes" expressing signatures of both podocytes and PECs, (5) endothelial cells, and (6) stromal cells (FIGS. 10A and 10B). Collectively, these six clusters comprised 60% of all cells analyzed by Drop-seq. The remaining ten clusters included neural, muscle, reproductive/endocrine, epithelial, undifferentiated, and proliferating cells, whereas a distinct population of collecting ducts was not identified (FIGS. 16A-16D). Similarly, specific markers of collecting duct principal and intercalated cells were not detected in bulk RNA-seq analysis (FIG. 16E).

Figure 10D:
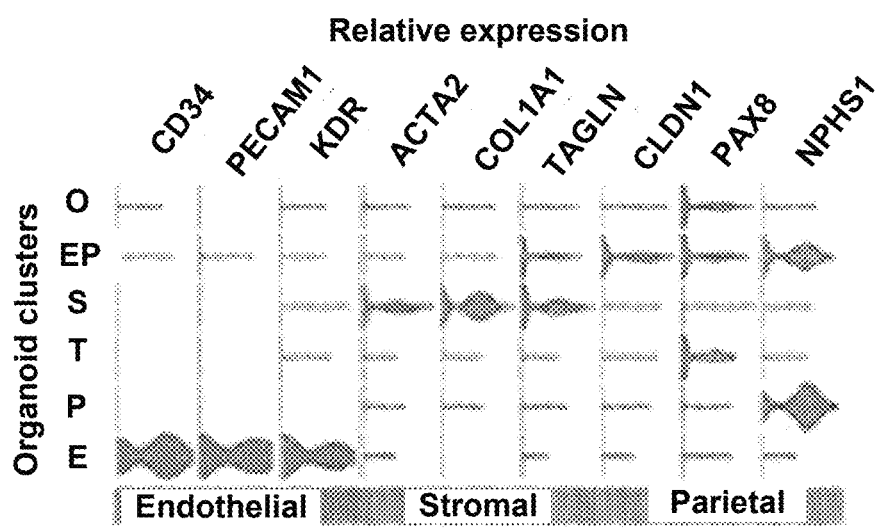

Average gene expression within each of the six kidney-relevant organoid clusters correlated well with its corresponding kidney compartment in vivo (FIG. 10C), based on comparison to scRNA-seq analysis of developing human kidneys (Menon et al., 2018). Notably, the endothelial cell cluster had a gene expression signature characteristic of ECs including PECAM1 (CD31), CD34, and KDR, and the overall gene expression of the cluster was clearly different from the stromal cell clusters (FIGS. 10A-10D). Relative to other cell clusters, an enhanced quantity of cells in the stromal cell cluster showed gene expression patterns characteristic of kidney interstitial myofibroblasts, pericytes, and mesangial cells (ACTA2, COL1A1, and TAGLN) (Brunskill et al., 2011; Daniel et al., 2012; Lin et al., 2008) (FIG. 10D). While there was no distinct cell cluster for parietal cells, co-expression of CLDN1, PAX8, and NPHS1 within the early podocyte cell cluster suggested that it may contain developing PECs (FIG. 10D).

Figure 10E:
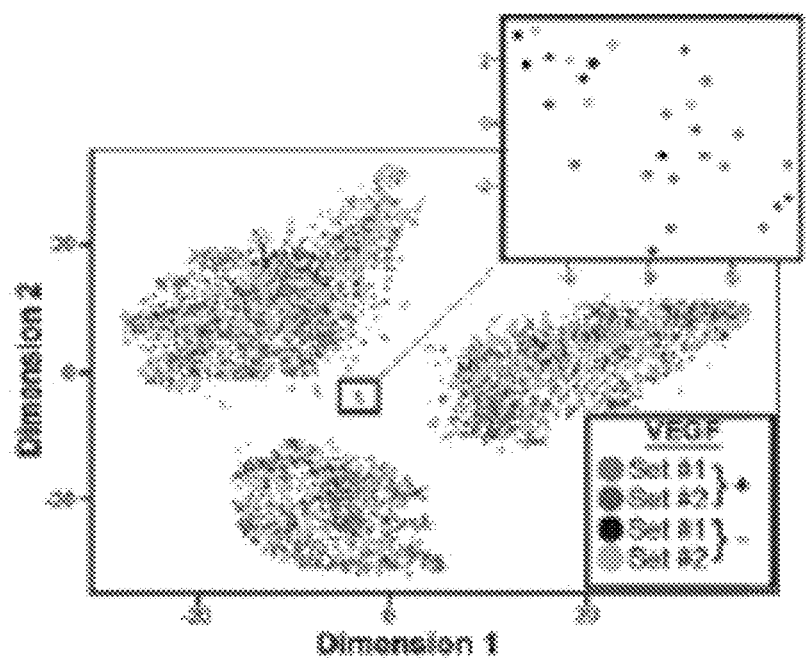
Figure 10F:
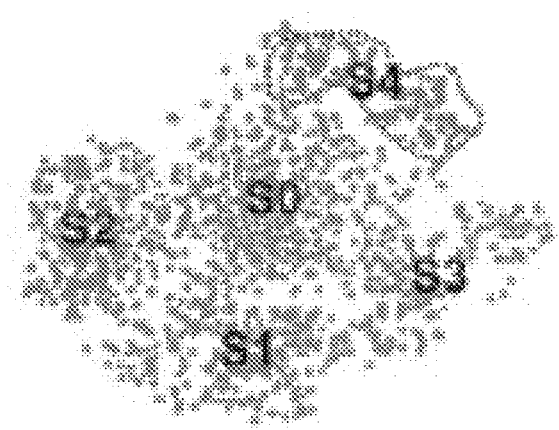
Figure 16F:
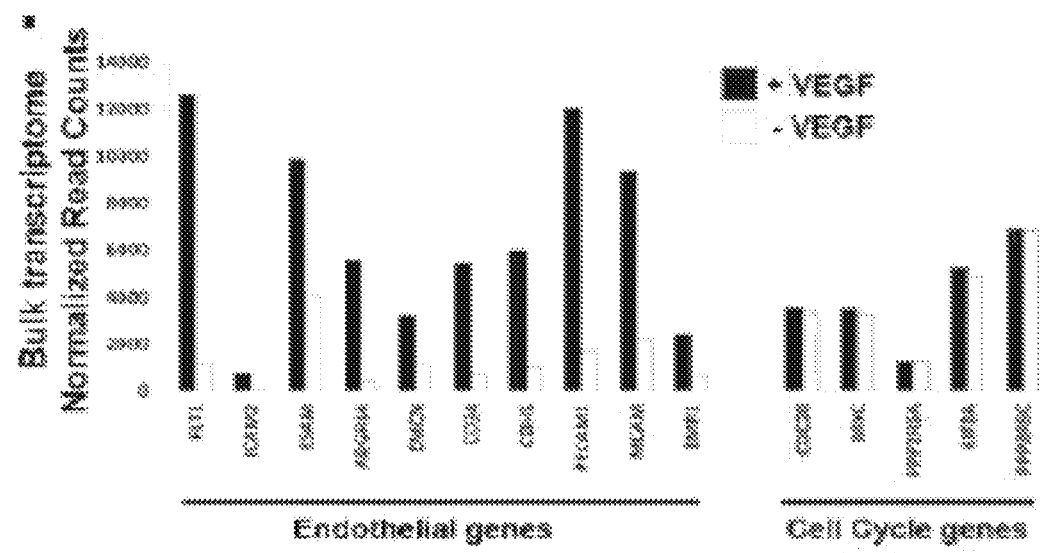
Figure 16G:
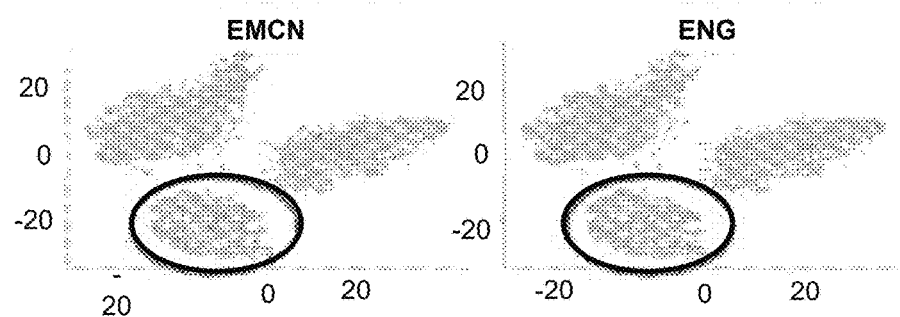

As organoids included in this analysis were generated by treatment both with and without VEGF, the contribution of cells to each cluster by each of the datasets was examined (FIG. 10E). Cells from each dataset were well dispersed within each cell cluster, confirming that organoids treated with VEGF generated a robust fraction of epithelial and stromal cells on par with organoids without VEGF treatment (FIG. 10E). Although VEGF clearly increased the number of ECs by immunofluorescence, relatively few ECs were captured by scRNA-seq and only a modest increase in ECs was observed (FIG. 10E). In contrast, bulk RNA-seq analysis from replicate wells detected marked (4-to 12-fold) upregulation of endothelial cell markers including PECAM1, CD34, CDH5, and FLT1 after VEGF treatment, validating the immunofluorescence analyses (FIG. 16F). The low abundance of ECs detected by scRNA-seq suggested either that a spectrum of maturation states was present in the cultures or that a substantial number of ECs were lost or destroyed during the processing steps prior to sequencing of Drop-seq isolates. The first possibility was supported by detection of EMCN and ENG expression in cells in the stromal cluster (FIG. 16G), both recently shown to be involved in angiogenesis (Jin et al., 2017; Park-Windhol et al., 2017; Sugden et al., 2017).

Figures 10G, 10H:
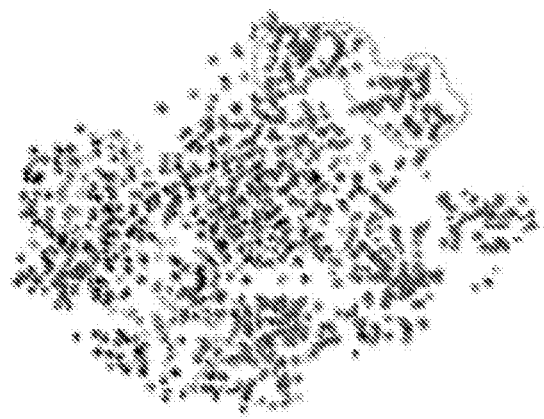
Figure 10I:
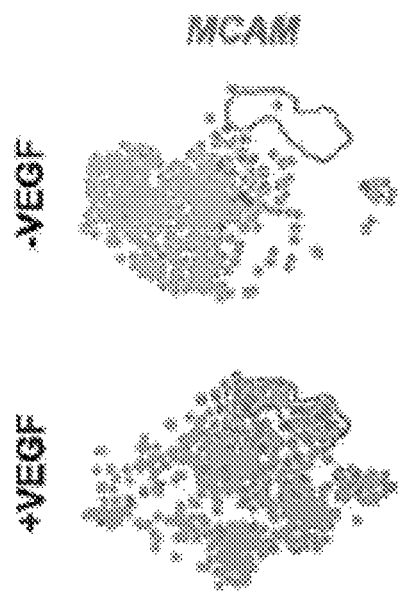
Figure 10J:
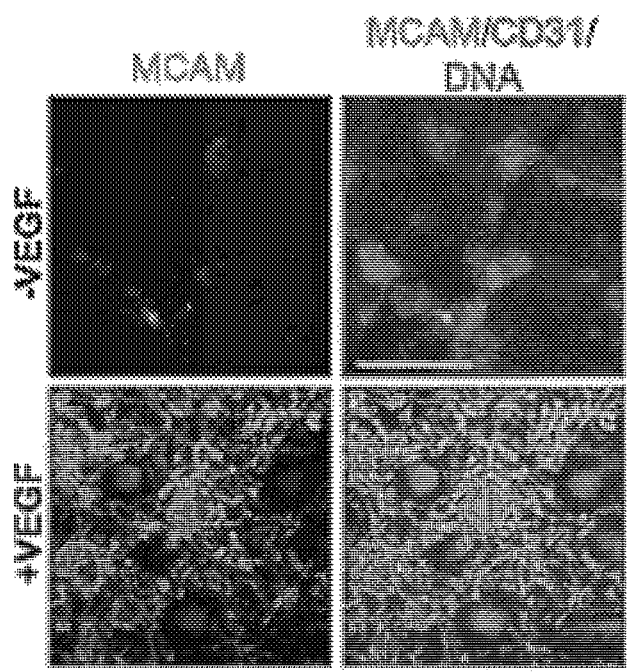
Figure 16H:
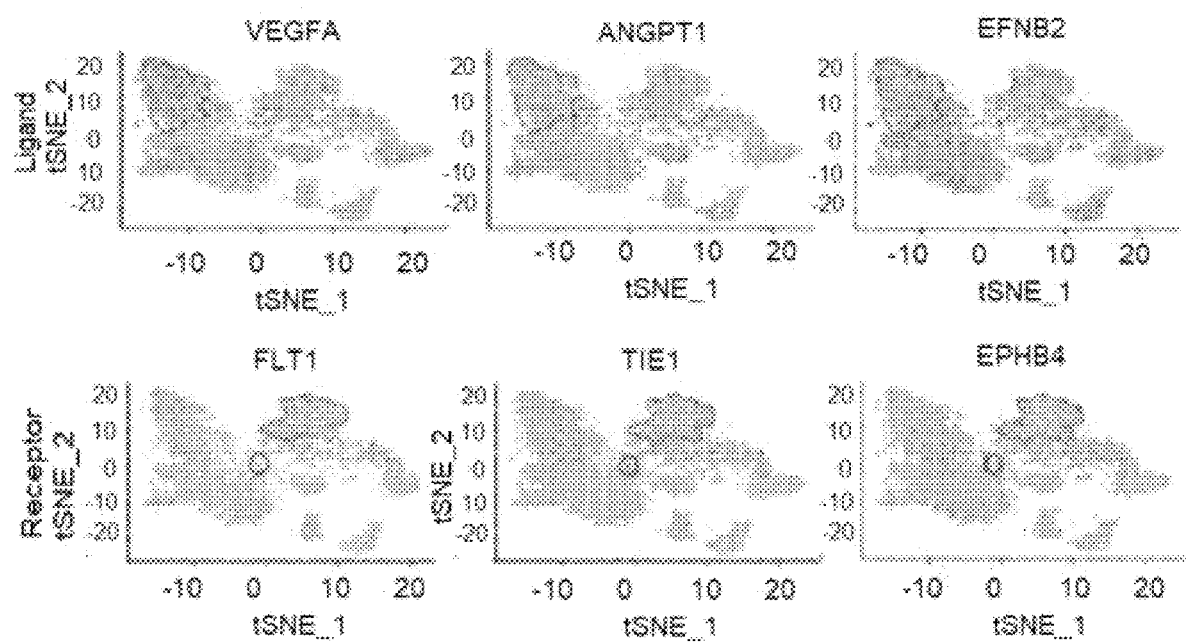

Subclustering of stromal cells further revealed a unique subpopulation, expressing the VEGF receptor FLT1, that arose specifically in VEGF-treated cultures but was entirely absent in untreated controls (FIGS. 10F-10I). MCAM, which was recently identified as a marker of endothelial cell progenitor cells within the developing kidneys (Halt et al., 2016), was strongly coexpressed within this subcluster (FIGS. 10F-10I). In the presence of VEGF, MCAM+ cells accounted for 9.5% of cells within the six kidney clusters, or 5% of all cells (FIG. 10G). In VEGF-treated cultures, MCAM protein was specifically expressed in CD31+ cells occupying large portions of the surface area, consistent with the identification of these cells as endothelial cell progenitors (FIG. 10J). Endothelial cell-specific growth receptors were detected at low levels by scRNAseq, despite substantial expression of their ligands from neighboring cells (FIG. 16H). Although FLT1 could be clearly detected by bulk RNA-seq, a method that involves less processing and increased sampling, it was difficult to detect by scRNA-seq (FIGS. 16F and 16H). Collectively, these findings suggest that, while VEGF treatment greatly increases the number of endothelial cell progenitors in organoid cultures, only a small minority of these cells reaches a mature endothelial cell differentiation state similar to that found in vivo. Furthermore, a substantial number of ECs may be lost during the scRNA-seq processing steps.

Organoid Plates Model Kidney Injury and Disease

Figure 11A:
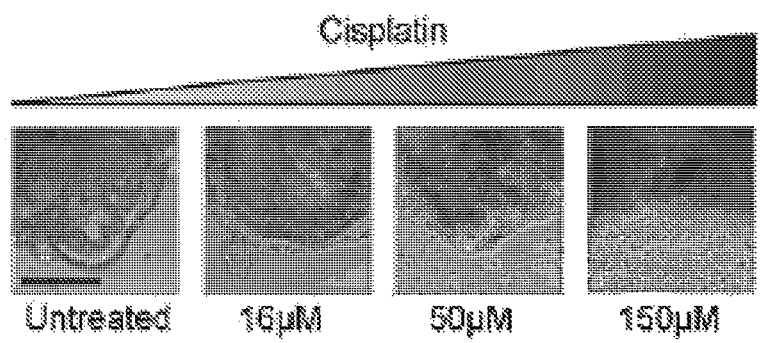
FIGS. 11A-11H show that organoid HTS plates model toxicity and disease phenotypes.
Figure 11B:
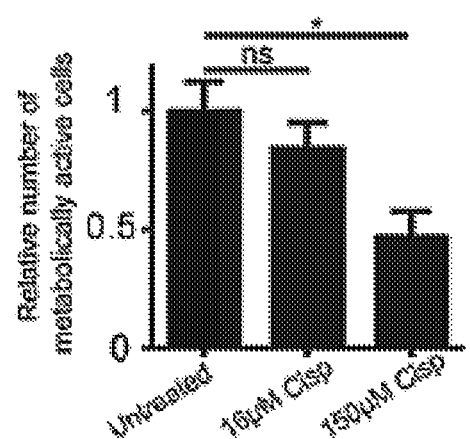
Figure 11C:
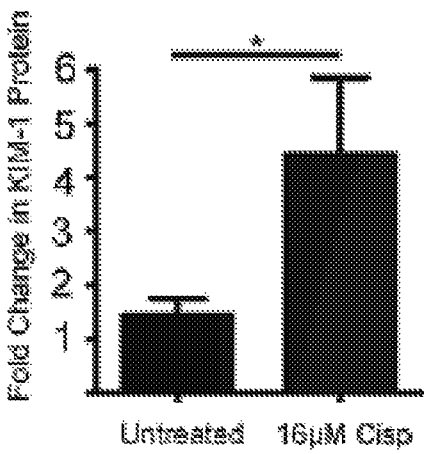
Figure 11D:
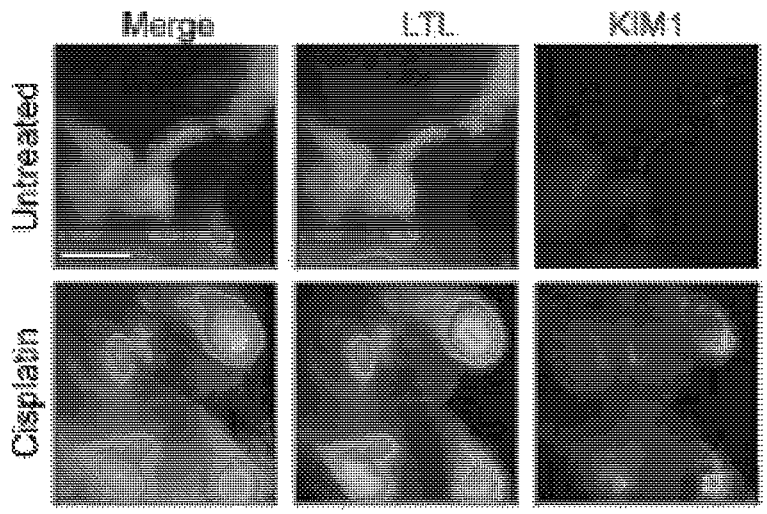

An important potential application for organoid-based microwell plates is to assess organ-specific toxicity and disease phenotypes using automated, HTS assays to predict safety and efficacy. In support of this approach, 384-well kidney organoid plates were first treated with increasing titrations of cis-diamineplatinum(II) dichloride (cisplatin), a chemotherapeutic with known nephrotoxic side effects (Freedman et al., 2015; Morizane et al., 2015; Pabla and Dong, 2008; Takasato et al., 2015). Using microscopy, it was observed that cisplatin induced apoptosis and caused destruction to tubule organization in kidney organoids in a dose-dependent manner (FIG. 11A and Video 2). This loss in cell viability could also be detected using a sensitive, luminescence-based assay appropriate for microwell formats (FIG. 11B). To extend this analysis to specific biomarkers, which are more sensitive than toxicity, kidney injury molecule-1 (KIM-1) expression was measured using an ELISA-based approach and succeeded in detecting high levels of expression at sub-lethal doses (FIG. 11C). Expression of KIM-1 specifically in the injured organoids was furthermore confirmed by immunofluorescence (FIG. 11D).

Figure 11E:
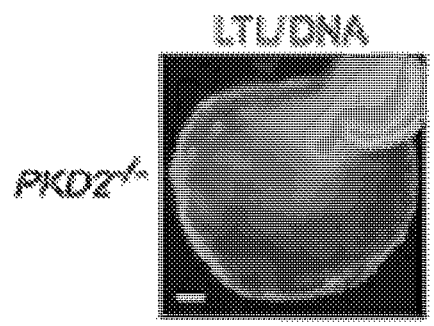
Figure 11F:
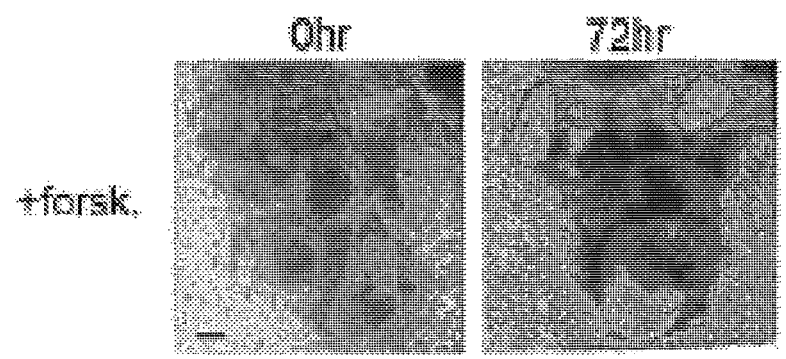
Figure 11G:
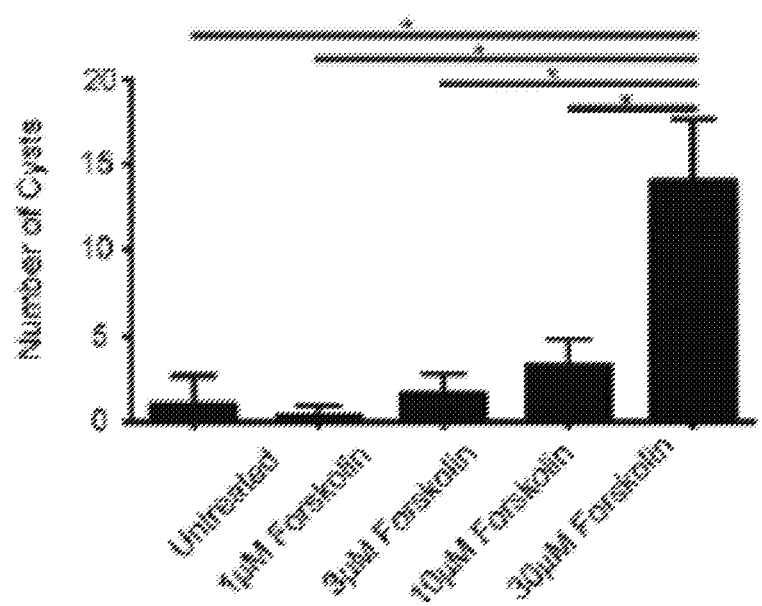
Figure 11H:
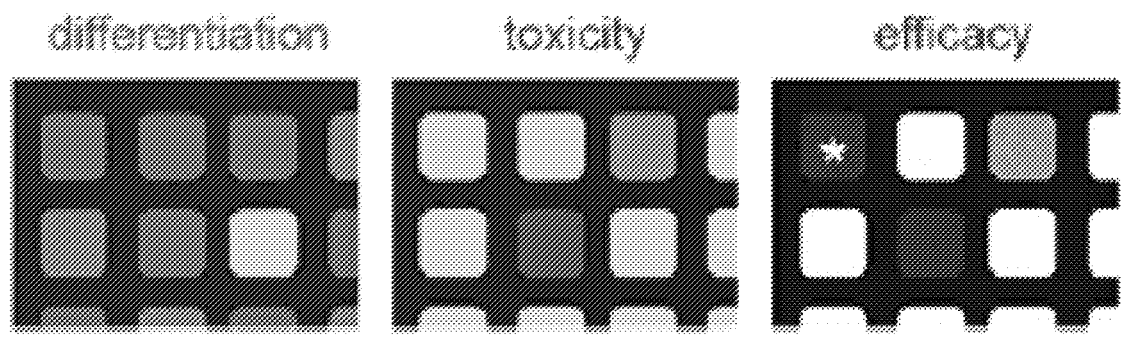

The potential of organoids in HTS formats to model genetic disease was also investigated. Cyst formation is a common endpoint in many different kidney diseases, including the most common genetic cause of kidney failure, polycystic kidney disease (PKD). Gene-edited kidney organoids with mutations in polycystin-1 or polycystin-2, loss of which causes PKD, produced cysts from kidney tubules in automated, 384-well cultures (FIG. 11E). To test their ability to respond physiologically to chemical stimuli, the organoids were treated with forskolin, which induces swelling by activating chloride channels such as CFTR. Forskolin treatment resulted in cystic swelling of HTS kidney organoid tubules in a dose-dependent manner (FIGS. 11F and 11G) (Cruz et al., 2017). These assays established a technological framework for assessing the effect of chemical or genetic treatments on organoids, to distinguish true therapeutic efficacy from differentiation- or toxicity-induced false positives or false negatives in HTS experiments (FIG. 11H).

Screening Reveals an Unexpected Role for Myosin in Organoid PKD

Figure 12A:
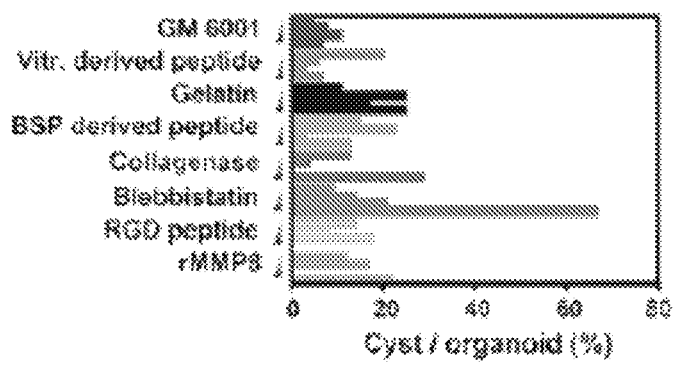
FIGS. 12A-12G illustrate that screening reveals blebbistatin increases PKD organoid cystogenesis.

To test whether the HTS organoid platform could provide insights into disease, a small-scale screen was performed to identify modifiers of PKD using eight candidate factors that may modulate interaction of cells with their surrounding microenvironment, which are important in organoid PKD (Cruz et al., 2017). HTS organoids derived from gene-edited hPSCs with mutations in polycystin-1 were treated on the 21st day of differentiation, a time point at which cysts had not yet formed, and maintained in the presence of each compound for 7 days. In most of the treatment conditions, cyst formation generally ranged from 5% to 20% of organoids, with no compound showing a dose-dependent decrease in cystogenesis. Interestingly, however, blebbistatin, a specific inhibitor of non-muscle myosin II, or NMII (Straight et al., 2003), induced a significant increase in cyst formation at the highest concentration, 12.5 mM (FIG. 12A). This was unexpected, as the myosin pathway was not known to be involved in PKD.

Figure 12B:
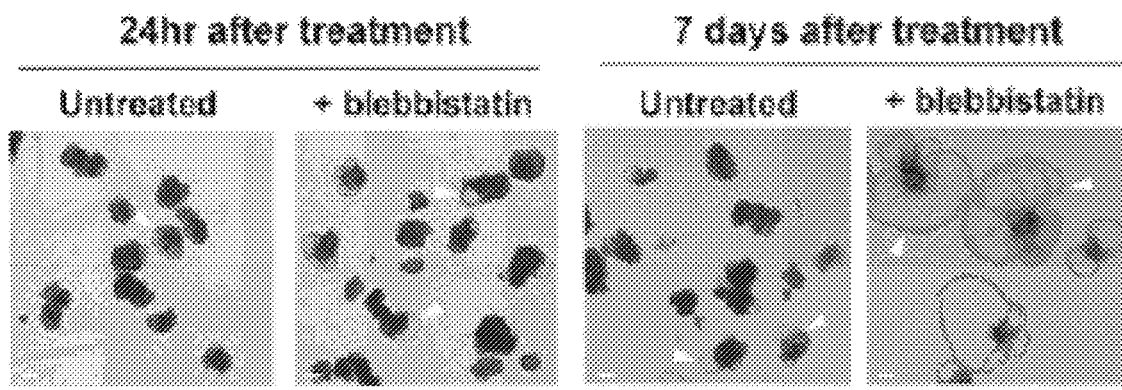
Figure 12C:
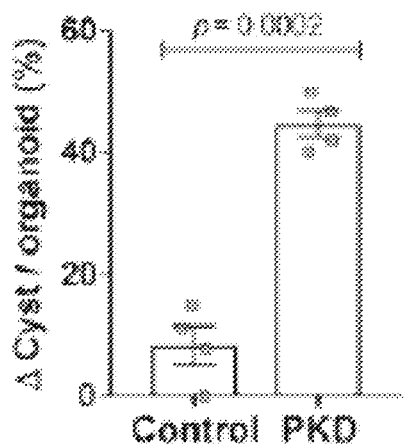
Figure 12D:
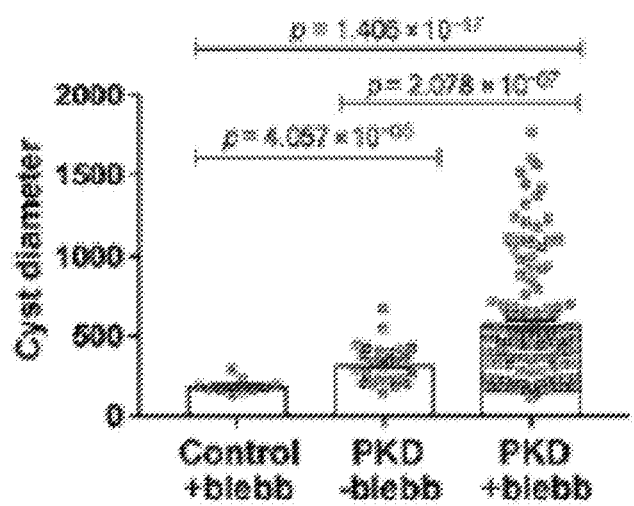
Figure 12E:
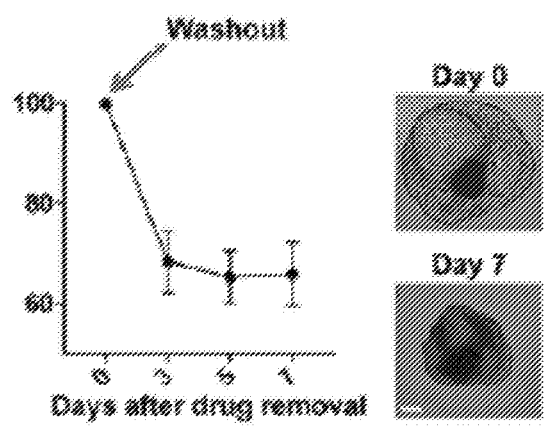
Figure 12F:
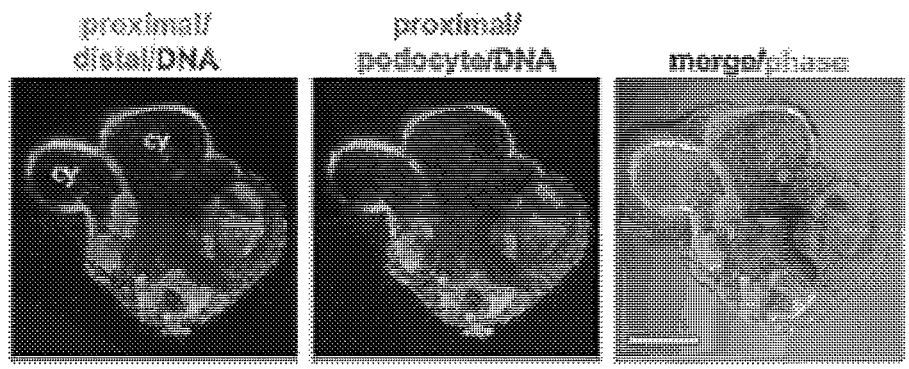
Figure 12G:
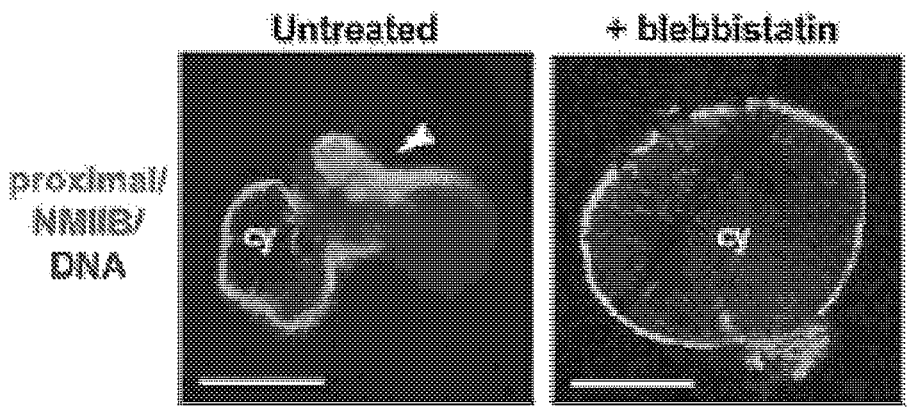
Figure 17A:
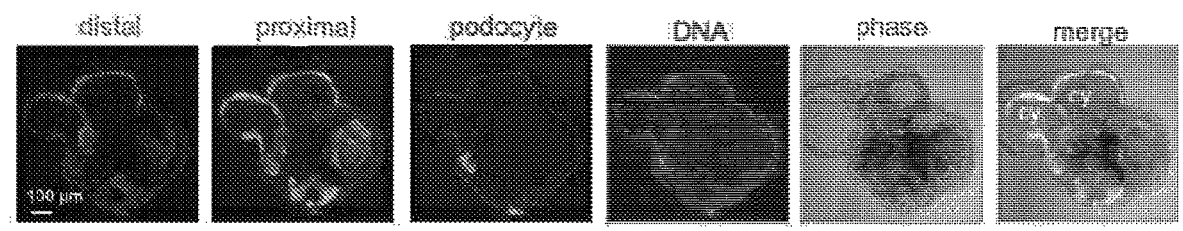
FIGS. 17A-17B show that NMIIB is expressed in cyst-lining epithelial cells.
Figure 17B:
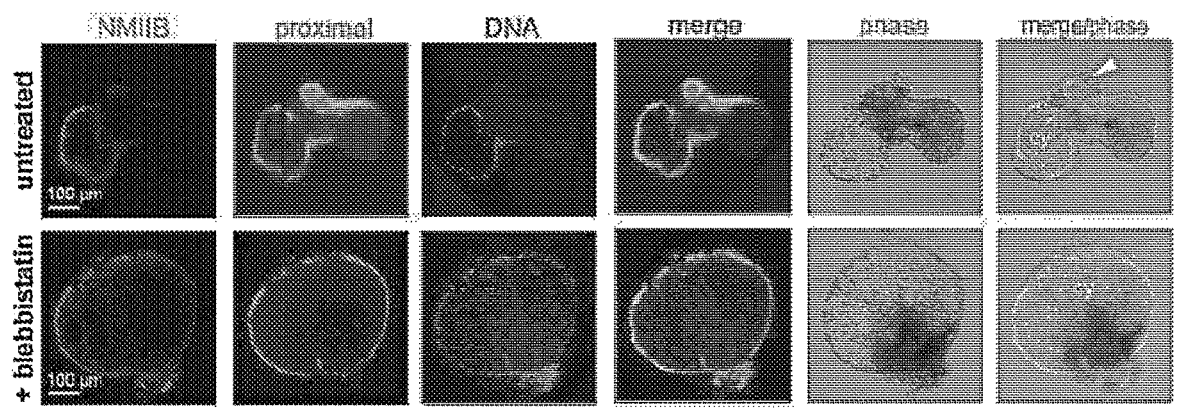

To validate this finding, blebbistatin was added to organoids in low-throughput suspension cultures, a condition that promotes robust cystogenesis from PKD organoids over the course of 14 days (Cruz et al., 2017). In blebbistatin-treated suspension cultures, PKD organoids formed cysts after only 24 hr, which continued to increase dramatically in diameter over the next week (FIG. 12B). In contrast to nephrotoxic compounds such as cisplatin, no damage to organoids was observed with blebbistatin treatment at this concentration and time frame (FIG. 12B). The rapid growth and expansion of blebbistatin-induced cysts suggested that they remained proliferative (FIG. 12B), similar to PKD cysts without blebbistatin (Cruz et al., 2017). Blebbistatin increased the rate of cystogenesis 40% in PKD organoids, but only 10% in control organoids of identical genetic background that lacked PKD mutations (FIG. 12C). Both the diameter and number of cysts were increased in blebbistatin-treated PKD organoids, compared to other conditions (FIG. 12D). When blebbistatin was removed from these cultures, cyst size declined, indicating that blebbistatin's effects were partially reversible and dependent upon sustained treatment with the drug (FIG. 12E). Immunofluorescence analysis indicated that blebbistatin-induced cysts arose from proximal and distal tubular epithelial cells, but not from podocytes (FIGS. 12F and 17A). Non-muscle myosin IIB (NMIIB) was expressed much more strongly within these cyst-lining epithelial cells than in non-cystic LTL+ tubular structures located inside the same organoids (FIGS. 12G and 17B). Collectively, these findings suggested that inhibition of NMII promoted cystogenesis in PKD organoids.

Discussion

Organoid cultures have significant advantages for HTS, including human species specificity, regenerative applications, and the ability to model complex phenotypes, but have been limited to lineages with robust, self-renewing stem cells, such as intestinal crypt cells or mammary tumors (Gracz et al., 2015; Sachs et al., 2018). hPSC-derived organoids are not known to have previously been generated in automated, HTS-compatible formats. Although the work described herein has focused on mini-kidney organoid differentiation as a representative lineage, it is likely that the same general techniques could be adapted to produce other types of organoids from hPSCs, such as mini-guts and mini-brains (Hayashi et al., 2016; McCracken et al., 2014; Spence et al., 2011). Importantly, all steps of differentiation, processing, imaging, and analysis can be performed automatically, using conventional cell-culture robots or by hand.

Using this system, it was shown that hPSC-derived organoids in HTS formats can be experimentally manipulated to enhance and optimize their own differentiation. A threshold concentration of CHIR99021 is required to induce kidney lineage differentiation, above which organoids form with similar subcompartment composition. Surprisingly, this induction threshold varies significantly between individual hPSC lines of identical genetic background. These organoids can be processed in multiplex fashion using low liquid volumes to identify previously unidentified cell types or subcompartments, such as PECs. scRNA-seq provides an unbiased mechanism to further assess the differentiation protocol, allowing us to confirm the immunostaining results and show that many of the cell types generated in the hPSC-derived organoids are indeed similar to those found in human kidneys during development.

One limitation of this work is that current organoid protocols produce fetal nephrons in which the tubules and vasculature are not fully mature (Freedman et al., 2015; Morizane et al., 2015; Taguchi et al., 2014; Takasato et al., 2015). This is most evident from the scRNA-seq analysis, which reveals significant clusters of early tubular cells and early podocytes, which are distinct from the more mature examples of these cell types. It was demonstrated that the number of ECs can be greatly increased in organoids by VEGF supplementation, a step toward vascularization that may be generalizable to other types of organoids derived from hPSCs. Many of these ECs are not yet fully mature, similar to the epithelial cells within these organoid cultures. Future HTS screening, complemented with unbiased scRNA-seq, may identify additional factors that push these cells to mature into podocytes, proximal tubules, and ECs, to promote more sophisticated architectures such as glomerular basement membranes. Notably, vascularization alone is insufficient to produce fully functioning kidneys from developing metanephroi transplanted in vivo, underscoring the need for HTS optimization of maturation state and purity to produce functional, engraftable stem cell populations (Dekel et al., 2003; Harari-Steinberg et al., 2013).

The combination of hPSCs and HTS has great potential for reducing costs and increasing success rates of clinical drug development (Grskovic et al., 2011). Although this work builds upon previous platforms in vitro using primary or hPSC-derived epithelial cells types for toxicity or disease modeling (Astashkina et al., 2012; Huang et al., 2015; Kandasamy et al., 2015; Ramm et al., 2016; Rinkevich et al., 2014), the system described herein is unique, in that it combines automated, HTS-compatible formats with complex, hPSC-derived organoids, which are self-organizing, highly complex, and include cell types that are challenging to cultivate from primary cultures (Freedman et al., 2015; Morizane et al., 2015; Taguchi et al., 2014; Takasato et al., 2015). hPSC-derived organoids in HTS formats efficiently model tissue-specific toxicity and disease phenotypes, such as KIM-1 expression and cyst formation. In combination with careful analysis of differentiation on a well-to-well basis, these techniques will enable proper interpretation of library-scale drug discovery experiments and "clinical trials in a dish" in large cohorts representing diverse patient populations (Doulatov et al., 2017; Huang et al., 2015; Sachs et al., 2018; Yang et al., 2013).

Despite many years of research, the molecular functions of the polycystin proteins remain enigmatic, which has hampered the development of targeted therapies for PKD. Applying the HTS platform, blebbistatin, an inhibitor of NMII ATPase activity, was identified as a specific activator of PKD cystogenesis in organoids. This suggests that the polycystins may normally function to positively regulate actomyosin activation within the tubular epithelium, strengthening and tightening the tubule and preventing it from deforming into a cyst. Actomyosin plays important roles in epithelial cell-cell adhesion at adherens junctions, tight junctions, and focal adhesions, including the formation of purse-string-like contractile rings (Conti et al., 2004; Vicente-Manzanares et al., 2009). During normal kidney development, myosin similarly promotes the proper elongation of nephron tubules (Lienkamp et al., 2012). In addition to epithelial cells, stromal myofibroblasts could also be affected by blebbistatin, as these constitute a significant subpopulation within organoids by scRNA-seq, and can be associated with PKD cysts (Cruz et al., 2017). Interestingly, recent work has identified a possible myosin heavy chain-like, calmodulin-binding domain at the carboxyl terminus of polycystin-1, which could potentially regulate myosin (Doerr et al., 2016). The precise mechanism whereby myosin and PKD pathways interact is an interesting area for future investigation, which may provide directions for therapy development. HTS organoids thus provide a screening tool to catalyze discoveries, which can be further evaluated in lower-throughput systems in vivo such as mouse models and human clinical trials.

In conclusion, organoid plates from hPSCs were produced in microwell formats capable of modeling complex human differentiation and disease states. These organoid plates bridge the gap between HTS-compatible experimental models, such as 2D cell lines and recombinant proteins, and low-throughput models, such as rodents. This balance of complexity and high throughput, coupled with their inherent species specificity, provides an attractive starting point for screening approaches focusing on therapeutic discovery, toxicology, and regenerative medicine.

Example 3: Treatment of Polycystic Kidney Disease Using Myosin Activators

A promising novel therapeutic approach for PKD—targeting NMII—has been identified herein, and would fill a strong need for therapeutics. Indirectly, the proposed studies will shed new light on PKD and NMII mechanism, which is important for intelligent development of compounds targeting these. Targeting myosin II activation, and involving not only animals but also human genotypic-phenotypic models, is highly innovative and well positioned for clinical trials in humans. This will have great significance for PKD and multiple organ systems from both a scientific and a medical perspective.

Polycystic kidney disease (PKD) is the most common genetic form of kidney disease, affecting twelve million people, in whom tiny tubes in the kidneys and other organs form balloon-like cysts, and for whom there remains no standard therapy to slow progression of the disease in a clinically beneficial way. Studies related to PKD have led to the surprising discovery that PKD involves specialized molecules that function as the kidney's 'muscles', helping long, thin tube structures to stay in shape and remain tightly coiled. The goal of the studies described below is to test out drugs that can strengthen these molecular muscles and thereby reduce cyst formation in PKD in both mice and human mini-kidney structures in the lab, so that those drugs' activity and safety can be optimized and can be prepared for successful clinical trials in humans.

The goal of these studies is to perform pre-clinical validation of a new therapeutic approach targeting the activation of myosin II for treatment of polycystic kidney disease (PKD). PKD is a major life-threatening Mendelian disorder with no known cure, in which tubular structures in the kidneys, liver, and other organs gradually expand into fluid-filled cysts, leading to organ failure. The disorder is commonly inherited as a loss-of-function mutation in PKD1 or PKD2, encoding polycystin-1 (PC1) or polycystin-2 (PC2), respectively.

Treatment for PKD typically involves controlling blood pressure and preparing for renal replacement therapy. Tolvaptan, a vasopressin receptor antagonist, can modestly slow cyst growth in aggressive cases of PKD, but has side effects that exclude many patients, and long-term benefit is not yet clear. Nevertheless, FDA approval of tolvaptan and associated trial endpoints has blazed a trail for clinical development for PKD.

A major barrier early in the PKD drug development pipeline has been a lack of phenotypic human models. To bridge this gap, human kidney organoids that express PKD-specific phenotypes were generated as described herein, the phenotypes including cyst formation from biallelic PKD1$^{-/-}$ or PKD2$^{-/-}$ tubules. As discussed above in the examples above, studies using human organoids, including high throughput phenotypic screening, have shown that microenvironment and myosin II activity play an important role in preventing PKD.

To that end, experiments described herein have identified a lead compound that activates myosin II and significantly rescues PKD cystogenesis in this system, without significant toxicity. The most recent screens have identified a lead compound, EMD 57033, that activates myosin II (inotrope) and significantly rescues PKD cystogenesis in human organoids, without overt toxicity. Preliminary work in a mouse model of PKD suggests that EMD can also be safe and efficacious in vivo. In addition to EMD, a back-up inotrope compound (4-HAP) has been identified. Notably, myosins are druggable targets in clinical trials for other indications. Here, the inotropic compounds identified may be further validated and optimized in pre-clinical human and animal models, to guide clinical trials in this area. Myosin activators may substitute for polycystins and rescue PKD cystogenesis by promoting the adhesion and contractility of kidney tubules, and preventing them from deforming into cysts, at doses that would be safe for clinical application.

In the studies described below, a new therapeutic strategy for PKD will be blueprinted by measuring the efficacy of myosin activators to reduce kidney cysts in vivo and in vitro. 'Lack of efficacy' is a major cause of drug failure. As cysts are the pathognomonic hallmark of PKD, it is critical to demonstrate that the new therapeutic strategy can reduce cystogenesis. The efficacy of EMD and alternative myosin activators can be measured in both preventing cyst formation (prophylactic), as well as shrinking pre-existing cysts (therapeutic), in a dose-dependent manner. Rescue will be assessed in a hypomorphic mouse mutant that genocopies and phenocopies human PKD, as well as in human PKD organoids. These experiments will establish a strong foundation for broad efficacy of the lead compound and therapeutic strategy for PKD.

Collectively, these studies, and those described below will validate the therapeutic strategy of myosin activation for polycystic kidney disease, so that it might be tested in human clinical trials towards the end of the project.

Background

PKD is commonly inherited as an autosomal dominant, loss-of-function mutation in either PKD1 or PKD2, encoding polycystin-1 (PC1) or polycystin-2 (PC2), respectively (The European PKD Consortium 1994; Mochizuki et al. 1996). Second-hit somatic mutations resulting in biallelic loss of either gene are thought to contribute to the severity of the disease over time (Qian et al. 1996; Watnick et al. 2000; Wu et al. 1998; Wu et al. 2002). The large, transmembrane PC1 and PC2 form a channel-receptor complex at cell sites including primary cilia (antenna-like apical projections of the plasma membrane) and basal focal adhesions (Nauli et al. 2003; Praetorius & Spring 2001). The complex appears to perform signaling and adhesion functions (Ma et al. 2013). Twenty years after the genes that cause PKD were first discovered, how exactly they function remains enigmatic. Indirectly, the drug development efforts described herein will shed light on this important question to guide iteration of the lead compound.

The work described herein will focus on the role of non-muscle myosin II (NMII) in PKD. NMII is present in many body cell types and organs, and is critical for many cellular processes. Less is known about NMII than about muscle myosins, and little therapeutic development has been done on NMII as a target. Specific modulators of NMII are lacking. These studies address this important pathway and need, with broad relevance beyond PKD.

Human PKD cystogenesis is a fundamental process that can be re-created in human cellular structures in a petri dish (Freedman et al. 2015a). Changing the three-dimensional microenvironment can greatly increase or reduce cyst formation in a PKD-specific way (Cruz et al. 2017; Czerniecki et al. 2018). By screening compounds that affect microenvironment, blebbistatin, a small molecule inhibitor of myosin II ATPase activity (Straight et al. 2003), was identified as a strong inducer of PKD cystogenesis (Czerniecki et al. 2018), which increased the rate of onset, size, and overall number of cysts in a PKD-specific and partially reversible manner.

Figures 18A, 18B:
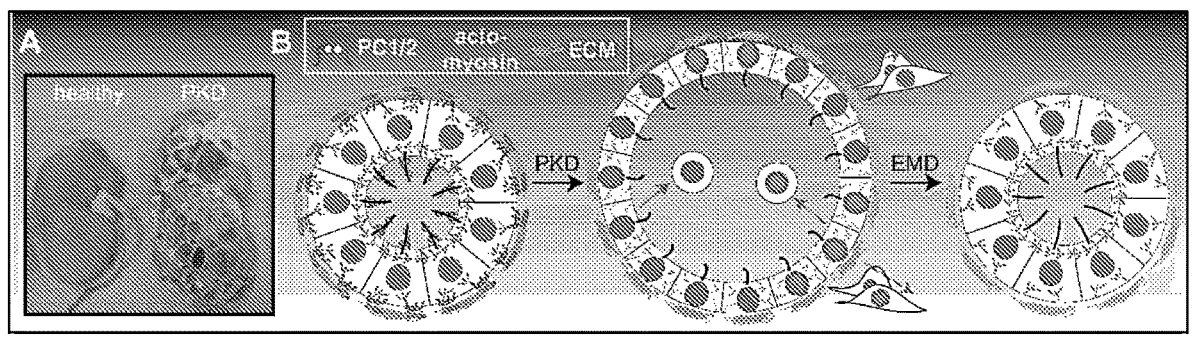
FIGS. 18A-18B show the bases underlying myosin therapy for PKD.

NMII within the kidney tubular epithelium appears to be the target of blebbistatin in these experiments and may be the enigmatic downstream target of polycystins in PKD. Several lines of evidence further support this connection. In epithelial cells, such as those of the kidney tubule, actomyosin localizes to adhesion sites and play key roles in shaping the epithelium, including the formation of purse-string-like contractile rings, cell migration, and wound healing (Vicente-Manzanares et al. 2009; Conti et al. 2004). A possible myosin heavy chain-like domain may exist at the PC1 carboxyl terminus (Doerr et al. 2016), which binds calmodulin, a myosin ATPase cofactor. Together with the findings described above, it may be possible that PC1 physically couples extracellular adhesion events with myosin regulatory activities (FIG. 18B).

PC2, believed to be a non-selective cation channel, could also play a role in myosin activation adjacent to PC1, by providing a source of calcium ions to activate calmodulin, or by chaperoning PC1 to the membrane (Gainullin et al. 2015; Cai et al. 2014). The cyclic AMP (cAMP) pathway is a modulator of myosin activity, thus many of the results in the literature linking cAMP to PKD could reflect a connection to myosin. Myosins are druggable targets, and inhibitors and activators of myosins have already been candidate therapeutics in the cardiology field for many years (Malik et al. 2011; Green et al. 2016). This led to the idea that activators of myosin II could have therapeutic effects for PKD.

The role of myosin has not previously been tested as a therapeutic strategy for PKD, and EMD has not previously been identified as a potential PKD therapeutic. This creates ample space for both scientific and commercial development.

Therapeutic Lead.

Figure 19:
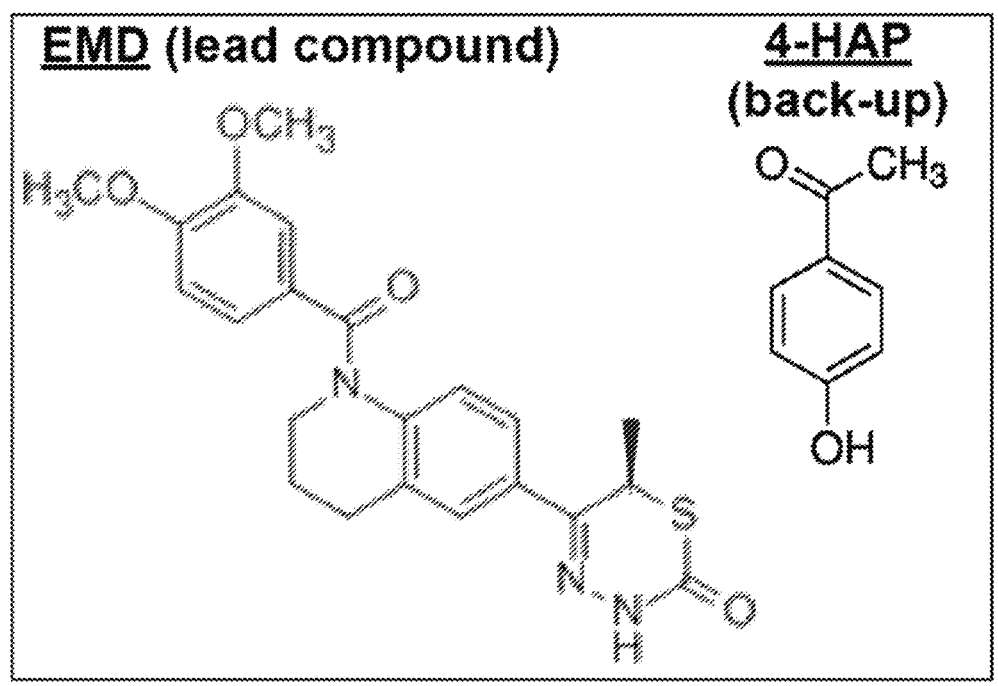
FIG. 19 shows the chemical structures of compounds EMD (lead compound, left) and 4-HAP (back-up, right).

In subsequent studies, follow-up screens of inotropes (myosin activators) were performed in human PKD organoids±blebbistatin. These screens identified EMD57033 (or EMD '57003'; henceforth, "EMD") as a novel lead compound for PKD (FIG. 19). EMD is a thiadiazinone derivative of 425.5 molecular weight that was identified over twenty years ago as a potent inotrope (myosin activator) and candidate drug for cardiomyopathy (Rodriguez et al. 2013; Lee et al. 1996; Tobias et al. 1996; Evans et al. 1995). EMD was first proposed to operate as a calcium sensitizer that binds to cardiac troponin C (Pan & Johnson 1996). However, EMD has since been shown to directly bind an allosteric pocket of the myosin motor domain (KD=7.3 µM), affect actomyosin cross-bridge binding force and stimulate actomyosin ATPase activity (AC50=7.0 µM for β-cardiac myosin and 15.1 µM for skeletal muscle myosin), and increase the thermostability of myosin (Rodriguez et al. 2013; Kraft & Brenner 1997; Radke et al. 2014). Thus, the effects of EMD may be dose-dependent and affect myosin as its primary target at low doses, and troponin at higher doses.

Preliminary data indicate that EMD can be efficacious for preventing and repairing PKD cystogenesis at non-toxic doses as discussed belos. That EMD has the opposite effect of blebbistatin further supports myosin as an important mechanistic pathway in PKD and an appropriate target.

EMD progressed through early development but trials in human were eventually halted due to concerns over solubility and arrhythmias resulting from interactions with troponin at high doses. However, EMD has since been shown to interact with myosin at lower doses that may not cause arrhythmias (Conti et al. 2004; Doerr et al. 2016). In this regard EMD bears resemblance to omecamtiv mercabil, which is a myosin activator currently in phase III clinical trials for heart disease (Malik et al. 2011). EMD differs from many drugs that affect muscle myosin indirectly e.g. phosphodiesterase inhibitors that increase calcium levels, and this may make it safer to use. As the therapeutic target in the studies described herein is the kidney, not the heart, and PKD patients generally have healthy cardiac function, it may be possible to avoid adverse effects by administering EMD at a lower dose that targets myosin and not troponin.

Thus, compounds that target and activate myosin II, such as EMD, can substitute for polycystins and rescue PKD cystogenesis by promoting the adhesion and contractility of kidney tubules, and preventing them from deforming into cysts, at doses that would be safe for clinical application.

Preliminary Studies.

Substantial preliminary trials of the new therapeutic strategy have been performed, the results of which are very encouraging. Initially, these studies were performed in human kidney organoids, which are convenient for drug addiction and screening, and proceeded into a PKD mouse model.

Figure 21A:
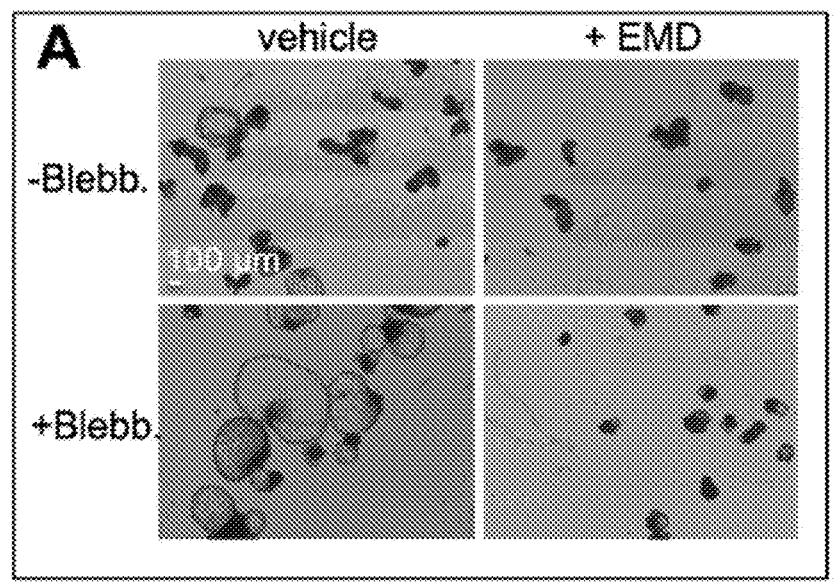
FIGS. 21A-21B show NMII modulation of PKD.
Figure 21B:
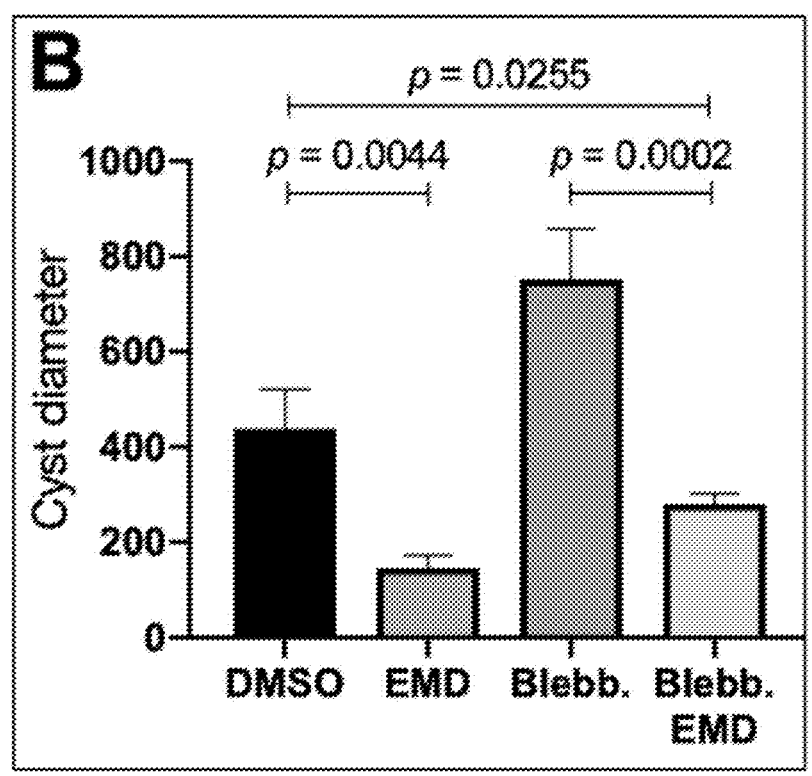
Figure 22:
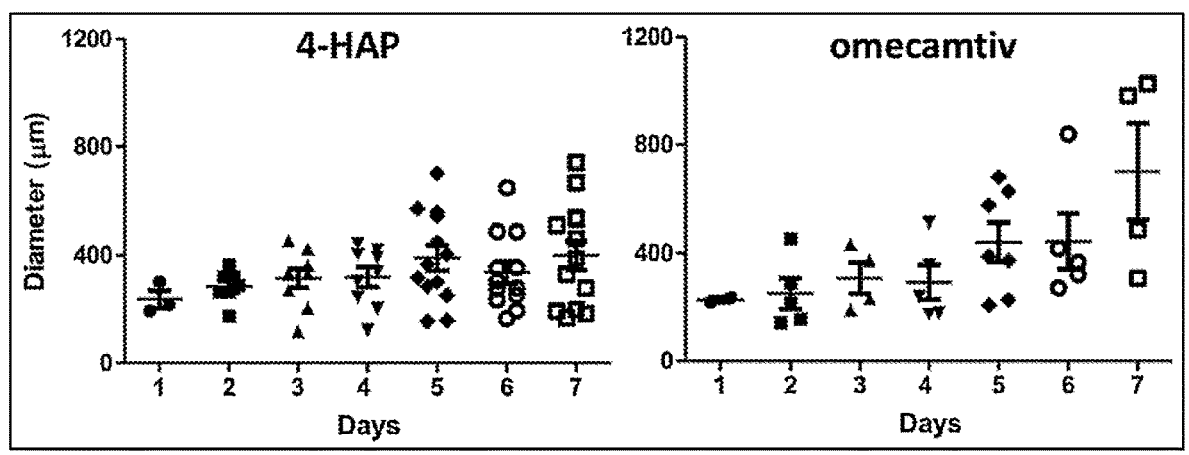
FIG. 22 shows the effect of back-up compounds 4-HAP (300 µM) vs. omecamtiv mecarbil (20 µM) on cyst growth in PKD1$^{-/-}$ organoids. Each data point represents one organoid.

Prophylactic Effect in Organoids: To assess prevention, pre-cystic human kidney organoids were treated in suspension, and found that EMD treatment effectively reduced the formation and size of the resultant cysts, compared to untreated controls (FIGS. 21A-21B). EMD was effective even in the presence of blebbistatin, a myosin II inhibitor that has been shown greatly increases cysts. EMD was efficient at rescuing cyst formation at the lowest dose tested (3 µM) and worked in both $PKD1^{-/-}$ and $PKD2^{-/-}$ mutant organoids. Positive effects have also been observed with the back-up compound 4-HAP in this system, whereas the cardiac myosin activator omecamtiv mercabil was ineffective at the highest dose that was tried (FIG. 22).

Figure 23A:
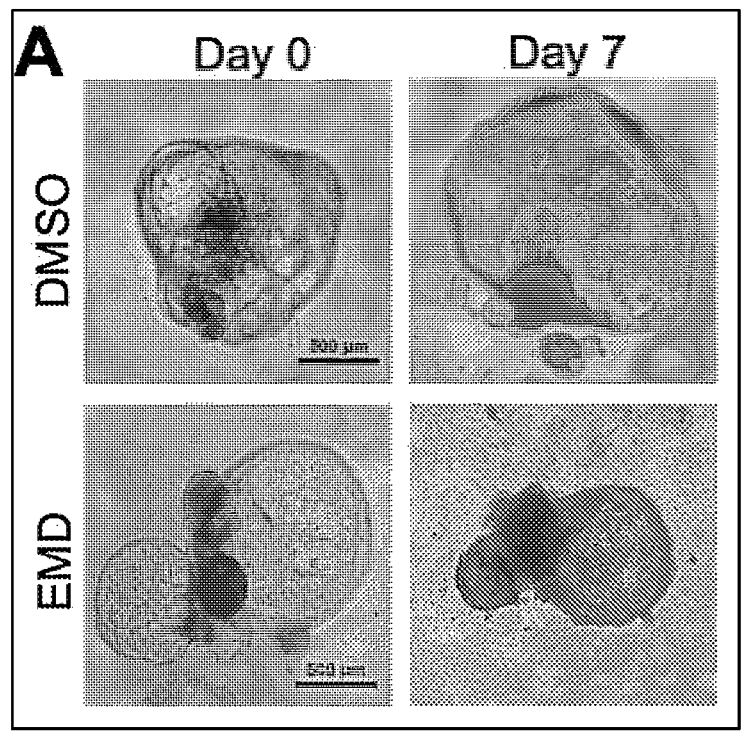
FIGS. 23A-23B show regression of cystic organoid growth after EMD treatment.
Figure 23B:
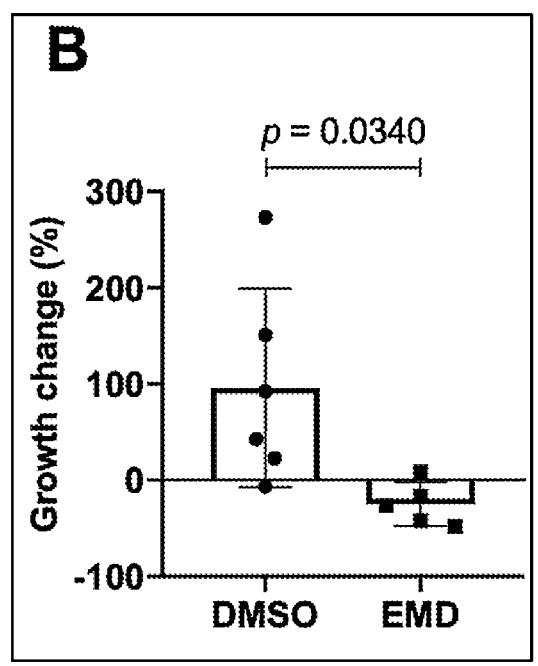

Regression of Pre-Existing Cysts: Encouraged by these findings, it was tested whether EMD can shrink pre-existing PKD cysts, a property that has yet to be demonstrated with other therapeutics. It was found that treatment of late-stage PKD organoids (day 37) with EMD caused an acute reduction in the size of pre-formed cysts over a period of one week (FIGS. 23A-23B). No overt toxicity was noted at these doses, which is further discussed below. Reduction of pre-existing cysts would be a major advantage over tolvaptan. In an acute setting, EMD could be used to reduce pain from swollen cysts, and in a chronic setting it could potentially reverse the course of disease.

Figure 24A:
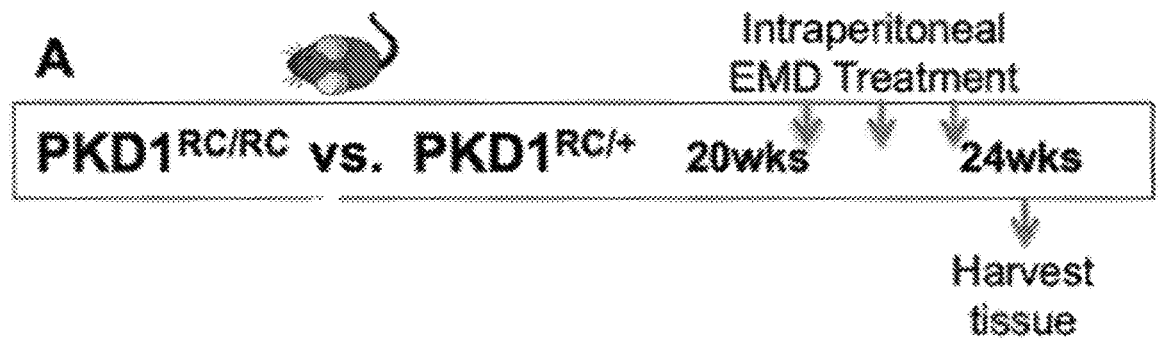
FIGS. 24A-24D show the effect of EMD in vivo.
Figure 24B:
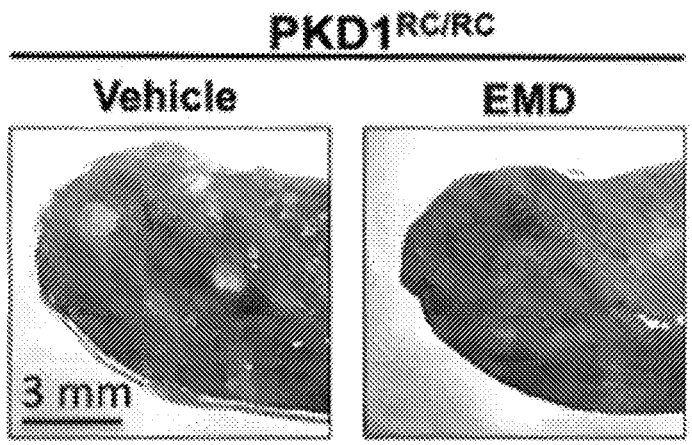
Figure 24C:
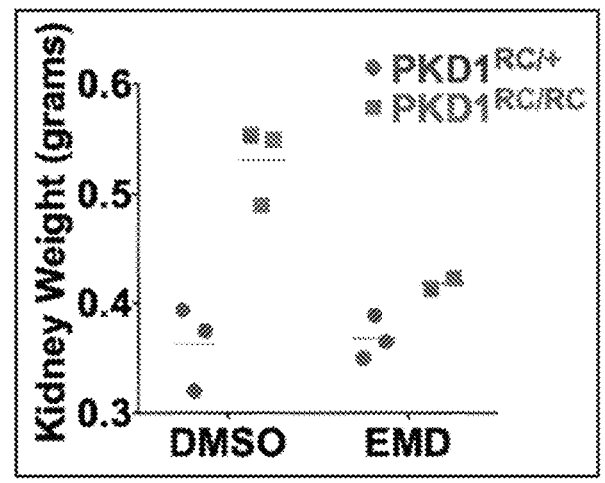
Figure 24D:
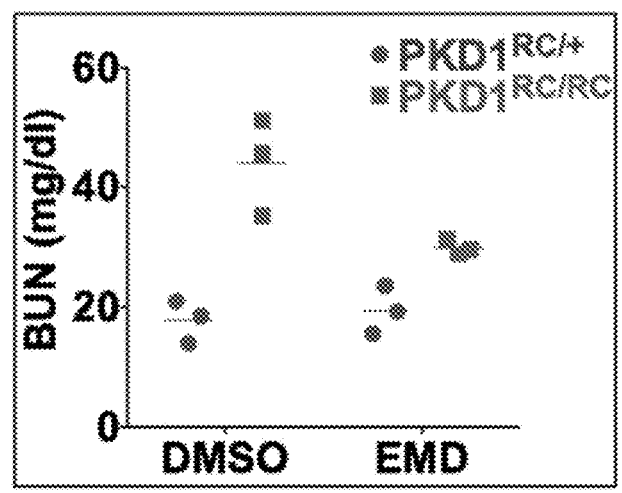

Efficacy In Vivo: To reproduce EMD's effects in an animal model, small pilot trial was performed in the PKD1RC/RC mouse. Animals at five months of age, a time point where cysts have already formed, were injected intraperitoneally with EMD four times over 2.5 weeks (FIG. 24A). EMD was dissolved in 400 µL PBS solution at 5 mg/kg (~25 µM in mouse blood). As negative controls, the same experiments were performed in PKD1 RC/+ animals, which do not form cysts. By gross morphology, EMD noticeably reduced superficial (renal cortical) cysts (FIG. 24B). Kidney weight and blood urea nitrogen levels (BUN, an inverse measure of kidney function) were also reduced (FIGS. 24C-24D).

Thus, treatment with a myosin activator in human or rodent PKD kidneys may prevent cyst initiation and reverse cystic expansion, resulting in improved kidney function.

Validation of Lead Compound and Experimental Design

The primary outcome of this project will be pre-clinical validation of a novel lead compound for PKD in a novel area of study for this disease (myosin). In addition to EMD, the lead compound, 4-HAP will be tested as a back-up myosin II activator. By pursuing the use of myosin activators in PKD, the use of this class of drugs will be advanced in general, and the first therapeutic compound of this nature can be developed.

Various drugs have been developed for PKD. With the exception of tolvaptan, all have failed in the clinic, due to both toxicity and efficacy issues. For tolvaptan, which is a vasopressin receptor antagonist, the mechanism of action is not yet fully clear, but likely relates to either dampening of cyclic AMP signaling and/or preventing fluid accumulation in kidney collecting ducts (Gattone et al. 2003; Reif et al. 2011). This has a relatively modest effect on PKD (3% year cyst growth in patients with severe disease), and requires high doses to achieve this effect compared to hyponatremia, the traditional indication for tolvaptan. This has substantial side effects and can damage the liver, which is already a sensitive organ in PKD patients, whose livers are frequently polycystic similar to the kidneys (Torres et al. 2012; Tangri et al. 2017; Torres et al. 2017; Gross et al. 2019). Thus, new therapeutics targeting the polycystin pathway would be a major therapeutic advance that would complement tolvaptan.

As discussed herein, preliminary data indicate NMII to be the target of EMD in PKD assays, rather than smooth muscle or cardiac muscle, for the following reasons: a) the same effect is not seem using omecamtiv mercabil, which is specific for cardiac myosin S1, or octreotide, which targets smooth muscle myosin (Malik et al. 2011; Chatila et al. 2000); b) organoids in PKD suspension cultures are purified away from other cell types by microdissection, which greatly reduces the presence of contaminating cardiac-like cells; c) an effect on kidney cysts is observed in vivo, where there are no contaminating cardiac cells.

The specific role of NMII has not been directly investigated in PKD. NMII has been linked to human disease, but not to PKD. Genetic redundancy between the three NMII isoforms (NMIIA, NMIIB, and NMIIC, corresponding to the MYH9, MYH10, and MYH14 genes), all of which contain SH3 domains that are highly conserved (Munnich et al. 2014). It has been confirmed that NMIIB is highly expressed in organoid tubules and in cysts as discussed below.

Dosage Determination In Vitro: To determine the minimal effective dose, multiple rounds of EMD treatment may be performed at different doses on human PKD organoids in suspension cultures, blebbistatin (half log concentrations ranging from 10 µM to 3.3 nM). There may be two treatment arms:

Prophylactic arm (prevention): Treatment and suspension culture will be initiated on day 21 of differentiation, a time point that precedes visible cyst formation by phase contrast microscopy. As a negative control, vehicle or EMD 57439, an (−) enantiomer of EMD that has reduced ability to activate myosin and operates via a different molecular pathway (phosphodiesterase III inhibition), will be utilized.

Therapeutic arm (rescue): PKD organoids on day 14 of suspension (~100 µm diameter cysts), or day 90 (~1 cm cysts), will be isolated into single wells of a 96-well plate and treated with EMD or vehicle control.

Assessment: On days 0, 1, 3, 7, and 14 after treatment, organoids will be imaged by phase-contrast microscopy. The number of cysts/organoid and their diameters will be measured and analyzed statistically (see C.1-5 below). In addition to EMD, other inotropes e.g. 4-HAP and omecamtiv mercabil will also be tested in dose curves to inhibit cystogenesis.

Pharmacokinetic Studies In Vivo: Using the organoid data as a basis for dosing in vivo, a pharmacokinetic analysis of EMD may be performed in the PKD1 RC/RC mouse. A regimen using a single administration of EMD at a range of doses (1 mg/kg-100 mg/kg) will be performed. At Cmax and Ctrough, animals will be sacrificed and sera, urine, and kidneys will be collected. Tissue will be sampled, extracted, and levels of EMD will be determined by nuclear magnetic resonance. This will enable us to establish absorption, distribution, metabolism, and excretion (ADME) profiles. Based on these data, it will be determined whether the effective minimal dose observed in organoids can be achieved in the mouse kidney in vivo.

Demonstration of Efficacy In Vivo: Having established the ideal dose in vivo, the PKD1 RC/RC mouse model can be utilized in a longer-term study to test efficacy. To test acute therapy, the trial described above may be repeated with greater numbers. To test prophylactic potential, animals will also be injected once per week with EMD, starting at two months of age. Urine and blood samples will be taken to calculate blood urea nitrogen levels and serum creatinine at weeks 0, 1, 2, 4, 8, and 12 after treatment. The animals are then sacrificed at five months, and kidneys and livers will be excised and sampled for cryosection and histology (sagittal sections) and protein and RNA lysates, and assessed for a) total weight, compared to body weight of the animal, in treated and untreated conditions; b) cystic index (cysts/field) and average cyst size; c) fibrosis as assessed by smooth muscle alpha-actin staining and Maisson's trichrome. Adverse events will be recorded, including any death or decline in physical appearance.

Pharmacokinetic and Biomarker Characterization.

As an integral part of these studies, the absorption and distribution of EMD and 4-HAP will be characterized on the body, about which little has been established (Vogt et al. 2008a). This will provide new insight into how these compounds are distributed to organs of therapeutic need. Further, side effects that could thwart clinical development can be studied using the HTS methods described above, and biomarkers may be identified to detect and determine strategies to avoid those side effects in both disease-affected and unaffected organ systems.

Phenotypic Human and Animal Models.

In a large retrospective study of phase II clinical trials, 'lack of efficacy' was found to be the top cause of drug attrition (Morgan et al. 2012). It is therefore important to address efficacy early on. As cysts are the pathognomonic hallmark of PKD, it is important to demonstrate that the new therapeutic strategy being explored can indeed reduce cystogenesis in target organs, and to identify the proper dose of EMD. This can be accomplished using human and rodent phenotypic models.

Animal and human genotype-phenotype pre-clinical models of autosomal dominant PKD may be used to assess safety and efficacy. To model PKD in vivo, the PKD1RC/RC mouse may be used (Hopp et al. 2012). Unlike Pkd1 homozygotes that are embryonic lethal, this hypomorph strain is viable and can breed. It develops kidney cysts between three and seven months of age, a slowly progressive PKD that specifically genocopies and partially phenocopies human autosomal dominant PKD, the most common kind. The disease produces both cysts and increased kidney weights for measuring TKV. This model has become quite popular since it was introduced in 2012 and is the basis for many current pre-clinical and mechanistic studies (Lakhia et al. 2018; Warner et al. 2016). Having a rodent model of PKD will be valuable for testing efficacy, as well as assessing PKD-specific safety concerns.

Figure 20A:
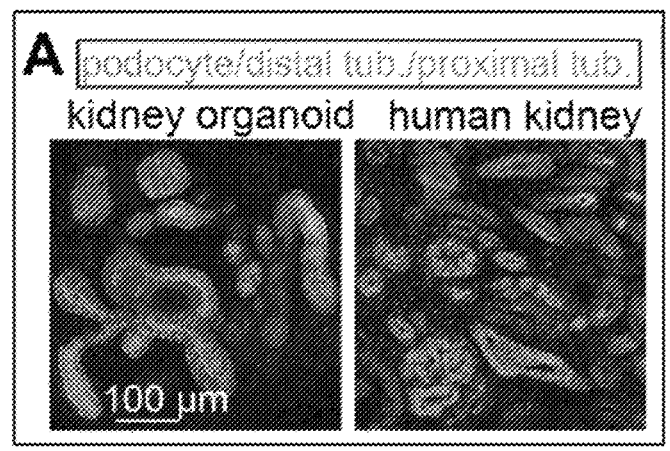
FIGS. 20A-20C illustrate that organoids reproduced key features of human PKD.

Rodent and other vertebrate models replicate certain features of PKD, but do not fully genocopy or phenocopy human PKD or its treatment. In vitro, polarized epithelial cells in 3D cultures can form hollow spheroids, but these 'cysts' arise even in non-mutant cells, and are therefore not PKD-specific (Neufeld et al. 1992; Carone et al. 1995; O'Brien et al. 2001; Kua et al. 2014; Boletta et al. 2000; Petersen et al. 1992; Jaffe et al. 2008). To bridge this gap, human kidney organoids were developed for studying PKD (Freedman et al. 2015a; Cruz et al. 2017; Freedman et al. 2013; Freedman et al. 2015b; Cruz et al. 2018). These were some of the first techniques to differentiate human pluripotent stem cells (hPSC) stepwise into the renal lineage, culminating in the generation of kidney organoids containing contiguous segments of distal tubules, proximal tubules, and podocytes along a distal-to-proximal axis (FIG. 20A) (Freedman et al. 2015a; Morizane et al. 2015; Takasato et al. 2015; Taguchi et al. 2014). The organoids furthermore demonstrate tissue-specific transport functions and responses to injury (Freedman et al. 2015a; Morizane et al. 2015; Takasato et al. 2015). As hPSC can be derived from adult patients by reprogramming, they have potential as individualized models of disease. In addition, a large cohort of patients with PKD is available, and whose organoids could be used as surrogates for personalized therapeutic predictions and enlisted in clinical trials.

To model PKD in organoids, a large and well-characterized cohort of PKD1 and PKD2 mutant lines has been established as a resource including homozygotes, heterozygotes, isogenic controls, and PKD patient PS cell lines (Table 1) (Freedman et al. 2015a; Cruz et al. 2017; Freedman et al. 2013; Freedman et al. 2015b; Cruz et al. 2018).

TABLE 1

Cohort of PKD hPSC

| genotype | distinct genotypes | distinct individuals |
|---|---|---|
| control | 14 | 4M, 4F |
| PKD1 +/− | 8 | 2M, 1F |
| PKD2 +/− | 4 | 1M, 1F |
| PKD1 +/− | 5 | 1M, 1F |
| PKD2 +/− | 9 | 1M, 1F |

Figure 20B:
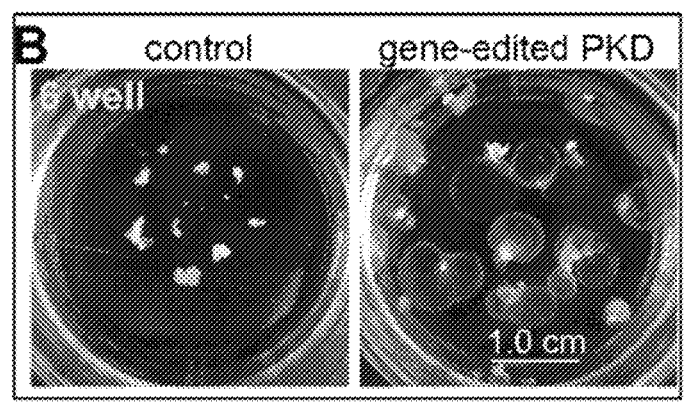
Figure 20C:
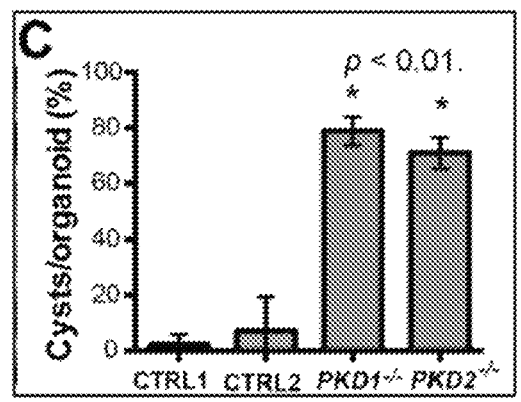

Organoids with biallelic mutations form cysts from kidney tubules, which are not observed in isogenic controls or mutants in other genes unrelated to PKD, thus reconstituting a key hallmark of the disease in vitro (FIGS. 20B-20C) (Freedman et al. 2015a; Cruz et al. 2017; Kim et al. 2017). Organoid cysts originate from both proximal and distal tubules, and closely resemble human PKD cyst tissue (Cruz et al. 2017; Rossetti et al. 2009). The expansive growth of these structures over time, reaching 1 cm diameters, provides a robust quantitative imaging biomarker similar to TKV (FIG. 20B). Several PKD phenotypes have been identified, and optimized methodologies and in vivo controls have been established as shown in Table 2 below.

TABLE 2

Phenotypes in polycystin-deficient hPSC

| phenotype | cell type | genotype |
|---|---|---|
| ↓ ciliary PC2 | hPSC, EB, liver, kidney | PKD1 +/−, PKD1 −/−, PKD2 −/− |
| ↑ cystogenesis | kidney | PKD1 −/−, PKD2 −/− |
| ↓ PC1 protein levels | hPSC, kidney | PKD1 −/−, PKD2 −/− |
| ↑ blebbistatin cysts | kidney | PKD1 −/−, PKD2 −/− |
| ↓ ECM compaction | kidney | PKD1 −/−, PKD2 −/− |

Of many molecules that have been screened, including many proposed PKD therapies close to the clinic, EMD is the primary compound that has been found to reduce cyst formation in the organoid model without toxicity. It not only prevents cysts, but also shrinks them, as shown below. Its study will establish an important positive control and benchmark for the discovery and testing of therapeutic compounds in this system.

This project will produce a key deliverable in the form of a well-characterized and validated lead compound targeting NMII for pre-clinical development for the treatment of PKD. The work is particularly innovative because it is focused on a myosin pathway that has only recently come to light as critical in PKD, and represents an attractive druggable target. This work establishes critical information regarding how the therapeutic is metabolized in the body and its safety profile.

Backup Lead.

Other screens have also identified 4-hydroxyacetophenone (4-HAP) as a back-up candidate to EMD (FIG. 18). 4-HAP is a compound that was identified relatively recently as an activator of myosin II paralogs, which appears to specifically affect non-muscle myosins IIB and IIC, but not IIA (Surcel et al. 2015). 4-HAP's precise AC50 for myosin II is unknown, but it shows effects on cell stiffness in the 5-50 µM range (Surcel et al. 2015). Although 4-HAP has less activity than EMD, it nevertheless appears to have a positive effect, as discussed below. In contrast, compounds such as octreotide (a somatostatin analog that stimulates contraction of smooth muscle myosin (Chatila et al. 2000)) and omecamtiv mercabil (which activates cardiac myosin S1 (Malik et al. 2011)) do not affect PKD cysts. 4-HAP is a newer inotrope and relatively simple compared to EMD. Its direct target binding characteristics and side effects are not yet fully known.

Discussion and Alternative Approaches

Study Populations and Sex as a Variable. Homozygous gene-edited hPSC and controls from the large cohort will be used, both male and female, and heterozygous or patient-derived lines may also be used (see Table 1). As PKD affects men and women of all races with approximately the same penetrance, the study population is similar to the general population. Both male and female animals will be used, as both develop PKD, and gender will be tracked, to account for any sex-related differences.

Power Analysis. The differences that have been observed with blebbistatin and EMD are substantial. Thus, it is likely that a significant phenotypic impact of no less than 20% will be observed, compared to the negative control. To measure such a change with 95% power and a p value of 0.01, 8 biological replicates will be used, using a Bonferroni correction method (see Table 3, below).

TABLE 3

Statistical Analysis Plan for Representative Experiments

| Aim | Measurement | PKD | WT control or EMD | N |
|---|---|---|---|---|
| 1 | Cystic organoids (%) | 75 ± 9 | 15 ± 6 | 8 |
|  | Cyst diameter (mm) | 0.60 ± 0.15 | 0.12 ± 0.04 | 7 |
|  | Kidney weight (g) | 0.55 ± 0.15 | 0.30 ± 0.1 | 9 |
|  | BUN (mg/dL) | 40 ± 8 | 20 ± 5 | 4 |
| 2 | alpha-SMA+ area (%) | 42 ± 7 | 25 ± 4 | 4 |
|  | KIM-1 ELISA (%) | 0.8 ± 0.2 | 0.4 ± 0.2 | 9 |
| 3 | NMII unfolding force (pN) | 22 ± 4 | 33 ± 5 | 6 |
|  | ATPase activity (s-1) | 0.4 ± 0.1 | 0.6 ± 1.0 | 9 |

Expected values for $p < 0.01$ (2-sided t-test, 95% power, $\alpha = 0.01$)

Biological replicates for organoids will be considered either a different cell line of equivalent genotype, the same cell line in a different experiment, or a combination of these two, and will be pooled, using no fewer than three cell different cell lines per condition. Every differentiation experiment is slightly different, due to minor variations between conditions over the course of the 30-day experiment and the complexity of the hPSC system. To reduce batch effects, differentiations will be performed side-by-side with positive and negative controls. For animal work, littermate experimental and control mice from at least three different litters will be used. Animals will be scored blinded in order to reduce human bias.

In canines and pigs in vivo treated with EMD for myocardial dysfunction, a positive inotropic efficacy was reported at ~0.4 mg/kg/min for 20 minutes (total 8 mg/kg)

(Satoh et al. 2002; Dunker et al. 2001; Senzaki et al. 2015). This is higher than the dose that was administered in the trials described above. Also in canines, orally administered EMD (optimized for dissolution) had an average Cmax of ~40 ng/ml and Tmax of ~150 min (Vogt et al 2008). Although the species of choice and route of administration may result in different kinetics, it is likely that EMD will be detectable, and will be effective in both preventing cysts from forming as well as shrinking pre-existing cysts. EMD does not cause overt toxicity to kidney epithelial cells at effective doses, and is unlikely to explain its beneficial effects, as will be further detailed below. One explanation is that EMD helps constrain the tubule in a tightly coiled conformation, preventing it from uncoiling and forming a cyst (see FIG. 18B, above).

The same experiments described may be adapted for the back-up lead compound, 4-HAP.

Correspondence with an In Vivo Biomarker for PKD: The organoids used in the studies described herein provide a powerful measure of phenotypic outcomes—cyst formation rate and size—that can be directly benchmarked to the same PKD metrics in vivo. Cyst formation may therefore be seen as an indirect measure of target engagement—a biomarker—which bridges the in vitro and in vivo paradigms. It should be noted that total kidney volume (TKV) is an approved FDA biomarker for PKD trials, the first of its kind (Tangri et al, 2017; Perrone et al. 2017). Thus, the biomarker relied upon here is quite closely linked to the FDA's approved biomarker for PKD clinical trials.

Figure 25A:
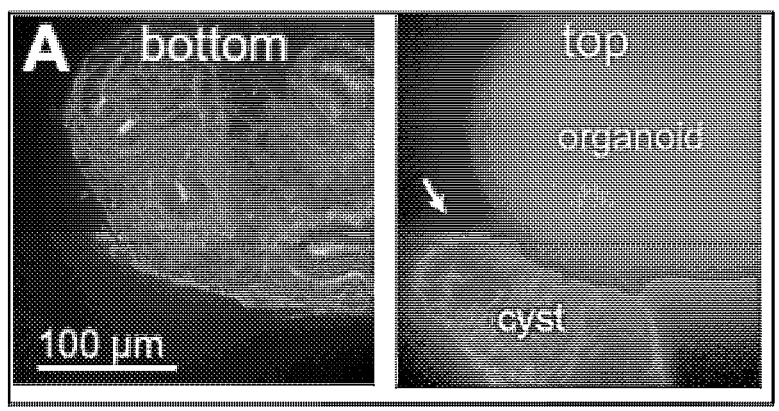
FIGS. 25A-25B show NMII expression in kidney.
Figure 25B:
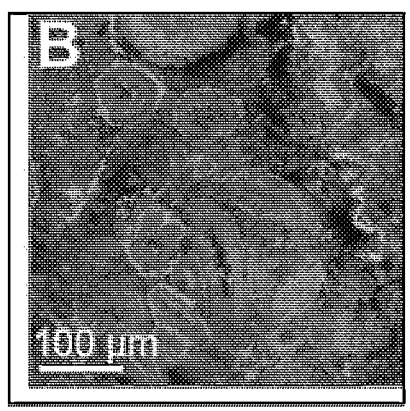

Alternative Approaches, Scientific Rigor, and Validation. In addition to the phenotypic biomarker of cyst size, a complementary approach is to develop a target engagement biomarker (Durham & Blanco 2015). For instance, it would be valuable to know what % of total NMII within a cell needs to be activated in order to produce rescue phenotypes in vitro and compare this to drug activation levels in vivo. There is no well-developed biomarker of this kind, but NMII intensity levels and localization patterns may be assessed to establish such a biomarker. Indeed, GFP-tagged NMIIB accumulates at the cortical membrane in cells acutely treated with 4-HAP in vitro (Surcel et al. 2015). To develop this biomarker, PKD2$^{-/-}$ organoids that express GFP-tagged NMIIB may be used from one of the endogenous alleles, which have been derived from existing Allen Institute PS cell lines (Roberts et al. 2017). NMII is normally expressed at both apical and basal junctions of human kidney tubules in organoids and in tissues (FIG. 25A). Cysts may show changes in NMIIB, e.g. a reduction in NMIIB intensity or localization (FIG. 25B). Organoids will be imaged every four minutes on organoids using a spinning disc confocal microscope to capture changes in NMIBI-GFP patterns after drug treatment in real time.

Having established the pattern, similar changes in NMIIA, NMIIB, and NMIIC can be assessed in fixed, immunostained samples at pre-cystic and post-cystic time points in both human organoids as well as PKD1 RC/RC mouse kidneys. Morphometry analysis will be performed on cell size and shape in epithelial populations, and line scans to quantify NMII intensity and co-localization. This will establish a target engagement marker to which the pharmacokinetic and efficacy data may be benchmarked. Assays for EMD activity on NMII may also be developed.

To more accurately reflect efficacy in humans, a rat model may be used or a model of efficacy in a larger domesticated species may be used—such as mini-pigs—where a genetic model of PKD with kidney and liver cysts has been established (He et al. 2015).

Example 4: Optimization of safety profiles for myosin activators by predicting and mitigating adverse events and tissue responses related to myosin activation in multiple organ systems.

The studies discussed below are performed to optimize safety profiles of PKD therapeutics by predicting and mitigating adverse events and tissue responses related to myosin activation in multiple organ systems. As PKD is a chronic, slowly progressing disease, it is important that treatments do as little harm as possible to the kidneys or other organs. To identify risks associated with myosin activation, EMD and alternate compounds will be tested in conventional rodent models of toxicity, as well as in human organoids. Survival will be quantified as well as adverse events in specific organs likely to be affected by myosin activity. Pharmacokinetic analysis will be performed to ensure proper dosing and determine safe levels of the drug, and protective strategies will be tested to ameliorate adverse pathway events based on analysis of specific tissues and organs.

Preliminary Studies.

Figure 26A:
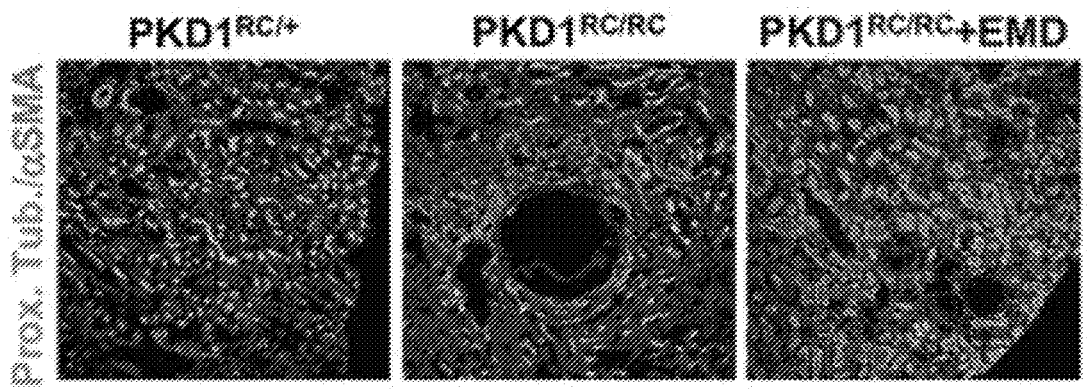
FIGS. 26A-26C show that EMD improves PKD without injuring kidneys.
Figure 26B:
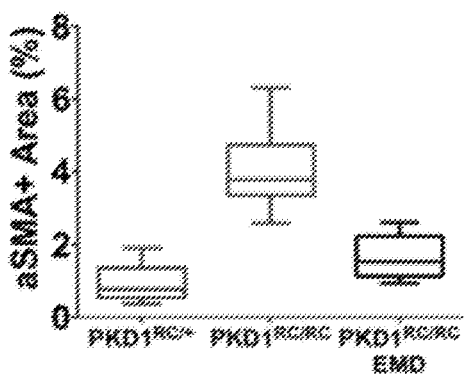
Figure 26C:
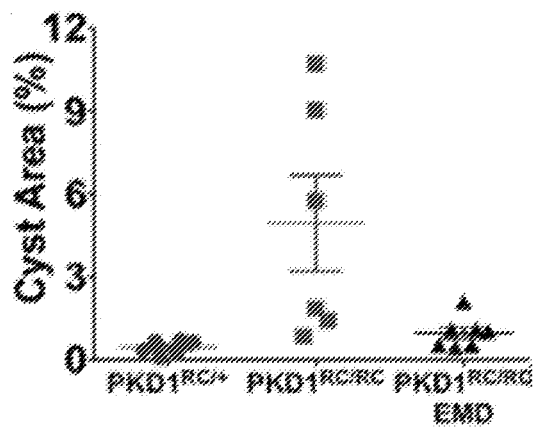

In preliminary studies performed with a high dose of EMD in the Pkd1RC/RC mouse model, all animals survived, and none showed any signs of distress due to treatment with the drug. These animals were sacrificed and analyzed their kidney tissue. Proximal tubules (LTL+) in treated kidneys appeared healthy and normal, with no evidence of acute tubular necrosis (FIG. 26A). Treated kidneys showed reduced expression of smooth muscle alpha-actin, a pre-fibrotic marker of myofibroblast differentiation prominent in areas surrounding cysts and had smaller cysts (FIGS. 26A-26C).

Figure 27A:
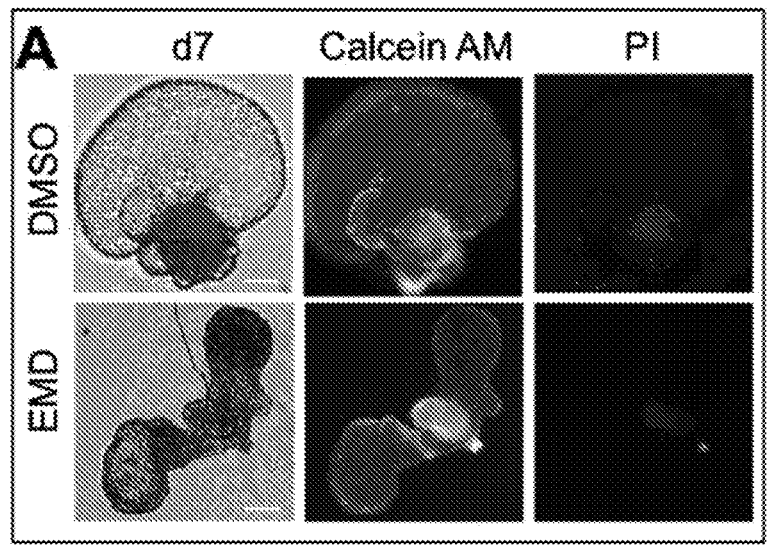
FIGS. 27A-27B show organoid viability after EMD treatment.
Figure 27B:
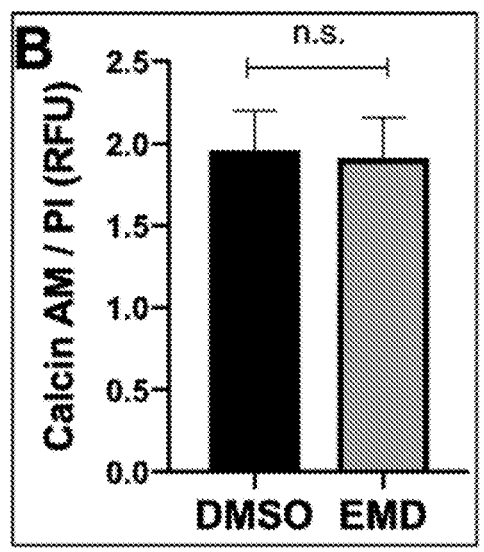

To assess potential toxicity in human organoids, morphology was examined by phase-contrast microscopy during the treatment time course and performed a live-dead analysis of organoids at the endpoint of treatment (10 μM EMD for two weeks). It was observed that no significant toxicity of the compound, even in organoids where efficacy was clearly demonstrated, compared to controls (FIGS. 27A-27B). Cumulatively, these studies suggest that EMD can be used safely in an acute setting.

Thus, myosin activators may be safely delivered into at-risk organs in PKD, although care must be taken to avoid over-dosing, particularly in settings of cardiovascular disease.

The primary experimental model in vivo will be the Pkd1 RC/RC mouse. The advantage of using this mouse is that it provides a setting in which to assess safety considerations relevant to PKD in multiple organ systems. These animals develop kidney cysts at three months, and demonstrate liver ductal plate malformations (pre-cystic hamartomas) and possible hepatic hypertrophy at 12 months (Hopp et al. 2012; Hopp et al. 2015). The hearts of these mice appear healthy, just as they are in most PKD patients.

Acute Pharmacokinetic Assessment.

The strategy in these studies is to establish low treatment doses at which EMD interacts primarily with myosin, and avoid high-dose interactions with troponin that could trigger arrhythmias (Conti et al. 20014; Doerr et al. 2016). To determine the limit of possible safety in animals, the pharmacokinetic studies described in the example above will be extended to include at-risk organs. Pkd1 RC/RC mice will be injected with a single administration of EMD at high doses (4 mg/kg-40 mg/kg, i.e. 10-100 μM) and assess the animals for both pharmacokinetic analysis and any sudden death or symptoms of disease. Vital organs including kidneys, liver, heart, and brain will be collected at Cmax and Ctrough to determine EMD levels by NMR. These experiments will also be performed in Pkd1 RC/+ mice without PKD, and wild-type C57/BL6R mice, to control for PKD-specific and strain-specific effects. Then ADME-Tox qualities of EMD and derived compounds will be determined through methods like QSPR and QSAR (quantitative structure-property or activity relationships).

Long-Term Safety Trial.

Having determined the maximum safe dose, homozygous Pkd1RC/RC animals will be subjected to long-term treatment with EMD, vehicle, or alternate compound at doses ranging from 0.4-4 mg/kg (0.5-5 µM), starting at four months of age, for six months, with weekly injections. In a subset of littermate animals, cardiovascular disease will be induced by cryoinjury to the left ventricle at two months of age, or mock injury will be performed with a room-temperature cryoprobe. Any adverse events necessitating sacrifice, or unplanned deaths, will be included in a Kaplan-Meier curve. Then, the animals will be carefully dosed and adverse events (e.g., cardiovascular events) will be detected.

Every month, animals from all treatment groups will be anesthetized for two hours and continuously monitored for surface electrocardiograms. At the conclusion of the study, the animals will be sacrificed and their livers, kidneys, and hearts will be removed, weighed compared to body weight, and analyzed histologically and by immunocytochemistry for evidence of injury, including a) live/dead or TUNEL staining, and upregulation of organ-specific injury biomarkers such as kidney injury molecule 1 (KIM-1) in tissue by immunofluorescence; b) fibrosis (increased smooth muscle α-actin in the interstitium and collagen deposition by Masson's trichrome and Sirius red staining).

Human Studies

To assess human toxicity, analogous analyses of PKD organoids±EMD (both PKD1 and PKD2) will be performed. Toxicity of these compounds on organoids will be assessed over a 100-fold range of dose by CellTiter-Glo luminescence or live-dead staining, compared to vehicle (negative) or 50 µM cisplatin (positive) control, an assay that was previously developed as discussed above (Freedman et al. 2015a; Czerniecki et al. 2018). hPSC from control and PKD backgrounds will further be differentiated into cardiomyocytes, using a protocol the PI has previously demonstrated (Freedman et al. 2015a; Czerniecki et al. 2018), to assess for effects of EMD on spontaneous beating rate in vitro. Effects of the myosin activators on cardiomyocytes from patients with MYH7 mutations may also be evaluated, in collaboration with the Regnier lab, to model effects on a disease sensitized background (Yang et al. 2018). Further, effects on human hepatoblast cells will be assessed, which were previously differentiated from hPSC with PKD mutations (Freedmen et al. 2013; Lam et al. 2014).

Results

As described above for efficacy, prior studies in large animals show EMD dose to be in the range of these studies, and that it has detectable bioavailability (Satoh et al. 2002; Dunker et al. 2001; Senzaki et al. 2015). In the pilot study, a high dose of EMD (5 mg/kg=25 µM) was applied repeatedly to PKD animals, and no adverse effects or mortality was observe. No fibrosis was observed in the kidneys—on the contrary, smooth muscle α-actin expression (diagnostic of myofibroblasts) was reduced after EMD treatment. A similar dose range was effective and non-toxic in organoids. In the acute trial, EMD could cause issues at high concentrations, although it is noted that solubility issues may preclude achieving a toxic dose. The PK studies discussed herein may to produce dose-dependent distribution measurements, which may be correlated with specific pathologies, for instance, arrhythmias could be tracked with electrocardiograms (by the Regnier lab) if accumulation is observed at Cmax in the heart. The target organs, kidneys and liver, are likely to benefit from myosin activation therapy if it reduces cyst formation as discussed above.

PKD hearts typically do not have the kind of obvious PKD-specific symptoms as seen in epithelial organs (Dagaard 1957; Greenberg & Cheung, 2009; Deltas & Papagregoriou; Chow & Ong 2009). If cardiovascular disease, induced by cryoinjury in a subset of the animals, results in greater susceptibility to long-term adverse effects of the drug, it would suggest that patients with a medical history of cardiac disease should be excluded from treatment with EMD until it is optimized. Conversely, if no deaths or arrhythmia phenotypes are observed, it may be safe even in humans with heart disease. Indeed, EMD can have a beneficial effect on the injured heart, as it can strengthen contractility without adverse effects (Rodriguez et al. 2013; Lee et al. 1996; Tobias et al. 1996; Evans et al. 1995; Satoh et al. 2002; Dunker et al. 2001; Senzaki et al. 2015).

Alternative Approaches, Scientific Rigor, and Validation.

PKD-Specific Safety Considerations: Patients with PKD may receive angiotensin converting enzyme (ACE) inhibitors to manage their hypertension. In addition to the cryoinjury model, it may be worthwhile to test the effect of ACE inhibitors together with myosin activators. Another consideration is whether the drug might have toxicity to the liver, similar to tolvaptan. A previous analysis of EMD in vitro found that it is metabolized by liver cells into demethylated and/or hydroxylated forms by CYP-dependent mechanisms (Gebhardt et al. 2003). NMII is present in many cell types, the long-term safety profile of drugs targeting NMII may take time to predict deterministically. Although these studies have focused on the organ systems most vulnerable or likely to be affected. Other organs could be profiled using the methods described here, in a similar way. The compounds will also be optimized as described below.

The method of single cell RNA-sequencing in organoids was previously established to detect individual cell types (Czerniecki et al. 2018; Harder et al. 2019). This may also be used ±EMD to assess signatures of gene expression changes in an unbiased manner. Such profiles can be mined for specific signatures of injury, including kidney biomarker expression and apoptotic markers, as a secondary measure of toxicity.

Blebbistatin as a Co-Drug: If general safety issues are identified, the effect of EMD may be blunted in this organ by co-administering blebbistatin, a myosin II inhibitor. Although this may seem counterintuitive, blebbistatin has previously been shown to have a protective effect on the heart in the setting of EMD treatment in mice (Baudenbacher et al. 2008). Supporting this, EMD+blebbistatin produces a substantial rescue of PKD in organoids, compared to untreated controls (above FIGS. 21A-21B). Although the precise mechanism underlying this remains poorly understood, it seems that blebbistatin and EMD work in different ways on muscle, and can potentially have cooperative and synergistic effects when administered together. Safer analogs of blebbistatin have been developed and could be highly suitable (Roman et al. 2018).

Alternative Systems: As organoids lack fluid flow, organ-on-chip microphysiological systems (MPS) may be utilized to gain insight into human-specific toxicities. The PI is part of a large Tissue Chips consortium to model human diseases in MPS, including PKD. The consortium includes a variety of organ- and disease-specific MPS, including kidney, liver, and heart, that can be used to assess toxicity with greater physiological relevance than simple monolayer cultures. These MPS largely incorporate primary cells, and can be linked in series, providing a useful complement to the organoid models (Sakolish et al. 2018; Vernetti et al. 2017; Weber et al. 2016). Compound screening in human cellular systems would thus progress from organoids into increasingly complex pre-clinical models.

Example 5: Optimizing Myosin Modulators for Improved Clinical Application

The purpose of this study is to develop a successful therapy development for PKD by establishing a second-generation myosin modulator optimized for clinical application. Recent studies reveal a path whereby chemical properties of myosin activators may be improved for clinical application. Medicinal chemistry and structural biophysics will be applied to optimize EMD (or its back-up) for safety and efficacy. This will involve developing a structure-activity relationship for myosin activation, selectivity amongst the different myosin isoforms, minimizing off-target toxicity, and improving physical properties such that appropriate DMPK attributes are attained (i.e. in vivo bioavailability, clearance and other ADME properties). These studies will produce an innovative, optimized lead compound well positioned to succeed in human clinical trials.

Recent studies suggest that EMD can be improved for clinical application, for instance to target specific isoforms such as NMII (Pan & Johnson 1996). As EMD was not previously identified as a compound to used for the purpose of treating PKD, it is important to ensure that the lead compound going into human trials has maximum potency, stability, and bioavailability.

Preliminary Studies

An analysis of EMD's major chemical properties was performed to identify two key areas whereby its drug safety and efficacy profile can be improved. One is solubility. EMD has an aqueous solubility of 5 μg/ml, which results in relatively low dissolution in the aqueous solutions most appropriate for advanced biological settings. This has been shown to affect bioavailability, and hampered the pre-clinical development of EMD as a cardiac drug (Vogt et al. 2008a). To explain the insolubility of the compound, the cLogP (a measure of lipophilicity) of EMD was calculated to be 3.5, which is on the high side (most drugs have a value of ~1-3). In the experiments in vivo, to achieve a high dose in the bloodstream, a concentrated solution of 25 μM EMD in PBS was successfully administered, which is above the limit of solubility. This was accomplished by warming the solution at 37 degrees Celsius for 30 minutes.

Figures 28A, 28B, 28C:
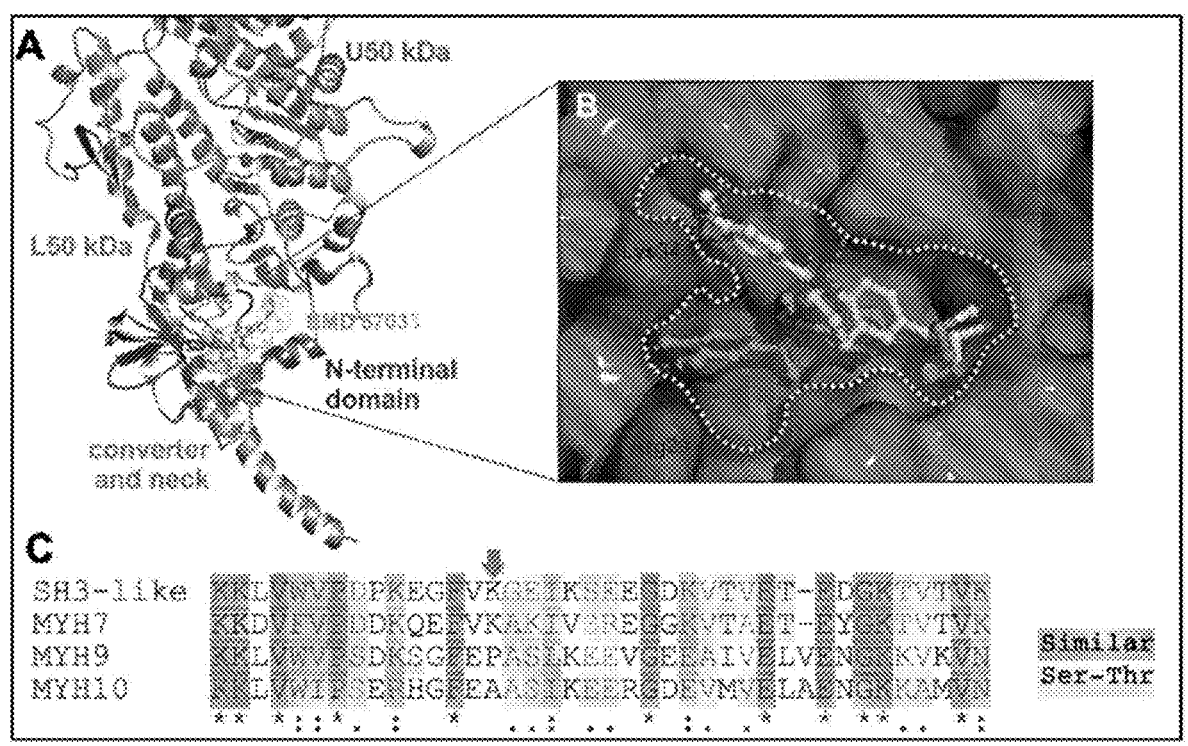
FIGS. 28A-28C show the structural basis of the EMD-NMII interaction.

The second area for improvement is the specificity and activity of EMD for the target NMII. This can affect its potency, which (like most myosin activators) currently rests in the low micromolar range, whereas nanomolar concentrations would be more desirable for treatment regimens. Although it can affect cardiac troponin (Pan & Johnson 1996), EMD's primary target is believed to be the globular head of myosin motor domains, including myosin II family members (FIGS. 28A-28B) (Radke et al. 2014). Binding to myosin II was shown to be dependent on the presence of the SH3-like domain, which is absent in myosin I, highly conserved, and is also present in all three NMII isoforms. However, EMD appears to have higher affinity for cardiac beta myosin than for other SH3-like domains (Radke et al. 2014), and has not been tested on the NMII SH3-like domain, which are the target in PKD. The in silico analysis, together with published structural comparisons (Munnich et al. 2014), reveals noticeable differences within this domain that could contribute to the lower activity of EMD on these motor domains (FIG. 28C). In particular, a key EMD-interacting lysine residue is absent, and the distribution of alcohol functional groups (serine and threonine) differs within the pocket. These finding suggest that EMD could potentially be optimized for improved interaction with NMII's SH3-like domain.

Optimization of EMD for solubility and NMII specificity may produce a second-generation therapeutic with significantly increased potency and bioavailability.

Experimental Design.

Studies may be designed to modify and improve the chemical and physical properties of EMD. Optimized compounds can be tested in the assays of efficacy and safety described above, and also in in vitro assays described below.

Improved Solubility: First, studies can be performed to lower the cLogP of EMD. By introducing additional polarity, solubility may be enhanced. In addition, EMD may be chemically modified to lower its melting temperature, which may enable sustained solubility in warm solutions and blood.

NMII Specificity: To improve EMD for the PKD indication, the compound may be optimized for binding to NMII, as opposed to cardiac myosin. The thiadiazinone scaffold will be modified to include elements that promote a specific interaction with the allosteric pocket within the motor domain of NMII, where EMD has been shown to bind at the SH3-like domain. There are substantial differences in the NMII SH3 domain that may contribute to the differential activity of EMD on this sub-family of myosins. A docking simulation may be performed to determine the proper alignment of EMD within the specific NMII pocket (FIGS. 28A-28B). Iterative development will be performed, utilizing a handful of compounds per iteration.

Target Function Assays: Having a better understanding the target-drug interactions of EMD is a valuable tool in the intelligent optimization of this compound. Functional assays may be developed to assess the activity of the optimized compounds on NMII. Human NMIIA will be expressed and purified with Spy-tag and Avi-tag (tags designed for single-molecule manipulation) on opposite sides from SF9 cells, which have been shown to express NMII proteins well (Billington et al. 2013). Alternatively, GFP affinity beads may be used to purify NMIIB-GFP from Allen Institute hPSC lines (Roberts et al. 2017).

Figure 29A:
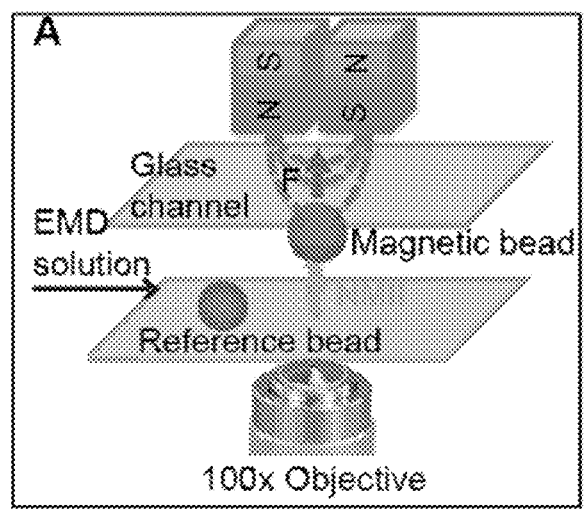
FIGS. 29A-29B illustrates single-molecule studies that reveal mechano-response in the presence of ligand.
Figure 29B:
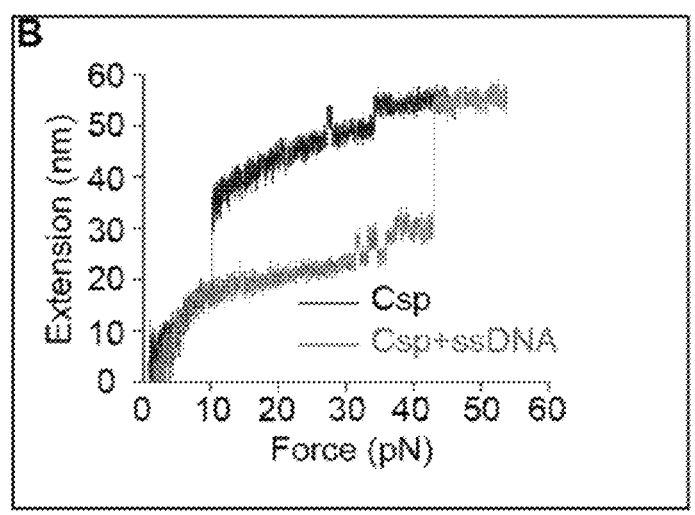

Purified NMIIA or NMIIB-GFP will be substituted into actin binding and polymerization kits in the presence of ATP, as well as ATPase assays developed based on actomyosin activity (commercially available kits from Cytoskeleton Inc., Denver CO) (De La Cruz & Ostap 2009). These NMII paralogs will be compared to positive controls of recombinant skeletal and cardiac myosin II (ibid). EMD or 4-HAP will be added into these assays in a dose titration from 0.1 to 10 μM. To assess unfolding, NMII paralogs will be tethered between Spy-catcher-coated glass channel surface and streptavidin-coated 2.8 μm-diameter magnetic bead, unfolded progressively under calibrated force, and allowed to re-fold in a vertical magnetic tweezers, in the presence or absence of EMD. The extension of NMIIA will be monitored and the changes of folding/unfolding forces will be measured under different doses of EMD. Dr. Fu has pioneered the vertical magnetic tweezers technique for such uses (FIGS. 29A-29B) (Fu et al. 2017; Fu et al. 2013; Zhang et al. 2012; Fu et al. 2011; Chen et al. 2011).

Study Populations. The same study populations will be used as described in the examples above Statistical Analysis. Studies will be powered with distinct organoid lines and sufficient samples as described above. Power analysis for these experiments is shown in Table 3 above.

Discussion

The development of myosin inhibitors and activators remains immature, which provides ample space for improvement (Bond et al. 2013). EMD is estimated to increase non-cardiac myosin II activity only three-fold (Radke et al. 2014). Optimization of EMD for binding and activity on NMII will likely reduce its interactions with cardiac myosins and increase its potency. In general, the potency of myosin II inhibitors and activators remains low. Active concentrations in the nanomolar range would be a significant outcome not only for PKD but also for the field of myosin activation as a whole. Second-generation scaffolds may be further used as the basis for subsequent improvements.

Notably, NMII is slowly processive, having evolved for tension-bearing and prolonged activity, in contrast to muscle myosins, which tend to be much quicker and have a shorter duty ratio. It is believed that NMII is the target of EMD, rather than other myosin isoforms, because other activators specific for smooth muscle or cardiac myosins do not have the same effect on PKD organoid cysts (see FIG. 22, above). Nevertheless, the mechanism of action is not yet fully understood. By optimizing EMD for binding to NMII in silico and more closely examining its effects at the cellular level in these in vitro assays, the comprehension of its mechanism of action will be improved. In turn this will help clarify the role of NMII in PKD, which is a new area of study, and the general pathophysiology of PKD.

Alternative Approaches, Scientific Rigor, and Validation. As an alternative to chemically modifying EMD to improve its solubility, a jet-milling protocol described for EMD in canines (Vogt et al. 2008a; Vogt et al. 2008b) may be used, or EMD may be suspended in propylene glycol (Duncker et al. 2001), to improve solubility.

In addition to myosin unfolding, the kinetic effects of drugs on actinomyosin activity can be measured using single molecule assays (Woody et al. 2018; Nagy et al. 2013). A TIRF microscope, may be used to directly monitor myosin processivity on actin filaments at the single molecule level, using a dual fluorescent labeling approach (Fu et al. 2017; Jiang et al. 2019). Changes of binding affinities between NMII and its partners may also be assessed using the Biacore T100 surface plasmon resonance (SPR).

As part of target validation, also it may also be investigated whether effects in organoids depend upon NMIIA, NMIIB, or NMIIC by knocking out these isoforms in hPSC with CRISPR. Assuming this is not lethal, the loss of NMII will phenocopy PKD, as was recently shown in a mouse model (Recuenco et al. 2015). In the scRNA-seq analyses described above, NMIIA and NMIIB were strongly expressed in kidney organoids, whereas NMIIC was expressed to a lesser degree (Czerniecki et al. 2018). If EMD is specific to one paralog, its loss should abrogate EMD's effect.

From the foregoing, it will be appreciated that specific embodiments of the invention have been described herein for purposes of illustration, but that various modifications may be made without deviating from the scope of the invention. Accordingly, the invention is not limited except as by the appended claims.

REFERENCES

Cruz, N. M., Song, X., Czerniecki, S. M., Gulieva, R. E., Churchill, A. J., Kim, Y. K., Winston, K., Diaz, M. A., Fu, H., Finn, L. S., Pei, Y., Himmelfarb, J., Freedman, B. S. Organoid cystogenesis reveals a critical role of microenvironment in human polycystic kidney disease. Nature Materials 16:1112-1119 (2017).

Czerniecki, S. M. et al. High-Throughput Screening Enhances Kidney Organoid Differentiation from Human Pluripotent Stem Cells and Enables Automated Multidimensional Phenotyping. Cell Stem Cell 22, 929-940 e924 (2018).

Dalgaard, O. Z. Bilateral polycystic disease of the kidneys; a follow-up of 284 patients and their families. Dan Med Bull 4, 128-133 (1957).

Daniel, C., L€udke, A., Wagner, A., Todorov, V. T., Hohenstein, B., and Hugo, C. (2012). Transgelin is a marker of repopulating mesangial cells after injury and promotes their proliferation and migration. Lab. Invest. 92, 812-826.

De La Cruz, E. M. & Ostap, E. M. Kinetic and equilibrium analysis of the myosin ATPase. Methods Enzymol 455, 157-192 (2009).

Dekel, B., Burakova, T., Arditti, F. D., Reich-Zeliger, S., Milstein, O., Aviel-Ronen, S., Rechavi, G., Friedman, N., Kaminski, N., Passwell, J. H., and Reisner, Y. (2003). Human and porcine early kidney precursors as a new source for transplantation. Nat. Med. 9, 53-60.

Dekkers, J. F., Wiegerinck, C. L., de Jonge, H. R., Bronsveld, I., Janssens, H. M., de Winter-de Groot, K. M., Brandsma, A. M., de Jong, N. W., Bijvelds, M. J., Scholte, B. J., et al. (2013). A functional CFTR assay using primary cystic fibrosis intestinal organoids. Nat. Med. 19, 939-945.

Deltas, C. & Papagregoriou, G. Cystic diseases of the kidney: molecular biology and genetics. Arch Pathol Lab Med 134, 569-582.

Doerr, N., Wang, Y., Kipp, K. R., Liu, G., Benza, J. J., Pletnev, V., Pavlov, T. S., Staruschenko, A., Mohieldin, A. M., Takahashi, M., et al. (2016). Regulation of polycystin-1 function by calmodulin binding. PLoS ONE 11, e0161525.

Doulatov, S., Vo, L. T., Macari, E. R., Wahlster, L., Kinney, M. A., Taylor, A. M., Barragan, J., Gupta, M., McGrath, K., Lee, H. Y., et al. (2017). Drug discovery for Diamond-Blackfan anemia using reprogrammed hematopoietic progenitors. Sci. Transl. Med. Published online Feb. 8, 2017. https://doi.org/10. 1126/scitranslmed.aah5645.

Duncker, D. J. et al. Beneficial effects of the Ca2+ sensitizer EMD 57033 in exercising pigs with infarction-induced chronic left ventricular dysfunction. Br J Pharmacol 134, 553-562 (2001).

Durham, T. B. & Blanco, M. J. Target engagement in lead generation. Bioorg Med Chem Lett 25, 998-1008 (2015).

Evans, S. J., Levi, A. J., Lee, J. A. & Jones, J. V. EMD 57033 enhances arrhythmias associated with increased wall-stress in the working rat heart. Clin Sci (Lond) 89, 59-67(1995).

Freedman, B. S. et al. Reduced ciliary polycystin-2 in induced pluripotent stem cells from polycystic kidney disease patients with PKD1 mutations. J. Am. Soc. Nephrol. 24, 1571-1586 (2013).

Freedman, B. S. et al. Modelling kidney disease with CRISPR-mutant kidney organoids derived from human pluripotent epiblast spheroids. Nat Commun 6, 8715 (2015a).

Freedman, B. S. Modeling Kidney Disease with iPS Cells. Biomark Insights 10, 153-169 (2015b).

Freedman, B. S. et al. Reduced ciliary polycystin-2 in induced pluripotent stem cells from polycystic kidney disease patients with PKD1 mutations. J Am Soc Nephrol 24, 1571-1586 (2013).

Fu, H. et al. Transition dynamics and selection of the distinct S-DNA and strand unpeeling modes of double helix overstretching. Nucleic Acids Res 39, 3473-3481 (2011).

Fu, H., Le, S., Chen, H., Muniyappa, K. & Yan, J. Force and ATP hydrolysis dependent regulation of RecA nucleoprotein filament by single-stranded DNA binding protein. Nucleic Acids Res 41, 924-932 (2013).

Fu, H. et al. Flow-induced elongation of von Willebrand factor precedes tension-dependent activation. Nat Commun 8, 324 (2017).

Gainullin, V. G., Hopp, K., Ward, C. J., Hommerding, C. J. & Harris, P. C. Polycystin-1 maturation requires polycystin-2 in a dose-dependent manner. J Clin Invest 125, 607-620 (2015).

Gattone, V. H., 2nd, Wang, X., Harris, P. C. & Torres, V. E. Inhibition of renal cystic disease development and progression by a vasopressin V2 receptor antagonist. Nat Med 9, 1323-1326 (2003).

Gebhardt, R. et al. New hepatocyte in vitro systems for drug metabolism: metabolic capacity and recommendations for application in basic research and drug development, standard operation procedures. Drug Metab Rev 35, 145-213 (2003).

Gracz, A. D., Williamson, I. A., Roche, K. C., Johnston, M. J., Wang, F., Wang, Y., Attayek, P. J., Balowski, J., Liu, X. F., Laurenza, R. J., et al. (2015). A high throughput platform for stem cell niche co-cultures and downstream gene expression analysis. Nat. Cell Biol. 17, 340-349.

Grantham, J. J., Geiser, J. L. & Evan, A. P. Cyst formation and growth in autosomal dominant polycystic kidney disease. Kidney Int. 31, 1145-1152 (1987).

Green, E. M. et al. A small-molecule inhibitor of sarcomere contractility suppresses hypertrophic cardiomyopathy in mice. Science 351, 617-621 (2016).

Greenberg, A. & Cheung, A. K. Primer on kidney diseases, Edn. 5th. (Saunders/Elsevier: National Kidney Foundation, Philadelphia, PA; 2009).

Gross, P., Schirutschke, H. & Paliege, A. Con: Tolvaptan for autosomal dominant polycystic kidney disease-do we know all the answers?Nephrol Dial Transplant 34, 35-37 (2019).

Grskovic, M., Javaherian, A., Strulovici, B., and Daley, G. Q. (2011). Induced pluripotent stem cells-opportunities for disease modelling and drug discovery. Nat. Rev. Drug Discov. 10, 915-929.

Halt, K. J., P€arssinen, H. E., Junttila, S. M., Saarela, U., Sims-Lucas, S., Koivunen, P., Myllyharju, J., Quaggin, S., Skovorodkin, I. N., and Vainio, S. J. (2016). CD146(+) cells are essential for kidney vasculature development. Kidney Int. 90, 311-324.

Harari-Steinberg, O., Metsuyanim, S., Omer, D., Gnatek, Y., Gershon, R., Pri-Chen, S., Ozdemir, D. D., Lerenthal, Y., Noiman, T., Ben-Hur, H., et al. (2013). Identification of human nephron progenitors capable of generation of kidney structures and functional repair of chronic renal disease. EMBO Mol. Med. 5, 1556-1568.

Harder, J. L. et al. Organoid single cell profiling identifies a transcriptional signature of glomerular disease. JCI Insight 4 (2019).

Hayashi, R., Ishikawa, Y., Sasamoto, Y., Katori, R., Nomura, N., Ichikawa, T., Araki, S., Soma, T., Kawasaki, S., Sekiguchi, K., et al. (2016). Co-ordinated ocular development from human PS cells and recovery of corneal function. Nature 531, 376-380.

He, J. et al. PKD1 mono-allelic knockout is sufficient to trigger renal cystogenesis in a mini-pig model. Int J Biol Sci 11, 361-369 (2015).

Hopp, K. et al. Functional polycystin-1 dosage governs autosomal dominant polycystic kidney disease severity. J Clin Invest 122, 4257-4273 (2012).

Hopp, K. et al. Tolvaptan plus pasireotide shows enhanced efficacy in a PKD1 model. J Am Soc Nephrol 26, 39-47 (2015).

Huang, L., Holtzinger, A., Jagan, I., BeGora, M., Lohse, I., Ngai, N., Nostro, C., Wang, R., Muthuswamy, L. B., Crawford, H. C., et al. (2015). Ductal pancreatic cancer modeling and drug screening using human pluripotent stem cell- and patient-derived tumor organoids. Nat. Med. 21, 1364-1371.

Ibraghimov-Beskrovnaya, O. et al. Strong homophilic interactions of the Ig-like domains of polycystin-1, the protein product of an autosomal dominant polycystic kidney disease gene, PKD1. Hum. Mol. Genet. 9, 1641-1649 (2000).

Jaffe, A. B., Kaji, N., Durgan, J. & Hall, A. Cdc42 controls spindle orientation to position the apical surface during epithelial morphogenesis. J Cell Biol 183, 625-633 (2008).

Jiang, Y., Fu, H., Springer, T. A. & Wong, W. P. Electrostatic Steering Enables Flow-Activated von Willebrand Factor to Bind Platelet Glycoprotein, Revealed by Single-Molecule Stretching and Imaging. J Mol Biol (2019).

Jin, Y., Muhl, L., Burmakin, M., Wang, Y., Duchez, A. C., Betsholtz, C., Arthur, H. M., and Jakobsson, L. (2017). Endoglin prevents vascular malformation by regulating flow-induced cell migration and specification through VEGFR2 signalling. Nat. Cell Biol. 19, 639-652.

Jinek, M. et al. A programmable dual-RNA-guided DNA endonuclease in adaptive bacterial immunity. Science 337, 816-821 (2012).

Kandasamy, K., Chuah, J. K., Su, R., Huang, P., Eng, K. G., Xiong, S., Li, Y., Chia, C. S., Loo, L. H., and Zink, D. (2015). Prediction of drug-induced nephrotoxicity and injury mechanisms with human induced pluripotent stem cell-derived cells and machine learning methods. Sci. Rep. 5, 12337.

Kim, Y. K., Refaeli, I., Brooks, C. R., Jing, P., Gulieva, R. E., Hughes, M. R., Cruz, N. M., Liu, Y., Churchill, A. J., Wang, Y., et al. (2017). Gene-edited human kidney organoids reveal mechanisms of disease in podocyte development. Stem Cells 35, 2366-2378.

Kraft, T. & Brenner, B. Force enhancement without changes in cross-bridge turnover kinetics: the effect of EMD 57033. Biophys J 72, 272-281 (1997).

Kuo, I. Y. et al. Cyst formation following disruption of intracellular calcium signaling. Proc Natl Acad Sci USA 111, 14283-14288 (2014).

Lakhia, R. et al. PPARalpha agonist fenofibrate enhances fatty acid beta-oxidation and attenuates polycystic kidney and liver disease in mice. Am J Physiol Renal Physiol 314, F122-F131 (2018).

Lam, A. Q. et al. Rapid and efficient differentiation of human pluripotent stem cells into intermediate mesoderm that forms tubules expressing kidney proximal tubular markers. J Am Soc Nephrol 25, 1211-1225 (2014).

Lancaster, M. A. et al. Cerebral organoids model human brain development and microcephaly. Nature 501, 373-379 (2013).

Lantinga-van Leeuwen, I. S. et al. Lowering of Pkd1 expression is sufficient to cause polycystic kidney disease. Hum. Mol. Genet. 13, 3069-3077 (2004).

Lee, J. A., Palmer, S. & Kentish, J. C. Photolysis of the novel inotropes EMD 57033 and EMD 57439: evidence that Ca2+ sensitization and phosphodiesterase inhibition depend upon the same enantiomeric site. Br J Pharmacol 118, 2037-2044 (1996).

Liberzon, A. et al. The Molecular Signatures Database (MSigDB) hallmark gene set collection. Cell Syst. 1, 417-425 (2015).

Lienkamp, S. S., Liu, K., Karner, C. M., Carroll, T. J., Ronneberger, O., Wallingford, J. B., and Walz, G. (2012). Vertebrate kidney tubules elongate using a planar cell polarity-dependent, rosette-based mechanism of convergent extension. Nat. Genet. 44, 1382-1387.

Lin, S. L., Kisseleva, T., Brenner, D. A., and Duffield, J. S. (2008). Pericytes and perivascular fibroblasts are the primary source of collagen-producing cells in obstructive fibrosis of the kidney. Am. J. Pathol. 173, 1617-1627.

Liu, C. P. et al. Targeting strategies for drug delivery to the kidney: From renal glomeruli to tubules. Med Res Rev 39, 561-578 (2019).

Ma, M., Tian, X., Igarashi, P., Pazour, G. J. & Somlo, S. Loss of cilia suppresses cyst growth in genetic models of autosomal dominant polycystic kidney disease. Nat Genet 45, 1004-1012 (2013).

Mae, S. I., Shono, A., Shiota, F., Yasuno, T., Kajiwara, M., Gotoda-Nishimura, N., Arai, S., Sato-Otubo, A., Toyoda, T., Takahashi, K., et al. (2013). Monitoring and robust induction of nephrogenic intermediate mesoderm from human pluripotent stem cells. Nat. Commun. 4, 1367.

Magenheimer, B. S. et al. Early embryonic renal tubules of wild-type and polycystic kidney disease kidneys respond to cAMP stimulation with cystic fibrosis transmembrane conductance regulator/Na+, K+, 2Cl-Co-transporter-dependent cystic dilation. J. Am. Soc. Nephrol. 17, 3424-3437 (2006).

Major, M. B., Roberts, B. S., Berndt, J. D., Marine, S., Anastas, J., Chung, N., Ferrer, M., Yi, X., Stoick-Cooper, C. L., von Haller, P. D., et al. (2008). New regulators of Wnt/beta-catenin signaling revealed by integrative molecular screening. Sci. Signal. 1, ra12.

Malik, F. I. et al. Cardiac myosin activation: a potential therapeutic approach for systolic heart failure. Science 331, 1439-1443 (2011).

Mangos, S. et al. The ADPKD genes pkd1a/b and pkd2 regulate extracellular matrix formation. Dis Model Mech. 3, 354-365 (2010).

McCracken, K. W., Cata, E. M., Crawford, C. M., Sinagoga, K. L., Schumacher, M., Rockich, B. E., Tsai, Y. H., Mayhew, C. N., Spence, J. R., Zavros, Y., and Wells, J. M. (2014). Modelling human development and disease in pluripotent stem-cell-derived gastric organoids. Nature 516, 400-404.

Menon, R., Otto, E. A., Kokoruda, A., Zhou, J., Zhang, Z., Yoon, E., Chen, Y.-C., Troyanscaya, O., Spence, J., Kretzler, M., et al. (2018). Single-cell analysis of progenitor cell dynamics and lineage specification of the human fetal kidney. bioRxiv. https://doi.org/10.1101/258798.

Mochizuki, T. et al. PKD2, a gene for polycystic kidney disease that encodes an integral membrane protein. Science 272, 1339-1342 (1996).

Morgan, P. et al. Can the flow of medicines be improved?Fundamental pharmacokinetic and pharmacological principles toward improving Phase II survival. Drug Discov Today 17, 419-424 (2012).

Morizane, R. et al. Nephron organoids derived from human pluripotent stem cells model kidney development and injury. Nat. Biotechnol. 33, 1193-1200 (2015).

Munnich, S., Pathan-Chhatbar, S. & Manstein, D. J. Crystal structure of the rigor-like human non-muscle myosin-2 motor domain. FEBS Lett 588, 4754-4760 (2014).

Nagy, A. et al. Kinetic characterization of nonmuscle myosin IIb at the single molecule level. J Biol Chem 288, 709-722 (2013).

Nakanishi, K., Sweeney, W. E. Jr, Zerres, K., Guay-Woodford, L. M. & Avner, E. D. Proximal tubular cysts in fetal human autosomal recessive polycystic kidney disease. J. Am. Soc. Nephrol. 11, 760-763 (2000).

Nauli, S. M. et al. Polycystins 1 and 2 mediate mechanosensation in the primary cilium of kidney cells. Nat Genet 33, 129-137 (2003).

Neufeld, T. K. et al. In vitro formation and expansion of cysts derived from human renal cortex epithelial cells. Kidney Int 41, 1222-1236 (1992).

O'Brien, L. E. et al. Rac1 orientates epithelial apical polarity through effects on basolateral laminin assembly. Nature cell biology 3, 831-838 (2001).

Olsan, E. E., Matsushita, T., Rezaei, M. & Weimbs, T. Exploitation of the Polymeric Immunoglobulin Receptor for Antibody Targeting to Renal Cyst Lumens in Polycystic Kidney Disease. J Biol Chem 290, 15679-15686 (2015).

Ong, A. C. et al. Polycystin-1 expression in PKD1, early-onset PKD1, and TSC2/PKD1 cystic tissue. Kidney Int. 56, 1324-1333 (1999).

Pabla, N., and Dong, Z. (2008). Cisplatin nephrotoxicity: Mechanisms and renoprotective strategies. Kidney Int. 73, 994-1007.

Pagliuca, F. W., Millman, J. R., G€urtler, M., Segel, M., Van Dervort, A., Ryu, J. H., Peterson, Q. P., Greiner, D., and Melton, D. A. (2014). Generation of functional human pancreatic b cells in vitro. Cell 159, 428-439.

Palpant, N. J., Pabon, L., Friedman, C. E., Roberts, M., Hadland, B., Zaunbrecher, R. J., Bernstein, I., Zheng, Y., and Murry, C. E. (2017). Generating high-purity cardiac and endothelial derivatives from patterned mesoderm using human pluripotent stem cells. Nat. Protoc. 12, 15-31.

Pan, B. S. & Johnson, R. G., Jr. Interaction of cardiotonic thiadiazinone derivatives with cardiac troponin C. J Biol Chem 271, 817-823 (1996).

Park-Windhol, C., Ng, Y. S., Yang, J., Primo, V., Saint-Geniez, M., and D'Amore, P. A. (2017). Endomucin inhibits VEGF-induced endothelial cell migration, growth, and morphogenesis by modulating VEGFR2 signaling. Sci. Rep. 7, 17138.

Patel, V. et al. Acute kidney injury and aberrant planar cell polarity induce cyst formation in mice lacking renal cilia. Hum. Mol. Genet. 17, 1578-1590 (2008).

Perrone, R. D. et al. Total Kidney Volume Is a Prognostic Biomarker of Renal Function Decline and Progression to End-Stage Renal Disease in Patients With Autosomal Dominant Polycystic Kidney Disease. Kidney Int Rep 2, 442-450 (2017).

Petersen, O. W., Ronnov-Jessen, L., Howlett, A. R. & Bissell, M. J. Interaction with basement membrane serves to rapidly distinguish growth and differentiation pattern of normal and malignant human breast epithelial cells. Proceedings of the National Academy of Sciences of the United States of America 89, 9064-9068 (1992).

Praetorius, H. A. & Spring, K. R. Bending the MDCK cell primary cilium increases intracellular calcium. J Membr Biol 184, 71-79 (2001).

Qian, F., Watnick, T. J., Onuchic, L. F. & Germino, G. G. The molecular basis of focal cyst formation in human autosomal dominant polycystic kidney disease type I. Cell 87, 979-987 (1996).

Radke, M. B. et al. Small molecule-mediated refolding and activation of myosin motor function. Elife 3, e01603 (2014).

Ramm, S., Adler, M., and Vaidya, V. S. (2016). A high-throughput screening assay to identify kidney toxic compounds. Curr. Protoc. Toxicol. 69, 9.10.1-9.10.26.

Recuenco, M. C. et al. Nonmuscle Myosin II Regulates the Morphogenesis of Metanephric Mesenchyme-Derived Immature Nephrons. J Am Soc Nephrol 26, 1081-1091 (2015).

Reif, G. A. et al. Tolvaptan inhibits ERK-dependent cell proliferation, Cl(−) secretion, and in vitro cyst growth of human ADPKD cells stimulated by vasopressin. Am J Physiol Renal Physiol 301, F1005-1013 (2011).

Rinkevich, Y., Montoro, D. T., Contreras-Trujillo, H., Harari-Steinberg, O., Newman, A. M., Tsai, J. M., Lim, X., Van-Amerongen, R., Bowman, A., Januszyk, M., et al. (2014). In vivo clonal analysis reveals lineage-restricted progenitor characteristics in mammalian kidney development, maintenance, and regeneration. Cell Rep. 7, 1270-1283.

Roberts, B. et al. Systematic gene tagging using CRISPR/Cas9 in human stem cells to illuminate cell organization. Mol Biol Cell 28, 2854-2874 (2017).

Rodriguez, A. G., Rodriguez, M. L., Han, S. J., Sniadecki, N. J. & Regnier, M. Enhanced contractility with 2-deoxy-ATP and EMD 57033 is correlated with reduced myofibril structure and twitch power in neonatal cardiomyocytes. Integr Biol (Camb) 5, 1366-1373 (2013).

Roman, B. I., Verhasselt, S. & Stevens, C. V. Medicinal Chemistry and Use of Myosin II Inhibitor (S)-Blebbistatin and Its Derivatives. J Med Chem 61, 9410-9428 (2018).

Rossetti, S. et al. Incompletely penetrant PKD1 alleles suggest a role for gene dosage in cyst initiation in polycystic kidney disease. Kidney Int 75, 848-855 (2009).

Sachs, N., de Ligt, J., Kopper, O., Gogola, E., Bounova, G., Weeber, F., Balgobind, A. V., Wind, K., Gracanin, A., Begthel, H., et al. (2018). A living biobank of breast cancer organoids captures disease heterogeneity. Cell 172, 373-386.e10.

Sakolish, C. et al. Technology Transfer of the Microphysiological Systems: A Case Study of the Human Proximal Tubule Tissue Chip. Sci Rep 8, 14882 (2018).

Satoh, S. et al. Post-beta-receptor impairment in the regulation of myofibrillar Ca2+ sensitivity in tachypacing-induced canine failing heart. J Cardiovasc Pharmacol 39, 88-97 (2002).

Schober, T. et al. Myofilament Ca sensitization increases cytosolic Ca binding affinity, alters intracellular Ca homeostasis, and causes pause-dependent Ca-triggered arrhythmia. Circ Res 111, 170-179 (2012).

Senzaki, H. et al. Improved mechanoenergetics and cardiac rest and reserve function of in vivo failing heart by calcium sensitizer EMD-57033. Circulation 101, 1040-1048 (2000).

Shankland, S. J., Freedman, B. S., and Pippin, J. W. (2017). Can podocytes be regenerated in adults?Curr. Opin. Nephrol. Hypertens. 26, 154-164.

Sharma, A., Burridge, P. W., McKeithan, W. L., Serrano, R., Shukla, P., Sayed, N., Churko, J. M., Kitani, T., Wu, H., Holmström, A., et al. (2017). High throughput screening of tyrosine kinase inhibitor cardiotoxicity with human induced pluripotent stem cells. Sci. Transl. Med. Published online Feb. 15, 2017. https://doi.org/10.1126/scitranslmed.aaf2584.

Shillingford, J. M. et al. The mTOR pathway is regulated by polycystin-1, and its inhibition reverses renal cystogenesis in polycystic kidney disease. Proc. Natl Acad. Sci. USA 103, 5466-5471 (2006).

Song, X. et al. Systems biology of autosomal dominant polycystic kidney disease (ADPKD): computational identification of gene expression pathways and integrated regulatory networks. Hum. Mol. Genet. 18, 2328-2343 (2009).

Spence, J. R., Mayhew, C. N., Rankin, S. A., Kuhar, M. F., Vallance, J. E., Tolle, K., Hoskins, E. E., Kalinichenko, V. V., Wells, S. I., Zorn, A. M., et al. (2011). Directed differentiation of human pluripotent stem cells into intestinal tissue in vitro. Nature 470, 105-109.

Straight, A. F. et al. Dissecting temporal and spatial control of cytokinesis with a myosin II Inhibitor. Science 299, 1743-1747 (2003).

Subramanian, A. et al. Gene set enrichment analysis: a knowledge-based approach for interpreting genome-wide expression profiles. Proc. Natl Acad. Sci. USA 102, 15545-15550 (2005).

Sugden, W. W., Meissner, R., Aegerter-Wilmsen, T., Tsaryk, R., Leonard, E. V., Bussmann, J., Hamm, M. J., Herzog, W., Jin, Y., Jakobsson, L., et al. (2017). Endoglin controls blood vessel diameter through endothelial cell shape changes in response to haemodynamic cues. Nat. Cell Biol. 19, 653-665.

Surcel, A. et al. Pharmacological activation of myosin II paralogs to correct cell mechanics defects. Proc Natl Acad Sci USA 112, 1428-1433 (2015).

Taguchi, A. et al. Redefining the in vivo origin of metanephric nephron progenitors enables generation of complex kidney structures from pluripotent stem cells. Cell Stem Cell 14, 53-67 (2014).

Takahashi, K., Tanabe, K., Ohnuki, M., Narita, M., Ichisaka, T., Tomoda, K., and Yamanaka, S. (2007). Induction of pluripotent stem cells from adult human fibroblasts by defined factors. Cell 131, 861-872.

Takakura, A. et al. Renal injury is a third h t promoting rapid development of adult polycystic kidney disease. Hum. Mol. Genet. 18, 2523-2531 (2009).

Takasato, M. et al. Kidney organoids from human iPS cells contain multiple lineages and model human nephrogenesis. Nature 526, 564-568 (2015).

Tangri, N. et al. Total Kidney Volume as a Biomarker of Disease Progression in Autosomal Dominant Polycystic Kidney Disease. Can J Kidney Health Dis 4, 2054358117693355 (2017).

The European Polycystic Kidney Disease Consortium. The polycystic kidney disease 1 gene encodes a 14 kb transcript and lies within a duplicated region on chromosome 16. Cell 78, 725 (1994).

The International Polycystic Kidney Disease Consortium. Polycystic kidney disease: the complete structure of the PKD1 gene and its protein. Cell 81, 289-298 (1995).

Thomson, J. A., Itskovitz-Eldor, J., Shapiro, S. S., Waknitz, M. A., Swiergiel, J. J., Marshall, V. S., and Jones, J. M. (1998). Embryonic stem cell lines derived from human blastocysts. Science 282, 1145-1147.

Tobias, A. H., Slinker, B. K., Kirkpatrick, R. D. & Campbell, K. B. Functional effects of EMD-57033 in isovolumically beating isolated rabbit hearts. Am J Physiol 271, H51-58 (1996).

Torres, V. E. et al. Tolvaptan in Later-Stage Autosomal Dominant Polycystic Kidney Disease. N Engl J Med 377, 1930-1942 (2017).

Torres, V. E. et al. Tolvaptan in patients with autosomal dominant polycystic kidney disease. N Engl J Med 367, 2407-2418 (2012).

Trudel, M. et al. C-myc-induced apoptosis in polycystic kidney disease is Bcl-2 and p53 independent. J. Exp. Med. 186, 1873-1884 (1997).

Vernetti, L. et al. Functional Coupling of Human Microphysiology Systems: Intestine, Liver, Kidney Proximal Tubule, Blood-Brain Barrier and Skeletal Muscle. Sci Rep 7, 42296 (2017).

Vicente-Manzanares, M., Ma, X., Adelstein, R. S. & Horwitz, A. R. Non-muscle myosin II takes centre stage in cell adhesion and migration. Nat Rev Mol Cell Biol 10, 778-790 (2009).

Vogt, M., Vertzoni, M., Kunath, K., Reppas, C. & Dressman, J. B. Cogrinding enhances the oral bioavailability of EMD 57033, a poorly water soluble drug, in dogs. Eur J Pharm Biopharm 68, 338-345 (2008a).

Vogt, M., Kunath, K. & Dressman, J. B. Dissolution improvement of four poorly water soluble drugs by cogrinding with commonly used excipients. Eur J Pharm Biopharm 68, 330-337 (2008b).

Vujic, M. et al. Incompletely penetrant PKD1 alleles mimic the renal manifestations of ARPKD. J. Am. Soc. Nephrol. 21, 1097-1102 (2010).

Warner, G. et al. Food Restriction Ameliorates the Development of Polycystic Kidney Disease. J Am Soc Nephrol 27, 1437-1447 (2016).

Watnick, T. et al. Mutations of PKD1 in ADPKD2 cysts suggest a pathogenic effect of trans-heterozygous mutations. Nat Genet 25, 143-144 (2000).

Weber, E. J. et al. Development of a microphysiological model of human kidney proximal tubule function. Kidney Int 90, 627-637 (2016).

Woody, M. S. et al. Positive cardiac inotrope omecamtiv mecarbil activates muscle despite suppressing the myosin working stroke. Nat Commun 9, 3838 (2018).

Wu, G. et al. Somatic inactivation of Pkd2 results in polycystic kidney disease. Cell 93, 177-188 (1998).

Wu, G. et al. Trans-heterozygous Pkd1 and Pkd2 mutations modify expression of polycystic kidney disease. Hum Mol Genet 11, 1845-1854 (2002).

Yang, K. C. et al. Novel Adult-Onset Systolic Cardiomyopathy Due to MYH7 E848G Mutation in Patient-Derived Induced Pluripotent Stem Cells. JACC Basic Transl Sci 3, 728-740 (2018).

Yang, Y. M., Gupta, S. K., Kim, K. J., Powers, B. E., Cerqueira, A., Wainger, B. J., Ngo, H. D., Rosowski, K. A., Schein, P. A., Ackeifi, C. A., et al. (2013). A small molecule screen in stem-cell-derived motor neurons identifies a kinase inhibitor as a candidate therapeutic for ALS. Cell Stem Cell 12, 713-726.

Zhang, J. H., Chung, T. D., and Oldenburg, K. R. (1999). A simple statistical parameter for use in evaluation and validation of high throughput screening assays. J. Biomol. Screen. 4, 67-73.

Zhang, X., Chen, H., Fu, H., Doyle, P. S. & Yan, J. Two distinct overstretched DNA structures revealed by single-molecule thermodynamics measurements. Proc Natl Acad Sci USA 109, 8103-8108 (2012).

We claim:

1. A method for testing effects of therapeutic compound candidates on a phenotypic organoid model comprising tubular structures, the method comprising:
   generating the phenotypic organoid model comprising tubular structures on a high throughput screening platform, comprising the steps of:
   plating each of a plurality of wells of a high throughput culture vessel with a population of human pluripotent stem cells (hPSCs);
   differentiating the population of hPSCs plated in each of the plurality of wells using only a single induction step without dissociating or replating the differentiated cells, wherein the single induction step comprises treating the population of hPSCs in each of the plurality of wells with a concentration of CHIR;
   treating the population of hPSCs plated in each of the plurality of wells with a therapeutic compound candidate among the therapeutic compound candidates; and
   testing one or more effects resulting from treatment with each of the therapeutic compound candidates;
   wherein the method is performed automatically by a liquid handling robot.

2. The method of claim 1, wherein the high throughput culture vessel comprises 384 or more wells and wherein the plurality of wells is the same as or less than a number of wells in the high throughput culture vessel.

3. The method of claim 2, wherein the population of hPSCs are plated at a density of less than 5,000 cells per well.

4. The method of claim 1, wherein the CHIR is CHIR99021.

5. The method of claim 4, wherein the concentration of CHIR99021 is 14 µM.

6. The method of claim 1, wherein generating the phenotypic organoid model further comprises treating the population of cells with VEGF.

7. The method of claim 1, wherein the one or more effects resulting from treatment with each of the therapeutic compound candidates comprise cell toxicity, cell differentiation, and efficacy.

8. The method of claim 1, wherein the organoid is a kidney organoid.

9. The method of claim 1, wherein the tubular structures comprise proximal tubules and distal tubules.

10. The method of claim 1, wherein the differentiation is directed differentiation.

11. The method of claim 1, wherein each cell has an organ lineage and each cell differentiates into the same organ lineage.

* * * * *